(12) United States Patent
Schunk et al.

(10) Patent No.: US 8,357,717 B2
(45) Date of Patent: Jan. 22, 2013

(54) SPIRO GROUP-CONTAINING AMIDE COMPOUNDS HAVING BRADYKININ 1 RECEPTOR (B1R) ACTIVITY

(75) Inventors: Stefan Schunk, Aachen (DE); Melanie Reich, Aachen (DE); Michael Engels, Turnhout (BE); Tieno Germann, Aachen (DE); Ruth Jostock, Stolberg (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/700,857

(22) Filed: Feb. 5, 2010

(65) Prior Publication Data

US 2010/0234340 A1 Sep. 16, 2010

Related U.S. Application Data

(60) Provisional application No. 61/150,413, filed on Feb. 6, 2009.

(30) Foreign Application Priority Data

Feb. 6, 2009 (EP) .................................. 09001659

(51) Int. Cl.
*A61K 31/40* (2006.01)
*A61K 31/47* (2006.01)
(52) U.S. Cl. .......... 514/414; 514/30; 514/314; 546/139; 546/152; 546/268.1; 548/469; 548/490; 548/950
(58) Field of Classification Search .................. 514/307, 514/314, 414; 546/139, 152, 268.1; 548/469, 548/490, 950
See application file for complete search history.

(56) References Cited

FOREIGN PATENT DOCUMENTS

| WO | WO 2007/101007 A | 9/2007 |
|---|---|---|
| WO | WO 2007/140383 | 12/2007 |
| WO | WO 2008/040492 A | 4/2008 |
| WO | WO 2008/046573 A | 4/2008 |

OTHER PUBLICATIONS

Bengtson et al., Kinin receptor expression during *Staphylococcus aureus* infection, *Blood*. 2006; 108: 2055-2063.
Calixto et al., Kinin B1 receptors: key G-protein-coupled receptors and their role in inflammatory and painful processes, *British Journal of Pharmacology*. 2004; 143: 803-818.

Gabra et al., The kinin system mediates hyperalgesia through the inducible bradykinin B1 receptor subtype: evidence in various experimental animal models of type 1 and type 2 diabetic neuropathy, *Biol. Chem.* vol. 387, pp. 127-143, Feb. 2006.
Hayashi et al., Bradykinin stimulates IL-6 and IL-8 production by human lung fibroblasts through ERK- and p38 MAPK-dependent mechanisms, *European Respiratory Journal*. 2000; 16: 452-458.
Hess et al., Generation and characterization of a humanized bradykinin B1 receptor mouse, *Biol. Chem.*, vol. 387, pp. 195-201, Feb. 2006.
Leeb-Lundberg et al., International Union of Pharmacology. XLV. Classification of the Kinin Receptor Family: from Molecular Mechanisms to Pathophysiological Consequences, *Pharmacological Reviews*. 57: 27-77, 2005.
Passos et al., Kinin B1 Receptor Up-Regulation after Lipopolysaccharide Administration: Role of Proinflammatory Cytokines and Neutrophil Influx, *The Journal of Immunology*. 2004, 172: 1839-1847.
Pesquero et al., Hypoalgesia and altered inflammatory responses in mice lacking kinin B1 receptors, *Proc. Natl. Acad. Sci.*, vol. 97, No. 14, pp. 8140-8145, Jul. 5, 2000.
Pesquero et al., Genetically altered animal models in the kallikrein-kinin system, *Biol. Chem.*, vol. 387, pp. 119-126, Feb. 2006.
Prat et al., Bradykinin B1 receptor expression and function on T lymphocytes in active multiple sclerosis, *Neurology*, vol. 53 (9), pp. 2087-2092, Dec. 10, 1999.
Stadnicki et al., Immunolocalization and expression of kinin B1R and B2R receptors in human inflammatory bowel disease, *Am. J. Physiol. Gastrointest. Liver Physiol.*, 289: G361-G366, 2005.

*Primary Examiner* — Douglas M Willis
(74) *Attorney, Agent, or Firm* — Crowell & Moring LLP

(57) ABSTRACT

Substituted spiroamide compounds corresponding to formula (I):

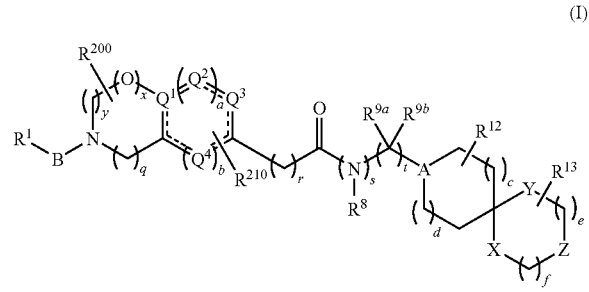

wherein A, B, $Q^1$, $Q^2$, $Q^3$, $Q^4$, $R^1$, $R^8$, $R^{9a}$, $R^{9b}$, $R^{12}$, $R^{13}$, $R^{200}$ and $R^{210}$ have defined meanings, processes for their preparation, pharmaceutical compositions containing such compounds, and the use of such compounds for treating or inhibiting pain or other conditions mediated at least in part by the bradykinin 1 receptor (B1R).

12 Claims, No Drawings

SPIRO GROUP-CONTAINING AMIDE COMPOUNDS HAVING BRADYKININ 1 RECEPTOR (B1R) ACTIVITY

CROSS REFERENCE TO RELATED APPLICATIONS

This application claims priority from U.S. provisional patent application No. 61/150,413, filed Feb. 6, 2009. Priority is also claimed based on European patent application no EP 09001659.3, also filed Feb. 6, 2009.

BACKGROUND OF THE INVENTION

The present invention relates to substituted spiroamides, to processes for their preparation, to pharmaceutical compositions comprising these compounds and to the use of substituted spiroamides in the preparation of medicaments and for the treatment and/or inhibition of pain, inflammatory diseases and other conditions mediated at least in part by Bradykinin 1 receptors (B1R).

Unlike the constitutive expression of the bradykinin 2 receptor (B2R), the bradykinin 1 receptor (B1R) is not expressed or is expressed only weakly in most tissues. However, the expression of B1R in various cells is inducible. For example, during inflammation reactions there is a rapid and pronounced induction of B1R in neuronal cells but also in various peripheral cells such as fibroblasts, endothelial cells, granulocytes, macrophages and lymphocytes. Accordingly, in the course of inflammation reactions there is a switch from B2R to B1R dominance in the cells that are involved. The cytokines interleukin-1 (IL-1) and tumour necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example, in enterocytes and macrophages in the affected tissue of patients with inflammatory intestinal diseases (Stadnicki et al., Am. J. Physiol. Gastrointest. Liver Physiol. 2005, 289, G361-366) or in T-lymphocytes of patients with multiple sclerosis (Prat et al., Neurology, 1999; 53, 2087-2092), or activation of the bradykinin B2R-B1R system is found in the course of infections with *Staphylococcus aureus* (Bengtson et al., Blood 2006, 108, 2055-2063). Infections with *Staphylococcus aureus* are responsible for symptoms such as superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

In addition, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143). They are also suitable for the treatment of migraine.

In the development of B1R modulators there is the problem, however, that the human and the rat B1 receptor differ so widely that many compounds that are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already led to the production of transgenic animals with human B1 receptors for animal pharmacology studies (Hess et al., Biol. Chem. 2006; 387(2):195-201). Working with transgenic animals is more expensive, however, than working with the unmodified animals.

Patent applications WO 2007/140383 and WO 2007/101007 describe compounds that exhibit an antagonistic activity on the macaque B1 receptor in in vitro assays. Experimental data relating to activity on the human B1 receptor or on the B1 receptor of the rat are not disclosed.

Patent applications WO 2008/040492 and WO 2008/046573 describe compounds that exhibit antagonistic activity both on the human B1 receptor and on the B1 receptor of the rat in in vitro assays.

Despite the efforts of the prior art, there remains a need for new B1R modulators, B1R modulators that bind both to the rat receptor and to the human receptor offering particular advantages.

SUMMARY OF THE INVENTION

An object of the present invention was, therefore, to provide novel compounds which are suitable in particular as pharmacological active ingredients in medicaments, especially in medicaments for the treatment of disorders or diseases that are mediated at least in part by B1R receptors.

This and other objects are achieved by the substituted spiroamides according to the invention.

The invention accordingly provides substituted spiroamides of the general formula (I)

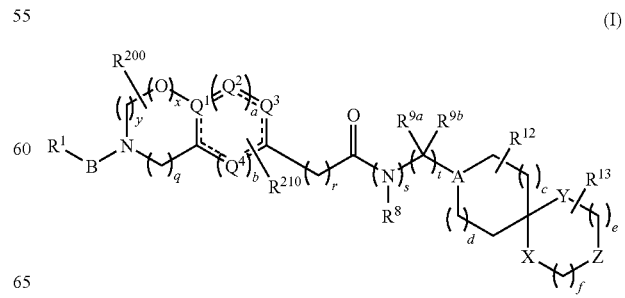

wherein $Q^1$ represents C or N;

$Q^2$ represents CH, N, O or S;

$Q^3$ represents CH, N, O or S;

$Q^4$ represents CH, N, O or S;

B represents C(=O), S(=O)$_2$ or represents the group —C(=O)—N(R$^4$), wherein the nitrogen atom is bonded to R$^1$;

a represents 0, 1 or 2;

b represents 0 or 1, with the proviso that a+b=1 or 2;

q represents 0 or 1;

x represents 0 or 1;

y represents 1, 2 or 3;

r represents 0, 1, 2 or 3;

$R^1$ represents aryl, heteroaryl or an aryl or heteroaryl bonded via a $C_{1-3}$-alkylene group or $C_{2-6}$-alkenylene group, wherein aryl and heteroaryl in each case optionally may be fused with a 4-, 5-, 6- or 7-membered carbocycle or heterocycle, wherein the carbocycle or heterocycle in each case may be saturated or mono- or polyunsaturated, for example mono- or di-unsaturated, but is not aromatic and in each case optionally may be substituted on one or more of its carbon ring members by one or more substituents independently selected from the group consisting of F, Cl, Br, I, —CF$_3$, —O—CF$_3$, $C_{1-6}$-alkyl and O—$C_{1-6}$-alkyl, and wherein the heterocycle contains one or more, for example 1, 2 or 3, heteroatoms or heteroatom groups independently selected from the group consisting of N, NR$^{50}$, O, S, S=O and S(=O)$_2$; wherein $R^{50}$ denotes H, $C_{1-6}$-alkyl, —C(=O)—R$^{51}$, $C_{3-8}$-cycloalkyl, aryl, heteroaryl or a $C_{3-8}$-cycloalkyl, aryl or heteroaryl bonded via a $C_{1-3}$-alkylene group, and $R^{51}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^4$ represents H, $C_{1-6}$-alkyl, aryl or an aryl bonded via a $C_{1-3}$-alkylene group;

$R^{200}$ represents from 0 to 4 substituents independently selected from the group consisting of $C_{1-6}$-alkyl, F, Cl, CF$_3$ and OCF$_3$;

$R^{210}$ represents from 0 to 4 substituents independently selected from the group consisting of $C_{1-6}$-alkyl, O—$C_{1-6}$-alkyl, F, Cl, CF$_3$ and OCF$_3$;

s=0 or 1, t=0, 1, 2 or 3, with the proviso that when s represents 0, then t represents 0;

$R^8$ represents H, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group;

$R^{9a}$ and $R^{9b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group;

A represents N or CH;

with the proviso that when s represents 1 and t represents 0, then A represents CH; and with the proviso that when s and t each represent 0, then A represents N;

c, d, e and f each independently represent 0, 1 or 2;

$R^{12}$ and $R^{13}$ each independently represent from 0 to 4 substituents independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent ones of the 0 to 4 substituents $R^{13}$ form a fused aryl or heteroaryl ring structure;

X represents CR$^{14a}$R$^{14b}$, NR$^{15}$, or O;

Y represents CR$^{16a}$R$^{16b}$, NR$^{17}$ or O;

with the proviso that if Y is NR$^{17}$, then X does not denote NR$^{15}$; and with the proviso that X and Y do not simultaneously denote O;

wherein $R^{14a}$, $R^{14b}$, $R^{16a}$ and $R^{16b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group; and/or $R^{14a}$ and $R^{14b}$ and/or $R^{16a}$ and $R^{16b}$, respectively, may together represent =O;

$R^{15}$ and $R^{17}$ each independently represent H, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group;

Z represents CR$^{18a}$R$^{18b}$; NR$^{19}$ or O; or if X represents O and f represents 0, then Z may represent —(C(R$^{124}$))=C (R$^{125}$)— or =(N(CR$^{126}$))—, wherein the N atom is singly bonded to the O atom, and wherein $R^{124}$ and $R^{125}$ together with the carbon atoms joining them form a fused aryl or heteroaryl ring structure;

$R^{126}$ represents H, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group; or wherein $R^{18a}$ represents H, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group; or $R^{18a}$ represents a structure corresponding to formula (II):

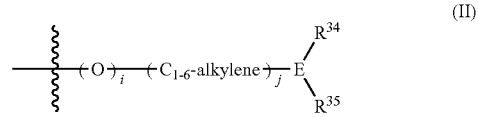

wherein i and j each independently represent 0 or 1;

E represents N or CH, with the proviso that if i is 1 and j is 0, then E represents CH;

$R^{34}$ and $R^{35}$ each independently denote H, $C_{1-6}$-alkyl, $C_{3-8}$-cycloalkyl, aryl or heteroaryl, or an aryl, heteroaryl or $C_{3-8}$-cycloalkyl bonded via a $C_{1-3}$-alkylene group; or $R^{34}$ and $R^{35}$ together with E form a 5- or 6-membered aryl or heteroaryl ring structure; or $R^{34}$ and $R^{35}$ together with E form a saturated heterocycle corresponding to formula (III):

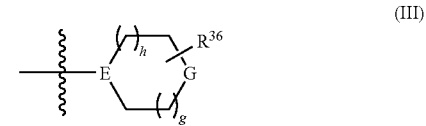

wherein h and g each independently denote 0, 1 or 2;

G represents CR$^{37a}$R$^{37b}$, NR$^{38}$, O, S, S=O or S(=O)$_2$, with the proviso that if E is CH, then G is not CR$^{37a}$R$^{37b}$;

$R^{36}$ represents from 0 to 4 substituents each independently selected from the group consisting of F, Cl, Br, I, OH, SH, =O, O—$C_{1-6}$-alkyl, $C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent substituents $R^{36}$ together represent a fused aryl or heteroaryl ring structure;

$R^{37a}$ and $R^{37b}$ each independently denote H, F, Cl, Br, I, OH, SH, =O, O—$C_{1-6}$-alkyl, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group;

$R^{38}$ represents H, $C_{1-6}$-alkyl, $C_{3-8}$-cycloalkyl, aryl or heteroaryl, or an aryl, heteroaryl or $C_{3-8}$-cycloalkyl bonded via a $C_{1-3}$-alkylene group;

$R^{18b}$ represents H, OH, $C_{1-6}$-alkyl, $C_{3-8}$-cycloalkyl, O—$C_{1-6}$-alkyl, O—($C_{3-8}$-cycloalkyl), ($C_{1-6}$-alkylene)-O—$C_{1-6}$-alkyl, ($C_{1-6}$-alkylene)-O—($C_{3-8}$-cycloalkyl), aryl, heteroaryl, O-aryl or O-heteroaryl, or an aryl, O-aryl, heteroaryl or O-heteroaryl bonded via a $C_{1-6}$-alkylene group; or $R^{18b}$ represents a structure corresponding to formula (IV):

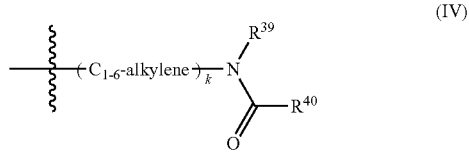

(IV)

wherein k represents 0 or 1;

$R^{39}$ represents H, $C_{1-6}$-alkyl, $C_{3-8}$-cycloalkyl, aryl or heteroaryl, or a $C_{3-8}$-cycloalkyl, aryl or heteroaryl bonded via a $C_{1-3}$-alkylene group;

$R^{40}$ represents $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group; or $R^{39}$ and $R^{40}$ together with the N—C(=O)— group joining them form a ring corresponding to formula (V):

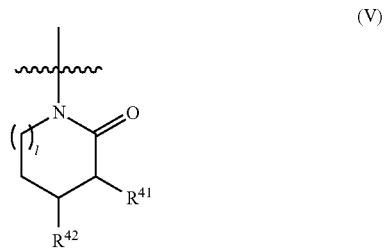

(V)

wherein l represents 0, 1 or 2; and $R^{41}$ and $R^{42}$ together with the carbon atoms joining them form a fused aryl or heteroaryl ring structure;

$R^{19}$ represents H; or $(P)_z$—$R^{22}$, wherein z represents 0 or 1;

P represents (C=O), S(=O)$_2$ or C(=O)—N($R^{24}$), wherein the N atom in C(=O)—N($R^{24}$) is bonded to $R^{22}$, and $R^{24}$ represents H, $C_{1-6}$-alkyl, $C_{3-8}$-cycloalkyl, or an aryl, heteroaryl or $C_{3-8}$-cycloalkyl bonded via a $C_{1-3}$-alkylene group;

$R^{22}$ represents $C_{1-6}$-alkyl, aryl or heteroaryl, or an aryl or heteroaryl bonded via a $C_{1-6}$-alkylene group; or $R^{22}$ represents a structure corresponding to formula (VI):

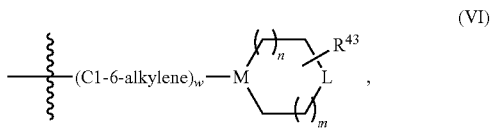

(VI)

wherein n represents 0, 1 or 2;

m represents 0, 1 or 2;

w represents 0 or 1,

M represents CH or N;

with the proviso that if P is C(=O)—NR$^{24}$ and w is 0, then M is CH; and with the proviso that if z and w simultaneously are 0, then M is CH;

L represents CR$^{44a}$R$^{44b}$, NR$^{45}$, O, S, S=O or S(=O)$_2$;

$R^{43}$ represents from 0 to 4 substituents each independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent ones of the 0 to 4 substituents $R^{43}$ together represent a fused aryl or heteroaryl ring structure;

$R^{44a}$ and $R^{44b}$ each independently represent H, F, Cl, Br, I, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group; or $R^{44a}$ and $R^{44b}$ together may represent =O; and $R^{45}$ represents H, $C_{1-6}$-alkyl, $C_{3-8}$-cycloalkyl, aryl or heteroaryl, or an aryl, heteroaryl or $C_{3-8}$-cycloalkyl bonded via a $C_{1-3}$-alkylene group;

wherein the above-mentioned $C_{1-6}$-alkyl, $C_{1-3}$-alkylene, $C_{1-6}$-alkylene, $C_{2-6}$-alkenylene, $C_{3-8}$-cycloalkyl, aryl and heteroaryl groups in each case may be unsubstituted, monosubstituted or polysubstituted by identical or different substituents, and the above-mentioned $C_{1-6}$-alkyl, $C_{1-3}$-alkylene, $C_{1-6}$-alkylene and $C_{2-6}$-alkenylene groups in each case may be branched or unbranched;

optionally in the form of an isolated enantiomer or of an isolated diastereoisomer, of the racemate, of the enantiomers, of the diastereoisomers, mixtures of enantiomers and/or diastereoisomers, as well as in each case in the form of their bases and/or physiologically acceptable salts.

Within the scope of this invention, the term "$C_{1-6}$-alkyl" includes acyclic saturated hydrocarbon groups having 1, 2, 3, 4, 5 or 6 carbon atoms, which may be branched- or straight-chained (unbranched) as well as unsubstituted or substituted one or more times, for example 2, 3, 4 or 5 times, by identical or different substituents. The alkyl groups can preferably be selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl groups are selected from the group consisting of methyl, ethyl, n-propyl, isopropyl, n-butyl, sec-butyl, isobutyl and tert-butyl.

Within the scope of this invention, the term "$C_{3-8}$-cycloalkyl" denotes cyclic saturated hydrocarbon groups having 3, 4, 5, 6, 7 or 8 carbon atoms, which may be unsubstituted or substituted on one or more ring members by one or more, for example by 2, 3, 4 or 5, identical or different substituents. $C_{3-8}$-Cycloalkyl is preferably selected from the group consisting of cyclopropyl, cyclobutyl, cyclopentyl, cyclohexyl, cycloheptyl and cyclooctyl.

Within the scope of this invention, the term "aryl" denotes aromatic hydrocarbons, in particular phenyls and naphthyls.

The aryl groups can also be fused with further saturated, (partially) unsaturated or aromatic ring systems. Each aryl group may be unsubstituted or substituted one or more times, for example 2, 3, 4 or 5 times, it being possible for the aryl substituents to be identical or different and to be at any desired and possible position of the aryl ring structure. Aryl is advantageously selected from the group consisting of phenyl, 1-naphthyl and 2-naphthyl, and may in each case be unsubstituted or substituted one or more times, for example by 2, 3, 4 or 5 substituents.

Within the scope of the present invention, the term "heteroaryl" denotes a 5-, 6- or 7-membered cyclic aromatic group containing at least 1, optionally also 2, 3, 4 or 5, heteroatom(s), it being possible for the heteroatoms to be identical or different and for the heteroaryl to be unsubstituted or substituted one or more times, for example 2, 3, 4 or 5 times, by identical or different substituents. The substituents may be bonded at any desired and possible position of the heteroaryl ring structure. The heterocycle may also be part of a bi- or poly-cyclic system, in particular of a mono-, bi- or tri-cyclic system, which can then be more than 7-membered in total, preferably up to 14-membered. Preferred heteroatoms are selected from the group consisting of N, O and S. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phthalazinyl, pyrazolyl, imidazolyl, thiazolyl, oxazolyl, oxadiazolyl, triazole, tetrazole, isoxazolyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, quinazolinyl, quinolinyl and isoquinolinyl, it being possible for the bonding to the general structure (I) to take place via any desired and possible ring member of the heteroaryl group. The heteroaryl group is particularly preferably selected from the group consisting of quinolinyl, isoquinolinyl, thienyl, imidazolyl, thiazolyl, triazolyl and pyridinyl.

Within the scope of the present invention, the expression "$C_{1-3}$-alkylene group" or "$C_{1-6}$-alkylene group" includes acyclic saturated hydrocarbon groups having 1, 2 or 3 or having 1, 2, 3, 4, 5 or 6 carbon atoms, which may be branched- or straight-chained (unbranched) as well as unsubstituted or substituted one or more times, for example 2, 3, 4 or 5 times, by identical or different substituents and which link a respective group to the general structure of higher order. The alkylene groups are preferably selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups are particularly preferably selected from the group consisting of —$CH_2$—, —$CH_2$—$CH_2$— and —$CH_2$—$CH_2$—$CH_2$—.

Within the scope of the present invention, the expression "$C_{2-6}$-alkenylene group" includes acyclic, mono- or poly-unsaturated, for example di-, tri- or tetra-unsaturated, hydrocarbon groups having 2, 3, 4, 5 or 6 carbon atoms, which may be branched- or straight-chained (unbranched) as well as unsubstituted or substituted one or more times, for example 2, 3, 4 or 5 times, by identical or different substituents and which contain at least one C=C double bond and link a respective group to the general structure of higher order. The alkenylene groups are preferably selected from the group consisting of —CH=CH—, —CH=CH—$CH_2$—, —$C(CH_3)$=$CH_2$—, —CH=CH—$CH_2$—$CH_2$—, —$CH_2$—CH=CH—$CH_2$—, —CH=CH—CH=CH—, —$C(CH_3)$=CH—$CH_2$—, —CH=$C(CH_3)$—$CH_2$—, —$C(CH_3)$=$C(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH=CH—$CH_2$—$CH_2$— and —CH=$CH_2$—CH—CH=$CH_2$—.

Within the scope of the present invention, the expression "aryl or heteroaryl bonded via a $C_{1-3}$-alkylene group, $C_{1-6}$-alkylene group or $C_{2-6}$-alkenylene group" means that the $C_{1-3}$-alkylene groups, $C_{1-6}$-alkylene groups or $C_{2-6}$-alkenylene groups as well as aryl or heteroaryl have the meanings defined above and the aryl or heteroaryl is bonded to the general structure of higher order via a $C_{1-3}$-alkylene group, $C_{1-6}$-alkylene group or $C_{2-6}$-alkenylene group. Benzyl, phenethyl and phenylpropyl may be mentioned as examples.

Within the scope of the present invention, the expression "$C_{3-6}$-cycloalkyl or $C_{3-8}$-cycloalkyl bonded via a $C_{1-3}$-alkylene group or $C_{1-6}$-alkylene group" means that the $C_{1-3}$-alkylene group or $C_{1-6}$-alkylene group, $C_{3-6}$-cycloalkyl and $C_{3-8}$-cycloalkyl have the meanings defined above and $C_{3-6}$-cycloalkyl or $C_{3-8}$-cycloalkyl is bonded to the general structure of higher order via a $C_{1-3}$-alkylene group or $C_{1-6}$-alkylene group.

In connection with "alkyl", "alkylene" and "cycloalkyl", the term "substituted" within the scope of this invention is understood as meaning the replacement of a hydrogen atom by F, Cl, Br, I, $CF_3$, $OCF_3$, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2$H, $CO_2$—$C_{1-6}$-alkyl, phenyl, phenoxy, benzyl, naphthyl, furyl, thienyl and pyridinyl, wherein polysubstituted groups are to be understood as being groups which are substituted multiple times, for example di- or tri-substituted, either on different atoms or on the same atom, for example trisubstituted on the same carbon atom, as in the case of $CF_3$ or $CH_2CF_3$, or at different positions, as in the case of CH(OH)—CH=CH—$CHCl_2$. Polysubstitution can be carried out with the same or with different substituents, such as, for example, in the case of CH(OH)—CH=CH—$CHCl_2$. In particular, it is here to be understood as meaning the replacement of one or more hydrogen atoms by F, Cl, $NH_2$, OH, O, —$CF_3$ or O—$C_{1-6}$-alkyl, in particular methoxy.

In relation to "aryl" and "heteroaryl", "substituted" within the scope of this invention is understood as meaning the replacement of one or more hydrogen atoms of the respective ring system, for example 2, 3, 4 or 5 hydrogen atoms, by F, Cl, Br, I, ON, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, ($C_{1-3}$-alkylene)-azetidinyl, ($C_{1-3}$-alkylene)-pyrrolinyl or ($C_{1-3}$-alkylene)-piperidinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, furyl, thienyl or pyridinyl, on one atom or on different atoms, wherein the above-mentioned substituents—unless indicated otherwise—may themselves optionally be substituted by the listed substituents. The polysubstitution of aryl and heteroaryl can be carried out with the same or with different substituents. Preferred substituents for aryl and heteroaryl are selected from the group consisting of —O—$C_{1-3}$-alkyl, unsubstituted $C_{1-6}$-alkyl, F, Cl, Br, I, ON, CF$_3$, OCF$_3$, OH, SH, —CH$_2$-azetidinyl, phenyl, naphthyl, furyl, thienyl and pyridinyl, in particular from the group consisting of F, Cl, Br, ON, CF$_3$, CH$_3$; OCH$_3$ and OCF$_3$.

In the chemical structural formulas which are used here to describe the compounds according to the invention, the symbol

is also used to describe one or more substitution patterns, that group, in contrast to the representation of a bond to a specific atom, not being bonded to a specific atom within the chemical structural formula ($R^a$ here represents, for example, a substituent R having a numbering represented by the variable "a"). Rather, the substituent can be bonded to any possible ring atom. This will be explained by way of example with reference to the group

from the general formula (I) shown above: The definition of $R^{13}$ states that $R^{13}$ can represent from 0 to 4 substituents. $R^{13}$ can, therefore, be absent, or 1, 2, 3 or 4 of the C-bonded hydrogen atoms within the partial structure represented by the general formula (I) can be replaced by a substituent provided in the definition of $R^{13}$, it being possible for the substituents in question to be independently selected, that is to say to have different meanings, and can replace C-bonded hydrogen atoms on one or more carbon atoms. As explained, for example, in the definition of $R^{13}$, it is also possible for in each case two of the substituents $R^{13}$ together to represent a fused aryl or heteroaryl (also known as annellated aryl or heteroaryl or fused/-annellated aryl or heteroaryl group).

Within the scope of the present invention, the symbol

used in formulas denotes the linking of a corresponding group to the respective general structure of higher order.

Persons skilled in the art will further understand that identical groups that are used to define different substituents are in each case independent of one another. Persons skilled in the art will further understand that the right-hand cycle of the following partial structure

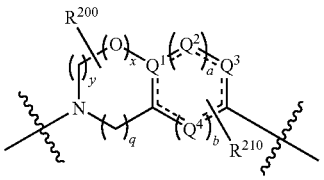

is aromatic, which is indicated by the broken line. $Q^2$, where it is present more than once (that is to say, where a represents 2) can at each occurrence be independently selected from the group consisting of CH, N, O and S.

Within the scope of this invention, the expression "physiologically acceptable salt" is understood as meaning preferably salts of the compounds according to the invention with inorganic or organic acids which are physiologically acceptable—in particular when used in humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. The salts of hydrochloric acid (hydrochlorides) and of citric acid (citrates) are particularly preferred.

Within the scope of this invention the term "isolated"' used with reference to a stereoisomer (i.e., an enantiomer or diasteromer) means that the stereoisomer is substantially completely separated from the opposite stereoisomer, but not necessarily from other substances.

In the compounds according to the invention, $R^1$ preferably represents phenyl, naphthyl, chromanyl, indolyl, benzofuranyl, benzothiophenyl (benzothienyl), 5,6-dihydro-4H-cyclopenta[b]thiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl), or a phenyl or naphthyl bonded via a $C_{1-3}$-alkylene group or a $C_{2-3}$-alkenylene group, particularly preferably phenyl, naphthyl, chromanyl, benzothiophenyl (benzothienyl), 5,6-dihydro-4H-cyclopenta[b]thiophenyl, benzooxadiazolyl, thienyl, pyridinyl, imidazothiazolyl, dibenzofuranyl, or a phenyl bonded via a $C_{1-3}$-alkylene group or a $C_{2-3}$-alkenylene group, most particularly preferably phenyl, naphthyl, chromanyl, benzothiophenyl (benzothienyl), 5,6-dihydro-4H-cyclopenta[b]thiophenyl, thienyl, or a phenyl bonded via a $C_{1\ or\ 2}$-alkylene group or —CH=CH— group, wherein the above-mentioned aryl or heteroaryl radicals are in each case unsubstituted or mono- or poly-substituted by identical or different substituents, the substituents being independently selected in particular from the group consisting of —O—$C_{1-3}$-alkyl, $C_{1-6}$-alkyl, F, Cl, Br, I, CF$_3$, OCF$_3$, OH, SH, phenyl, phenoxy, naphthyl, furyl, thienyl and pyridinyl, and wherein the above-mentioned alkylene and alkenylene groups are in each case unsubstituted or mono- or poly-substituted by identical or different substituents, the substituents being independently selected in particular from the group consisting of —O—$C_{1-3}$-alkyl, F, Cl, Br, I, CF$_3$, OCF$_3$, OH, SH, phenyl, phenoxy, naphthyl, furyl, thienyl and pyridinyl. $R^1$ can in particular represent phenyl or naphthyl, wherein the phenyl or naphthyl is unsubstituted or substituted one or more times, for example 2, 3, 4 or 5 times, by identical or different radicals selected from methyl, methoxy, CF$_3$, OCF$_3$, F and Cl.

In embodiments of the compounds according to the invention that are likewise preferred, R¹ is selected from the group consisting of 4-methoxy-2,3,6-trimethylphenyl, 4-methoxy-2,6-dimethylphenyl, 2,4,6-trimethylphenyl, 2,6-dichloro-4-(trifluoromethyl)phenyl, 2-chloro-6-methylphenyl, 2,4,6-trichlorophenyl, 2,4,5-trichlorophenyl, 4-fluoro-2,6-dimethylphenyl, 2,6-dichloro-4-methoxyphenyl, 2,6-dichlorophenyl, 2,6-dichloro-3-methylphenyl, 6-methoxy-2-naphthyl, 2-methyl-1-naphthyl, 2-chloro-1-naphthyl, 2-fluoro-1-naphthyl, 2-chloro-4-(trifluoromethoxy)-phenyl, 4-chloro-2,5-dimethylphenyl, 2-chlorophenyl, 3-chlorophenyl, 4-chlorophenyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 4-methyl-1-naphthyl, 5-chloro-1-naphthyl, 4-chloro-1-naphthyl, 4-fluoro-1-naphthyl, 4-methoxy-1-naphthyl, 1-naphthyl, 2-naphthyl, benzothiophenyl, 2,2-diphenylethanyl and 2,2-dimethylchroman-6-yl. In particular, R¹ can represent 4-methoxy-2,6-dimethylphenyl.

In further preferred embodiments of the compounds according to the invention, B represents S(=O)₂, so that the general formula (I) assumes the following form (I'):

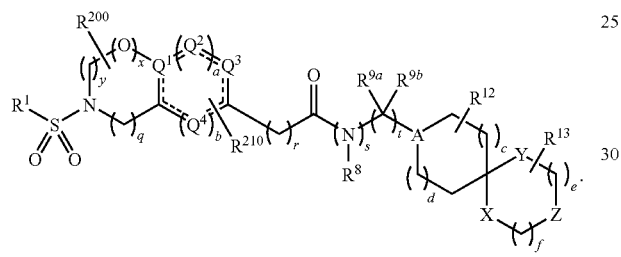

In embodiments of the compounds according to the invention that are likewise preferred, R⁴ represents H or $C_{1-4}$-alkyl.

In further preferred embodiments of the compounds according to the invention, the substituents $R^{200}$ and/or $R^{210}$ can be absent.

In embodiments of the compounds of the general formula (I) according to the invention that are likewise preferred, the following partial structure (Ac):

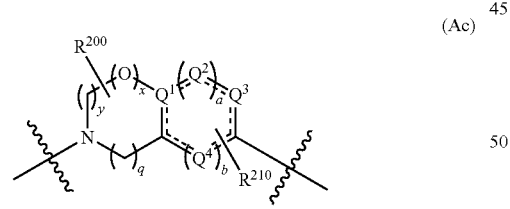

represents a partial structure selected from the group consisting of

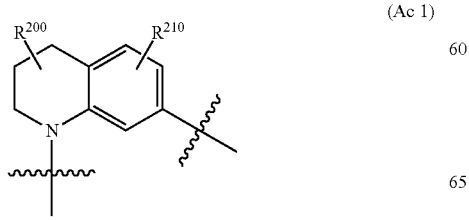

(Ac 1)

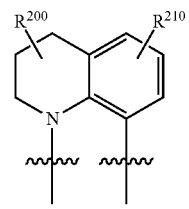

(Ac 2)

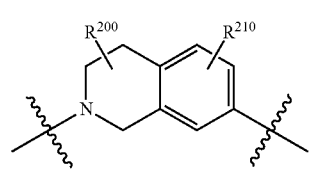

(Ac 3)

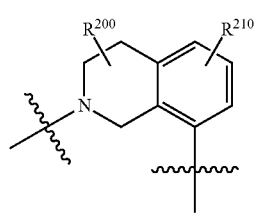

(Ac 4)

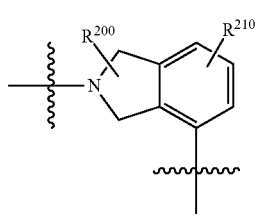

(Ac 5)

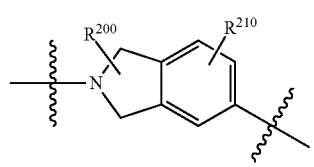

(Ac 6)

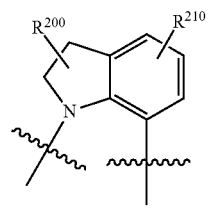

(Ac 7)

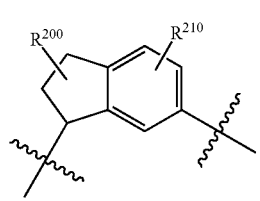

(Ac 8)

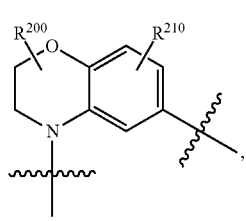

(Ac 9)

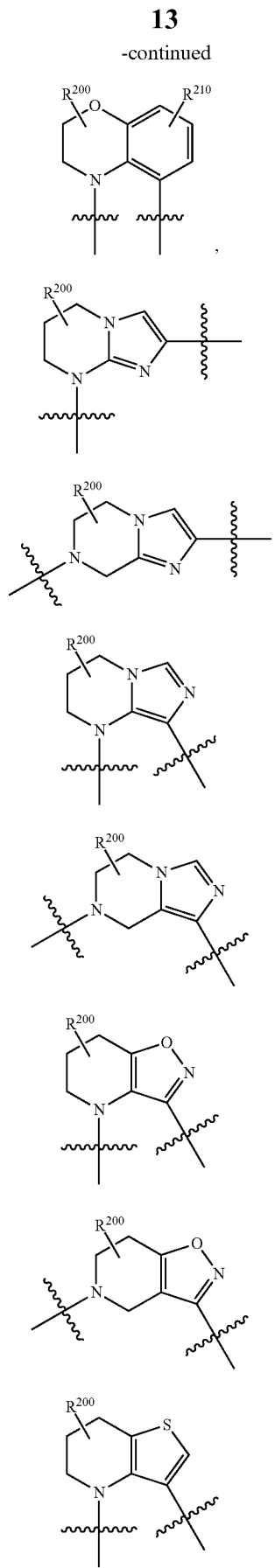
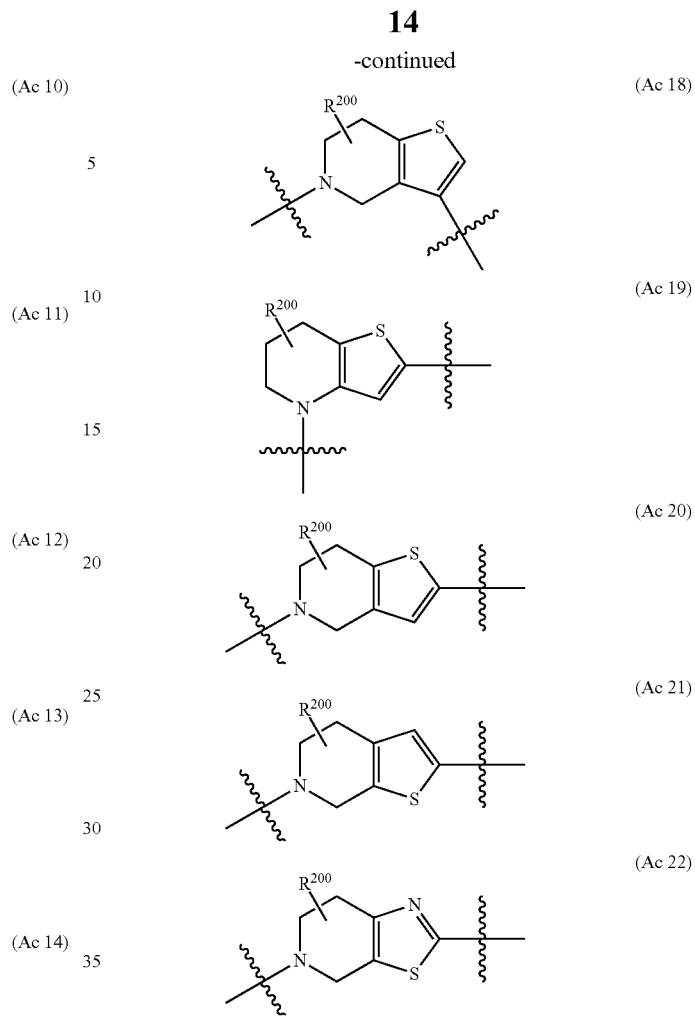

In particular, the partial structure Ac can be selected from the group consisting of partial structures Ac 1, Ac 3, Ac 6, Ac 8, Ac 9, Ac 16 and Ac 20.

In embodiments of the compounds according to the invention that are likewise preferred, r represents 0 or 1, in particular in each case in connection with partial structures Ac1-Ac22 shown above.

Embodiments of the compounds according to the invention that are likewise preferred are those in which $R^8$ represents H; $C_{1-6}$-alkyl, in particular methyl, ethyl, n-propyl, isopropyl, n-butyl, isobutyl, sec-butyl or tert-butyl; cyclopropyl, cyclobutyl, cyclopentyl, cyclohexyl, —$CH_2CF_3$, phenyl, benzyl, phenylethyl, phenylpropyl, or a cyclopropyl, cyclobutyl, cyclopentyl, cyclohexyl bonded via a $C_{1-3}$-alkylene group, in each case unsubstituted or mono- or poly-substituted by identical or different substituents.

Further preferred embodiments of the compounds according to the invention are those in which $R^{9a}$ and $R^{9b}$ each independently represent H; F; methyl; ethyl, isopropyl, $CF_3$, methoxy; cyclopropyl; phenyl; benzyl, phenylethyl, $C_{1-3}$-alkylene-cyclopropyl, $C_{1-3}$-alkylene-cyclobutyl, $C_{1-3}$-alkylene-cyclopentyl, $C_{1-3}$-alkylene-cyclohexyl, $C_{1-3}$-alkylene-$CF_3$, in each case unsubstituted or mono- or poly-substituted by identical or different substituents. Preferably both $R^{9a}$ and $R^{9b}$ simultaneously represent H.

In further preferred embodiments of the compounds according to the invention, A represents N.

In embodiments of the compounds according to the invention that are likewise preferred, s and t in each case represent 0 and A represents N.

Further preferred embodiments of the compounds according to the invention are those in which X represents $CR^{14a}R^{14b}$; $NR^{15}$ or O;
Y represents $CR^{16a}R^{16b}$;
$R^{14a}$, $R^{14b}$, $R^{16a}$ and $R^{16b}$ each independently denote H, F, Cl, OH, $C_{1-6}$-alkyl, O—$C_{1-6}$-alkyl, $C_{3-8}$-cycloalkyl, aryl or heteroaryl, or represents a $C_{3-8}$-cycloalkyl, aryl or heteroaryl bonded via a $C_{1-6}$-alkylene group, and/or
$R^{14a}$ and $R^{14b}$ together can represent =O; and/or
$R^{16a}$ and $R^{16b}$ together can represent =O;
$R^{15}$ represents H, $C_{1-6}$-alkyl, $C_{3-8}$-cycloalkyl, aryl or heteroaryl, or denotes a $C_{3-8}$-cycloalkyl, aryl or heteroaryl bonded via a $C_{1-6}$-alkylene group;
Z represents $CR^{18a}R^{18b}$ or $NR^{19}$; or
if X represents O and f represents 0, then Z may denote =$(N(CR^{126}))$—, wherein the N atom is singly bonded to the O atom, and
$R^{126}$ represents H, $C_{1-6}$-alkyl, $C_{3-8}$-cycloalkyl, aryl or heteroaryl, or a $C_{3-8}$-cycloalkyl, aryl or heteroaryl bonded via a $C_{1-6}$-alkylene group;
$R^{18a}$ represents H, $C_{1-6}$-alkyl, $C_{3-8}$-cycloalkyl, —NH($C_{1-6}$-alkyl), —N($C_{1-6}$-alkyl)$_2$, phenyl, pyridyl, imidazolyl, triazolyl, pyrimidyl, thiazolyl or thienyl, in each case unsubstituted or mono- or poly-substituted; or phenyl, pyridyl, imidazolyl, triazolyl, pyrimidyl, thiazolyl or thienyl bonded via a —(O)$_{0-1}$—$C_{1-6}$-alkylene group, in each case unsubstituted or mono- or poly-substituted; or
$R^{18a}$ represents a structure corresponding to formula (VII):

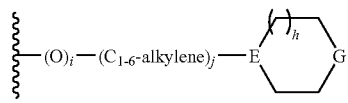

(VII)

wherein
i represents 0 or 1;
j represents 0 or 1;
h represents 0 or 1;
E represents N or CH; with the proviso that if i is 1 and j is 0, then E is CH;
G represents $CR^{37a}R^{37b}$ or $NR^{38}$; wherein
$R^{37a}$ and $R^{37b}$ each independently represent H; F or $C_{1-6}$-alkyl, in each case unsubstituted or mono- or poly-substituted by identical or different substituents;
$R^{38}$ represents H; $C_{1-6}$-alkyl, $C_{3-6}$-alkyl or pyridyl;
$R^{18b}$ represents H, OH, $C_{1-6}$-alkyl, phenyl, pyridyl, imidazolyl, triazolyl, pyrimidyl, thiazolyl or thienyl, in each case unsubstituted or mono- or poly-substituted by identical or different substituents, phenyl, pyridyl, imidazolyl, triazolyl, pyrimidyl, thiazolyl or thienyl bonded via a $C_{1-6}$-alkylene group, in each case unsubstituted or mono- or poly-substituted by identical or different substituents; O-phenyl or O-pyridyl, in each case unsubstituted or mono- or poly-substituted by identical or different substituents; $C_{1-6}$-alkylene-NH(C=O)-bridged phenyl, pyridyl or thienyl, in each case unsubstituted or mono- or poly-substituted by identical or different substituents;
$R^{19}$ represents H, $C_{1-6}$-alkyl, $C_{3-8}$-cycloalkyl, —(C=O)—$C_{1-6}$-alkyl, phenyl, pyridyl, thienyl, thiazolyl, triazolyl, pyrimidinyl or imidazolyl; in each case unsubstituted or mono- or poly-substituted by identical or different substituents; or phenyl, pyridyl, thienyl, thiazolyl, pyrimidinyl, triazolyl or imidazolyl bonded via a $C_{1-6}$-alkylene group, in each case unsubstituted or mono- or poly-substituted by identical or different substituents; or $R^{19}$ represents a structure corresponding to formula (VIII):

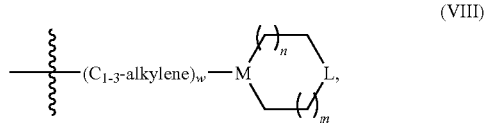

(VIII)

wherein
w represents 0 or 1;
n represents 0 or 1;
m represents 0 or 1;
M represents CH or N, with the proviso that if w represents 0, then M is CH;
L represents $CR^{44a}R^{44b}$ or $NR^{45}$; wherein
$R^{44a}$ and $R^{44b}$ each independently represent H; F or $C_{1-6}$-alkyl, in each case unsubstituted or mono- or poly-substituted by identical or different substituents; and
$R^{45}$ represents H, $C_{1-6}$-alkyl, $C_{3-8}$-alkyl or pyridyl.

Further preferred embodiments of the compounds according to the invention are those in which s and t each represent 0, and the following partial structure (SP)

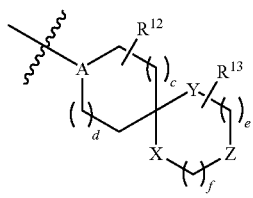

(SP)

is selected from the group consisting of:

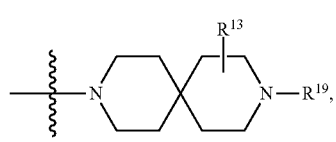

SP 1

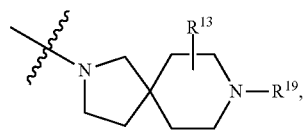

SP 2

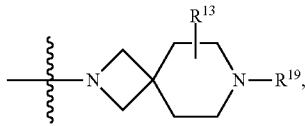

SP 3

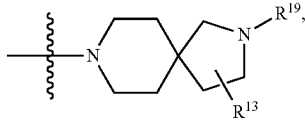

SP 4

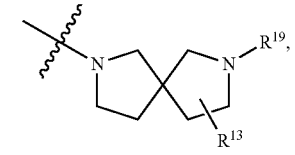

SP 5

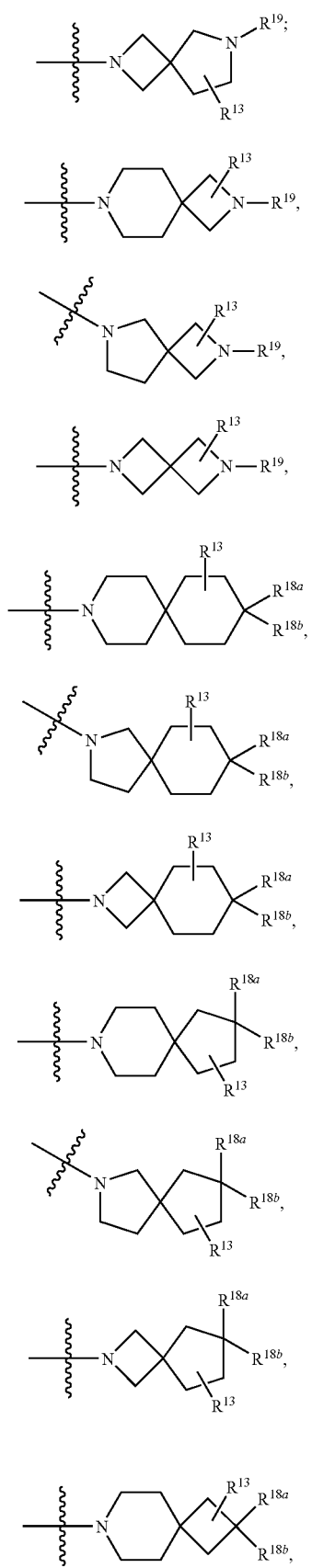
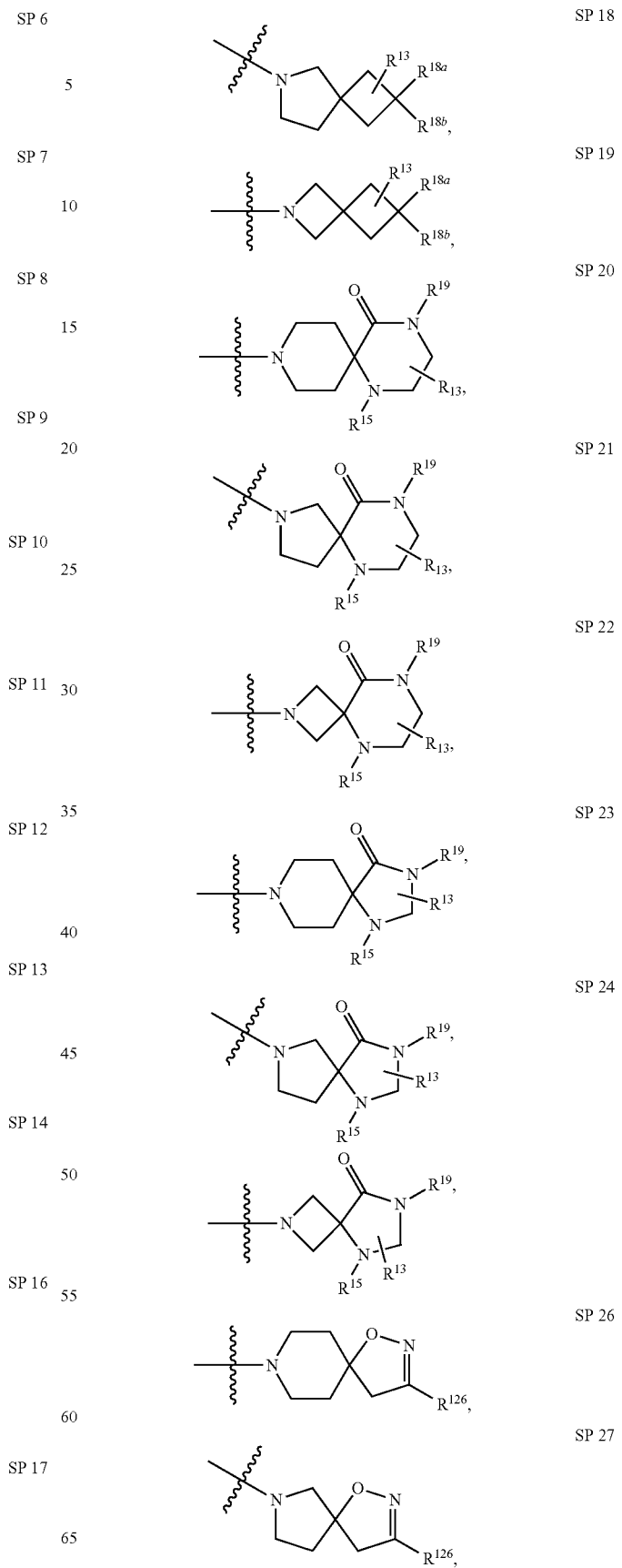

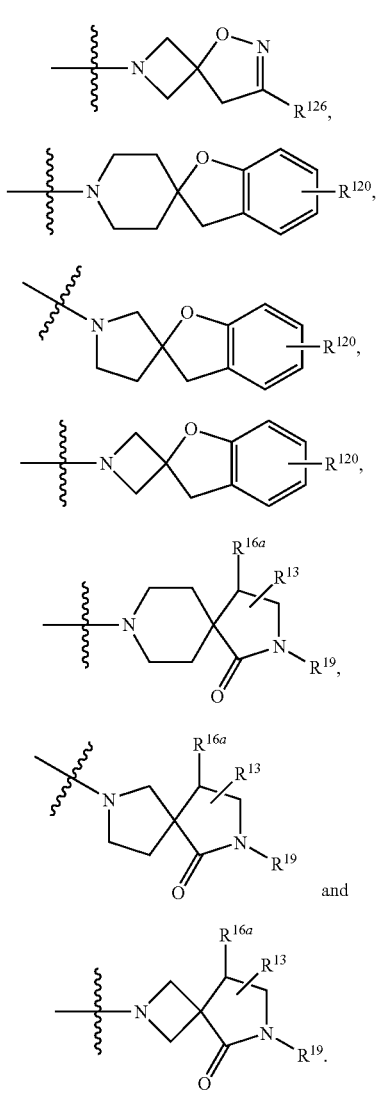

wherein
R[13] represents 1 or 2 substituents selected from the group consisting of H and unsubstituted, monosubstituted or identically or differently polysubstituted phenyl; and/or two substituents R[13] together form =O and/or two adjacent substituents R[13] together form a fused aryl or heteroaryl ring structure, in particular a benzo group, in each case unsubstituted or mono- or poly-substituted by identical or different substituents;

R[15] represents H; $C_{1-6}$-alkyl; $C_{3-8}$-cycloalkyl, phenyl, pyridyl, in each case unsubstituted or mono- or poly-substituted by identical or different substituents; or phenyl or pyridyl bonded via a $C_{1-6}$-alkylene group and in each case unsubstituted or mono- or poly-substituted by identical or different substituents;

R[16a] represents H, $C_{1-6}$-alkyl, phenyl or pyridyl, in each case unsubstituted or mono- or poly-substituted by identical or different substituents;

R[18a] represents H; $C_{1-6}$-alkyl; $C_{3-8}$-cycloalkyl, $N(C_{1-6}$-alkyl)$_2$; $NH(C_{1-6}$-alkyl), azetidinyl; pyrrolidinyl, piperidinyl, 4-($C_{1-6}$-alkyl)piperazinyl; phenyl or pyridyl, in each case unsubstituted or mono- or poly-substituted by identical or different substituents; or $N(C_{1-6}$-alkyl)$_2$; $NH(C_{1-6}$-alkyl), azetidinyl; pyrrolidinyl, piperidinyl, 4-($C_{1-6}$-alkyl)-piperazinyl; phenyl, imidazolyl, triazolyl, or pyridyl bonded via a —(O)$_{0/1}$—$C_{1-6}$-alkylene group and in each case unsubstituted or mono- or poly-substituted by identical or different substituents;

R[18b] represents H; OH; $C_{1-6}$-alkyl; phenyl or pyridyl, in each case unsubstituted or mono- or poly-substituted by identical or different substituents; O-phenyl or O-pyridyl, in each case unsubstituted or mono- or poly-substituted by identical or different substituents, or phenyl or pyridyl bonded via a $C_{1-6}$-alkylene group and in each case unsubstituted or mono- or poly-substituted by identical or different substituents;

R[19] represents H; $C_{1-6}$-alkyl; $C_{3-8}$-cycloalkyl, phenyl, pyridyl, thienyl, imidazolyl, thiazolyl or triazolyl, in each case unsubstituted or mono- or poly-substituted by identical or different substituents; or phenyl or pyridyl bonded via a $C_{1-6}$-alkylene group or (C=O)— group and in each case unsubstituted or mono- or poly-substituted by identical or different substituents;

R[120] represents H; F; Cl; OH; OCH$_3$, O—CF$_3$, $C_{1-6}$-alkyl; CF$_3$ or unsubstituted or mono- or poly-substituted phenyl;

R[126] represents H; $C_{1-6}$-alkyl; $C_{3-6}$-cycloalkyl; phenyl or pyridyl; or $C_{3-6}$-cycloalkyl, phenyl or pyridyl bonded via a $C_{1-3}$-alkylene group and in each case unsubstituted or mono- or poly-substituted by identical or different substituents.

The partial structures SP1, SP2, SP4, SP5, SP10, SP23, SP26 and SP32 shown above are preferred.

Further preferred embodiments of the compounds according to the invention are those in which s and t each represent 0 and the following partial structure (SP):

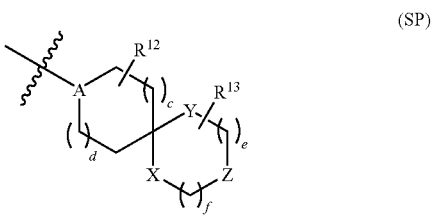

is selected from the group consisting of:

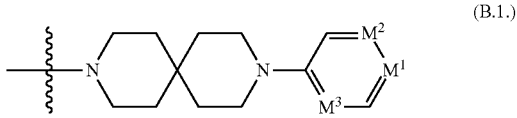

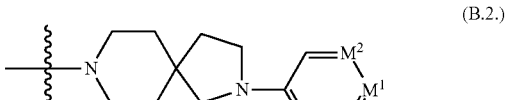

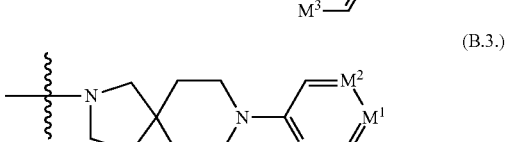

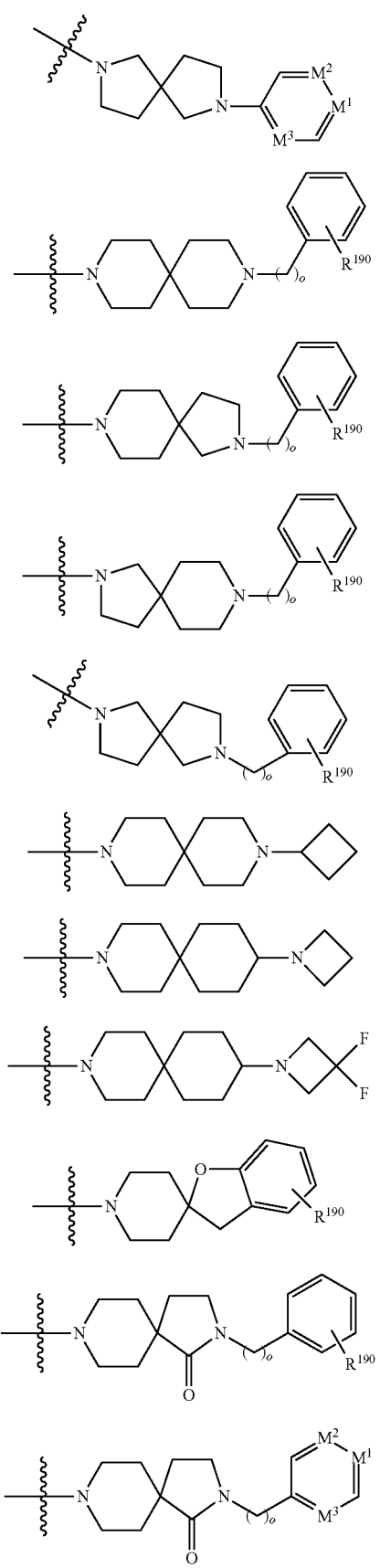
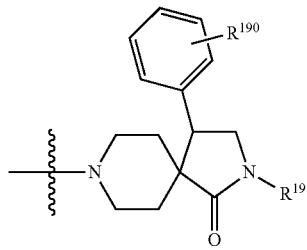
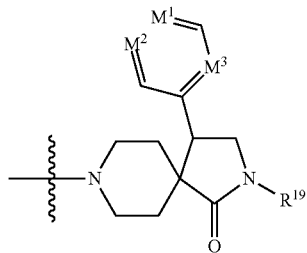
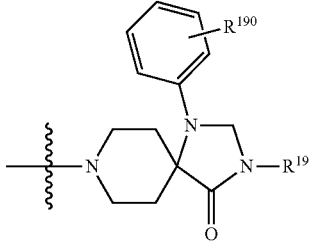
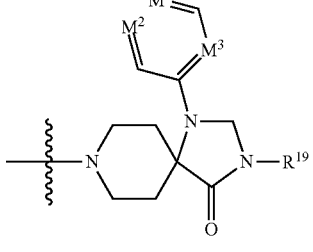
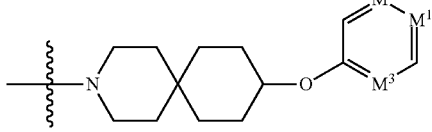
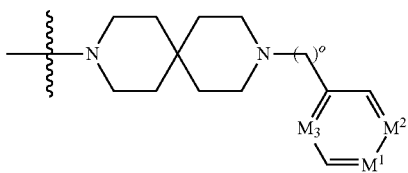
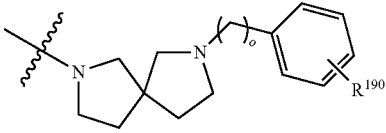

o=0, 1, 2 or 3;

$M^1$, $M^2$ and $M^3$ each represent N or CH, wherein one of $M^1$, $M^2$ and $M^3$ represents N and the others both represent CH;

$R^{19}$ is selected from the group consisting of H; $C_{1-6}$-alkyl, in particular methyl, ethyl, n-propyl, isopropyl, n-butyl, sec-butyl, isobutyl and tert-butyl; $C_{3-6}$-cycloalkyl, in each case unsubstituted or mono- or poly-substituted by identical or different substituents; and $R^{190}$ represents from 0 to 4 substituents independently selected from F, Cl, O—$CF_3$, $CF_3$ and CN.

The foregoing partial structures B.1., B.2., B.3., B.13., B.15., B.17., B.19., B.20., B.21., B.22. and B.25. are preferred. In partial structures B.1., B.2., B.3., B.19., B.21., B.25. preferably $M^1$ represents N, and each of $M^2$ and $M^3$ represents CH. In partial structure B.13. preferably o represents 1, and $R^{190}$ is absent or represents F in the 4-position. In partial structure B.15. preferably $R^{19}$ represents methyl, and $R^{190}$ is absent. In partial structure B.17. preferably $R^{19}$ represents H, and $R^{190}$ is absent. In partial structure B.22. preferably o represents 1, and $R^{190}$ is absent.

Further embodiments of the compounds according to the invention are those which are represented by the following general formulas C1 through C14:

-continued

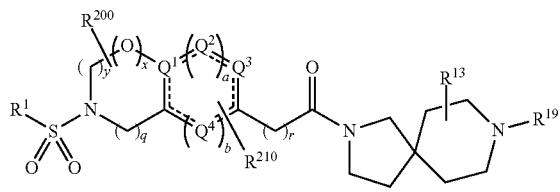
C9

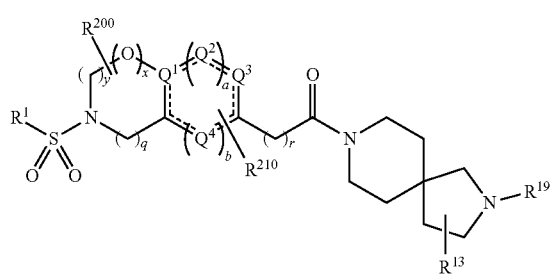
C10

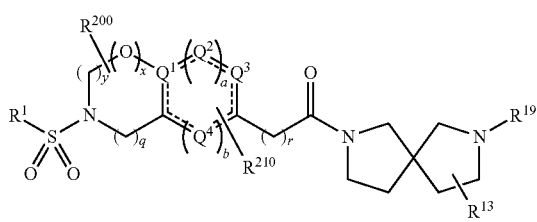
C11

-continued

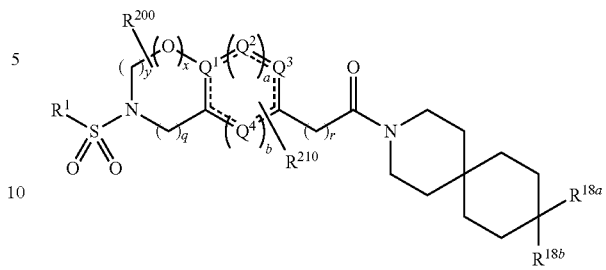
C12

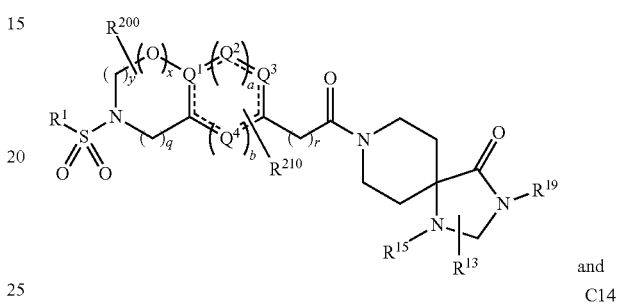
C13 and

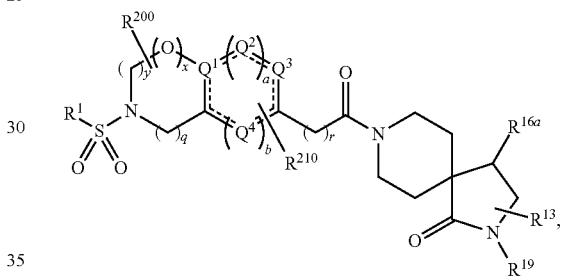
C14 wherein the substituent groups, variables and indices have the meanings described above.

In a further preferred embodiment of the present invention, the substituted compounds according to the invention are selected from the group consisting of:

| Compound | Name |
|---|---|
| G-04 | (2-(4-Methoxy-2,6-dimethylphenylsulfonyl)-1,2,3,4-tetrahydroisoquinolin-7-yl)(9-(pyridin-4-yl)-3,9-diazaspiro[5.5]undecan-3-yl)methanone |
| G-09 | 2-(1-(4-Methoxy-2,6-dimethylphenylsulfonyl)-1,2,3,4-tetrahydroquinolin-7-yl)-1-(2-(pyridin-4-yl)-2,8-diazaspiro[4.5]decan-8-yl)ethanone |
| G-10 | 1-(2-Cyclobutyl-2,8-diazaspiro[4.5]decan-8-yl)-2-(1-(4-methoxy-2,6-dimethylphenylsulfonyl)-1,2,3,4-tetrahydroquinolin-7-yl)ethanone |
| G-11 | 2-(1-(4-Methoxy-2,6-dimethylphenylsulfonyl)-1,2,3,4-tetrahydroquinolin-7-yl)-1-(8-(pyridin-4-yl)-2,8-diazaspiro[4.5]decan-2-yl)ethanone |
| G-12 | 2-(1-(4-Methoxy-2,6-dimethylphenylsulfonyl)-1,2,3,4-tetrahydroquinolin-7-yl)-1-(7-(pyridin-4-yl)-2,7-diazaspiro[4.4]nonan-2-yl)ethanone |
| G-13 | (5-(2-Chlorobenzoyl)-4,5,6,7-tetrahydroisoxazolo[4,5-c]pyridin-3-yl)(9-(pyridin-4-yl)-3,9-diazaspiro[5.5]undecan-3-yl)methanone |
| G-14 | (5-(4-Methoxy-2,6-dimethylphenylsulfonyl)-4,5,6,7-tetrahydrothieno[3,2-c]pyridin-2-yl)(9-(pyridin-4-yl)-3,9-diazaspiro[5.5]undecan-3-yl)methanone |
| G-15 | (5-(2-Chlorobenzoyl)-4,5,6,7-tetrahydrothieno[3,2-c]pyridin-2-yl)(9-(pyridin-4-yl)-3,9-diazaspiro[5.5]undecan-3-yl)methanone |
| G-16 | 1-(9-(Pyridin-4-yl)-3,9-diazaspiro[5.5]undecan-3-yl)-2-(1-(2-(trifluoromethyl)phenylsulfonyl)-1,2,3,4-tetrahydroquinolin-7-yl)ethanone |
| G-17 | 2-(1-(Naphthalin-1-ylsulfonyl)-1,2,3,4-tetrahydroquinolin-7-yl)-1-(9-(pyridin-4-yl)-3,9-diazaspiro[5.5]undecan-3-yl)ethanone |
| G-18 | 2-(1-(2-Chloro-6-methylphenylsulfonyl)-1,2,3,4-tetrahydroquinolin-7-yl)-1-(9-(pyridin-4-yl)-3,9-diazaspiro[5.5]undecan-3-yl)ethanone |
| G-19 | 2-(4-(4-Methoxy-2,6-dimethylphenylsulfonyl)-3,4-dihydro-2H-benzo[b][1,4]oxazin-6-yl)-1-(9-(pyridin-4-yl)-3,9-diazaspiro[5.5]undecan-3-yl)ethanone |

-continued

| Compound | Name |
|---|---|
| G-20 | 2-(1-(4-Methoxy-2,6-dimethylphenylsulfonyl)indolin-6-yl)-1-(9-(pyridin-4-yl)-3,9-diazaspiro[5.5]undecan-3-yl)ethanone |
| G-21 | (1-(2-Chlorobenzoyl)-1,2,3,4-tetrahydroquinolin-7-yl)(9-(pyridin-4-yl)-3,9-diazaspiro[5.5]undecan-3-yl)methanone |
| G-24 | (1-(4-Methoxy-2,6-dimethylphenylsulfonyl)-1,2,3,4-tetrahydroquinolin-7-yl)(9-(pyridin-4-yl)-3,9-diazaspiro[5.5]undecan-3-yl)methanone |
| G-25 | 2-(1-(4-Methoxy-2,6-dimethylphenylsulfonyl)-1,2,3,4-tetrahydroquinolin-7-yl)-1-(9-(pyridin-4-yl)-3,9-diazaspiro[5.5]undecan-3-yl)ethanone |
| G-26 | (5-(4-Methoxy-2,6-dimethylphenylsulfonyl)-4,5,6,7-tetrahydroisoxazolo[4,5-c]pyridin-3-yl)(9-(pyridin-4-yl)-3,9-diazaspiro[5.5]undecan-3-yl)methanone |
| G-30 | 2-(1-(4-Methoxy-2,6-dimethylphenylsulfonyl)-1,2,3,4-tetrahydroquinolin-7-yl)-1-(9-(pyridin-4-yloxy)-3-azaspiro[5.5]undecan-3-yl)ethanone |
| G-32 | 1-(9-(Azetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone |
| G-33 | 2-(1-(4-Methoxy-2,6-dimethylphenylsulfonyl)-1,2,3,4-tetrahydroquinolin-7-yl)-1-(3-(pyridin-4-yl)-1-oxa-2,8-diazaspiro[4.5]dec-2-en-8-yl)ethanone |
| G-34 | 1-(9-(3,3-Difluoroazetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone |
| G-35 | 2-(1-(2-Chloro-4-(trifluoromethoxy)phenylsulfonyl)-1,2,3,4-tetrahydroquinolin-7-yl)-1-(9-(pyridin-4-yl)-3,9-diazaspiro[5.5]undecan-3-yl)ethanone |
| G-36 | (2-(4-Methoxy-2,6-dimethylphenylsulfonyl)-1,2,3,4-tetrahydroisoquinolin-8-yl)(9-(pyridin-4-yl)-3,9-diazaspiro[5.5]undecan-3-yl)methanone |
| G-37 | (2-(2-Chloro-6-methylphenylsulfonyl)-1,2,3,4-tetrahydroisoquinolin-8-yl)(9-(pyridin-4-yl)-3,9-diazaspiro[5.5]undecan-3-yl)methanone |
| G-38 | (2-(2,3-Dichlorophenylsulfonyl)-1,2,3,4-tetrahydroisoquinolin-8-yl)(9-(pyridin-4-yl)-3,9-diazaspiro[5.5]undecan-3-yl)methanone |
| G-39 | 2-(2-(4-Methoxy-2,6-dimethylphenylsulfonyl)-1,2,3,4-tetrahydroisoquinolin-7-yl)-1-(9-(pyridin-4-yl)-3,9-diazaspiro[5.5]undecan-3-yl)ethanone |
| G-40 | (7-(4-Methoxy-2,6-dimethylphenylsulfonyl)-5,6,7,8-tetrahydroimidazo[1,2-a]pyrazin-2-yl)(9-(pyridin-4-yl)-3,9-diazaspiro[5.5]undecan-3-yl)methanone |
| G-41 | 3-(2-Chlorophenyl)-1-(7-(9-(pyridin-4-yl)-3,9-diazaspiro[5.5]undecane-3-carbonyl)-3,4-dihydroisoquinolin-2(1H)-yl)prop-2-en-1-one |
| G-42 | (5-Chlorothiophen-2-yl)(7-(9-(pyridin-4-yl)-3,9-diazaspiro[5.5]undecane-3-carbonyl)-3,4-dihydroisoquinolin-2(1H)-yl)methanone |
| G-43 | 2-(2-Chlorophenyl)-1-(7-(9-(pyridin-4-yl)-3,9-diazaspiro[5.5]undecane-3-carbonyl)-3,4-dihydroisoquinolin-2(1H)-yl)ethanone |
| G-44 | (5-Chlorothiophen-2-yl)(8-(9-(pyridin-4-yl)-3,9-diazaspiro[5.5]undecane-3-carbonyl)-3,4-dihydroisoquinolin-2(1H)-yl)methanone |
| G-45 | N-(2-Chlorobenzyl)-7-(9-(pyridin-4-yl)-3,9-diazaspiro[5.5]undecane-3-carbonyl)-3,4-dihydroisoquinoline-2(1H)-carboxamide |
| G-46 | N-(3,4-Dichlorophenyl)-3-(9-(pyridin-4-yl)-3,9-diazaspiro[5.5]undecane-3-carbonyl)-6,7-dihydroisoxazolo[4,5-c]pyridine-5(4H)-carboxamide |
| G-47 | (2-(4-Methylnaphthalin-1-ylsulfonyl)-1,2,3,4-tetrahydroisoquinolin-7-yl)(9-(pyridin-4-yl)-3,9-diazaspiro[5.5]undecan-3-yl)methanone |
| G-48 | (2-(4-Methoxynaphthalin-1-ylsulfonyl)-1,2,3,4-tetrahydroisoquinolin-7-yl)(9-(pyridin-4-yl)-3,9-diazaspiro[5.5]undecan-3-yl)methanone |
| G-49 | 2,2-Diphenyl-1-(7-(9-(pyridin-4-yl)-3,9-diazaspiro[5.5]undecane-3-carbonyl)-3,4-dihydroisoquinolin-2(1H)-yl)ethanone |
| G-50 | (2-(4-Chloronaphthalin-1-ylsulfonyl)-1,2,3,4-tetrahydroisoquinolin-7-yl)(9-(pyridin-4-yl)-3,9-diazaspiro[5.5]undecan-3-yl)methanone |
| G-51 | 2-(1-(2-Chloro-6-methylphenylsulfonyl)-1,2,3,4-tetrahydroquinolin-7-yl)-1-(8-(pyridin-4-yl)-2,8-diazaspiro[4.5]decan-2-yl)ethanone |
| G-52 | 2-(1-(Naphthalin-1-ylsulfonyl)-1,2,3,4-tetrahydroquinolin-7-yl)-1-(8-(pyridin-4-yl)-2,8-diazaspiro[4.5]decan-2-yl)ethanone |
| G-53 | 2-(1-(Naphthalin-1-ylsulfonyl)-1,2,3,4-tetrahydroquinolin-7-yl)-1-(7-(pyridin-4-yl)-2,7-diazaspiro[4.4]nonan-2-yl)ethanone |
| G-54 | 1-(9-(Azetidin-1-yl)-3-azaspiro[5.5]undecan-3-yl)-2-(1-(naphthalin-1-ylsulfonyl)-1,2,3,4-tetrahydroquinolin-7-yl)ethanone |
| G-55 | N-(3,4-dichlorophenyl)-7-(9-(pyridin-4-yl)-3,9-diazaspiro[5.5]undecane-3-carbonyl)-3,4-dihydroisoquinoline-2(1H)-carboxamide |
| G-56 | (2-(4-Fluoronaphthalin-1-ylsulfonyl)-1,2,3,4-tetrahydroisoquinolin-7-yl)(9-(pyridin-4-yl)-3,9-diazaspiro[5.5]undecan-3-yl)methanone |
| G-57 | 1-(8-(Pyridin-4-yl)-2,8-diazaspiro[4.5]decan-2-yl)-2-(1-(2-(trifluoromethyl)phenylsulfonyl)-1,2,3,4-tetrahydroquinolin-7-yl)ethanone |
| G-58 | (5-Methylthiophen-2-yl)(7-(9-(pyridin-4-yl)-3,9-diazaspiro[5.5]undecane-3-carbonyl)-3,4-dihydroisoquinolin-2(1H)-yl)methanone |
| G-59 | Benzo[b]thiophen-2-yl(7-(9-(pyridin-4-yl)-3,9-diazaspiro[5.5]undecane-3-carbonyl)-3,4-dihydroisoquinolin-2(1H)-yl)methanone |
| G-60 | (5,6-Dihydro-4H-cyclopenta[b]thiophen-2-yl)(7-(9-(pyridin-4-yl)-3,9-diazaspiro[5.5]undecane-3-carbonyl)-3,4-dihydroisoquinolin-2(1H)-yl)methanone |
| G-61 | (3-Chloro-6-methoxybenzo[b]thiophen-2-yl)(7-(9-(pyridin-4-yl)-3,9-diazaspiro[5.5]undecane-3-carbonyl)-3,4-dihydroisoquinolin-2(1H)-yl)methanone |

| Compound | Name |
|---|---|
| G-62 | (2-(5-Chloronaphthalin-1-ylsulfonyl)-1,2,3,4-tetrahydroisoquinolin-7-yl)(9-(pyridin-4-yl)-3,9-diazaspiro[5.5]undecan-3-yl)methanone |
| G-63 | (5-tert-Butylthiophen-2-yl)(7-(9-(pyridin-4-yl)-3,9-diazaspiro[5.5]undecane-3-carbonyl)-3,4-dihydroisoquinolin-2(1H)-yl)methanone |
| G-64 | 2-[1-(2-Chloro-benzoyl)-1,2,3,4-tetrahydro-quinolin-7-yl]-1-(9-pyridin-4-yl-3,9-diazaspiro[5.5]undecan-3-yl)-ethanone |
| G-66 | 2-[1-[(2,6-Dichloro-3-methyl-phenyl)sulfonyl]-1,2,3,4-tetrahydro-quinolin-7-yl]-1-(9-pyridin-4-yl-3,9-diazaspiro[5.5]undecan-3-yl)-ethanone |
| G-67 | [2-[(4-Methoxy-2,6-dimethyl-phenyl)sulfonyl]-2,3-dihydro-1H-isoindol-5-yl]-(9-pyridin-4-yl-3,9-diazaspiro[5.5]undecan-3-yl)-methanone |
| G-68 | [2-[(2-Chloro-6-methyl-phenyl)sulfonyl]-2,3-dihydro-1H-isoindol-5-yl]-(9-pyridin-4-yl-3,9-diazaspiro[5.5]undecan-3-yl)-methanone |
| G-69 | [2-(5-Chloro-thiophene-2-carbonyl)-2,3-dihydro-1H-isoindol-5-yl]-(9-pyridin-4-yl-3,9-diazaspiro[5.5]undecan-3-yl)-methanone |
| G-70 | 2-[8-[(4-Methoxy-2,6-dimethyl-phenyl)sulfonyl]-5,6,7,8-tetrahydro-[1,8]naphthyridin-2-yl]-1-(9-pyridin-4-yl-3,9-diazaspiro[5.5]undecan-3-yl)-ethanone |
| G-71 | [7-(5-Chloro-thiophene-2-carbonyl)-5,6,7,8-tetrahydro-imidazo[1,2-a]pyrazin-2-yl]-(9-pyridin-4-yl-3,9-diazaspiro[5.5]undecan-3-yl)-methanone |
| G-72 | [7-[(4-Methoxy-2,6-dimethyl-phenyl)sulfonyl]-5,6,7,8-tetrahydro-imidazo[1,5-a]pyrazin-1-yl]-(9-pyridin-4-yl-3,9-diazaspiro[5.5]undecan-3-yl)-methanone |
| G-73 | [2-(4-Methoxy-2,6-dimethyl-benzoyl)-2,3-dihydro-1H-isoindol-5-yl]-(9-pyridin-4-yl-3,9-diazaspiro[5.5]undecan-3-yl)-methanone |
| G_CC-006 | 2-(4-Fluorobenzyl)-8-(1-(4-methoxy-2,6-dimethylphenylsulfonyl)indoline-6-carbonyl)-2,8-diazaspiro[4.5]decan-1-one |
| G_CC-007 | (7-Benzyl-2,7-diazaspiro[4.4]nonan-2-yl)(1-(4-methoxy-2,6-dimethylphenylsulfonyl)indoline-6-yl)methanone |
| G_CC-008 | (1-(4-Methoxy-2,6-dimethylphenylsulfonyl)indolin-6-yl)(9-(pyridin-4-yl)-3,9-diazaspiro[5.5]undecan-3-yl)methanone |
| G_CC-009 | (1-(2-Chlorobenzoyl)indolin-6-yl)(9-(pyridin-4-yl)-3,9-diazaspiro[5.5]undecan-3-yl)methanone |
| G_CC-013 | (1-(4-Chloro-2,5-dimethylphenylsulfonyl)indolin-6-yl)(9-(pyridin-4-yl)-3,9-diazaspiro[5.5]undecan-3-yl)methanone |
| G_CC-018 | 8-(2-(2-Chlorobenzoyl)isoindoline-5-carbonyl)-2-(4-fluorobenzyl)-2,8-diazaspiro[4.5]decan-1-one |
| G_CC-025 | 4-(4-Fluorophenyl)-8-(1-(4-methoxy-2,6-dimethylphenylsulfonyl)-1,2,3,4-tetrahydroquinoline-7-carbonyl)-2-methyl-2,8-diazaspiro[4.5]decan-1-one |
| G_CC-026 | 2-Benzyl-8-(1-(4-methoxy-2,6-dimethylphenylsulfonyl)-1,2,3,4-tetrahydroquinoline-7-carbonyl)-2,8-diazaspiro[4.5]decan-1-one |
| G_CC-027 | (7-Benzyl-2,7-diazaspiro[4.4]nonan-2-yl)(1-(4-methoxy-2,6-dimethylphenylsulfonyl)-1,2,3,4-tetrahydroquinolin-7-yl)methanone |
| G_CC-039 | 2-(4-Fluorobenzyl)-8-(2-(4-methoxy-2,6-dimethylphenylsulfonyl)-1,2,3,4-tetrahydroisoquinoline-7-carbonyl)-2,8-diazaspiro[4.5]decan-1-one |
| G_CC-040 | 2-Benzyl-8-(2-(4-methoxy-2,6-dimethylphenylsulfonyl)-1,2,3,4-tetrahydroisoquinoline-7-carbonyl)-2,8-diazaspiro[4.5]decan-1-one |
| G_CC-041 | (7-Benzyl-2,7-diazaspiro[4.4]nonan-2-yl)(2-(4-methoxy-2,6-dimethylphenylsulfonyl)-1,2,3,4-tetrahydroisoquinolin-7-yl)methanone |
| G_CC-043 | 8-(2-(4-Methoxy-2,6-dimethylphenylsulfonyl)-1,2,3,4-tetrahydroisoquinoline-7-carbonyl)-1-phenyl-1,3,8-triazaspiro[4.5]decan-4-one |
| G_CC-045 | (2-(2-Chlorobenzoyl)-1,2,3,4-tetrahydroisoquinolin-7-yl)(9-(pyridin-4-yl)-3,9-diazaspiro[5.5]undecan-3-yl)methanone |
| G_CC-053 | 2-Benzyl-8-(2-(1-(4-methoxy-2,6-dimethylphenylsulfonyl)-1,2,3,4-tetrahydroquinolin-7-yl)acetyl)-2,8-diazaspiro[4.5]decan-1-one |
| G_CC-054 | 1-(7-Benzyl-2,7-diazaspiro[4.4]nonan-2-yl)-2-(1-(4-methoxy-2,6-dimethylphenylsulfonyl)-1,2,3,4-tetrahydroquinolin-7-yl)ethanone |
| G_CC-055 | 2-[1-[(4-Methoxy-2,6-dimethyl-phenyl)sulfonyl]-1,2,3,4-tetrahydro-quinolin-7-yl]-1-(3-pyridin-4-yl-3,9-diazaspiro[5.5]undecan-9-yl)-ethanone |
| G_CC-056 | [1-[(4-Methoxy-2,6-dimethyl-phenyl)sulfonyl]-1,2,3,4-tetrahydro-quinolin-7-yl]-(3-pyridin-4-yl-3,9-diazaspiro[5.5]undecan-9-yl)-methanone | optionally in the form of an isolated enantiomer or of an isolated diastereoisomer, of the racemate, of the enantiomers, of the diastereoisomers, mixtures of enantiomers or diastereoisomers, in each case in the form of their bases and/or physiologically acceptable salts, in particular the hydrochloride salts.

The numbering of the individual embodiments of the compounds according to the invention that has been used above is retained in the explanations of the present invention given hereinbelow, in particular in the description of the examples.

According to one aspect of the present invention, the compounds according to the invention preferably exhibit an antagonistic activity on the human B1R receptor or the B1R receptor of the rat. In a preferred embodiment of the invention, the compounds according to the invention exhibit an antagonistic activity both on the human B1R receptor (hB1R) and on the B1R receptor of the rat (rB1R).

In a preferred embodiment of the present invention, the compounds according to the invention exhibit an inhibition of at least 15%, 25%, 50%, 70%, 80% or 90% on the human B1R receptor and/or on the B1R receptor of the rat in the FLIPR assay at a concentration of 10 µM. Most particular preference is given to compounds that exhibit an inhibition of at least 70%, in particular of at least 80% and particularly preferably of at least 90%, on the human B1R receptor and on the B1R receptor of the rat at a concentration of 10 µM.

The agonistic or antagonistic activity of substances can be quantified on the bradykinin receptor 1 (B1R) of the species human and rat using ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-$Arg^9$-bradykinin (0.5 nM) or Des-$Arg^9$-bradykinin (100 nM). Antagonists lead to suppression of the $Ca^{2+}$ influx after the addition of the agonist. % Inhibition compared with the maximum achievable inhibition is indicated.

The substances according to the invention act especially, for example, on B1R, which is relevant in connection with various diseases, so that they are suitable as a pharmaceutical active ingredient in medicaments. The invention accordingly further provides pharmaceutical compositions comprising at least one substituted spiroamide according to the invention as well as, optionally, suitable additives and/or auxiliary substances and/or optionally further active ingredients.

The pharmaceutical compositions according to the invention are suitable especially for controlling pain, in particular pain selected from the group consisting of acute pain, neuropathic pain, visceral pain, chronic pain and inflammatory pain; or for the treatment of migraine; diabetes; respiratory diseases; inflammatory intestinal diseases; neurological diseases; septic shock; reperfusion syndrome; obesity and also as an angiogenesis inhibitor.

The pharmaceutical compositions according to the invention optionally comprise, in addition to at least one substituted spiroamide according to the invention, suitable additives and/or auxiliary substances, that is to say also carriers, fillers, solvents, diluents, colorings and/or binders, and can be administered as liquid medicament forms in the form of injection solutions, drops or juices, or as semi-solid medicament forms in the form of granules, tablets, pellets, patches, capsules, plasters/spray-on plasters or aerosols. The choice of the auxiliary substances etc. and the amounts thereof to be employed depend on whether the medicament is to be administered orally, perorally, parenterally, intravenously, intraperitoneally, intradermally, intramuscularly, nasally, buccally, rectally or topically, for example to the skin, the mucous membranes or into the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Substituted spiroamides according to the invention in a depot, in dissolved form or in a plaster, optionally with the addition of agents which promote penetration through the skin, are suitable formulations for percutaneous administration. Forms of preparation which can be used orally or percutaneously can release the substituted spiroamides according to the invention in a delayed manner. The substituted spiroamides according to the invention can also be used in parenteral long-term depot forms, such as, for example, implants or implanted pumps. In principle, other further active ingredients known to the person skilled in the art can be added to the medicaments according to the invention.

The amount of active ingredient to be administered to the patient varies depending on the weight of the patient, the manner of administration, the indication and the severity of the disease. From 0.00005 to 50 mg/kg, preferably from 0.01 to 5 mg/kg, of at least one substituted spiroamide according to the invention are conventionally administered. In a preferred form of the pharmaceutical composition, a substituted spiroamide according to the invention that is present can be in the form of an isolated diastereoisomer and/or enantiomer, in the form of the racemate or in the form of a non-equimolar or equimolar mixture of the diastereoisomers and/or enantiomers.

B1R is involved in particular in the occurrence of pain. Accordingly, the substituted spiroamides according to the invention can be used in the preparation of a medicament for the treatment of pain, in particular of acute, visceral, neuropathic or chronic pain. Accordingly, the invention further provides the use of a substituted spiroamide according to the invention in the preparation of a medicament for the treatment of pain, in particular of acute, visceral, neuropathic or chronic pain. A specific embodiment of the present invention is the use of at least one of the substituted spiroamides according to the invention in the preparation of a medicament for the treatment of inflammatory pain.

The invention further provides the use of a substituted spiroamide according to the invention in the preparation of a medicament for the treatment of diabetes, respiratory diseases, for example asthma bronchiale, allergies, COPD/chronic-obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke, obesity; and as an angiogenesis inhibitor.

It may be preferred in one of the above uses to use a substituted spiroamide in the form of an isolated diastereoisomer and/or enantiomer, in the form of the racemate or in the form of a non-equimolar or equimolar mixture of the diastereoisomers and/or enantiomers.

The invention further provides a method of treating, in particular in one of the above-mentioned indications, a non-human mammal or a human in need of treatment, by administration of a therapeutically effective dose of a substituted spiroamide according to the invention, or of a medicament according to the invention.

The invention further provides a process for the preparation of the substituted spiroamides according to the invention, in particular as specified in the following description, examples and claims. The process according to the invention is shown in the following reaction Scheme 1:

Scheme 1

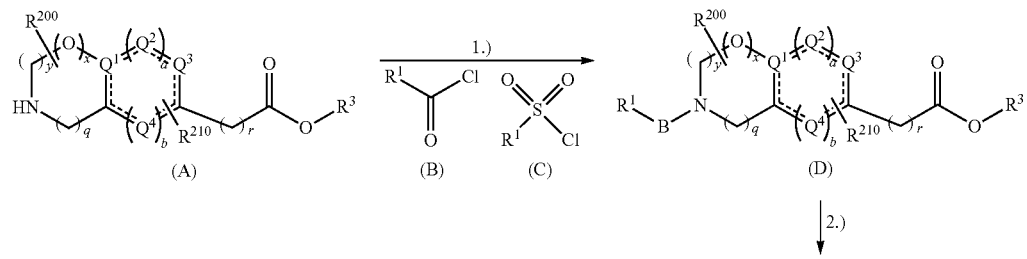

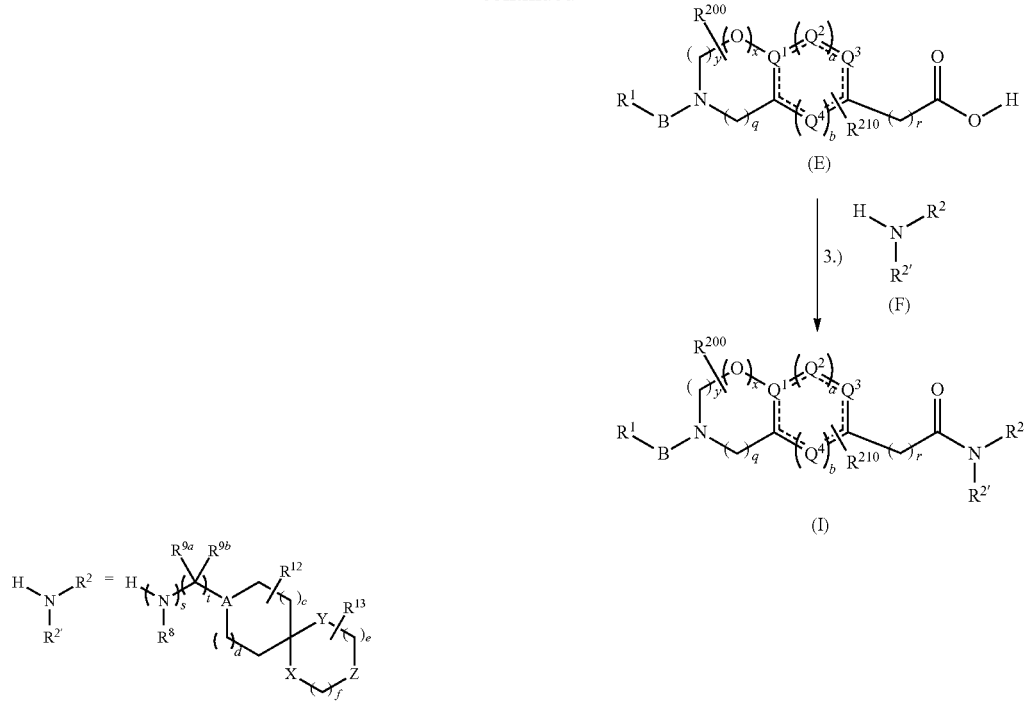

In stage 1, a carboxylic acid chloride of the general formula (B), wherein $R^1$ has the meaning given above, or a sulfonyl chloride of the general formula (C), wherein $R^1$ has the meaning given above, is reacted in at least one solvent, preferably selected from the group consisting of dichloromethane, acetonitrile, dimethylformamide, diethyl ether, dioxane, tetrahydrofuran, methanol, ethanol and isopropanol, with amino acid esters (A), in the presence of at least one inorganic base, preferably selected from the group consisting of potassium carbonate and caesium carbonate, or organic base, preferably selected from the group consisting of triethylamine, diisopropylethylamine and pyridine, and optionally with the addition of 4-(dimethylamino)pyridine or 1-hydroxybenzotriazole, at temperatures of preferably from −15° C. to 50° C., to give compounds having the general formula (D).

In step 1 it is optionally possible to use instead of the carboxylic acid chloride (B) also the corresponding carboxylic acids. These acids of the general formula $R^1CO_2H$, wherein $R^1$ has the meaning given above, are reacted in at least one solvent, preferably selected from the group consisting of dichloromethane, acetonitrile, dimethylformamide, diethyl ether, dioxane and tetrahydrofuran, with amino acid esters (A) with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCl), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or organic base, preferably selected from the group consisting of triethylamine, diisopropylethylamine and pyridine, and optionally with the addition of 4-(dimethylamino)pyridine or 1-hydroxybenzotriazole, to give compounds having the general formula (D).

In stage 2, compounds of the general formula (D) are reacted in at least one solvent, preferably selected from the group consisting of water, methanol, ethanol, isopropanol, diethyl ether, tetrahydrofuran, toluene, acetonitrile, dimethylformamide, dioxane and dimethyl sulfoxide, with an inorganic base, preferably selected from the group consisting of lithium hydroxide, sodium hydroxide, potassium hydroxide, potassium tert-butanolate, lithium propanethiolate and sodium phenylselenolate, optionally with the addition of HMPA or lithium chloride, or with a Lewis acid, preferably selected from the group consisting of trimethylsilyl chloride, boron tribromide and aluminium trichloride, optionally with the addition of thiols, sodium iodide or lithium chloride, at temperatures of preferably from 0° C. to 100° C., to give compounds of the general formula (E).

In stage 3, compounds of the general formula (E) are reacted in at least one solvent, preferably selected from the group consisting of dichloromethane, acetonitrile, dimethylformamide, diethyl ether, dioxane and tetrahydrofuran, with amine (F), with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-Methylcarbodiimide (EDCl), O-(benzotriazol-1-yl)-N,N,N',N'-tetramethyluronium tetrafluoroborate (TBTU), N,N' dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or organic base, preferably selected from the group consisting of triethylamine, diisopropylethylamine and pyridine, and optionally with the addition of 4-(dimethylamino)pyridine or 1-hydroxybenzotriazole, to give compounds having the general formula (G).

Pharmacological Methods
1. Functional Study on the Bradykinin Receptor 1 (B1R)

The agonistic or antagonistic activity of substances can be determined on the bradykinin receptor 1 (B1R) of the species human and rat using the following assay. According to this assay, the $Ca^{2+}$ influx through the channel is quantified with the aid of a $Ca^{2+}$-sensitive dye (Fluo-4 type, Molecular Probes Europe BV, Leiden, Netherlands) using a Fluorescent Imaging Plate Reader (FLIPR, Molecular Devices, Sunnyvale, USA).

2. Method:

Chinese hamster ovary cells (CHO K1 cells) which have been stably transfected with the human B1R gene (hB1R cells) or with the B1R gene of the rat (rB1R cells) are used. For functional studies, the cells are plated out on black 96-well plates having a clear base (BD Biosciences, Heidelberg, Germany or Greiner, Frickenhausen, Germany) in a density of 20,000-35,000 cells/well. The cells are left overnight at 37° C. and with 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany), with 10 vol. % FBS (fetal bovine serum, Gibco Invitrogen GmbH, Karlsruhe, Germany or PAN Biotech GmbH, Aidenbach, Germany). On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR for $Ca^{2+}$ measurement. Alternatively, washing is carried out with buffer A (15 mM HEPES, 80 mM NaCl, 5 mM KCl, 1.2 mM $CaCl_2$, 0.7 mM $MgSO_4$, 2 g/l glucose, 2.5 mM probenecid) followed by loading with buffer A with added 2.5 µM Fluo-4 and 0.025% Pluronic F127 (Sigma-Aldrich, Taufkirchen, Germany). The cells are then washed twice with buffer A and incubated for 30 minutes at room temperature with buffer A additionally containing 0.05% BSA and 0.05% gelatin and are then inserted into the FLIPR for $Ca^{2+}$ measurement. The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

3. FLIPR Assay:

The FLIPR protocol consists of two substance additions. Test substances (10 µM) are first pipetted onto the cells and the $Ca^{2+}$ influx is compared with the control (hB1R: Lys-Des-$Arg^9$-bradykinin >=50 nM; rB1R: Des-$Arg^9$-bradykinin 10 µM). This gives the activation in %, based on the $Ca^{2+}$ signal after addition of Lys-Des-$Arg^9$-bradykinin (>=50 nM) or Des-$Arg^9$-bradykinin (10 µM). After 10-20 minutes' incubation, Lys-Des-$Arg^9$-bradykinin (hB1R) or Des-$Arg^9$-bradykinin (rB1R) is applied in the concentration of the $EC_{80}$, and the influx of $Ca^{2+}$ is likewise determined. Antagonists lead to suppression of the $Ca^{2+}$ influx. The % inhibition compared with the maximum achievable inhibition is calculated. In order to determine the $IC_{50}$ value, the substances are added in various concentrations. Duplicate or triplicate determinations (n=2 or n=3) are carried out, and these are repeated in at least one further independent experiment (N>=2). The compounds exhibit especially a B1R antagonistic activity on the human receptor and/or on the rat receptor. The following data are indicated by way of example in the table below: (in the table, "% inh. (rat B1R) 10 µM" stands for "% inhibition rat B1R at 10 µM" and "% inh. (hum. B1R) 10 µM" stands for "% inhibition human B1R at 10 µM".

The invention is explained hereinafter with reference to examples. These explanations are given only by way of example and do not limit the overall scope of the inventive concept.

EXAMPLES

| List of abbreviations: | |
|---|---|
| DIPEA | diisopropylethylamine |
| EDCl | N-ethyl-N'-(3-dimethylaminopropyl)-carbodiimide hydrochloride |
| h | hour(s) |
| HOBt | 1-hydroxy-1H-benzotriazole |
| conc. | concentrated |
| min. | minute(s) |
| N | normal |
| RT | room temperature |
| THF | tetrahydrofuran |
| TFA | trifluoroacetic acid |
| abs. | absolute |
| eq. | equivalent(s) |
| equiv. | equivalent(s) |
| Boc | tert-butylcarbamate |
| DCM | dichloromethane |
| M | molar |
| EtOAc | ethyl acetate |
| $Et_3N$ | triethylamine |
| Cbz | benzylcarbamate |
| DMF | dimethylformamide |
| DBU | 1,8-diazabicyclo[5.4.0]undec-7-ene |

The chemicals and solvents used were obtained commercially from conventional suppliers (Acros, Aldrich, Fluka, Lancaster, Maybridge, TCI, Fluorochem, Tyger, ABCR, Fulcrum, FrontierScientific, Milestone etc.). The yields of the prepared compounds are not optimized. The mixing ratios of solvents are always given in the ratio volume/volume. Quantitative equivalents of the reagents used, as well as amounts of solvent, reaction temperatures and times, can vary slightly in different reactions that are carried out by the same method. Methods of working up and purifying were adapted to the characteristic properties of the compounds. The compounds were analyzed by HPLC-MS and/or NMR:

NMR: Bruker 440 MHz or 600 MHz device

Materials and methods for LC-MS analysis: HPLC: Waters Alliance 2795 with PDA Waters 2998; MS: Micromass Quattro Micro™ API; column: Waters Atlantis® T3, 3 µm, 100 Å, 2.1×30 mm; column temperature: 40° C., eluant A: water+0.1% formic acid; eluant B: acetonitrile+0.1% formic acid; gradient: 0% B to 100% B in 8.8 min, 100% B for 0.4 min, 100% B to 0% B in 0.01 min, 0% B for 0.8 min; flow: 1.0 ml/min; ionisation: ES+, 25 V; make up: 100 µl/min 70% methanol+0.2% formic acid; UV: 200-400 nm.

Syntheses of Structural Units
1) Synthesis of the Amino Acid Esters A Structural unit A-01:
Methyl indoline-6-carboxylate Stage 1: 4-Methyl-3-nitrobenzoic acid Conc. sulfuric acid (25 ml; 0.5 equiv.) was added over a period of 10 minutes to nitric acid at 0° C. (69-72%; 25 ml; 0.5 equiv.). The resulting mixture was stirred for 30 minutes at 0° C. Conc. sulfuric acid (75 ml; 1.5 equiv.) was added at room temperature, over a period of 20 minutes, to 4-methylbenzoic acid (50 g; 1 equiv.). The resulting suspension was cooled to 0° C., and the nitrating acid was added thereto over a period of 45 minutes. The resulting reaction mixture was stirred for 1 hour at 10-20° C. When the conversion was complete, the reaction mixture was poured onto ice-water and the resulting white solid was filtered out and dried. 4-Methyl-3-nitrobenzoic acid (66.5 g; 82.7%) was obtained in the form of a white solid.

Stage 2: 4-(2-(Dimethylamino)vinyl)-3-nitrobenzoic acid

DMF-DMA (45.4 g; 2.3 equiv.) was added under a nitrogen atmosphere to a solution of 4-methyl-3-nitrobenzoic acid (30 g; 1 equiv.) in dimethylformamide (150 ml). The resulting reaction mixture was heated for 17 h at 140° C. When the conversion was complete, the DMF was distilled off; 150 ml of methanol were added to the residue, and the mixture was stirred for 2 hours at room temperature and then crystallised overnight at 0-4° C. The resulting solid was filtered out and washed with ice-cold methanol and then with hexane. Drying yielded 4-(2-(dimethylamino)vinyl)-3-nitrobenzoic acid (28 g; 71.79%) in the form of a red solid.

Stage 3: Methyl 1H-indole-6-carboxylate

Sodium dithionate (164.4 g; 16 equiv.) was added over a period of 20 minutes to a solution of 4-(2-(dimethylamino) vinyl)-3-nitrobenzoic acid (14 g; 1 equiv.) in a mixture of THF (42 ml), ethanol (42 ml) and water (140 ml). The reaction mixture was heated for 90 min. at reflux and then stirred for 12 hours at room temperature. When the conversion was complete, dichloromethane was added, the phases were separated and the aqueous phase was extracted with dichloromethane. The combined organic phases were dried over sodium sulfate. After removal of the solvent under reduced pressure, purification was carried out by column chromatography (silica gel, 10% ethyl acetate/hexane). Methyl 1H-indole-6-carboxylate (8 g; 40%) was obtained in the form of a solid.

Stage 4: Methyl indoline-6-carboxylate

NaCNBH$_3$ (11.49 g; 0.04 equiv.) was added at 0° C., over a period of 10 minutes, to a solution of methyl 1H-indole-6-carboxylate (8 g; 1 equiv.) in acetic acid (80 ml). The reaction mixture was stirred at 0° C. for 20 minutes and then warmed to room temperature and stirred for 1 hour at room temperature. When the conversion was complete, the acetic acid was distilled off under reduced pressure and the resulting residue was dissolved in dichloromethane. The resulting phases were separated. The organic phase was washed with 1N sodium hydroxide solution and dried over sodium sulfate. After removal of the solvent under reduced pressure, purification was carried out by column chromatography (silica gel, 10-15% ethyl acetate/hexane). Methyl indoline-6-carboxylate (6 g; 75%) was obtained in the form of a solid.
Structural unit A-02: Methyl isoindoline-5-carboxylate hydrochloride Stage 1: Methyl 3,4-dimethylbenzoate Thionyl chloride (80 ml; 2 equiv.) was added at room temperature to a solution of 3,4-dimethylbenzoic acid (35 g; 1 equiv.) and dimethylformamide (1 ml) in 227 ml of methanol. The resulting reaction mixture was stirred for 12 h at room temperature and then concentrated under reduced pressure. The resulting residue was taken up in dichloromethane and washed with 5% sodium carbonate solution. The organic phase was dried over magnesium sulfate and concentrated under reduced pressure. The methyl 3,4-dimethylbenzoate so obtained (38.2 g) was used in the next stage without further purification.

Stage 2: Methyl 3,4-bis(bromomethyl)benzoate

A catalytic amount of benzyl peroxide and NBS (82.9 g; 2 equiv.) was added to a solution of methyl 3,4-dimethylbenzoate (38.2 g; 1 equiv.) in 458.4 ml of dichloromethane. The resulting reaction mixture was stirred for 15 minutes at room temperature and then heated for 18 hours at reflux (110-120° C.). The reaction mixture was cooled to room temperature, filtered and concentrated under reduced pressure. The residue was taken up in dichloromethane, washed with 5% sodium carbonate solution, dried over sodium sulfate and again concentrated under reduced pressure. The methyl 3,4-bis(bromomethyl)benzoate so obtained (73.9 g) was used in the next stage without further purification.

Stage 3: Methyl 2-benzylisoindoline-5-carboxylate

TEA was added at room temperature, in the course of 15 minutes, to a solution of methyl 3,4-bis(bromomethyl)benzoate (9.3 g; 1 equiv.) and benzylamine (4.3 g; 1.4 equiv.) in 83.7 ml of benzene. The resulting reaction mixture was first stirred for 30 minutes at room temperature and then heated for 20 hours at reflux (110-120° C.). When the conversion was complete, the reaction mixture was cooled to room temperature and filtered. The filtrate was taken up in 100 ml of dichloromethane and washed 2× with 5% sodium carbonate solution. The combined organic phases were dried over sodium sulfate and the solvent was removed under reduced pressure. Purification by column chromatography (silica gel, 5% ethyl acetate/hexane) yielded methyl 2-benzylisoindoline-5-carboxylate (2.2 g; 28.3%) in the form of a solid.

Stage 4: Methyl 2-benzylisoindoline-5-carboxylate hydrochloride (AL/7102/S04)

HCl gas was passed through a solution of methyl 2-benzylisoindoline-5-carboxylate (56 g; 1 equiv.) in 560 ml of dichloromethane until a solid formed. The solid was filtered out, washed with hexane and dried. Methyl 2-benzylisoindoline-5-carboxylate hydrochloride (43 g) was obtained in the form of a white solid.

Stage 5: Methyl isoindoline-5-carboxylate hydrochloride

10% Pd/C (4.3 g) was added to a solution of methyl 2-benzylisoindoline-5-carboxylate hydrochloride (43 g; 1 equiv.) in 800 ml of methanol. The mixture was hydrogenated for 90 minutes at 60 mm hydrogen. When the conversion was complete, the reaction mixture was filtered, the filtrate was concentrated under reduced pressure and the crude product was recrystallised from chloroform. In this manner the desired product (25.39 g; 84%) was obtained in the form of a white solid having a purity of 98.63%.
Structural unit A-03: Methyl 1,2,3,4-tetrahydroquinoline-7-carboxylate

Stage 1: 7-(Trifluoromethyl)quinoline

Conc. sulfuric acid (4.56 g; 1.5 equiv.) was added dropwise to a mixture of 3-(trifluoromethyl)aniline (5 g; 1 equiv.), glycerol (5.14 g; 1.8 equiv.) and iodine (150 mg). The resulting reaction mixture was stirred for 1 hour at 80-90° C. and for 3 hours at 160-170° C. When the conversion was complete, the reaction mixture was diluted at room temperature with 100 ml of water, neutralised with sodium carbonate and extracted 4× with 200 ml of dichloromethane. The combined organic phases were dried over sodium sulfate, the solvent was removed under reduced pressure and the crude product was purified by column chromatography (silica gel, 10% EtOAc/hexane). 7-(Trifluoromethyl)quinoline (1.35 g; 22.13%) was obtained in the form of a white crystalline solid.

Stage 2: Methyl quinoline-7-carboxylate

A mixture of 7-(trifluoromethyl)quinoline (8.9 g; 1 equiv.) and 35.6 ml of 10% oleum was heated for 3 hours at 150° C. and then cooled to room temperature; 90 ml of methanol were added and the mixture was heated overnight at 80° C. When the conversion was complete, methanol was distilled off and the residue was taken up in 200 ml of water, neutralized with sodium carbonate and extracted 3 times with ethyl acetate. The combined organic phases were dried over sodium sulfate and concentrated under reduced pressure, and the crude product was washed with petroleum ether. Methyl quinoline-7-carboxylate (7.4 g; 88%) was obtained in the form of a white solid.

Stage 3: Methyl 1,2,3,4-tetrahydroquinoline-7-carboxylate $BF_3$ etherate (30.5 g; 2 equiv.) was first added dropwise to a solution of methyl quinoline-7-carboxylate (20.1 g; 1 equiv.) in 200 ml of methanol. Sodium cyanoboro-hydride (13.5 g; 2 equiv.) was then added in portions. The resulting reaction mixture was stirred for 20 minutes at room temperature and heated overnight at reflux (70-80° C.). When the conversion was complete, the reaction mixture was cooled to room temperature, the solvent was removed under reduced pressure and the residue was taken up in 300 ml of water and extracted 3× with EtOAc. The combined organic phases were dried over sodium sulfate and concentrated under reduced pressure, and the crude product was recrystallised from isopropanol. Methyl 1,2,3,4-tetrahydro-quinoline-7-carboxylate (14 g; 67.3%) was obtained in the form of a colorless solid.

Structural unit A-04: Methyl 1,2,3,4-tetrahydroisoquinoline-7-carboxylate

Stage 1: 7-Nitro-1,2,3,4-tetrahydroisoquinoline hydrochloride 1,2,3,4-Tetrahydroisoquinoline (50 g; 1 equiv.) was added at 0° C., in the course of 90 minutes, to 185 ml of sulfuric acid, and the reaction mixture was stirred for 30 minutes at 0° C. Potassium nitrate (40.7 g; 1.2 equiv.) was then added in portions, and stirring was carried out for 15 hours at room temperature. When the conversion was complete, the reaction mixture was shaken on 500 g of ice and adjusted to pH 8-9 with ammonia solution. Extraction with chloroform was then carried out 3 times, and the combined organic phases were dried over sodium sulfate and concentrated under reduced pressure. The residue was taken up in IPA (500 ml) and cooled to 0° C., and hydrochloric acid (2 equiv.) was added. The resulting solid was filtered out and recrystallised from methanol. 7-Nitro-1,2,3,4-tetrahydroisoquinoline (35 g; 52.3%) was obtained in the form of a white solid.

Stage 2: 1,2,3,4-Tetrahydroisoquinoline-7-amine

10% Pd/C (1.9 g) was added to a solution of 7-nitro-1,2,3,4-tetrahydroisoquinoline hydrochloride (19 g; 1 equiv.) in 300 ml of methanol, and the reaction mixture was hydrogenated for 2 hours at 60 PSI. When the conversion was complete, filtration over Celite was carried out, the filter cake was then washed 4 times with methanol, the filtrate was concentrated under reduced pressure, and the residue was taken up in 100 ml of water. The aqueous solution was adjusted to a pH value of 8-9 with potassium hydroxide solution and extracted 3× with chloroform. The combined organic phases were dried over sodium sulfate and reduced under reduced pressure. 1,2,3,4-Tetrahydroisoquinoline-7-amine (9 g; 69.2%) was obtained in the form of a pale-brown solid.

Stage 3: 1,2,3,4-Tetrahydroisoquinoline-7-carbonitrile (AL/7103/S04)

Hydrochloric acid (30.6 ml; 2 equiv.) was added at 0° C. to a solution of 1,2,3,4,-tetrahydroisoquinoline-7-amine (15.3 g; 1 equiv.) in 40 ml of water, and the reaction mixture was stirred for 10 minutes at −5° C. Sodium nitrate solution (7.13 g of sodium nitrate in 35 ml of water) was added dropwise at 0° C. in the course of 30 minutes, and the resulting reaction mixture was stirred for 30 minutes at 0° C. Finally, urea (1.86 g; 0.3 equiv.) was added. A mixture of sodium hydroxide solution (10.3 g of NaOH in 70 ml of $H_2O$), potassium cyanide solution (33.5 g (5 equiv.) of KCN in 50 ml of $H_2O$) and 76.5 ml of benzene was cooled to 0° C.; a nickel sulfate solution (32.6 g (1.2 equiv.) of $NiSO_4*6H_2O$ in 50 ml of $H_2O$) was added slowly, and stirring was carried out for 30 min. at 0° C. The diazonium solution was slowly added dropwise at 0° C., and the resulting reaction mixture was stirred first for 2 h at room temperature and then for 1 h at 50° C. When the conversion was complete, the mixture was cooled to 0° C., adjusted to a pH value of 8-9 with sodium hydroxide solution and filtered over Celite, and the filter cake was then washed with dichloromethane. The aqueous solution was extracted 3 times with dichloromethane. The combined organic phases were dried over sodium sulfate and concentrated under reduced pressure. The crude product was purified by column chromatography (silica gel, 10% methanol/chloroform). 1,2,3,4-Tetrahydroisoquinoline-7-carbonitrile (4 g; 24.5%) was obtained in the form of a solid.

Stage 4: Methyl 1,2,3,4-tetrahydroisoquinoline-7-carboxylate 240 ml of methanolic hydrochloric acid (hydrogen chloride was passed over methanol for 4 hours) were added to a solution of 1,2,3,4-tetrahydroisoquinoline-7-carbonitrile (12 g; 1 equiv.). The resulting reaction mixture was heated for 18 hours at reflux (80° C.). When the conversion was complete, the methanol was distilled off and the residue was taken up in 100 ml of water and adjusted to a pH value of 8-9 with sodium carbonate. The reaction mixture was extracted 3× with dichloromethane and the combined organic phases were dried over sodium sulfate and concentrated under reduced pressure. The crude product was purified by column chromatography (silica gel, 50% ethanol/heptane). Methyl 1,2,3,4- tetrahydroisoquinoline-7-carboxylate (8 g; 55%) was obtained in the form of a brownish oil.

Structural unit A-05: Methyl 2-(1,2,3,4-tetrahydroquinolin-7-yl)acetate

Stage 1: 1-(3,4-Dihydroquinolin-1(2H)-yl)ethanone

Acetic anhydride (55.5 g; 1.05 equiv.) was slowly added dropwise, at 0° C., to a solution of 1,2,3,4-tetrahydroquinoline (69 g; 1 equiv.) in 690 ml of dichloromethane. The reaction mixture was stirred for 30 minutes at room temperature and, when the conversion was complete, was washed with cold water and sodium hydrogen carbonate solution. The organic phase was dried over sodium sulfate and concentrated under reduced pressure. 1-(3,4-Dihydroquinolin-1(2H)-yl)ethanone (85 g; 94.4%) was obtained in the form of a colorless oil.

Stage 2: 1,1'-(3,4-Dihydroquinolin-1,6(2H)-diyl)diethanone and 1,1'-(3,4-dihydroquinolin-1,7(2H)-diyl)diethanone 1-(3,4-Dihydroquinolin-1(2H)-yl)ethanone (85 g; 1 equiv.) was added dropwise to aluminium chloride (194.4 g; 3 equiv.); stirring was carried out for 30 minutes and then distilled acetyl chloride (76.2 g; 2 equiv.) was added in the course of 30 minutes. The resulting reaction mixture was heated for 10 hours at reflux (60° C.) then quenched at 0° C. with cold water and extracted with ethyl acetate. The combined organic phases were dried over sodium sulfate and concentrated under reduced pressure. The crude product was purified by column chromatography (silica gel, 75% ethyl acetate/hexane). The desired regioisomer mixture (54 g; 60.9%) was obtained in the form of a yellow oil.

Stage 3: 1-(1,2,3,4-Tetrahydroquinolin-6-yl)ethanone & 1-(1,2,3,4-tetrahydroquinolin-7-yl)ethanone 270 ml of conc. hydrochloric acid were added dropwise in the course of 15 minutes to a solution of the regioisomer mixture obtained above (stage 2; 54 g; 1 equiv.) in 540 ml of methanol. The reaction mixture was heated for 6 hours at reflux. When the conversion was complete, the methanol was distilled off, the residue was dissolved in 300 ml of water, and this solution was rendered basic at 0° C. with sodium carbonate and finally extracted 2× with 200 ml of ethyl acetate. The combined organic phases were dried over sodium sulfate and concentrated under reduced pressure. Purification by column chromatography (silica gel, 8% ethyl acetate/hexane) yielded 18 g of the desired 1-(1,2,3,4-tetrahydroquinolin-7-yl)ethanone in the form of a pale-yellow solid.

Stage 4: 1-Morpholino-2-(1,2,3,4-tetrahydroquinolin-7-yl)ethanethione

Sulfur (4.7 g; 0.25 equiv.) was added in portions to a solution of 1-(1,2,3,4-tetrahydroquinolin-7-yl)ethanone (12 g; 1 equiv.) in morpholine (16.1 g; 2.5 equiv.) and the mixture was heated for 12 hours at reflux (160° C.). When the conversion was complete, the solvent was removed under reduced pressure and the crude product was purified by column chromatography (silica gel, 40% EtOAc/hexane). 1-Morpholino-2-(1,2,3,4-tetrahydroquinolin-7-yl)ethanethione (11 g; 58.8%) was obtained in the form of a yellow oil.

Stage 5: 2-(1,2,3,4-Tetrahydroquinolin-7-yl)acetic acid 110 ml of a 20% barium hydroxide solution were added dropwise to a solution of 1-morpholino-2-(1,2,3,4-tetrahydroquinolin-7-yl)-ethanethione (11 g; 1 equiv.) in 55 ml of ethanol, and the resulting reaction mixture was heated for 10 hours at reflux. When the conversion was complete, the solvent was removed under reduced pressure and the residue was taken up in 100 ml of water and heated to 80° C. The reaction mixture was then neutralised carefully with dry ice, filtered over Celite and concentrated under reduced pressure. The resulting crude product (14 g) was used in the next stage without further purification.

Stage 6: Methyl 2-(1,2,3,4-tetrahydroquinolin-7-yl)acetate

Thionyl chloride (13 g; 1.5 equiv.) was added dropwise at 0° C., in the course of 5-10 minutes, to a solution of crude 2-(1,2,3,4-tetrahydroquinolin-7-yl)acetic acid (stage 5; 14 g; 1 equiv.) in 140 ml of methanol, and the resulting reaction mixture was then heated for 6 hours at reflux (70° C.). When the conversion was complete, the reaction solution was concentrated under reduced pressure and the residue was taken up in 150 ml of water, rendered basic (pH 7-8) with sodium carbonate and finally extracted with 2×150 ml of chloroform. The combined organic phases were dried over sodium sulfate and concentrated under reduced pressure. The crude product was purified by column chromatography (silica gel, 10-12% ethyl acetate/-hexane). Methyl 2-(1,2,3,4-tetrahydroquinolin-7-yl)acetate (4 g) was obtained in the form of a colorless oil.

Structural unit A-06: Ethyl 4,5,6,7-tetrahydroisoxazolo[4,5-c]pyridine-3-carboxylate

Stage 1: tert-Butyl 4-(pyrrolidin-1-yl)-5,6-dihydropyridine-1(2H)-carboxylate Catalytic amounts of p-toluenesulfonic acid (0.47 g, 0.27 mmol) were added to a solution of N-Boc-4-piperidone (5 g, 25.12 mmol) and pyrrolidine (1.96 g, 27.63 mmol) in toluene (100 ml), and the mixture was stirred for 2 hours under reflux with a water separator. The resulting solution was concentrated to dryness in vacuo and the resulting residue was used directly in the following stage.

Stage 2: 5-tert-Butyl 3-ethyl 7a-(pyrrolidin-1-yl)-3a,4,7,7a-tetrahydroisoxazolo-[4,5-c]pyridine-3,5(6H)-dicarboxylate The crude product from the preceding stage was dissolved in dichloromethane (50 ml), and a solution of 2-chlorohydroxyiminoacetic acid ethyl ester (5.3 g, 35.17 mmol) in dichloromethane (50 ml) was added slowly at RT (optionally with cooling), with vigorous stirring. Triethylamine (4.8 ml, 35.17 mmol) was then slowly added dropwise at 0° C. The reaction mixture was stirred for 16 hours at room temperature and terminated by addition of 10% citric acid. The mixture was extracted with dichloromethane and the organic phases were washed with NaHCO$_3$ solution and NaCl solution, dried over Na$_2$SO$_4$ and concentrated in vacuo. Purification of the crude product was carried out by column chromatography (silica gel, 8% acetone in hexane). Yield: 60%

Stage 3: Ethyl 4,5,6,7-tetrahydroisoxazolo[4,5-c]pyridine-3-carboxylate

Trifluoroacetic acid (6.67 ml, 89.9 mmol) was added at 0° C. to a solution of 5-tert-butyl 3-ethyl 7a-(pyrrolidin-1-yl)-3a,4,7,7a-tetrahydroisoxazolo[4,5-c]pyridine-3,5(6H)-dicarboxylate (5.5 g, 14.98 mmol) in DCM (100 ml), and the mixture was stirred for 16 hours under reflux. Cooling to 0° C. was then carried out and NaHCO₃ solution was added. The phases were separated and the aqueous phase was extracted with dichloromethane. The combined organic phases were dried over Na₂SO₄, filtered and concentrated in vacuo. Purification of the crude product was carried out by column chromatography (silica gel, 16% methanol in ethyl acetate). Yield: 62% [Alternatively, ethyl 4,5,6,7-tetrahydroisoxazolo[4,5-c]pyridine-3-carboxylate A-06 can be synthesised as described in WO2006105945.]

Structural unit A-08: Methyl 2-(3,4-dihydro-2H-benzo[b][1,4]oxazin-6-yl)acetate

Stage 1: Methyl 2-(3-oxo-3,4-dihydro-2H-benzo[b][1,4]oxazin-6-yl)acetate

Chloroacetyl chloride (1 equiv.) was added at room temperature to a mixture of methyl (3-amino-4-hydroxyphenyl)acetate (5.5 mmol) and sodium hydrogen carbonate (1.1 equiv.) in ethyl acetate (5 ml)/water (5 ml). The reaction mixture was stirred for 1 h, then the phases were separated and the organic phase was washed with water and saturated sodium chloride solution, dried over sodium sulfate and concentrated in vacuo. The crude product was dissolved in DMF (11 ml); activated potassium carbonate was added, and the mixture was stirred overnight at room temperature. The reaction mixture was then diluted with water and extracted with ethyl acetate. The organic phase was again washed with water and saturated sodium chloride solution, dried over sodium sulfate and concentrated in vacuo. The crude product was purified by column chromatography (silica gel, ethyl acetate/hexane). Yield: 90%

Stage 2: Methyl 2-(3,4-dihydro-2H-benzo[b][1,4]oxazin-6-yl)acetate

Borane dimethylsulfide solution (0.3 ml, 94% in THF) was added at room temperature to a solution of the product from stage 1 (2.7 mmol) in dry THF (14 ml), and the mixture was refluxed for 2 h. Hydrolysis with methanol (1 ml) was carried out, followed by refluxing for a further 15 min. The reaction mixture was then cooled to room temperature and concentrated in vacuo. The crude product was purified by column chromatography (silica gel, ethyl acetate/hexane). Yield: 62%

Structural unit A-09: Ethyl 5,6,7,8-tetrahydroimidazo[1,2-a]pyrazine-2-carboxylate hydrochloride available commercially from, e.g., Activate Scientific Structural unit A-10: Methyl 2-(5,6,7,8-tetrahydro-1,8-naphthyridin-2-yl)acetate hydrochloride tert-Butyl 7-(2-methoxy-2-oxoethyl)-3,4-dihydro-1,8-naphthyridine-1(2H)-carboxylate (1 eq.) (CAS [925889-81-2], available commercially from Fluorochem, for example) was dissolved in methanol (1.6 ml); hydrogen chloride in methanol (1.25 M, 5 equiv.) was added, and the mixture was heated to boiling temperature. After 1 h, the solvent was removed in vacuo and the residue so obtained was used directly in the following stage. Yield: >99%

2) Synthesis of the Acid Chlorides (B) and Sulfonic Acid Chlorides (C)

The sulfonic acid chlorides used according to the invention are available commercially or can be prepared by conventional methods known to Persons skilled in the art. The numbers given in square brackets hereinbelow are the CAS numbers.

Acid chloride B-01: 2-Chlorobenzoyl chloride [609-65-4] available commercially from Aldrich, for example.

Sulfonyl chloride C-01: 4-Methoxy-2,6-dimethylphenyl-1-sulfonyl chloride

Chlorosulfonic acid (1.83 ml, 2.3 equiv.) in dichloromethane (10 ml) was added dropwise at 0° C., over a period of 20 minutes, to a solution of 3,5-dimethylanisole (1.632 g, 11.982 mmol) in dichloromethane (15 ml). The reaction mixture was then stirred for 10 min. at room temperature. The reaction mixture was added to ice-water (3 ml, 5 equiv. based on chlorosulfonic acid) and the aqueous phase was extracted with dichloromethane (3×100 ml). The organic phase was dried (Na₂SO₄) and concentrated in vacuo. Yield: 2.6 g (92%)

Sulfonyl chloride C-02: 4-Chloro-2,5-dimethylphenyl-1-sulfonyl chloride [88-49-3] available commercially from ABCR, for example.

Sulfonyl chloride C-03: 2-(Trifluoromethyl)phenyl-1-sulfonyl chloride [776-04-5] available commercially from Aldrich, for example.

Sulfonyl chloride C-04: Naphthalene-1-sulfonyl chloride [85-46-1] available commercially from ACROS, for example.

Sulfonyl chloride C-05: 2-Chloro-6-methylphenyl-1-sulfonyl chloride [25300-37-2] available commercially from Fluorochem, for example.

Sulfonyl chloride C-06: 4-Methoxy-2,3,6-trimethylphenyl-1-sulfonyl chloride [80745-07-9] available commercially from ABCR, for example.

Sulfonyl chloride C-07: 2-Chloro-4-(trifluoromethoxy)benzene-1-sulfonyl chloride available commercially from ABCR, for example.

Sulfonyl chloride C-08: 2,6-Dichloro-3-methylphenyl-1-sulfonyl chloride available commercially from Akos, for example.

3) Synthesis of the Acylated or Sulfonylated Amino Acid Esters D

General Method for the Synthesis of the Sulfonylated Amino Acid Esters D

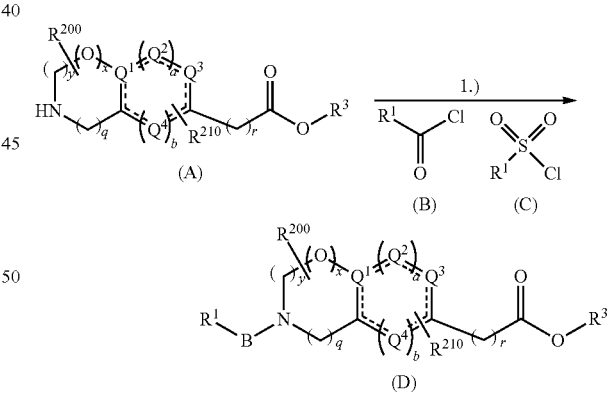

Synthesis of the Sulfonylated Amino Acid Esters D

General working procedure GWP I—sulfonylation: A solution of the sulfonyl chloride C (1 equiv.) in dichloromethane was added at room temperature to a solution of the amino acid ester A (1.2 equiv.) and diisopropylethylamine (1 to 3 equiv.) in dichloromethane. The reaction mixture was stirred for 12 h at room temperature, then washed 3× with a 1N HCl solution, dried over sodium sulfate and concentrated under reduced pressure. Purification by column chromatography (silica; ethyl acetate/-hexane) yielded the desired product.

General working procedure GWP II—acylation: A solution of the acid chloride B (2 equiv.) was added at room temperature to a solution of the amino acid ester A (1 equiv.) and diisopropylethylamine (1 to 3 equiv.) in dichloromethane. The reaction mixture was stirred for 12 h at room temperature, N,N-dimethylethane-1,2-diamine (1 to 3 equiv.) was added, and stirring was carried out for 1 h at room temperature. The mixture is then washed 3× with a 1N HCl solution, dried over sodium sulfate and concentrated under reduced pressure. Purification by column chromatography (silica; ethyl acetate/hexane) yielded the desired product.

General working procedure GWP III—sulfonylation: Amino acid ester A (1 equiv.) was dissolved in dichloromethane and triethylamine (1-2 equiv.) and cooled with an ice bath. The sulfonyl chloride B (1-2 equiv.), dissolved in dichloromethane, was added slowly at 0° C. The cooling bath was removed and the reaction mixture was stirred for 15 h. Saturated sodium hydrogen carbonate solution was then added and the phases were separated. The aqueous phase was extracted with dichloromethane, and the combined organic phases were washed with water or HCl solution (0.05 mol/l) and saturated sodium chloride solution, dried over sodium sulfate and concentrated in vacuo. The crude product was purified by column chromatography (silica gel).

General working procedure GWP IV—sulfonylation: Triethylamine (1-3 equiv.), optionally DMAP (cat.) and then sulfonyl chloride B (1.2-2 equiv.), optionally dissolved in dichloromethane, were added to an ice-cooled solution of the amino acid ester A (1 equiv.) in DCM. The reaction mixture was stirred for 1-15 h at room temperature, diluted with water or saturated sodium hydrogen carbonate solution and extracted with dichloromethane. The combined organic phases were washed with water or hydrochloric acid (0.05 mol/l) and with saturated sodium chloride solution, dried over sodium sulfate and concentrated in vacuo. The crude product was purified by column chromatography (silica gel).

General working procedure GWP V—acylation: Amino acid ester A (1 equiv.) was dissolved in dichloromethane and triethylamine (1.5 equiv.), cooled with an ice bath and stirred for 15 min. The carboxylic acid chloride B (1 equiv.), dissolved in dichloromethane, was added slowly at 0° C. The cooling bath was removed and the reaction mixture was stirred for 15 h at RT. Saturated sodium hydrogen carbonate solution was then added and the phases were separated. The aqueous phase was extracted with dichloromethane, and the combined organic phases were washed with saturated sodium chloride solution, dried over sodium sulfate and concentrated in vacuo. The crude product was purified by column chromatography (silica gel).

General working procedure GWP Va—acylation: Amino acid ester A (1 equiv.) was dissolved in dichloromethane and triethylamine (2 equiv.) and cooled with an ice bath. The carboxylic acid chloride B (1.2 equiv.), dissolved in dichloromethane, was added slowly at 0° C. The cooling bath was removed and the reaction mixture was stirred for 1 h at RT. Pyridine was then added catalytically, and the mixture was heated for 3 h at boiling temperature and stirred for 48 h at RT. Pyridine (about 1 ml/mmol) was added and the mixture was heated for 6 h at boiling temperature. The reaction mixture was then washed with copper sulfate solution (aq.) (20 ml) and sat. NaCl solution (20 ml), dried over sodium sulfate and concentrated in vacuo. The resulting crude product was purified by column chromatography (silica gel).

TABLE 1

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-01 | 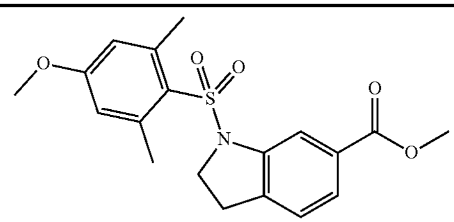 | Methyl 1-(4-methoxy-2,6-dimethylphenyl)-indoline-6-carboxylate (D-01) | Methyl indoline-6-carboxylate (A-01) | 4-Methoxy-2,6-dimethylphenyl-1-sulfonyl chloride (C-01) | GWP I | 99% (21 mmol) |
| D-02 | 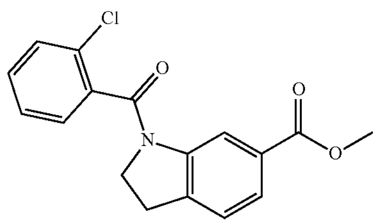 [SMILES: COC(=O)c1ccc2c(c1)N(C(=O)c1ccccc1Cl)CC2] | Methyl 1-(2-chlorobenzoyl)indoline-6-carboxylate (D-02) | Methyl indoline-6-carboxylate (A-01) | 2-Chlorobenzoyl chloride (B-01) | GWP II | 71% (20 mmol) |
| D-03 | 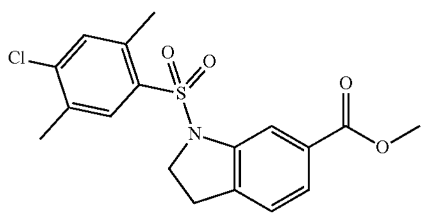 [SMILES: COC(=O)c1ccc2c(c1)N(S(=O)(=O)c1cc(C)c(Cl)cc1C)CC2] | Methyl 1-(4-chloro-2,5-dimethylphenylsulfonyl)-indoline-6-carboxylate (D-03) | Indoline-6-carboxylic acid (A-01) | 4-Chloro-2,5-dimethylphenyl-1-sulfonyl chloride (C-02) | GWP I | 94% (17.6 mmol) |
| D-04 | 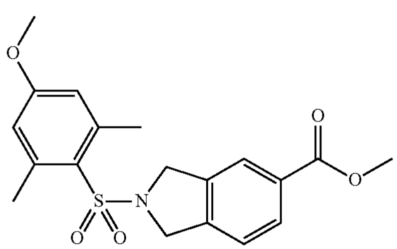 [SMILES: COC(=O)c1ccc2c(c1)CN(S(=O)(=O)c1c(C)cc(OC)cc1C)C2] | Methyl 2-(4-methoxy-2,6-dimethylphenylsulfonyl)-isoindoline-5-carboxylate (D-04) | Methyl isoindoline-5-carboxylate (A-02) | 4-Methoxy-2,6-dimethylphenyl-1-sulfonyl chloride (C-01) | GWP I | 78% (16.6 mmol) |

TABLE 1-continued

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-05 | 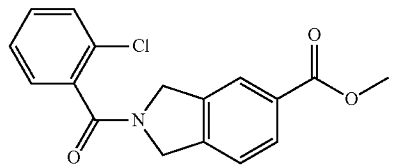 [SMILES: COC(=O)c1ccc2c(c1)CN(C(=O)c1ccccc1Cl)C2] | Methyl 2-(2-chlorobenzoyl)isoindoline-5-carboxylate (D-05) | Methyl isoindoline-5-carboxylate (A-02) | 2-Chlorobenzoyl chloride (B-01) | GWP II | 68% (16 mmol) |
| D-06 | 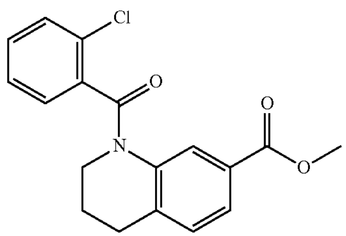 [SMILES: COC(=O)c1ccc2c(c1)N(C(=O)c1ccccc1Cl)CCC2] | Methyl 1-(2-chlorobenzoyl)-1,2,3,4-tetrahydroquinoline-7-carboxylate (D-06) | Methyl 1,2,3,4-tetrahydroquinoline-7-carboxylate (A-03) | 2-Chlorobenzoyl chloride (B-01) | GWP II | 62% (13.6 mmol) |
| D-07 | 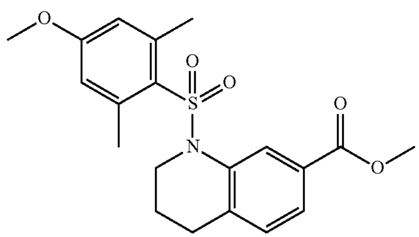 | Methyl 1-(4-methoxy-2,6-dimethylphenylsulfonyl)-1,2,3,4-tetrahydroquinoline-7-carboxylate (D-07) | Methyl 1,2,3,4-tetrahydroquinoline-7-carboxylate (A-03) | 4-Methoxy-2,6-dimethylphenyl-1-sulfonyl chloride (C-01) | GWP I | 72% (15.3 mmol) |
| D-08 | 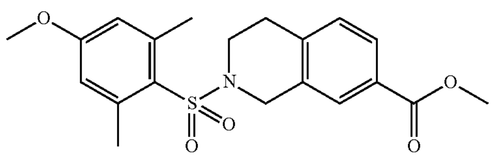 | Methyl 2-(4-methoxy-2,6-dimethylphenylsulfonyl)-1,2,3,4-tetrahydroisoquinoline-7-carboxylate (D-08) | Methyl 1,2,3,4-tetrahydroisoquinoline-7-carboxylate (A-04) | 4-Methoxy-2,6-dimethylphenyl-1-sulfonyl chloride (C-01) | GWP I | 64% (11 mmol) |
| D-09 | 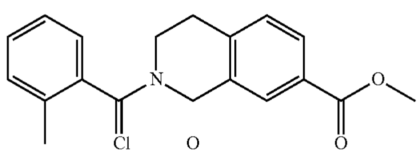 | Methyl 2-(2-chlorobenzoyl)-1,2,3,4-tetrahydroisoquinoline-7-carboxylate (D-09) | Methyl 1,2,3,4-tetrahydroisoquinoline-7-carboxylate (A-04) | 2-Chlorobenzoyl chloride (B-01) | GWP II | 89% (18.6 mmol) |

TABLE 1-continued

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-10 | 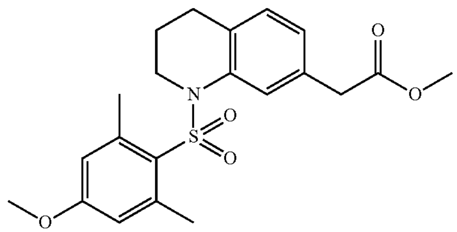 | Methyl 2-(1-(4-methoxy-2,6-dimethylphenylsulfonyl)-1,2,3,4-tetrahydroquinolin-7-yl)acetate (D-10) | Methyl 2-(1,2,3,4-tetrahydroquinolin-7-yl)acetate (A-05) | 4-Methoxy-2,6-dimethylphenyl-1-sulfonyl chloride (C-01) | GWP I | 40% (8.5 mmol) |
| D-11 | 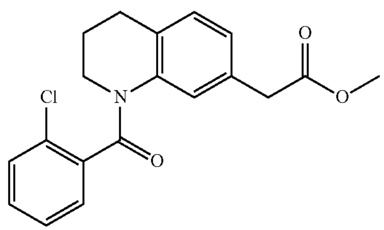 [SMILES: COC(=O)Cc1ccc2c(c1)N(C(=O)c1ccccc1Cl)CCC2] | Methyl 2-(1-(2-chlorobenzoyl)-1,2,3,4-tetrahydroquinolin-7-yl)acetate (D-11) | Methyl 2-(1,2,3,4-tetrahydroquinolin-7-yl)acetate (A-05) | 2-Chlorobenzoyl chloride (B-01) | GWP II | 100% (19.5 mmol) |
| D-12 | 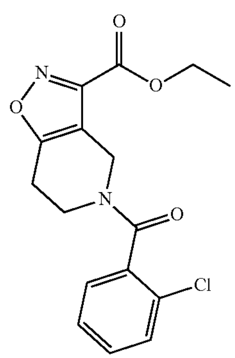 [SMILES: CCOC(=O)c1noc2c1CN(C(=O)c1ccccc1Cl)CC2] | Ethyl 5-(2-chlorobenzoyl)-4,5,6,7-tetrahydroisoxazolo[4,5-c]pyridine-3-carboxylate (D-12) | Ethyl 4,5,6,7-tetrahydroisoxazolo[4,5-c]pyridine-3-carboxylate (A-06) | 2-Chlorobenzoyl chloride (B-01) | GWP V | 94% (0.40 g) |

TABLE 1-continued

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-15 | 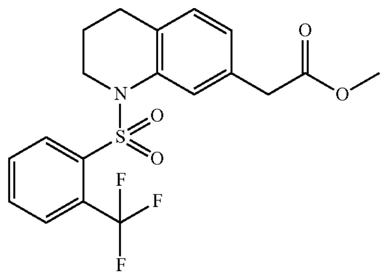 [SMILES: COC(=O)Cc1ccc2c(c1)N(S(=O)(=O)c1ccccc1C(F)(F)F)CCC2] | Methyl 2-(1-(2-(trifluoromethyl)phenyl-sulfonyl)-1,2,3,4-tetrahydroquinolin-7-yl)acetate (D-15) | Methyl 2-(1,2,3,4-tetrahydroquinolin-7-yl)acetate (A-05) | 2-(Trifluoromethyl)phenyl-1-sulfonyl chloride (C-03) | GWP III | 34% (0.34 g) |
| D-16 | 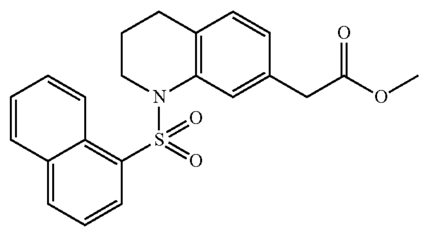 [SMILES: COC(=O)Cc1ccc2c(c1)N(S(=O)(=O)c1cccc3ccccc13)CCC2] | Methyl 2-(1-(naphthalin-1-ylsulfonyl)-1,2,3,4-tetrahydroquinolin-7-yl)acetate (D-16) | Methyl 2-(1,2,3,4-tetrahydroquinolin-7-yl)acetate (A-05) | Naphthalin-1-sulfonyl chloride (C-04) | GWP III | >99% (1.03 g) |
| D-17 | 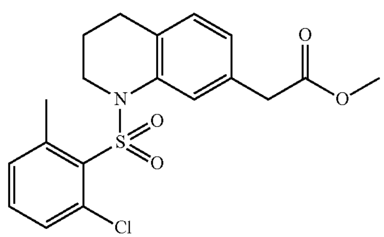 [SMILES: COC(=O)Cc1ccc2c(c1)N(S(=O)(=O)c1c(C)cccc1Cl)CCC2] | Methyl 2-(1-(2-chloro-6-methylphenylsulfonyl)-1,2,3,4-tetrahydroquinolin-7-yl)acetate (D-17) | Methyl 2-(1,2,3,4-tetrahydroquinolin-7-yl)acetate (A-05) | 2-Chloro-6-methylphenyl-1-sulfonyl chloride (C-05) | GWP III | 53% (0.51 g) |
| D-18 | 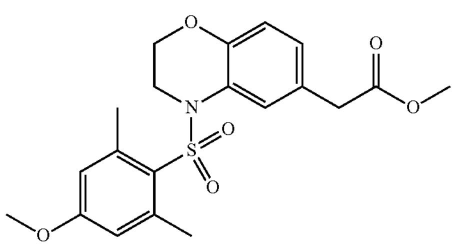 | Methyl 2-(4-(4-methoxy-2,6-dimethylphenylsulfonyl)-3,4-dihydro-2H-benzo[b][1,4]oxazin-6-yl)acetate (D-18) | Methyl 2-(3,4-dihydro-2H-benzo[b][1,4]oxazin-6-yl)acetate (A-08) | 4-Methoxy-2,6-dimethylphenyl-1-sulfonyl chloride (C-01) | GWP IV | 48% |

TABLE 1-continued

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-20 | 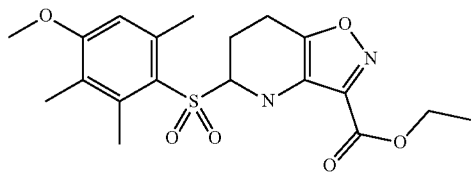 [SMILES: CCOC(=O)c1noc2c1NC(S(=O)(=O)c1c(C)cc(OC)c(C)c1C)CC2] | Ethyl 5-(4-methoxy-2,3,6-trimethylphenylsulfonyl)-4,5,6,7-tetrahydroisoxazolo[4,5-c]pyridine-3-carboxylate (D-20) | Ethyl 4,5,6,7-tetrahydroisoxazolo[4,5-c]pyridine-3-carboxylate (A-06) | 4-Methoxy-2,3,6-trimethylphenyl-1-sulfonyl chloride (C-06) | GWP IV | 47% |
| D-21 | 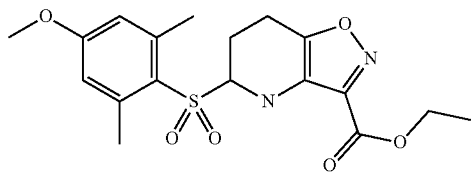 [SMILES: CCOC(=O)c1noc2c1NC(S(=O)(=O)c1c(C)cc(OC)cc1C)CC2] | Ethyl 5-(4-methoxy-2,6-dimethylphenylsulfonyl)-4,5,6,7-tetrahydroisoxazolo[4,5-c]pyridine-3-carboxylate (D-21) | Ethyl 4,5,6,7-tetrahydroisoxazolo[4,5-c]pyridine-3-carboxylate (A-06) | 4-Methoxy-2,6-dimethylphenyl-1-sulfonyl chloride (C-01) | GWP IV | 92% |
| D-22 | 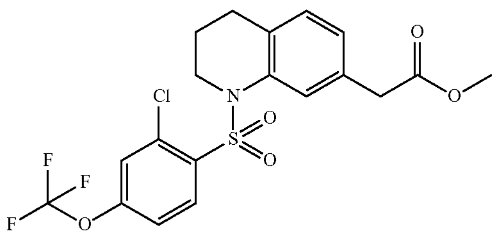 [SMILES: COC(=O)Cc1ccc2c(c1)N(S(=O)(=O)c1ccc(OC(F)(F)F)cc1Cl)CCC2] | Methyl 2-(1-(2-chloro-4-(trifluoromethoxy)phenyl-sulfonyl)-1,2,3,4-tetrahydroquinolin-7-yl)acetate (D-22) | Methyl 2-(1,2,3,4-tetrahydroquinolin-7-yl)acetate (A-05) | 2-Chloro-4-(trifluoromethoxy)benzene-1-sulfonyl chloride (C-07) | GWP III | 78% |
| D-27 | 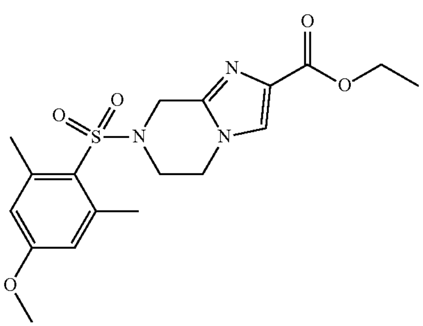 [SMILES: CCOC(=O)c1cn2c(n1)CN(S(=O)(=O)c1c(C)cc(OC)cc1C)CC2] | Ethyl 7-(4-methoxy-2,6-dimethylphenylsulfonyl)-5,6,7,8-tetrahydroimidazo[1,2-a]pyrazine-2-carboxylate (D-27) | Ethyl 5,6,7,8-tetrahydroimidazo[1,2-a]pyrazine-2-carboxylate hydroxychloride (A-09) | 4-Methoxy-2,6-dimethylphenyl-1-sulfonyl chloride (C-01) | GWP V | 65% |

TABLE 1-continued

Synthesis of the acylated or sulfonylated amino acid esters D

| Ester No. | Structure | Name | Amino acid ester (A) | Carboxylic acid chloride (B) or sulfonic acid chloride (C) | Synthesis according to: | Yield |
|---|---|---|---|---|---|---|
| D-28 | 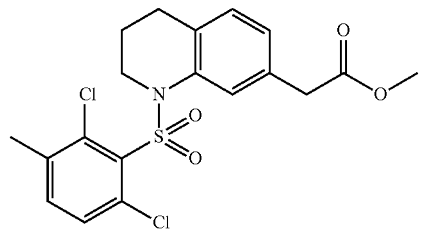 | Methyl 2-(1-(2,6-dichloro-3-methylphenyl)sulfonyl-1,2,3,4-tetrahydroquinolin-7-yl)acetate (D-28) | Methyl 2-(1,2,3,4-tetrahydroquinolin-7-yl)acetate (A-05) | 2,6-Dichloro-3-methylphenyl-1-sulfonyl chloride (C-08) | GWP V | 26% (0.11 g) |
| D-29 | 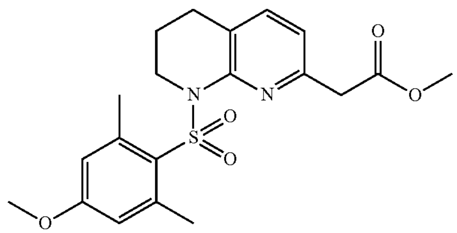 | Methyl 2-(8-(4-methoxy-2,6-dimethylphenylsulfonyl)-5,6,7,8-tetrahydro-1,8-naphthyridin-2-yl)acetate (D-29) | Methyl 2-(5,6,7,8-tetrahydro-1,8-naphthyridin-2-yl)acetate hydrochloride (A-10) | 4-Methoxy-2,6-dimethylphenyl-1-sulfonyl chloride (C-01) | GWP Va | 15% (0.1 g) |

4) Synthesis of the Acylated or Sulfonylated Amino Acids E
General Method for the Synthesis of the Acylated or Sulfonylated Amino Acids E

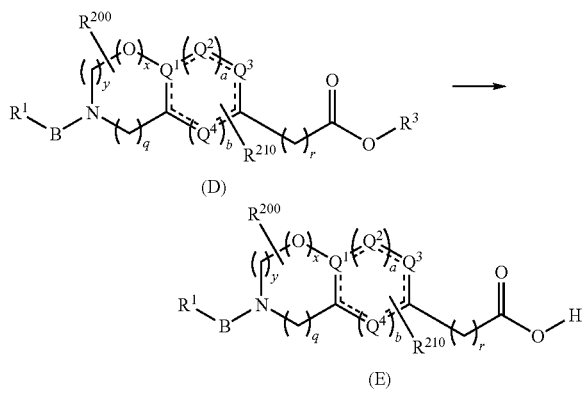

General working procedure GWP VI: Lithium hydroxide (2 to 5 equiv.) was added to a solution of ester D (1 equiv.) in methanol/water (1.5/1) and the mixture was heated for 12 to 24 hours at reflux. The reaction mixture was then concentrated under reduced pressure, the residue was taken up in water and the aqueous phase was acidified with 1N HCl solution. The resulting solid was filtered out and dried.

General working procedure GWP VII: The carboxylic acid ester D (1 equiv.) was dissolved in water/methanol, and lithium hydroxide monohydrate (1.5-4 equiv.) was added. The reaction mixture was stirred for 1-15 h (TLC monitoring) at room temperature, then the solvent was distilled off in vacuo. Ethyl acetate and 1N hydrochloric acid or 10% citric acid were added to the residue, the phases were separated, and the aqueous phase was extracted with ethyl acetate (2-3×). The combined organic phases were dried over sodium sulfate or magnesium sulfate and concentrated in vacuo.

General working procedure GWP VIII: Lithium hydroxide monohydrate (5 equiv.) was added to a solution of the carboxylic acid ester D (1 equiv.) in tetrahydrofuran/water (1:1) and the mixture was stirred for 2 h. The solvent was removed in vacuo and the residue was taken up in dilute HCl solution and extracted with ethyl acetate. The organic phase was washed with water and saturated sodium chloride solution, dried over sodium sulfate and concentrated in vacuo.

TABLE 2

Synthesis of the acylated or sulfonylated amino acids E

| Amino acid No. | Structure | Name | Amino acid ester (D) | Synthesis according to/ Comments: | Yield |
|---|---|---|---|---|---|
| E-01 | 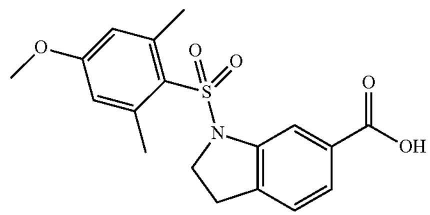 [SMILES: COc1cc(C)c(S(=O)(=O)N2CCc3ccc(C(=O)O)cc32)c(C)c1] | 1-(4-Methoxy-2,6-dimethylphenylsulfonyl)indoline-6-carboxylic acid (E-01) | Methyl 1-(4-methoxy-2,6-dimethylphenylsulfonyl)indoline-6-carboxylate (D-01) | GWP VI | 97% (20.5 mmol) |
| E-02 | 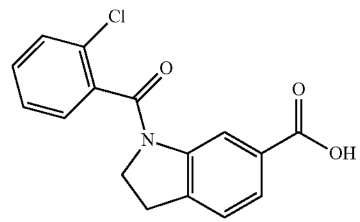 [SMILES: O=C(O)c1ccc2c(c1)N(C(=O)c1ccccc1Cl)CC2] | 1-(2-Chlorobenzoyl)indoline-6-carboxylic acid (E-02) | Methyl 1-(2-chlorobenzoyl)indoline-6-carboxylate (D-02) | GWP VI | 99% (22 mmol) |
| E-03 | 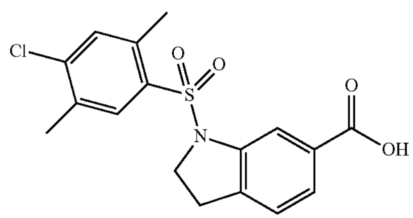 [SMILES: Cc1cc(S(=O)(=O)N2CCc3ccc(C(=O)O)cc32)c(C)cc1Cl] | 1-(4-Chloro-2,5-dimethylphenylsulfonyl)indoline-6-carboxylic acid (E-03) | Methyl 1-(4-chloro-2,5-dimethylphenylsulfonyl)indoline-6-carboxylate (D-03) | GWP VI | 92% (17.4 mmol) |
| E-04 | 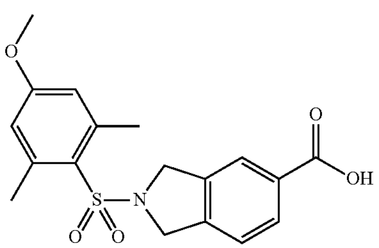 [SMILES: COc1cc(C)c(S(=O)(=O)N2Cc3ccc(C(=O)O)cc3C2)c(C)c1] | 2-(4-Methoxy-2,6-dimethylphenylsulfonyl)isoindoline-5-carboxylic acid (E-04) | Methyl 2-(4-methoxy-2,6-dimethylphenylsulfonyl)isoindoline-5-carboxylate (D-04) | GWP VI | 97% (16 mmol) |

TABLE 2-continued

Synthesis of the acylated or sulfonylated amino acids E

| Amino acid No. | Structure | Name | Amino acid ester (D) | Synthesis according to/ Comments: | Yield |
|---|---|---|---|---|---|
| E-05 | 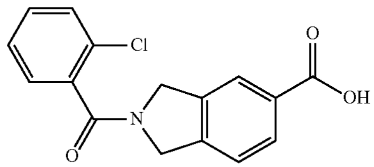 [SMILES: O=C(O)c1ccc2c(c1)CN(C(=O)c1ccccc1Cl)C2] | 2-(2-Chlorobenzoyl)isoindoline-5-carboxylic acid (E-05) | Methyl 2-(2-chlorobenzoyl)isoindoline-5-carboxylate (D-05) | GWP VI | >100% (>15.9 mmol) |
| E-06 | 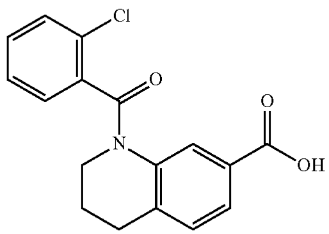 [SMILES: O=C(O)c1ccc2c(c1)N(C(=O)c1ccccc1Cl)CCC2] | 1-(2-Chlorobenzoyl)-1,2,3,4-tetrahydroquinoline-7-carboxylic acid (E-06) | Methyl 1-(2-chlorobenzoyl)-1,2,3,4-tetrahydroquinoline-7-carboxylate (D-06) | GWP VI | >100% (>13.7 mmol) |
| E-07 | 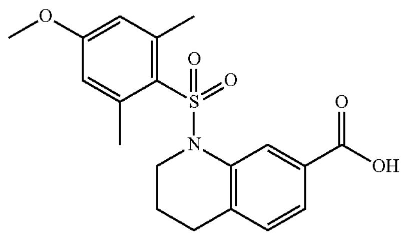 [SMILES: COc1cc(C)c(S(=O)(=O)N2CCCc3ccc(C(=O)O)cc32)c(C)c1] | 1-(4-Methoxy-2,6-dimethylphenylsulfonyl)-1,2,3,4-tetrahydroquinoline-7-carboxylic acid (E-07) | Methyl 1-(4-methoxy-2,6-dimethylphenylsulfonyl)-1,2,3,4-tetrahydroquinoline-7-carboxylate (D-07) | GWP VI | 100% (15.4 mmol) |
| E-08 | 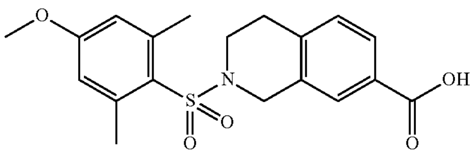 [SMILES: COc1cc(C)c(S(=O)(=O)N2CCc3ccc(C(=O)O)cc3C2)c(C)c1] | 2-(4-Methoxy-2,6-dimethylphenylsulfonyl)-1,2,3,4-tetrahydroisoquinoline-7-carboxylic acid (E-08) | Methyl 2-(4-methoxy-2,6-dimethylphenylsulfonyl)-1,2,3,4-tetrahydroisoquinoline-7-carboxylate (D-08) | GWP VI | 91% (10 mmol) |
| E-09 | 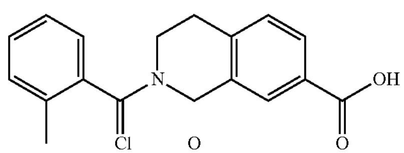 | 2-(2-Chlorobenzoyl)-1,2,3,4-tetrahydroisoquinoline-7-carboxylic acid (E-09) | Methyl 2-(2-chlorobenzoyl)-1,2,3,4-tetrahydroisoquinoline-7-carboxylate (D-09) | GWP VI | 86% (16 mmol) |

TABLE 2-continued

Synthesis of the acylated or sufonylated amino acids E

| Amino acid No. | Structure | Name | Amino acid ester (D) | Synthesis according to/ Comments: | Yield |
|---|---|---|---|---|---|
| E-10 | 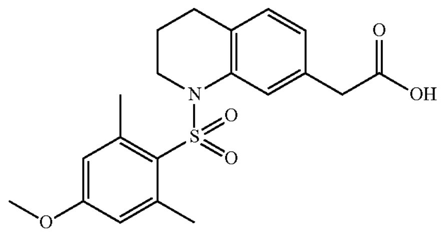 [SMILES: COc1cc(C)c(S(=O)(=O)N2CCCc3ccc(CC(=O)O)cc32)c(C)c1] | 2-(1-(4-Methoxy-2,6-dimethylphenylsulfonyl)-1,2,3,4-tetrahydroquinolin-7-yl)acetic acid (E-10) | Methyl 2-(1-(4-methoxy-2,6-dimethylphenylsulfonyl)-1,2,3,4-tetrahydroquinolin-7-yl)acetate (D-10) | GWP VI | 83% (7 mmol) |
| E-11 | 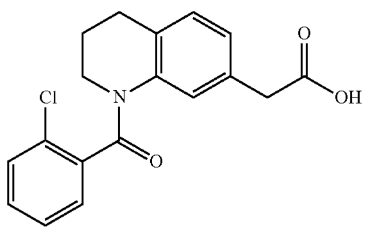 [SMILES: O=C(O)Cc1ccc2c(c1)N(C(=O)c1ccccc1Cl)CCC2] | 2-(1-(2-Chlorobenzoyl)-1,2,3,4-tetrahydroquinolin-7-yl)acetic acid (E-11) | Methyl 2-(1-(2-chlorobenzoyl)-1,2,3,4-tetrahydroquinolin-7-yl)acetate (D-11) | GWP VI | 78% (15.6 mmol) |
| E-12 | 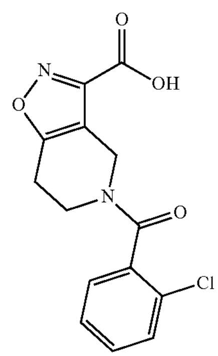 [SMILES: O=C(O)c1noc2c1CN(C(=O)c1ccccc1Cl)CC2] | 5-(2-Chlorobenzoyl)-4,5,6,7-tetrahydroisoxazolo[4,5-c]pyridine-3-carboxylic acid (E-12) | Ethyl 5-(2-chlorobenzoyl)-4,5,6,7-tetrahydroisoxazolo[4,5-c]pyridine-3-carboxylate (D-12) | GWP VII | 90% (0.33 g) |

TABLE 2-continued

Synthesis of the acylated or sufonylated amino acids E

| Amino acid No. | Structure | Name | Amino acid ester (D) | Synthesis according to/ Comments: | Yield |
|---|---|---|---|---|---|
| E-15 | 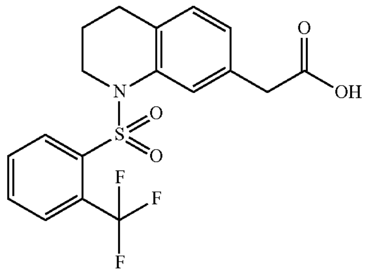 [SMILES: O=C(O)Cc1ccc2c(c1)N(S(=O)(=O)c1ccccc1C(F)(F)F)CCC2] | 2-(1-(2-(Trifluoromethyl)phenylsulfonyl)-1,2,3,4-tetrahydroquinolin-7-yl)acetic acid (E-15) | Methyl 2-(1-(2-(trifluoormethyl)phenylsulfonyl)-1,2,3,4-tetrahydroquinolin-7-yl)acetate (D-15) | GWP VII | 85% (0.27 g) |
| E-16 | 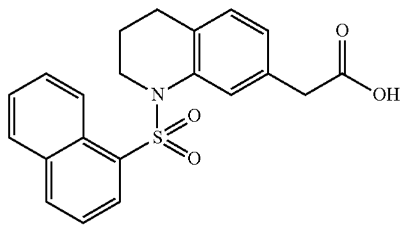 [SMILES: O=C(O)Cc1ccc2c(c1)N(S(=O)(=O)c1cccc3ccccc13)CCC2] | 2-(1-(Naphthalin-1-ylsulfonyl)-1,2,3,4-tetrahydroquinolin-7-yl)acetic acid (E-16) | Methyl 2-(1-(naphthalin-1-ylsulfonyl)-1,2,3,4-tetrahydroquinolin-7-yl)acetate (D-16) | GWP VII | >99% (1.00 g) |
| E-17 | 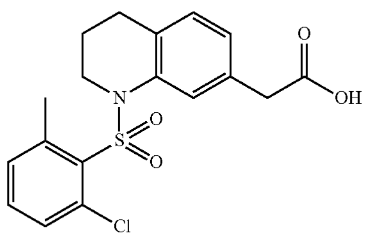 [SMILES: Cc1cccc(Cl)c1S(=O)(=O)N1CCCc2ccc(CC(=O)O)cc21] | 2-(1-(2-Chloro-6-methylphenylsulfonyl)-1,2,3,4-tetrahydroquinolin-7-yl)acetic acid (E-17) | Methyl 2-(1-(2-chloro-6-methylphenylsulfonyl)-1,2,3,4-tetrahydroquinolin-7-yl)acetate (D-17) | GWP VII | 89% (0.43 g) |

TABLE 2-continued

Synthesis of the acylated or sufonylated amino acids E

| Amino acid No. | Structure | Name | Amino acid ester (D) | Synthesis according to/ Comments: | Yield |
|---|---|---|---|---|---|
| E-18 | 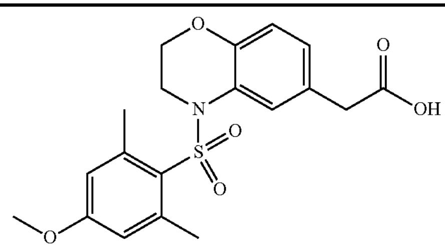 | 2-(4-(4-Methoxy-2,6-dimethylphenylsulfonyl)-3,4-dihydro-2H-benzo[b][1,4]oxazin-6-yl)acetic acid (E-18) | Methyl 2-(4-(4-methoxy-2,6-dimethylphenylsulfonyl)-3,4-dihydro-2H-benzo[b][1,4]oxazin-6-yl)acetate (D-18) | GWP VIII | 77% |
| E-20 | 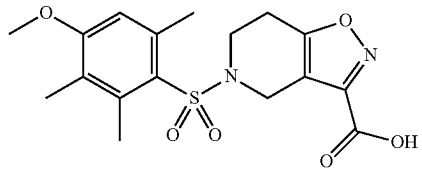 [SMILES: COc1cc(C)c(S(=O)(=O)N2CCc3onc(C(=O)O)c3C2)c(C)c1C] | 5-(4-Methoxy-2,3,6-trimethylphenylsulfonyl)-4,5,6,7-tetrahydroisoxazolo[4,5-c]pyridine-3-carboxylic acid (E-20) | Ethyl 5-(4-methoxy-2,3,6-trimethylphenylsulfonyl)-4,5,6,7-tetrahydroisoxazolo[4,5-c]pyridine-3-carboxylate (D-20) | GWP VII | >99% |
| E-21 | 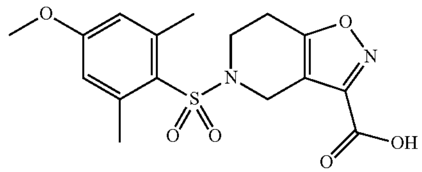 [SMILES: COc1cc(C)c(S(=O)(=O)N2CCc3onc(C(=O)O)c3C2)c(C)c1] | 5-(4-methoxy-2,6-dimethylphenylsulfonyl)-4,5,6,7-tetrahydroisoxazolo[4,5-c]pyridine-3-carboxylic acid (E-21) | Ethyl 5-(4-methoxy-2,6-dimethylphenylsulfonyl)-4,5,6,7-tetrahydroisoxazolo[4,5-c]pyridine-3-carboxylate (D-21) | GWP VII | >99% |
| E-22 | 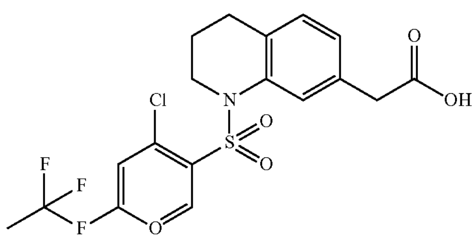 | 2-(1-(2-Chloro-4-(trifluoromethoxy)phenylsulfonyl)-1,2,3,4-tetrahydroquinolin-7-yl)acetic acid (E-22) | Methyl 2-(1-(2-chloro-4-(trifluoromethoxy)phenylsulfonyl)-1,2,3,4-tetrahydroquinolin-7-yl)acetate (D-22) | GWP VII | 81% |

TABLE 2-continued

Synthesis of the acylated or sufonylated amino acids E

| Amino acid No. | Structure | Name | Amino acid ester (D) | Synthesis according to/ Comments: | Yield |
|---|---|---|---|---|---|
| E-26 | 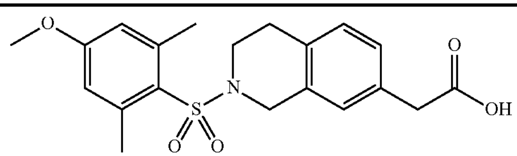 | 2-(2-(4-Methoxy-2,6-dimethylphenylsulfonyl)-1,2,3,4-tetrahydroisoquinolin-7-yl)acetic acid (E-26) | | for synthesis see below | |
| E-27 | 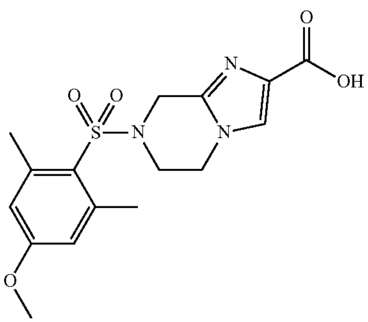 [SMILES: COc1cc(C)c(S(=O)(=O)N2CCn3cc(C(=O)O)nc3C2)c(C)c1] | 7-(4-Methoxy-2,6-dimethylphenylsulfonyl)-5,6,7,8-tetrahydroimidazo[1,2-a]pyrazine-2-carboxylic acid (E-27) | Ethyl 7-(4-methoxy-2,6-dimethylphenylsulfonyl)-5,6,7,8-tetrahydroimidazo[1,2-a]pyrazine-2-carboxylate (D-27) | GWP VII | >99% |
| E-28 | 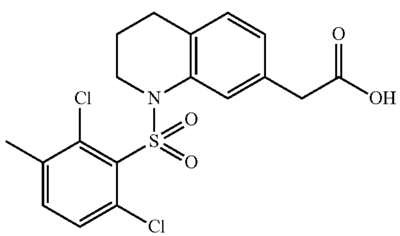 [SMILES: Cc1ccc(Cl)c(S(=O)(=O)N2CCCc3ccc(CC(=O)O)cc32)c1Cl] | 2-(1-(2,6-Dichloro-3-methylphenylsulfonyl)-1,2,3,4-tetrahydroquinolin-7-yl)acetic acid (E-28) | Methyl 2-(1-(2,6-dichloro-3-methylphenylsulfonyl)-1,2,3,4-tetrahydroquinolin-7-yl)acetate (D-28) | GWP VII | 89% (0.31 g) |
| E-29 | 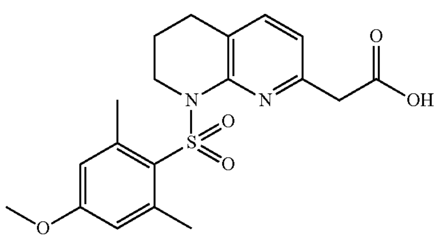 | 2-(8-(4-Methoxy-2,6-dimethylphenylsulfonyl)-5,6,7,8-tetrahydro-1,8-naphthyridin-2-yl)acetic acid (E-29) | Methyl 2-(8-(4-methoxy-2,6-dimethylphenylsulfonyl)-5,6,7,8-tetrahydro-1,8-naphthyridin-2-yl)acetate (D-29) | GWP VII | 83% (0.08 g) |

TABLE 2-continued

Synthesis of the acylated or sufonylated amino acids E

| Amino acid No. | Structure | Name | Amino acid ester (D) | Synthesis according to/ Comments: | Yield |
|---|---|---|---|---|---|
| E-30 | 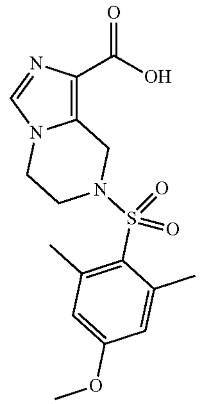 [SMILES: COc1cc(C)c(S(=O)(=O)N2CCn3cnc(C(=O)O)c3C2)c(C)c1] | 7-(4-Methoxy-2,6-dimethylphenylsulfonyl)-5,6,7,8-tetrahydroimidazo[1,5-a]pyrazine-1-carboxylic acid (E-30) | | for synthesis see below | |

Structural unit E-26: 2-(2-(4-Methoxy-2,6-dimethylphenyl-sulfonyl)-1,2,3,4-tetrahydroisoquinolin-7-yl)acetic acid Stage 1: Methyl 2-(4-methoxy-2,6-dimethylphenyl-sulfonyl)-1,2,3,4-tetrahydroisoquinoline-7-carboxy-late TEA (3 equiv.) was added at 25° C. to a solution of methyl 1,2,3,4-tetrahydroisoquinoline-7-carboxylate hydrochloride (4.4 mmol, 1 equiv.) in DCM, and the mixture was stirred for 30 min. 4-Methoxy-2,6-dimethylphenyl-1-sulfonyl chloride (4.4 mmol, 1 equiv.) was then added, and the reaction mixture was stirred for 12 h at 25° C. $NH_4Cl$ solution was added to the mixture, and the organic phase was extracted with water and sat. NaCl solution. The organic phase was dried over $Na_2SO_4$, and the solvent was removed in vacuo. The resulting crude product was used in the following stage without further purification.

Stage 2: (2-(4-Methoxy-2,6-dimethylphenylsulfo-nyl)-1,2,3,4-tetrahydroisoquinolin-7-yl)methanol A solution of methyl 2-(4-methoxy-2,6-dimethylphenyl-sulfonyl)-1,2,3,4-tetrahydroisoquinoline-7-carboxylate (3.85 mmol, 1 equiv.) in THF (10 ml) was added dropwise to a cold suspension of LAH (7.7 mmol, 2 equiv.) in THF (30 ml), and the resulting mixture was stirred for 1 h. THF/water was added to the reaction mixture, and filtration over Celite was carried out. The filtrate was concentrated and the yellow oil so obtained was used in the following stage without further purification.

Stage 3: (2-(4-Methoxy-2,6-dimethylphenylsulfo-nyl)-1,2,3,4-tetrahydroisoquinolin-7-yl)methyl meth-anesulfonate MsCl (3.32 mmol, 1.5 equiv.) was added at 0° C. to a solution of (2-(4-methoxy-2,6-dimethylphenylsulfonyl)-1,2,3,4-tetrahydroisoquinolin-7-yl)methanol (2.22 mmol, 1 equiv.) and TEA (2.5 equiv.) in DCM (16 ml), and the mixture was stirred for 1 h. The reaction mixture was diluted with DCM, extracted with sat. sodium hydrogen carbonate solution, water and sat. NaCl solution and dried over $Na_2SO_4$. The solvent was removed in vacuo and the crude product was purified by column chromatography (silica gel).

Stage 4: 2-(2-(4-Methoxy-2,6-dimethylphenylsulfo-nyl)-1,2,3,4-tetrahydroisoquinolin-7-yl)acetonitrile KCN (2.73 mmol, 1.2 equiv.) was added to a solution of (2-(4-methoxy-2,6-dimethylphenylsulfonyl)-1,2,3,4-tet-rahydroisoquinolin-7-yl)methyl methanesulfonate (2.28 mmol, 1 equiv.) in EtOH/water (10 ml), and the mixture was refluxed for 24 h. The reaction mixture was then cooled and diluted with ethyl acetate. Extraction with sat. $FeSO_4$ solution, water and sat. NaCl solution was carried out, and the organic phase was dried over $Na_2SO_4$ and concentrated in vacuo. The resulting crude product was purified by column chromatography (silica gel). Yield: 71%

Stage 5: 2-(2-(4-Methoxy-2,6-dimethylphenylsulfo-nyl)-1,2,3,4-tetrahydroisoquinolin-7-yl)acetic acid 2-(2-(4-Methoxy-2,6-dimethylphenylsulfonyl)-1,2,3,4-tetrahydroisoquinolin-7-yl)acetonitrile (2.7 mmol) was refluxed for 16 h in 25% aqueous KOH solution (20 ml). The reaction mixture was cooled, adjusted to an acidic pH value with 50% HCl solution and then extracted with DCM. The organic phase was extracted with water and sat. NaCl solution and dried over $Na_2SO_4$. The solvent was removed in vacuo, and the desired product was thus obtained in the form of a white solid. This was used in the following stage without further purification.

Structural unit E-30: 7-(4-Methoxy-2,6-dimethylphenylsul-fonyl)-5,6,7,8-tetrahydroimidazo[1,5-a]pyrazine-1-car-boxylic acid Stage 1: Methyl 4-(diethoxymethyl)-1H-imidazole-5-carboxylate A mixture of diethoxyacetonitrile (38.72 mmol, 1 equiv.) and methyl isocyanoacetate (99.1 mmol, 1.4 equiv.) in dry bis(2-methoxyethyl)ether (20 ml) was added to a suspension of 30-35% KH (54.2 mmol, 1.4 equiv.) in dry bis(2-methoxy-ethyl)ether (30 ml). The resulting mixture was heated overnight at 70-80° C. The reaction mixture was then cooled to 25° C., and sat. $NH_4Cl$ solution (20 ml) was added. DCM (100 ml) was added, and the phases were separated. The aqueous phase was extracted with DCM (2×75 ml) and the combined organic phases were dried over $Na_2SO_4$ and filtered, and the solvent was removed in vacuo. Cold ether (10 ml) was added to the brown oil so obtained, and the resulting solid was filtered out and washed with ether. The desired product was thus obtained in the form of a yellow solid. Yield: 26%

Stage 2: Methyl 4-formyl-1H-imidazole-5-carboxylate

Acetic acid (244 mmol, 34.7 equiv.) was added to a solution of methyl 4-(diethoxy-methyl)-1H-imidazole-5-car-boxylate (7.04 mmol, 1 equiv.) in water (4.2 ml), and the resulting mixture was stirred for 6 h at 25° C. under nitrogen. Toluene was added to the reaction mixture, and the solvent was removed in vacuo in order thus to yield the desired product in the form of a yellow solid. This was used in the following stage without further purification. Yield: quantitative Stage 3: Methyl 4-((benzyl(2-hydroxyethyl)amino) methyl)-1H-imidazole-5-carboxylate Methyl 4-formyl-1H-imidazole-5-carboxylate (1.68 mmol, 1 equiv.) was taken up in dry THF (10 ml). Dry $Na_2SO_4$ (15.53 mmol, 9.2 equiv.) and N-benzylethanolamine (1.99 mmol, 1.18 equiv.) were added, and the mixture was stirred for 1 h at 25° C. under nitrogen. $NaBH(OAc)_3$ (2.36 mmol, 1.4 equiv.) was then added in portions, and the reaction mixture was stirred for 16 h. Then water (5 ml) was added, and the mixture was neutralised with sat. $NaHCO_3$ solution (10 ml). Extraction with DCM (2×20 ml) was carried out, and the combined organic phases were dried over $Na_2SO_4$, filtered and concentrated in vacuo. The resulting crude product was purified by column chromatography (silica gel, 5-10% MeOH in DCM), and the desired product was thus obtained in the form of a white solid. Yield: 99%

Stage 4: Methyl 4-((benzyl(2-chloroethyl)amino) methyl)-1H-imidazole-5-carboxylate Thionyl chloride (0.5 ml, 4 equiv.) was added to a solution of methyl 4-((benzyl(2-hydroxyethyl)amino)methyl)-1H-imidazole-5-carboxylate (1.7 mmol, 1 equiv.) in DCM (10 ml), and the mixture was stirred for 16 h at 45° C. The reaction mixture was cooled to 25° C. and concentrated in vacuo. The residue was taken up in acetonitrile, the solvent was removed, and the residue was dried for 24 h in vacuo. The desired product was thus obtained in the form of a white solid. This was used in the following stage without further purification. Yield: quantitative Stage 5: Methyl 7-benzyl-5,6,7,8-tetrahydroimidazo[1,5-a]pyrazine-1-carboxylate TEA (28.66 mmol, 4 equiv.) was added at 0° C. to a solution of methyl 4-((benzyl(2-chloroethyl)amino)methyl)-1H-imidazole-5-carboxylate (7.16 mmol, 1 equiv.) in acetonitrile (50 ml). The resulting mixture was heated for 16 h at 80° C. It was then cooled and filtered, and the filtrate was concentrated in vacuo. The crude product was taken up in DCM and sat. sodium hydrogen carbonate solution, and the organic phase was dried and concentrated in vacuo. The resulting crude product was purified by column chromatography (silica gel, 5% MeOH in DCM), and the desired product was thus obtained in the form of a brown solid. Yield: 64%

Stage 6: Methyl 5,6,7,8-tetrahydroimidazo[1,5-a]pyrazine-1-carboxylate

Methyl 7-benzyl-5,6,7,8-tetrahydroimidazo[1,5-a]pyrazine-1-carboxylate (3.69 mmol) was dissolved in MeOH (20 ml), and the solution was flushed with nitrogen. Pd(OH)$_2$ (250 mg) and a cat. amount of AcOH were added, and the mixture was again flushed with nitrogen for 20 min. The reaction mixture was reacted under a hydrogen atmosphere (50 psi) for 5 h on a Parr hydrogenation apparatus. Filtration over Celite was then carried out, followed by washing with methanol. The resulting crude product was purified by column chromatography (silica gel, 3-5% MeOH in DCM), and the desired product was thus obtained in the form of a yellow solid. Yield: 99%

Stage 7: Methyl 7-(4-methoxy-2,6-dimethylphenylsulfonyl)-5,6,7,8-tetrahydroimidazo[1,5-a]pyrazine-1-carboxylate Methyl 5,6,7,8-tetrahydroimidazo[1,5-a]pyrazine-1-carboxylate (0.55 mmol, 1.0 equiv.) was dissolved in DCM (6 ml), and TEA (7.21 mmol, 2.5 equiv.) was added at 0° C., followed by 4-methoxy-2,6-dimethylphenyl-1-sulfonyl chloride (0.66 mmol, 1.2 equiv.) in DCM (3 ml). The reaction mixture was stirred for 4 h at 25° C. and then diluted with DCM (50 ml) and washed with water (10 ml) and sat. NaCl solution (10 ml). The organic phase was dried over Na$_2$SO$_4$ and concentrated in vacuo. The resulting crude product was purified by column chromatography (silica gel, 3% MeOH in DCM), and the desired product was thus obtained in the form of a white solid. Yield: 31%

Stage 8: 7-(4-Methoxy-2,6-dimethylphenylsulfonyl)-5,6,7,8-tetrahydroimidazo[1,5-a]pyrazine-1-carboxylic acid A mixture of methyl 7-(4-methoxy-2,6-dimethylphenyl-sulfonyl)-5,6,7,8-tetrahydroimidazo[1,5-a]pyrazine-1-carboxylate (0.13 mmol, 1 equiv.), MeOH/H$_2$O (1:1, 4 ml), and LiOH (0.551 mmol, 6 equiv.) was stirred for 16 h at 25° C. The organic solvent was removed in vacuo, and the resulting suspension was diluted with water (5 ml) and adjusted to an acidic pH value with 1N HCl at 0° C. Extraction with ethyl acetate (2×15 ml) was then carried out, and the combined organic phases were washed with sat. NaCl solution. The organic phase was dried over Na$_2$SO$_4$ and concentrated in vacuo to yield the product in the form of a light-yellow solid. This was used in the following stage without further purification. Yield: 63%

5) Synthesis of the Amine Structural Units F

Amine F-09: 3-(Pyridin-4-yl)-3,9-diazaspiro[5.5]undecane dihydrochloride

Stage (i): tert-Butyl 9-(pyridin-4-yl)-3,9-diazaspiro[5.5]undecane-3-carboxylate tert-Butyl-3,9-diazaspiro[5.5]undecane-3-carboxylate (1 g, 3.931 mmol), 4-chloro-pyridinium chloride (1.765 g, 11.794 mmol) and triethylamine (2.2 ml, 15.725 mmol) were refluxed for 15 h in 1-butanol (50 ml). Saturated sodium hydrogen carbonate solution (30 ml) and ethyl acetate (80 ml) were added, the phases were separated, and the aqueous phase was extracted with ethyl acetate (2×80 ml). The combined organic phases were dried over magnesium sulfate and concentrated in vacuo. The crude product was purified by column chromatography (silica gel, ethyl acetate/-hexane/methanol/ammonia (25% aq.), 400:40:40:1). Yield: 0.52 g (39%)

Stage (ii): 3-(Pyridin-4-yl)-3,9-diazaspiro[5.5]undecane dihydrochloride

Hydrogen chloride in methanol (1.25 mol/l, 6.3 ml) was added to tert-butyl-9-(pyridin-4-yl)-3,9-diazaspiro[5.5]undecane-3-carboxylate (0.52 g, 1.569 mmol), and the mixture was refluxed for 1 h. The solvent was removed in vacuo, and the residue was taken up in ethanol (3 ml) and cooled. Acetone (80 ml) was added and stirring was carried out for 30 min. in an ice bath. The precipitate was filtered out with suction, washed with diethyl ether and dried in vacuo. Yield: 0.4 g (83%) Alternatively, the deprotection can also be carried out under the action of TFA in DCM in order to obtain the amine (F-09) in the form of the free base.

Amine F-14: 1-Phenyl-1,3,8-triazaspiro[4.5]decan-4-one [1021-25-6] is available commercially from Acros, for example Amine F-16: 4-(4-Fluorophenyl)-2-methyl-2,8-diazaspiro[4.5]decan-1-one hydrochloride [MDL No.: MFCD08460813] is available commercially from ASWMEDCHEM, for example Amine F-17: 2-(4-Fluorobenzyl)-2,8-diazaspiro[4.5]decan-1-one hydrochloride
[MDL No.: MFCD08461093] is available commercially from ASWMEDCHEM, for example.

Amine F-18: 2-Benzyl-2,8-diazaspiro[4.5]decan-1-one hydrochloride [MDL No.: MFCD02179153] is available commercially from ASWMEDCHEM, for example Amine F-19: 2-Benzyl-2,7-diazaspiro[4.4]nonane [MDL No.: MFCD04115133] is available commercially from Tyger, for example Amine F-23: 8-(Pyridin-4-yl)-2,8-diazaspiro[4.5]decane dihydrochloride The synthesis was carried out analogously to the synthesis of amine F-09. To this end, in stage (i) tert-butyl 2,8-diazaspiro[4.5]decane-2-carboxylate was reacted with 4-chloro-pyridinium chloride (yield: 22%). Then, in stage (ii), the Boc protecting group was cleaved. After completion of the reaction and removal of the methanol in vacuo, the residue was taken up in ethanol and cooled, and acetone was added. The resulting suspension was stirred for 30 min. in an ice bath and the precipitate was filtered out with suction, washed with acetone and dried in vacuo (yield of amine F-23: 92%).

Amine F-24: 2-(Pyridin-4-yl)-2,7-diazaspiro[4.4]nonane dihydrochloride

The synthesis was carried out analogously to the synthesis of amine F-09. To this end, in stage (i) tert-butyl 2,7-diazaspiro[4.4]nonane-2-carboxylate was reacted with 4-chloropyridinium chloride (yield: 50%). Then, in stage (ii), the Boc protecting group was cleaved. After completion of the reaction and removal of the methanol in vacuo, the residue was taken up in ethanol and cooled, and acetone was added. The resulting suspension was stirred for 30 min. in an ice bath and the precipitate was filtered out with suction, washed with acetone and dried in vacuo (yield of amine F-24: 73%).

Amine F-26: tert-Butyl 1,8-diazaspiro[4.5]decane-1-carboxylate [336191-17-4] available commercially from JW-Pharmalab, for example Amine F-30: 9-(Pyridin-4-yloxy)-3-azaspiro[5.5]undecane dihydrochloride Stage (i):
1-(Benzyloxycarbonyl)piperidine-4-carboxylic acid Water (75 ml), followed by sodium bicarbonate (30.8 g), was added to piperidine-4-carboxylic acid (25 g) in THF (75 ml). The mixture was cooled to 0° C., and Cbz chloride (38.9 ml) was added dropwise. The reaction mixture was then stirred for 5 h at room temperature (TLC monitoring). When the conversion was complete, the organic solvent was distilled off and the residue was taken up in water (200 ml) and washed with ethyl acetate (2×150 ml). The aqueous phase was acidified with dilute aqueous HCl solution and extracted with ethyl acetate. The organic phase was dried ($Na_2SO_4$) and concentrated in vacuo. Yield: 48.5 g (96%)

Stage (ii): 1-Benzyl 4-methyl piperidine-1,4-dicarboxylate 1-(Benzyloxycarbonyl)piperidine-4-carboxylic acid (48.5 g) in methanol (485 ml) was cooled to 0° C., and thionyl chloride (13.34 ml) was added dropwise. The mixture was then refluxed for 20 min. (TLC monitoring). When the conversion was complete, the methanol was distilled off and the residue was taken up in water (15 ml) and extracted with ethyl acetate (2×150 ml). The combined organic phases were extracted with water and sat. sodium chloride solution, dried ($Na_2SO_4$) and concentrated in vacuo. Yield: 38 g (67%)

Stage (iii): Benzyl 4-formylpiperidine-1-carboxylate

A solution of 1-benzyl-4-methyl piperidine-1,4-dicarboxylate (10 g) in toluene (100 ml) under nitrogen was cooled to −78° C. DIBAL-H (60.9 ml) was then added dropwise at −78° C. and the mixture was stirred for 1 h at that temperature (TLC monitoring). Because the conversion was incomplete, a further 0.2 eq. of DIBAL-H was added and stirring was carried out for a further 30 min. (TLC monitoring: some starting material and the corresponding alcohol were detectable). Methanol (40 ml) followed by sat. sodium chloride solution (40 ml) were added slowly to the reaction mixture at −78° C. The mixture was filtered over Celite and the solvent was removed in vacuo. The residue was extracted with ethyl acetate (3×75 ml), dried ($Na_2SO_4$) and concentrated in vacuo. The resulting crude product was purified by column chromatography (silica gel, 20% ethyl acetate/hexane). Yield: 4.3 g (49%)

Stage (iv): Benzyl 9-oxo-3-azaspiro[5.5]undec-7-ene-3-carboxylate

Methyl vinyl ketone (1.64 ml), ethanol (5 ml) and water (5 ml) were added to benzyl 4-formylpiperidine-1-carboxylate (5 g). The mixture was then added to a boiling solution of potassium hydroxide (0.22 g) in ethanol (10 ml) and the resulting reaction mixture was refluxed for 1 h (TLC monitoring). When the conversion was complete, the mixture was added to water (25 ml) and extracted with ethyl acetate (2×50 ml). The combined organic phases were dried ($Na_2SO_4$) and concentrated in vacuo. The resulting crude product was purified by column chromatography (silica gel, 25% ethyl acetate/hexane). Yield: 2.8 g (46%)

Stage (v): tert-Butyl 9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was then added, and hydrogenolysis was carried out for 4 h at 80 psi (TLC monitoring). When the conversion was complete, the mixture was filtered over Celite and then rinsed with ethanol and ethyl acetate. The filtrate was dried ($Na_2SO_4$) and concentrated in vacuo. The residue was taken up in ethyl acetate and water, and the aqueous phase was extracted with ethyl acetate. The combined organic phases were dried ($Na_2SO_4$) and concentrated in vacuo. The resulting crude product was purified by column chromatography (silica gel, 20% ethyl acetate/hexane). Yield: 2.92 g, 40%

Stage (vi): tert-Butyl 9-hydroxy-3-azaspiro[5.5]undecane-3-carboxylate tert-Butyl 9-oxo-3-azaspiro[5.5]undecane-3-carboxylate (1.5 g) was dissolved in THF (7.5 ml) and cooled to −5° C. $NaBH_4$ (0.212 g) was then added and the mixture was stirred for 1 h at room temperature (TLC monitoring). When the conversion was complete, acetic acid was added to the mixture and the methanol was then distilled off. The residue was taken up in water (50 ml) and extracted with ethyl acetate (2×50 ml). The combined organic phases were dried ($Na_2SO_4$) and concentrated in vacuo. The resulting crude product was purified by column chromatography (silica gel, 30% ethyl acetate/hexane). Yield: 1.2 g (80%)

Stage (vii): tert-Butyl 9-(pyridin-4-yloxy)-3-azaspiro[5.5]undecane-3-carboxylate 4-Chloropyridine hydrochloride (1.3 g) was added to sodium hydride (0.89 g) in DMSO (20 ml), and the mixture was stirred for 10 min. tert-Butyl 9-hydroxy-3-azaspiro[5.5]undecane-3-carboxylate (2.0 g) in DMSO (20 ml) was then added slowly, and the mixture was stirred overnight (TLC monitoring: conversion about 30-35%). A catalytic amount of sodium iodide was added, and the reaction mixture was stirred for 8 h at 80° C. (TLC monitoring). Methanol and $NaHCO_3$ solution were added to the reaction mixture, and stirring was carried out for 20 min. The mixture was then extracted with ethyl acetate and again washed with $NaHCO_3$ solution and cold water. The organic phase was dried ($Na_2SO_4$) and concentrated in vacuo. The resulting crude product was purified by column chromatography (silica gel, 70% ethyl acetate/hexane). Yield: 1.0 g (40%)

Stage (viii): 9-(Pyridin-4-yloxy)-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml); hydrogen chloride in methanol (1.25 mol/l, 11.5 ml) was added, and the mixture was refluxed for 30 min. The solvent was removed in vacuo and the residue was dissolved in a small amount of ethanol. Acetone (about 25 ml) was then added, the mixture was stirred for 30 min. at 0° C. and finally the resulting solid was filtered out with suction. Yield: 0.96 g (>99%)

Amine F-32: 9-(Azetidin-1-yl)-3-azaspiro[5.5]undecane dihydrochloride

Stage (i): tert-Butyl 9-(azetidin-1-yl)-3-azaspiro[5.5]undecane-3-carboxylate tert-Butyl 9-oxo-3-azaspiro[5.5]undecane-3-carboxylate (stage (iv) Amine F-30) (1 g, 3.74 mmol) and azetidine (0.25 ml, 3.74 mmol) were placed in 1,2-dichloroethane (15 ml), and sodium triacetoxyborohydride (1.1 g, 5.23 mmol) was added thereto. The reaction mixture was stirred for 3 d at room temperature, and then saturated sodium hydrogen carbonate solution was added thereto. After phase separation, the aqueous phase was extracted with dichloromethane (2×). The combined organic phases were washed with saturated sodium chloride solution (1×), dried over magnesium sulfate and concentrated in vacuo. The crude product was purified by column chromatography (silica gel, ethyl acetate/methanol/ammonia (25% aq.), 100:10:1). Yield: 1 g (89%)

Stage (ii): 9-(Azetidin-1-yl)-3-azaspiro[5.5]undecane

Hydrogen chloride in methanol (1.25 mol/l, 15.5 ml) was added to tert-butyl 9-(azetidin-1-yl)-3-azaspiro[5.5]undecane-3-carboxylate (1 g, 3.24 mmol), and the mixture was refluxed for 45 min. The solvent was removed in vacuo and the residue was dissolved in a small amount of ethanol. A solid was then precipitated by addition of acetone, and finally diethyl ether was added and the resulting precipitate was filtered out with suction. Yield: 0.87 g (95%)

Amine F-33: 3-(Pyridin-4-yl)-1-oxa-2,8-diazaspiro[4.5]dec-2-ene bis(2,2,2-trifluoroacetate)

Stage (i): tert-Butyl 4-methylenepiperidine-1-carboxylate

In a thoroughly heated apparatus flooded with protecting gas, methyltriphenyl-phosphonium bromide (53.82 g, 150 mmol) was suspended in diethyl ether (300 ml) and cooled to 0° C. Potassium tert-butylate (15.78 g, 140 mmol) was added in portions, and the suspension was stirred for 30 min. Boc-4-piperidone (20 g, 100 mmol), dissolved in diethyl ether (200 ml), was slowly added dropwise, and then the mixture was warmed to room temperature and stirred for 15 h. The reaction mixture was cooled, and ammonium chloride solution (300 ml, 10%) was added thereto; after phase separation, the aqueous phase was extracted with ether (3×200 ml), and the combined organic phases were dried ($MgSO_4$) and concentrated in vacuo. The crude product was purified by column chromatography (silica gel) with ether/hexane (1:1). Yield: 18.57 g (93%)

Stage (ii): tert-Butyl 3-(pyridin-4-yl)-1-oxa-2,8-diazaspiro[4.5]dec-2-ene-8-carboxylate (a): (Z)-N-Hydroxyisonicotinimidoyl chloride: Pyridine-4-carbaldoxime (1 g, 8.19 mmol) was dissolved in DMF (10 ml); a solution of N-chlorosuccinimide (1.31 g, 9.83 mmol) in DMF (5 ml) was slowly added dropwise, and the reaction mixture was stirred at room temperature. When the conversion was complete (monitoring by thin layer chromatography, here 6 h), diethyl ether (50 ml) and water (20 ml) were added, the phases were separated, and the aqueous phase was extracted with diethyl ether (5×30 ml). The combined organic phases were washed with water (50 ml) and saturated sodium chloride solution (50 ml), dried ($MgSO_4$) and concentrated in vacuo. The crude substance was reacted without being purified and analyzed further. Yield: 0.74 g (100%)

(b): tert-Butyl 4-methylenepiperidine-1-carboxylate (0.7 g, 3.55 mmol) was dissolved in dichloromethane (10 ml) and cooled under protecting gas to 0° C. (Z)-N-Hydroxyisonicotinimidoyl chloride (1.67 g, 10.64 mmol), dissolved in dichloromethane (15 ml), was added, followed by triethylamine (1.2 ml, 8.5 mmol) in dichloromethane (10 ml). The reaction mixture was slowly warmed to room temperature and stirred for 15 h. It was diluted with dichloromethane (50 ml) and washed with water, 10% citric acid and saturated sodium chloride solution (in each case 30 ml), dried ($MgSO_4$) and concentrated in vacuo. The crude product was purified by column chromatography (silica gel) with ethyl acetate/hexane 10/1. Yield: 0.48 g (42%)

Stage (iii): 3-(Pyridin-4-yl)-1-oxa-2,8-diazaspiro[4.5]dec-2-ene bis(2,2,2-trifluoroacetate)

tert-Butyl 3-(pyridin-4-yl)-1-oxa-2,8-diazaspiro[4.5]dec-2-ene-8-carboxylate (0.48 g, 1.5 mmol) was dissolved in dichloromethane (10 ml) and cooled, and trifluoroacetic acid (1.2 ml, 15 mmol) was added slowly thereto. After refluxing for 2 h, the solvent was removed in vacuo and the residue was co-evaporated with 30 ml of each of toluene and methanol. Yield: 0.74 g (100%)

Amine F-34: 9-(3,3-Difluoroazetidin-1-yl)-3-azaspiro[5.5]undecane dihydrochloride

Stage (i): tert-Butyl 9-(3,3-difluoroazetidin-1-yl)-3-azaspiro[5.5]undecane-3-carboxylate tert-Butyl 9-oxo-3-azaspiro[5.5]undecane-3-carboxylate (stage (iv) Amine F30) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 min., and then sodium triacetoxyborohydride (1.1 g, 5.23 mmol) was added thereto and stirring was carried out for 3 d at room temperature. Saturated sodium hydrogen carbonate solution was added and, after phase separation, the aqueous phase was extracted with dichloromethane (2×). The combined organic phases were washed with saturated sodium chloride solution (1×), dried over magnesium sulfate and concentrated in vacuo. Yield: 1.26 g (98%)

Stage (ii): 9-(3,3-Difluoroazetidin-1-yl)-3-azaspiro[5.5]undecane dihydrochloride tert-Butyl 9-(3,3-difluoroazetidin-1-yl)-3-azaspiro[5.5]undecane-3-carboxylate (1.26 g, 3.66 mmol) was dissolved in hydrogen chloride in methanol (1.25 mol/l, 29 ml) and refluxed for 45 min. The solvent was removed in vacuo and the residue was dissolved in a small amount of ethanol. A solid was then precipitated by addition of acetone. The mixture was stirred for 10 min. at room temperature, then diethyl ether was added and stirring was carried out for a further 30 min. at room temperature. The resulting precipitate was filtered out with suction, washed with diethyl ether and dried in vacuo. Yield: 1.1 g (95%)

| Amine | Structure | Name |
|---|---|---|
| F-09 | 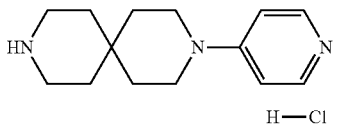 | 3-(Pyridin-4-yl)-3,9-diazaspiro[5.5]undecane dihydrochloride (F-09) |
| F-14 | 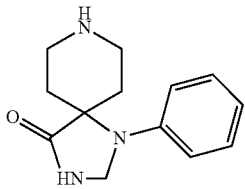 [SMILES: O=C1NCN(c2ccccc2)C12CCNCC2] | 1-Phenyl-1,3,8-triazaspiro[4.5]decan-4-one (F-14) |
| F-16 | 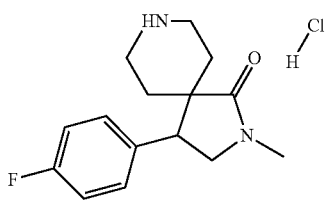 | 4-(4-Fluorophenyl)-2-methyl-2,8-diazaspiro[4.5]decan-1-one hydrochloride (F-16) |
| F-17 | 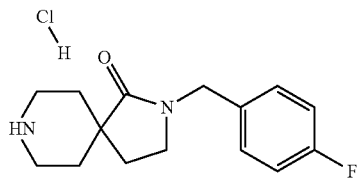 | 2-(4-Fluorobenzyl)-2,8-diazaspiro[4.5]decan-1-one hydrochloride (F-17) |
| F-18 | 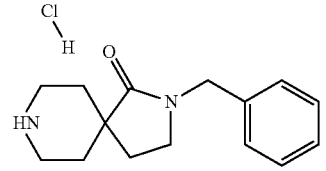 | 2-Benzyl-2,8-diazaspiro[4.5]decan-1-one hydrochloride (F-18) |
| F-19 | 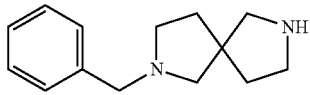 [SMILES: c1ccc(CN2CCC3(CCNC3)C2)cc1] | 2-Benzyl-2,7-diazaspiro[4.4]nonane (F-19) |
| F-23 | 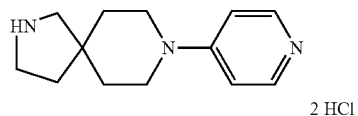 [SMILES: c1cc(N2CCC3(CCNC3)CC2)ccn1] | 8-(Pyridin-4-yl)-2,8-diazaspiro-[4.5]decane dihydrochloride (F-23) |
| F-24 | 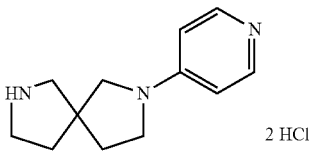 [SMILES: c1cc(N2CCC3(CCNC3)C2)ccn1] | 2-(Pyridin-4-yl)-2,7-diazaspiro-[4.4]nonane dihydrochloride (F-24) |
| F-26 | 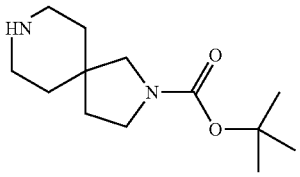 [SMILES: CC(C)(C)OC(=O)N1CCC2(CCNCC2)C1] | tert-Butyl 2,8-diazaspiro[4.5]decane-2-carboxylate (F-26) |

-continued

| Amine | Structure | Name |
|---|---|---|
| F-30 | 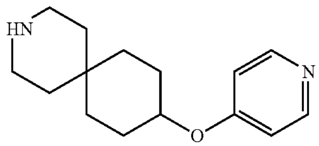 | 9-(Pyridin-4-yloxy)-3 azaspiro[5.5]undecane dihydrochloride (F-30) |
| F-32 | 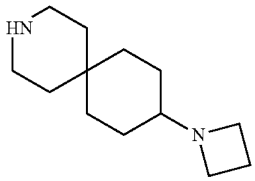 | 9-(Azetidin-1-yl)-3-azaspiro[5.5]undecane dihydrochloride (F-32) |
| F-33 | 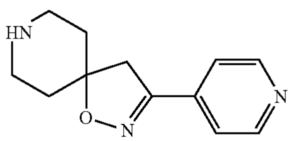 | 3-(Pyridin-4-yl)-1-oxa-2,8-diazaspiro[4.5]dec-2-ene bis(trifluoroacetate) (F-33) |
| F-34 | 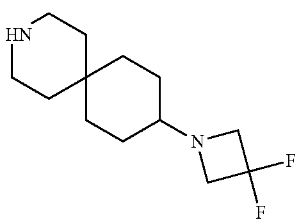 | 9-(3,3-Difluoroazetidin-1-yl)-3-azaspiro[5.5]undecane dihydrochloride (F-34) |

Syntheses of Individual Substances

6) Synthesis of the Compounds of the General Formula (I) According to the Invention

General Method for the Synthesis of the Amides G

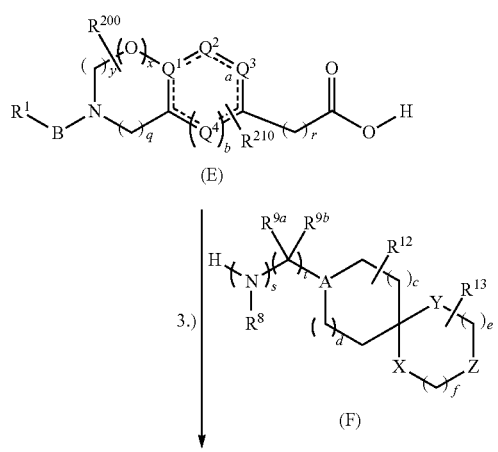

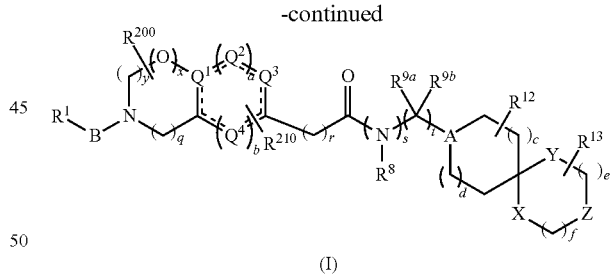

General working procedure GWP IX—CDI coupling: A solution of acid E (1 equiv.), diisopropylethylamine (2 equiv.) and carbonyldiimidazole (1.1 equiv.) in dichloromethane was stirred for 1 h at room temperature; amine F (1 equiv.; when using amine hydrochloride, the amount of diisopropylethylamine used is adapted accordingly) was then added thereto and stirring was carried out for 12 h at room temperature. Ethyl acetate was added to the reaction solution; the mixture was washed 1× with sat. sodium chloride solution, 1× with sat. sodium hydrogen carbonate solution and 3× with saturated sodium hydrogen carbonate solution, dried over sodium sulfate and concentrated under reduced pressure. Purification by column chromatography (Alox neutral, ethyl acetate/hexane or silica, DCM/MeOH optionally NEt$_3$) yielded the desired product.

General working procedure GWP IXa—CDI coupling: A solution of acid E (1 equiv.), diisopropylethylamine (2 equiv.) and carbonyldiimidazole (1.05 equiv.) in dichloromethane was stirred for 1 h at room temperature; then amine F (1 equiv.; when amine hydrochloride is used, the amount of diisopropylethylamine used is adjusted accordingly) is added and the mixture is stirred for 12 h at room temperature. The reaction solution was diluted with DCM, and sat. sodium hydrogen carbonate solution was added. The phases were separated, the aqueous phase was extracted 2× with DCM, and the combined org. phases were washed 1× with sat. NaCl solution, dried over sodium sulfate and concentrated under reduced pressure. Purification by column chromatography (silica gel) yielded the desired product.

General working procedure GWP X—TBTU coupling: TBTU (1.2 equiv.) was added to a solution of acid E (1 equiv.), amine F (1 equiv.), HOBt (1.1 equiv.) and diisopropylethylamine (3 equiv.; when using amine hydrochloride, the amount of diisopropylethylamine used is adapted accordingly) in THF, and stirring was carried out for 12 h at room temperature. Ethyl acetate was added to the reaction solution; the mixture was washed 1× with sat. ammonium chloride solution, 1× with sat. sodium hydrogen carbonate solution and 1× with saturated sodium chloride solution, dried over sodium sulfate and concentrated under reduced pressure. Purification by column chromatography (Alox neutral, ethyl acetate/hexane or silica, DCM/MeOH optionally NEt$_3$) yielded the desired product.

General working procedure GWP XI—TBTU coupling: The carboxylic acid E (1 equiv.), 0-(1H-benzotriazol-1-yl)-N,N,N',N'-tetramethyluronium tetrafluoroborate (1 equiv.) and 1-hydroxybenzotriazole hydrate (1 equiv.) were placed, under a protecting gas, in tetrahydrofuran and stirred for 30 min. at room temperature. A solution of the amine F (optionally in the form of the corresponding hydrochloride (xHCl)) (1 equiv.) and diisopropylethylamine (DIPEA) (3-5 equiv.) in tetrahydrofuran was added, and the reaction mixture was stirred for 15 h to 3 d at room temperature. Tetrahydrofuran was then removed in vacuo, the residue was taken up in ethyl acetate and saturated sodium hydrogen carbonate solution, and the phases were separated. The aqueous phase was extracted with ethyl acetate and the combined organic phases were again washed with saturated sodium chloride solution, dried over sodium sulfate and concentrated in vacuo. The crude product was purified by column chromatography (silica gel).

General working procedure GWP XII—EDCl—HCl coupling: EDCl.HCl (1.5 equiv.), HOBt (1 equiv.) and DIPEA (4 equiv.) were added to an ice-cooled solution of the carboxylic acid E (1 equiv.) in DCM, and stirring was carried out for 30 min. A solution of the amine F (1.2 equiv.) in DCM was then added, the ice bath was removed, and stirring was carried out overnight at room temperature. The reaction mixture was diluted with dichloromethane and washed with saturated ammonium chloride solution, saturated sodium chloride solution, saturated sodium carbonate solution and again with saturated sodium chloride solution, dried over sodium sulfate and concentrated in vacuo. The crude product was purified by column chromatography (silica gel).

General working procedure GWP XIII—CDI coupling: 1,1'-Carbonyldiimidazole (1.05 equiv.) and carboxylic acid E (1 equiv.) were dissolved in dichloromethane or a dichloromethane/N,N-dimethylformamide (3:2) mixture and stirred for 1 h at room temperature. The amine F (optionally in the form of the corresponding hydrochloride (xHCl)) (1.5 equiv.), dissolved in a mixture of dichloromethane/N,N-dimethylformamide (3:2) and triethylamine (1-3 equiv.), was then added dropwise and the reaction mixture was stirred for up to 3 days at room temperature (TLC monitoring). A small amount of water was added to the mixture, and concentration in vacuo was carried out. The residue was then taken up in dichloromethane and washed with saturated sodium hydrogen carbonate solution and with saturated sodium chloride solution. The aqueous phase was extracted with dichloromethane (2×) and the combined organic phases were again washed with saturated sodium chloride solution. Drying over sodium sulfate and concentration in vacuo were then carried out. The crude product was purified by column chromatography (silica gel).

General working procedure GWP XIV—EDCl—HCl coupling: The carboxylic acid E (1 equiv.) and N-ethyl-N'-(3-dimethylaminopropyl)carbodiimide hydrochloride (EDCl—HCl) (2 equiv.) were dissolved in dichloromethane and stirred for 30 min. N-Hydroxybenzotriazole (HOBt) (0.05 equiv.) was added, followed by a solution of the amine F (optionally in the form of the corresponding hydrochloride (xHCl)) (1 equiv.) and triethylamine (1-4 equiv.) in dichloromethane. The resulting reaction mixture was stirred for 15 h at room temperature. The mixture was diluted with dichloromethane; saturated sodium hydrogen carbonate solution was added and the phases were separated. The aqueous phase was extracted with dichloromethane (2×), then the combined organic phases were washed with saturated sodium chloride solution, dried over sodium sulfate and concentrated in vacuo. The crude product was purified by column chromatography (silica gel).

General working procedure GWP XV—Castro coupling: The carboxylic acid E (1 equiv.) and the amine F (1 equiv.) were dissolved in DMF, and there was added 4-methylmorpholine (3 equiv.) followed by benzotriazol-1-yloxytris(dimethylamino)-phosphonium hexafluorophosphate (1.3 equiv.). The reaction mixture was stirred for 4 d at room temperature, and then the solvent was removed in vacuo. The residue was taken up in ethyl acetate and saturated sodium hydrogen carbonate solution and the phases were separated. The aqueous phase was extracted with ethyl acetate and the combined organic phases were dried over magnesium sulfate and concentrated in vacuo The crude product was purified by column chromatography (silica gel).

General working procedure GWP XVI—HATU coupling: The carboxylic acid E (1 equiv.) was dissolved at 0° C. in THF, and DIPEA (3.0 equiv.) and HATU (2.0 equiv.) were added. The reaction mixture was stirred for 15 min at 25° C. and then cooled to 0° C. again. The amine F (1.0 equiv.), dissolved in THF, was added, and the resulting mixture was stirred for 16 h at 25° C. The solvent was removed in vacuo, and the residue was diluted with DCM and washed with sat. sodium carbonate solution, sat. ammonium chloride solution, water and sat. sodium chloride solution, dried over sodium sulfate and concentrated in vacuo. The crude product was purified by column chromatography (silica gel).

TABLE 3

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-04 | 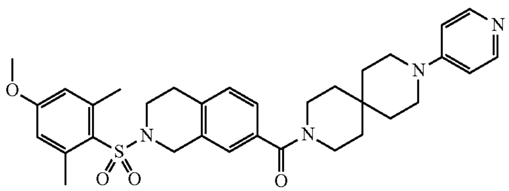 [SMILES: COc1cc(C)c(S(=O)(=O)N2CCc3ccc(C(=O)N4CCC5(CC4)CCN(c4ccncc4)CC5)cc3C2)c(C)c1] | (2-(4-Methoxy-2,6-dimethylphenylsulfonyl)-1,2,3,4-tetrahydroisoquinolin-7-yl)(9-(pyridin-4-yl)-diazaspiro[5.5]undecan-3-yl)methanone (G-04) | 2-(4-Methoxy-2,6-dimethylphenylsulfonyl)-1,2,3,4-tetrahydroisoquinoline-7-carboxylic acid (E-08) | 3-(Pyridin-4-yl)-3,9-diazaspiro[5.5]-undecane dihydrochloride (F-09) | 17% (0.09 mmol) | $R_t$ = 3.4 min; Purity (UV 200-400 nm) 95%; m/z = 589.1 [MH]$^+$ | GWP X |
| G-11 | 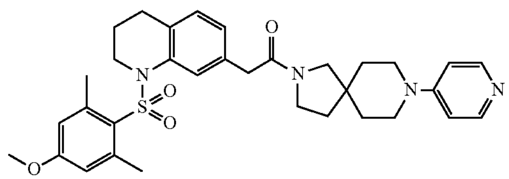 [SMILES: COc1cc(C)c(S(=O)(=O)N2CCCc3ccc(CC(=O)N4CCC5(CCN(c6ccncc6)CC5)C4)cc32)c(C)c1] | 2-(1-(4-Methoxy-2,6-dimethylphenylsulfonyl)-1,2,3,4-tetrahydroquinolin-7-yl)-1-(8-(pyridin-4-yl)-2,8-diazaspiro[4.5]decan-2-yl)ethanone (G-11) | 2-(1-(4-Methoxy-2,6-dimethylphenylsulfonyl)-1,2,3,4-tetrahydroquinolin-7-yl)acetic acid (E-10) | 8-(Pyridin-4-yl)-2,8-diazaspiro[4.5]decane (F-23) | 66% (0.15 g) | $R_t$ = 3.5 min; m/z = 589.3 [MH]$^+$ | GWP XI |
| G-12 | 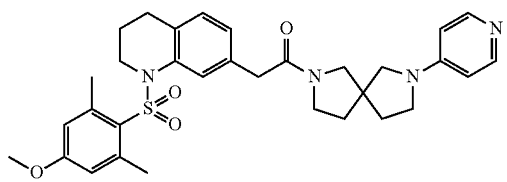 [SMILES: COc1cc(C)c(S(=O)(=O)N2CCCc3ccc(CC(=O)N4CCC5(CCN(c6ccncc6)C5)C4)cc32)c(C)c1] | 2-(1-(4-Methoxy-2,6-dimethylphenylsulfonyl)-1,2,3,4-tetrahydroquinolin-7-yl)-(7-(pyridin-4-yl)-2,7-diazaspiro[4.4]nonan-2-yl)ethanone (G-12) | 2-(1-(4-Methoxy-2,6-dimethylphenylsulfonyl)-1,2,3,4-tetrahydroquinolin-7-yl)acetic acid (E-10) | 2-(Pyridin-4-yl)-diazaspiro[4.4]nonane (F-24) | 90% (0.20 g) | $R_t$ = 3.4 min; m/z = 575.3 [MH]$^+$ | GWP XI |
| G-13 | 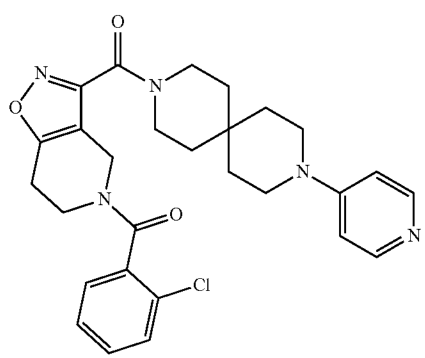 [SMILES: O=C(c1ccccc1Cl)N1CCc2onc(C(=O)N3CCC4(CC3)CCN(c3ccncc3)CC4)c2C1] | (5-(2-Chlorobenzoyl)-4,5,6,7-tetrahydroisoxazolo[4,5-c]pyridin-3-yl)(9-(pyridin-4-yl)-3,9-diazaspiro[5.5]undecan-3-yl)methanone (G-13) | 5-(2-Chlorobenzoyl)-4,5,6,7-tetrahydroisoxazolo[4,5-c]pyridine-3-carboxylic acid (E-12) | 3-(Pyridin-4-yl)-3,9-diazaspiro[5.5]-undecane dihydrochloride (F-09) | 84% (0.17 g) | $R_t$ = 2.8 min; m/z = 520.2 [MH]$^+$ | GWP XIII |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-16 | 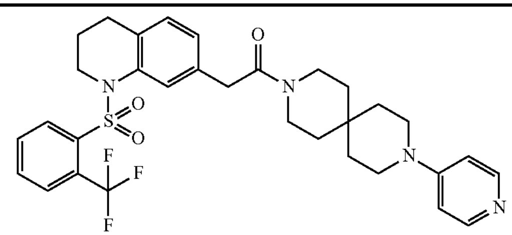 | 1-(9-(Pyridin-4-yl)-3,9-diazaspiro[5.5]undecan-3-yl)-2-(1-(2-(trifluoromethyl)phenylsulfonyl)-1,2,3,4-tetrahydroquinolin-7-yl)ethanone (G-16) | 2-(1-(2-(Trifluoromethyl)-phenylsulfonyl)-1,2,3,4-tetrahydroquinolin-7-yl)acetic acid (E-15) | 3-(Pyridin-4-yl)-3,9-diazaspiro[5.5]-undecane dihydrochloride (F-09) | 87% (0.21 g) | R$_t$ = 3.5 min; m/z = 613.3 [MH]$^+$ | GWP XI |
| G-17 | 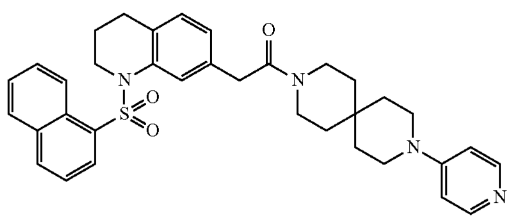 [SMILES: O=C(Cc1ccc2c(c1)N(S(=O)(=O)c1cccc3ccccc13)CCC2)N1CCC2(CC1)CCN(c1ccncc1)CC2] | 2-(1-(Napthalin-1-ylsulfonyl)-1,2,3,4-tetrahydroquinolin-7-yl)-1-(9-(pyridin-4-yl)-3,9-diazaspiro[5.5]undecan-3-yl)ethanone (G-17) | 2-(1-(Napthalin-1-ylsulfonyl)-1,2,3,4-tetrahydroquinolin-7-yl)acetic acid (E-16) | 3-(Pyridin-4-yl)-3,9-diazaspiro[5.5]-undecane dihydrochloride (F-09) | 73% (0.17 g) | R$_t$ = 3.5 min; m/z = 595.4 [MH]$^+$ | GWP XI |
| G-18 | 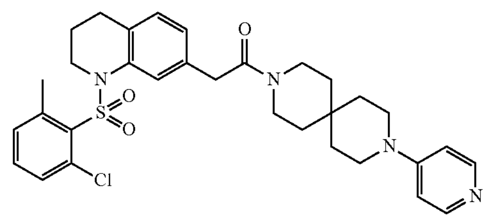 [SMILES: Cc1cccc(Cl)c1S(=O)(=O)N1CCCc2ccc(CC(=O)N3CCC4(CC3)CCN(c3ccncc3)CC4)cc21] | 2-(1-(2-Chloro-6-methylphenylsulfonyl)-1,2,3,4-tetrahydroquinolin-7-yl)-1-(9-pyridin-4-yl)-3,9-diazaspiro[5.5]undecan-3-yl)ethanone (G-18) | 2-(1-(2-Chloro-6-methylphenylsulfonyl)-1,2,3,4-tetrahydroquinolin-7-yl)acetic acid | 3-(Pyridin-4-yl)-3,9-diazaspiro[5.5]-undecane dihydrochloride (F-09) | 85% (0.20 g) | R$_t$ = 3.5 min; m/z = 593.3 [MH]$^+$ | GWP XI |
| G-19 | 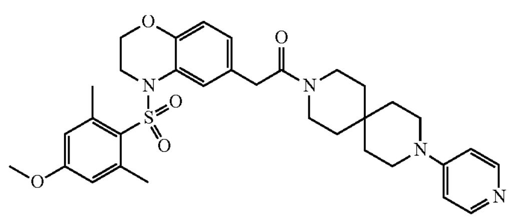 [SMILES: COc1cc(C)c(S(=O)(=O)N2CCOc3ccc(CC(=O)N4CCC5(CC4)CCN(c4ccncc4)CC5)cc32)c(C)c1] | 2-(4-(4-Methoxy-2,6-dimethylphenylsulfonyl)-3,4-dihydro-2H-benzo[b][1,4]oxazin-6-yl)-1-(9-(pyridin-4-yl)-3,9-diazaspiro[5.5]undecan-3-yl)ethanone (G-19) | 2-(4-(4-Methoxy-2,6-dimethylphenylsulfonyl)-3,4-dihydro-2H-benzo[b][1,4]oxazin-6-yl)acetic acid (E-18) | 3-(Pyridin-4-yl)-3,9-diazaspiro[5.5]-undecane dihydrochloride (F-09) | 52% | R$_t$ = 3.3 min; m/z = 605.3 [MH]$^+$ | GWP XII |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-21 | 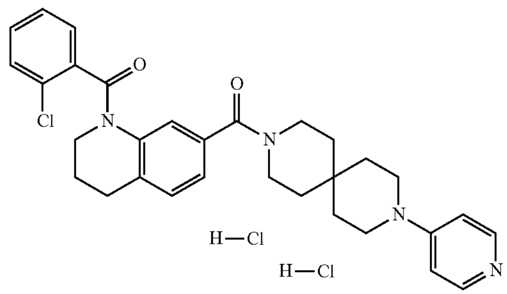 | (1-(2-Chlorobenzoyl)-1,2,3,4-tetrahydroquinolin-7-yl)(9-(pyridin-4-yl)-3,9-diazaspiro[5.5]undecan-3-yl)methanone dihydrochloride (G-21) | (1-(2-Chlorobenzoyl)-1,2,3,4-tetrahydroquinoline-7-carboxylic acid (E-06) | 3-(Pyridin-4-yl)-3,9-diazaspiro[5.5]-undecane dihydrochloride (F-09) | 59% (0.1 g) | $R_t$ = 3.0 min; m/z = 529.1 [MH]+ | GWP XI HCl precipitation |
| G-24 | 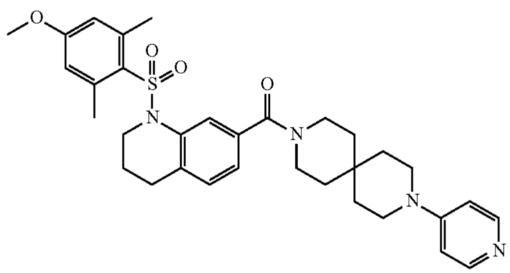 [SMILES: COc1cc(C)c(S(=O)(=O)N2CCCc3ccc(C(=O)N4CCC5(CC4)CCN(c4ccncc4)CC5)cc32)c(C)c1] | (1-(4-Methoxy-2,6-dimethylphenylsulfonyl)-1,2,3,4-tetrahydroquinolin-7-yl)-1-(9-(pyridin-4-yl)-3,9-diazaspiro[5.5]undecan-3-yl)methanone (G-24) | (1-(4-Methoxy-2,6-dimethylphenylsulfonyl)-1,2,3,4-tetrahydroquinoline-7-carboxylic acid (E-07) | 3-(Pyridin-4-yl)-3,9-diazaspiro[5.5]-undecane dihydrochloride (F-09) | 83% (0.14 g) | $R_t$ = 3.5 min; m/z = 589.1 [MH]+ | GWP XI |
| G-25 | 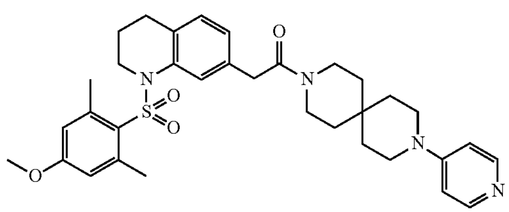 [SMILES: COc1cc(C)c(S(=O)(=O)N2CCCc3ccc(CC(=O)N4CCC5(CC4)CCN(c4ccncc4)CC5)cc32)c(C)c1] | 2-(1-(4-Methoxy-2,6-dimethylphenylsulfonyl)-1,2,3,4-tetrahydroquinolin-7-yl)-1-(9-pyridin-4-yl)-3,9-diazaspiro[5.5]undecan-3-yl)ethanone (G-25) | 2-(1-(4-Methoxy-2,6-dimethylphenylsulfonyl)-1,2,3,4-tetrahydroquinolin-7-yl)acetic acid (E-10) | 3-(Pyridin-4-yl)-3,9-diazaspiro[5.5]-undecane dihydrochloride (F-09) | 83% (0.13 g) | $R_t$ = 3.5 min; m/z = 603.1 [MH]+ | GWP XI |

TABLE 3-continued

Synthesis of the amides G

| Example No. | Name | Structure | Amino acid (E) | Amine (F) | Yield | Analyzis (LC/MS)[1] | Synthesised according to/ Comments |
|---|---|---|---|---|---|---|---|
| G-26 | (5-(4-Methoxy-2,6-dimethylphenylsulfonyl)-4,5,6,7-tetrahydroisoxazolo[4,5-c]pyridin-3-yl)(9-(pyridin-4-yl)-3,9-diazaspiro[5.5]undecan-3-yl)methanone (G-26) | 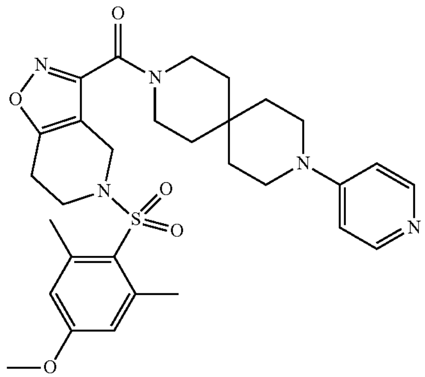 [SMILES: COc1cc(C)c(S(=O)(=O)N2CCc3onc(C(=O)N4CCC5(CC4)CCN(c4ccncc4)CC5)c3C2)c(C)c1] | 5-(4-Methoxy-2,6-dimethylphenylsulfonyl)-4,5,6,7-tetrahydroisoxazolo[4,5-c]pyridine-3-carboxylic acid (E-21) | 3-(Pyridin-4-yl)-3,9-diazaspiro[5.5]-undecane dihydrochloride (F-09) | 34% (0.11 g) | $R_t$ = 3.2 min; m/z = 580.0 [MH]$^+$ | GWP XIII |
| G-30 | 2-(1-(4-Methoxy-2,6-dimethylphenylsulfonyl)-1,2,3,4-tetrahydroquinolin-7-yl)-1-(9-(pyridin-4-yloxy)-3-azaspiro[5.5]undecan-3-yl)ethanone (G-30) | 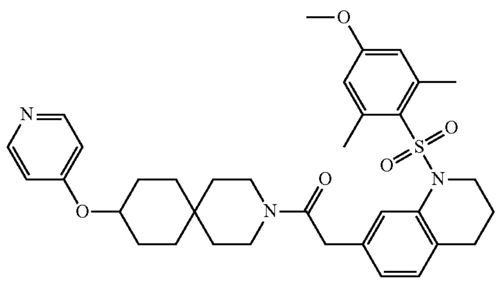 [SMILES: COc1cc(C)c(S(=O)(=O)N2CCCc3ccc(CC(=O)N4CCC5(CCC(Oc6ccncc6)CC5)CC4)cc32)c(C)c1] | 2-(1-(4-Methoxy-2,6-dimethylphenylsulfonyl)-1,2,3,4-tetrahydroquinolin-7-yl)acetic acid (E-10) | 9-(Pyridin-4-yloxy)-3-azaspiro[5.5]-undecane (F-30) | 76% (0.12 g) | $R_t$ = 3.7 min; m/z = 618.4 [MH]$^+$ | GWP XI |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-32 | 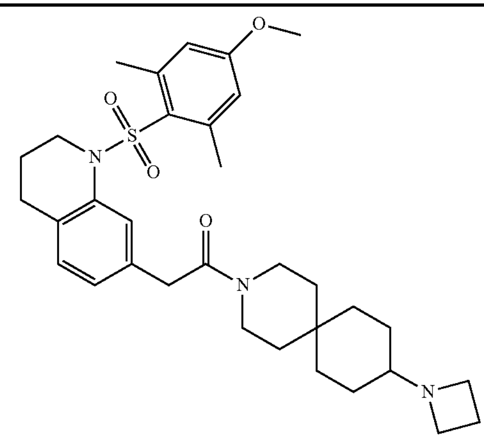 | 1-(9-(Azetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone (G-32) | 2-(1-(4-Methoxy-2,6-dimethylphenylsulfonyl)-1,2,3,4-tetrahydroquinolin-7-yl)acetic acid (E-10) | 9-(Azetidin-1-yl)-3-azaspiro[5.5]undecane (F-32) | 72% (0.16 g) | $R_t$ = 3.4 min; m/z = 580.5 [MH]$^+$ | GWP XI |
| G-33 | 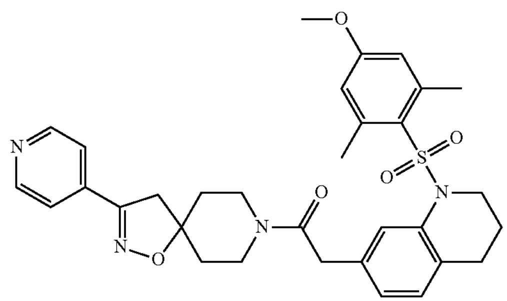 [SMILES: COc1cc(C)c(S(=O)(=O)N2CCCc3ccc(CC(=O)N4CCC5(CC4)CC(c4ccncc4)=NO5)cc32)c(C)c1] | 2-(1-(4-Methoxy-2,6-dimethylphenylsulfonyl)-1,2,3,4-tetrahydroquinolin-7-yl)-1-(3-(pyridin-4-yl)-1-oxa-2,8-diazaspiro[4.5]dec-2-en-8-yl)ethanone (G-33) | 2-(1-(4-Methoxy-2,6-dimethylphenylsulfonyl)-1,2,3,4-tetrahydroquinolin-7-yl)acetic acid (E-10) | 3-(Pyridin-4-yl)-1-oxa-2,8-diazaspiro[4.5]dec-2-ene (F-33) | 53% (0.08 g) | $R_t$ = 4.2 min; m/z = 589.3 [MH]$^+$ | GWP XI |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-34 | 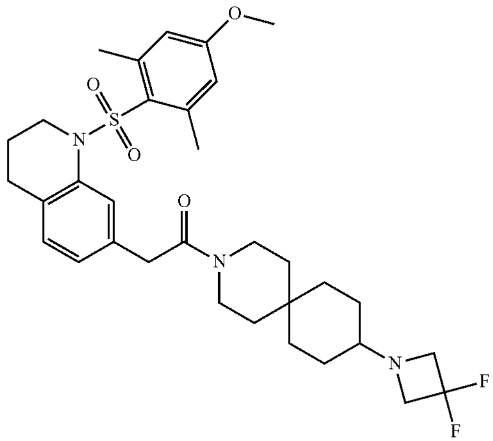 [SMILES: COc1cc(C)c(S(=O)(=O)N2CCCc3ccc(CC(=O)N4CCC5(CCC(N6CC(F)(F)C6)CC5)CC4)cc32)c(C)c1] | 1-(9-(3,3-Difluoroazetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone (G-34) | 2-(1-(4-Methoxy-2,6-dimethylphenylsulfonyl)-1,2,3,4-tetrahydroquinolin-7-yl)acetic acid (E-10) | 9-(3,3-Difluoroazetidin-1-yl)-3-azaspiro[5.5]undecane (F-34) | 67% (0.16 g) | $R_t$ = 3.7 min; m/z = 616.4 [MH]$^+$ | GWP IXa |
| G-35 | 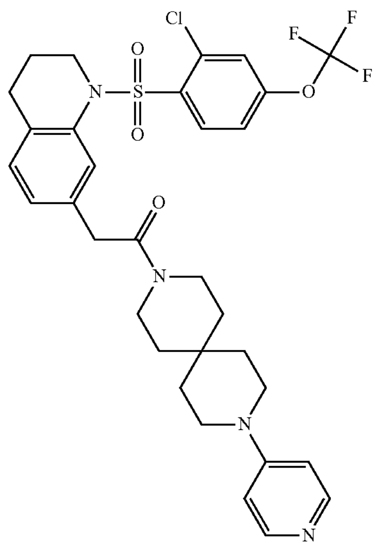 [SMILES: O=C(Cc1ccc2c(c1)N(S(=O)(=O)c1ccc(OC(F)(F)F)cc1Cl)CCC2)N1CCC2(CC1)CCN(c1ccncc1)CC2] | 2-(1-(2-Chloro-4-(trifluoromethoxy)phenylsulfonyl)-1,2,3,4-tetrahydroquinolin-7-yl)-1-(9-(pyridin-4-yl)-3,9-diazaspiro[5.5]undecan-3-yl)ethanone (G-35) | 2-(1-(2-Chloro-4-(trifluoromethoxy)phenylsulfonyl)-1,2,3,4-tetrahydroquinolin-7-yl)acetic acid (E-22) | 3-(Pyridin-4-yl)-3,9-diazaspiro[5.5]undecane dihydrochloride (F-09) | 69% (0.26 g) | $R_t$ = 3.9 min; m/z = 663.4 [MH]$^+$ | GWP XI |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-36 | 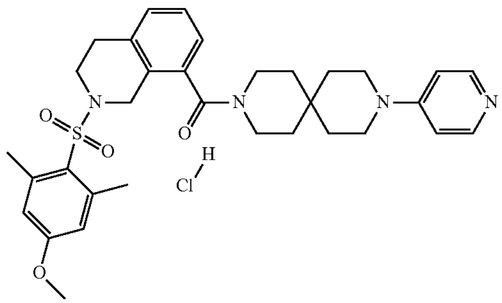 | (2-(4-Methoxy-2,6-dimethylphenylsulfonyl)-1,2,3,4-tetrahydroisoquinolin-8-yl)(9-(pyridin-4-yl)-3,9-diazaspiro[5.5]undecan-3-yl)methanone hydrochloride (G-36) | (2-(4-Methoxy-2,6-dimethylphenylsulfonyl)-1,2,3,4-tetrahydroisoquinoline-8-carboxylic acid (E-23) | 3-(Pyridin-4-yl)-3,9-diazaspiro[5.5]-undecane dihydrochloride (F-09) | | | |
| G-37 | 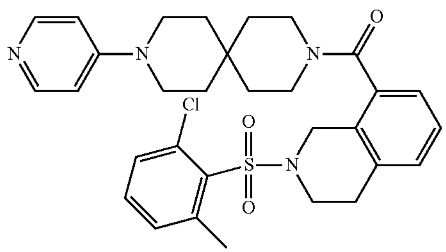 [SMILES: Cc1cccc(Cl)c1S(=O)(=O)N1CCc2cccc(C(=O)N3CCC4(CC3)CCN(c3ccncc3)CC4)c2C1] | (2-(2-Chloro-6-methylphenylsulfonyl)-1,2,3,4-tetrahydroisoquinolin-8-yl)(9-(pyridin-4-yl)-3,9-diazaspiro[5.5]undecan-3-yl)methanone (G-37) | (2-(2-Chloro-6-methylphenylsulfonyl)-1,2,3,4-tetrahydroisoquinoline-8-carboxylic acid (E-24) | 3-(Pyridin-4-yl)-3,9-diazaspiro[5.5]-undecane dihydrochloride (F-09) | | | |
| G-38 | 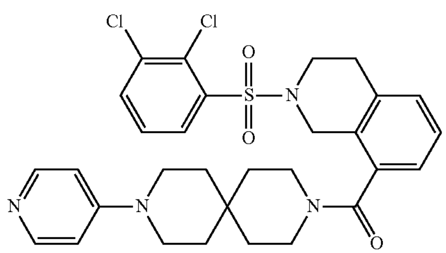 [SMILES: O=C(c1cccc2c1CN(S(=O)(=O)c1cccc(Cl)c1Cl)CC2)N1CCC2(CC1)CCN(c1ccncc1)CC2] | (2-(2,3-Dichlorophenylsulfonyl)-1,2,3,4-tetrahydroisoquinolin-8-yl)(9-(pyridin-4-yl)-3,9-diazaspiro[5.5]undecan-3-yl)methanone (G-38) | (2-(2,3-Dichlorophenylsulfonyl)-1,2,3,4-tetrahydroisoquinoline-8-carboxylic acid (E-25) | 3-(Pyridin-4-yl)-3,9-diazaspiro[5.5]-undecane dihydrochloride (F-09) | | | |

TABLE 3-continued

Synthesis of the amides G

| Example No. | Name | Structure | Amino acid (E) | Amine (F) | Yield | Analyzis (LC/MS)[1] | Synthesised according to/ Comments |
|---|---|---|---|---|---|---|---|
| G-39 | 2-(2-(4-Methoxy-2,6-dimethylphenylsulfonyl)-1,2,3,4-tetrahydroisoquinolin-7-yl)-1-(9-(pyridin-4-yl)-3,9-diazaspiro[5.5]undecan-3-yl)ethanone (G-39) | 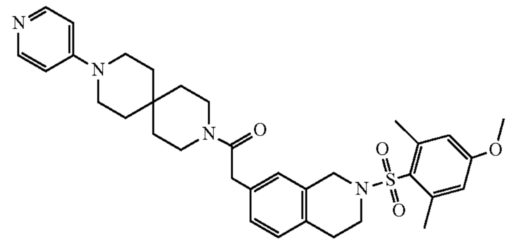 [SMILES: COc1cc(C)c(S(=O)(=O)N2CCc3ccc(CC(=O)N4CCC5(CC4)CCN(c4ccncc4)CC5)cc3C2)c(C)c1] | 2-(2-(4-Methoxy-2,6-dimethylphenylsulfonyl)-1,2,3,4-tetrahydroisoquinolin-7-yl)acetic acid (E-26) | 3-(Pyridin-4-yl)-3,9-diazaspiro[5.5]-undecane (F-09) | 66% | $R_t$ = 3.6 min; m/z = 603.5 [MH]+ | GWP XII |
| G-40 | (7-(4-Methoxy-2,6-dimethylphenylsulfonyl)-5,6,7,8-tetrahydroimidazo[1,2-a]pyrazin-2-yl)(9-(pyridin-4-yl)-3,9-diazaspiro[5.5]undecan-3-yl)methanone (G-40) | 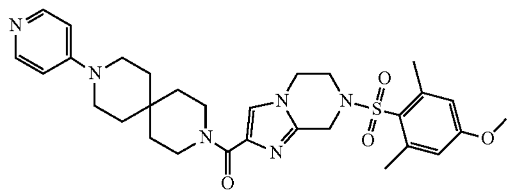 [SMILES: COc1cc(C)c(S(=O)(=O)N2CCn3cc(C(=O)N4CCC5(CC4)CCN(c4ccncc4)CC5)nc3C2)c(C)c1] | (7-(4-Methoxy-2,6-dimethylphenylsulfonyl)-5,6,7,8-tetrahydroimidazo[1,2-a]pyrazine-2-carboxylic acid (E-27) | 3-(Pyridin-4-yl)-3,9-diazaspiro[5.5]-undecane dihydrochloride (F-09) | 21% (0.04 g) | $R_t$ = 2.9 min; m/z = 579.4 [MH]+ | GWP XV |
| G-41 | 3-(2-Chlorophenyl)-1-(7-(9-(pyridin-4-yl)-3,9-diazaspiro[5.5]undecane-3-carbonyl)-3,4-dihydroisoquinolin-2(1H)-yl)prop-2-en-1-one (G-41) | 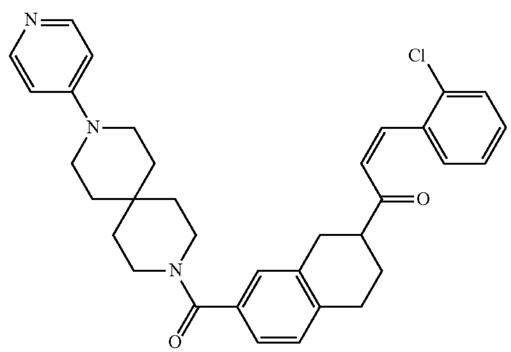 [SMILES: O=C(/C=C\c1ccccc1Cl)C1CCc2ccc(C(=O)N3CCC4(CC3)CCN(c3ccncc3)CC4)cc2C1] | 2-(3-(2-Chlorophenyl)acryloyl)-1,2,3,4-tetrahydroisoquinoline-7-carboxylic acid (E-28) | 3-(Pyridin-4-yl)-3,9-diazaspiro[5.5]-undecane dihydrochloride (F-09) | | | |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-42 | 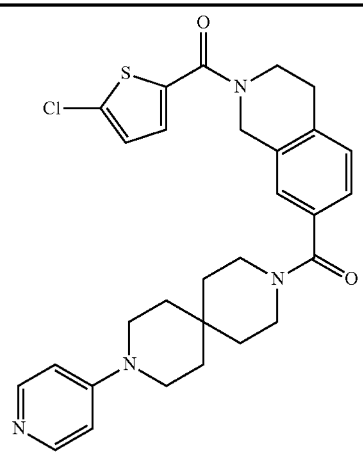 | (5-Chlorothiophen-2-yl)(7-(9-(pyridin-4-yl)-3,9-diazaspiro[5.5]undecane-3-carbonyl)-3,4-dihydroisoquinolin-2(1H)-yl)methanone (G-42) | 2-(5-Chlorothiophene-2-carbonyl)-1,2,3,4-tetrahydroisoquinoline-7-carboxylic acid (E-29) | 3-(Pyridin-4-yl)-3,9-diazaspiro[5.5]-undecane dihydrochloride (F-09) | | | |
| G-43 | 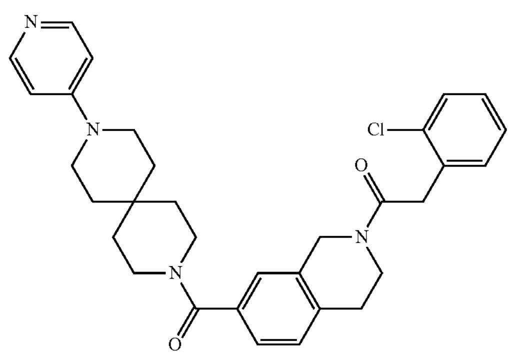 [SMILES: O=C(Cc1ccccc1Cl)N1CCc2ccc(C(=O)N3CCC4(CC3)CCN(c3ccncc3)CC4)cc2C1] | 2-(2-Chlorophenyl)-1-(7-(9-(pyridin-4-yl)-3,9-diazaspiro[5.5]undecane-3-carbonyl)-dihydroisoquinolin-2(1H)-yl)ethanone (G-43) | 2-(2-Chlorophenyl)acetyl)-1,2,3,4-tetrahydroisoquinoline-7-carboxylic acid (E-30) | 3-(Pyridin-4-yl)-3,9-diazaspiro[5.5]-undecane dihydrochloride (F-09) | | | |
| G-51 | 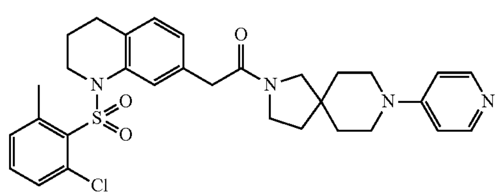 [SMILES: Cc1cccc(Cl)c1S(=O)(=O)N1CCCc2ccc(CC(=O)N3CCC4(CCN(c5ccncc5)CC4)C3)cc21] | 2-[1-{(2-Chloro-6-methylphenyl)sulfonyl]-1,2,3,4-tetrahydroquinolin-7-yl]-1-(8-pyridin-4-yl-3,8-diazaspiro[4.5]decan-3-yl)-ethanone (G-51) | 2-(1-(2-Chloro-6-methylphenylsulfonyl)-1,2,3,4-tetrahydroquinolin-7-yl)acetic acid (E-17) | 8-(Pyridin-4-yl)-2,8-diazaspiro[4.5]decane (F-23) | 94% (0.23 g) | $R_t$ = 3.4 min; m/z = 579.3 [MH]+ | GWP XI |

TABLE 3-continued

Synthesis of the amides G

| Example No. | Name | Amino acid (E) | Amine (F) | Yield | Analyzis (LC/MS)[1] | Synthesised according to/ Comments |
|---|---|---|---|---|---|---|
| G-52 | 2-[1-(Naphthalin-1-ylsulfonyl)-1,2,3,4-tetrahydro-quinolin-7-yl]-1-(8-pyridin-4-yl-3,8-diazaspiro[4.5]decan-3-yl)-ethanone (G-52) | 2-(1-(Naphthalin-1-ylsulfonyl)-1,2,3,4-tetrahydroquinolin-7-yl)acetic acid (E-16) | 8-(Pyridin-4-yl)-2,8-diazaspiro[4.5]decane (F-23) | 61% (0.14 g) | $R_t$ = 3.6 min; m/z = 581.3 [MH]$^+$ | GWP XI |
| G-53 | 2-[1-(Naphthalin-1-ylsulfonyl)-1,2,3,4-tetrahydro-quinolin-7-yl]-1-(8-pyridin-4-yl-3,8-diazaspiro[4.5]nonan-3-yl)-ethanone (G-53) | 2-(1-(Naphthalin-1-ylsulfonyl)-1,2,3,4-tetrahydroquinolin-7-yl)acetic acid (E-16) | 2-(Pyridin-4-yl)-2,7-diazaspiro[4.5]nonane (F-24) | 76% (0.17 g) | $R_t$ = 3.4 min; m/z = 567.3 [MH]$^+$ | GWP XI |
| G-54 | 1-[9-(Azetidin-1-yl)-3-azaspiro[5.5]undecan-3-yl]-2-[1-(naphthalin-1-ylsulfonyl)-1,2,3,4-tetrahydro-quinolin-7-yl]-ethanone (G-54) | 2-(1-(Naphthalin-1-ylsulfonyl)-1,2,3,4-tetrahydroquinolin-7-yl)acetic acid (E-16) | 9-(Azetidin-1-yl)-3-azaspiro[5.5]undecane (F-32) | 76% (0.17 g) | $R_t$ = 3.5 min; m/z = 572.3 [MH]$^+$ | GWP XI |
| G-57 | 1-(8-Pyridin-4-yl-3,8-diazaspiro[4.5]decan-3-yl)-2-[1-[[2-(trifluoromethyl)-phenyl]sulfonyl]-1,2,3,4-tetrahydro-quinolin-7-yl]-ethanone (G-57) | 2-(1-(2-(Trifluoromethyl)phenyl-sulfonyl)-1,2,3,4-tetrahydroquinolin-7-yl)acetic acid (E-15) | 8-(Pyridin-4-yl)-2,8-diazaspiro[4.5]decane (F-23) | 93% (0.14 g) | $R_t$ = 3.4 min; m/z = 599.3 [MH]$^+$ | GWP XI |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-64 | 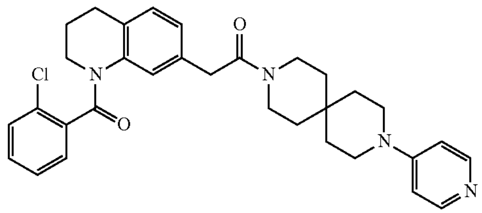 [SMILES: O=C(Cc1ccc2c(c1)N(C(=O)c1ccccc1Cl)CCC2)N1CCC2(CC1)CCN(c1ccncc1)CC2] | 2-[1-(2-Chloro-benzoyl)-1,2,3,4-tetrahydro-quinolin-7-yl]-1-(9-pyridin-4-yl-3,9-diazaspiro[5.5]undecan-3-yl)-ethanone (G-64) | 2-(1-(2-Chlorobenzoyl)-1,2,3,4-tetrahydroquinolin-7-yl)acetic acid (E-11) | 3-(Pyridin-4-yl)-3,9-diazaspiro[5.5]-undecane dihydrochloride (F-09) | 91% (0.15 g) | $R_t$ = 3.1 min; m/z = 543.1 [MH]+ | GWP XI |
| G-66 | 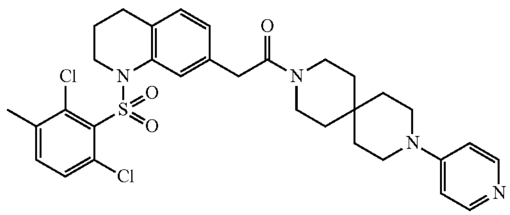 [SMILES: Cc1ccc(Cl)c(S(=O)(=O)N2CCCc3ccc(CC(=O)N4CCC5(CC4)CCN(c4ccncc4)CC5)cc32)c1Cl] | 2-[1-[(2,6-Dichloro-3-methylphenyl)sulfonyl]-1,2,3,4-tetrahydro-quinolin-7-yl]-1-(9-pyridin-4-yl-3,9-diazaspiro[5.5]undecan-3-yl)-ethanone (G-66) | 2-(1-(2,6-Dichloro-3-methylphenylsulfonyl)-1,2,3,4-tetrahydroquinolin-7-yl)acetic acid (E-28) | 3-(Pyridin-4-yl)-3,9-diazaspiro[5.5]-undecane dihydrochloride (F-09) | 88% (0.4 g) | $R_t$ = 3.9 min; m/z = 627.2 [MH]+ | GWP XI |
| G-70 | 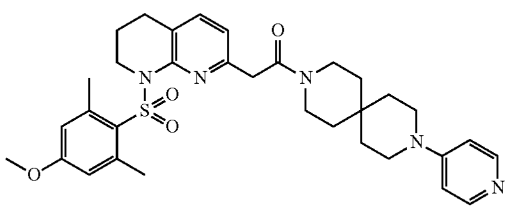 [SMILES: COc1cc(C)c(S(=O)(=O)N2CCCc3ccc(CC(=O)N4CCC5(CC4)CCN(c4ccncc4)CC5)nc32)c(C)c1] | 2-[8-[(4-Methoxy-2,6-dimethyl-phenyl)sulfonyl]-5,6,7,8-tetrahydro-[1,8]naphthyridin-2-yl]-1-(9-pyridin-4-yl-3,9-diazaspiro[5.5]undecan-3-yl)-ethanone (G-70) | 2-(8-(4-Methoxy-2,6-dimethylphenylsulfonyl)-5,6,7,8-tetrahydro-1,8-naphthyridin-2-yl)acetic acid (E-29) | 3-(Pyridin-4-yl)-3,9-diazaspiro[5.5]-undecane dihydrochloride (F-09) | 32% (0.04 g) | $R_t$ = 3.5 min; m/z = 604.4 [MH]+ | GWP XI |

TABLE 3-continued

Synthesis of the amides G

| Example No. | Structure | Name | Amino acid (E) | Amine (F) | Yield | Analyzis (LC/MS)[1] | Synthesised according to/ Comments |
|---|---|---|---|---|---|---|---|
| G-72 | 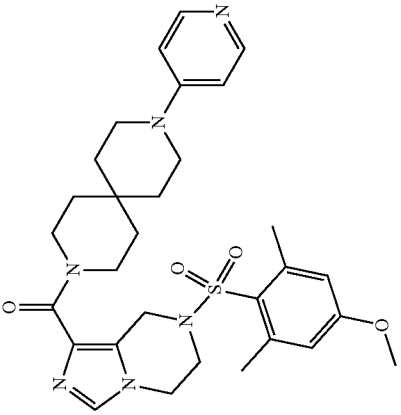 | [7-[(4-Methoxy-2,6-dimethyl-phenyl)sulfonyl]-5,6,7,8-tetrahydro-imidazo[1,5-a]pyrazin-1-yl]-(9-pyridin-4-yl-3,9-diazaspiro[5.5]undecan-3-yl)-methanone (G-72) | 7-(4-Methoxy-2,6-dimethylphenylsulfonyl)-5,6,7,8-tetrahydroimidazo[1,5-a]pyrazine-1-carboxylic acid (E-30) | 3-(Pyridin-4-yl)-3,9-diazaspiro[5.5]undecane (F-09) | 32% | $R_t$ = 3.3 min; m/z = 579.5 [MH]$^+$ | GWP XVI |

[1] Equipment and methods for HPLC-MS analyzis: HPLC: Waters Alliance 2795 with PDA Waters 2998; MS: Micromass Quattro Micro ™ API; Column: Waters Atlantis ® T3, 3 µm, 100 Å, 2.1 × 30 mm; column temperature: 40° C., eluant A: purified water + 0.1% formic acid; eluant B: acetonitrile (gradient grade) + 0.1% formic acid; gradient: 0% B to 100% B in 8.8 min, 100% B for 0.4 min, 100% B to 0% B in 0.01 min, 0% B for 0.8 min; flow: 1.0 ml/min; ionization: ES+, 25V; make up: 100 µl/min 70% methanol +0.2% formic acid; UV: 200-400 nm.

(a) The hydrochloride precipitation was carried out by addition of 2 M HCl in diethyl ether to an acetone/diethyl ether solution of the corresponding free base and subsequent filtration.

$^1$H NMR (600 MHz, DMSO-$d_6$) d ppm 2.09 (s, 3 H) 2.44 (s, 3 H) 2.60 (s, 3H) 2.90 (t, J=5.29 Hz, 2 H) 3.52 (t, J=5.67 Hz, 2 H) 3.56-3.62 (m, 2 H) 3.65 (d, J=6.04 Hz, 2 H) 3.74-3.83 (m, 2 H) 3.86 (s, 3 H) 3.94-4.04 (m, 2 H) 4.22 (s, 2 H) 6.88 (s, 1 H) 6.99 (d, J=6.80 Hz, 2 H) 8.24 (d, J=5.29 Hz, 2H)

Exemplary Compound G-09: 2-(1-(4-Methoxy-2,6-dimethylphenylsulfonyl)-1,2,3,4-tetrahydroquinolin-7-yl)-1-(2-(pyridin-4-yl)-2,8-diazaspiro[4.5]decan-8-yl)ethanone and Exemplary compound G-10: 1-(2-Cyclobutyl-2,8-diazaspiro[4.5]decan-8-yl)-2-(1-(4-methoxy-2,6-dimethylphenylsulfonyl)-1,2,3,4-tetrahydroquinolin-7-yl)ethanone hydrochloride reaction mixture was refluxed for 1 h. The solvent was removed in vacuo and the residue was taken up in a small amount of acetone and added dropwise to cooled diethyl ether. Stirring was then carried out for 30 min. in an ice bath, and the resulting solid was filtered out and dried. Yield: 0.32 g (71%)

Stage (iii): 2-(1-(4-Methoxy-2,6-dimethylphenylsulfonyl)-1,2,3,4-tetrahydroquinolin-7-yl)-1-(2-(pyridin-4-yl)-2,8-diazaspiro[4.5]decan-8-yl)ethanone (G-09)

A mixture of 2-(1-(4-methoxy-2,6-dimethylphenylsulfonyl)-1,2,3,4-tetrahydroquinolin-7-yl)-1-(2,8-diazaspiro[4.5]decan-8-yl)ethanone hydrochloride (0.15 g, 0.274 mmol), 4-chloropyridinium chloride (0.12 g, 0.821 mmol) and triethylamine (0.15 ml, 1.09 mmol) was refluxed for 15 h in

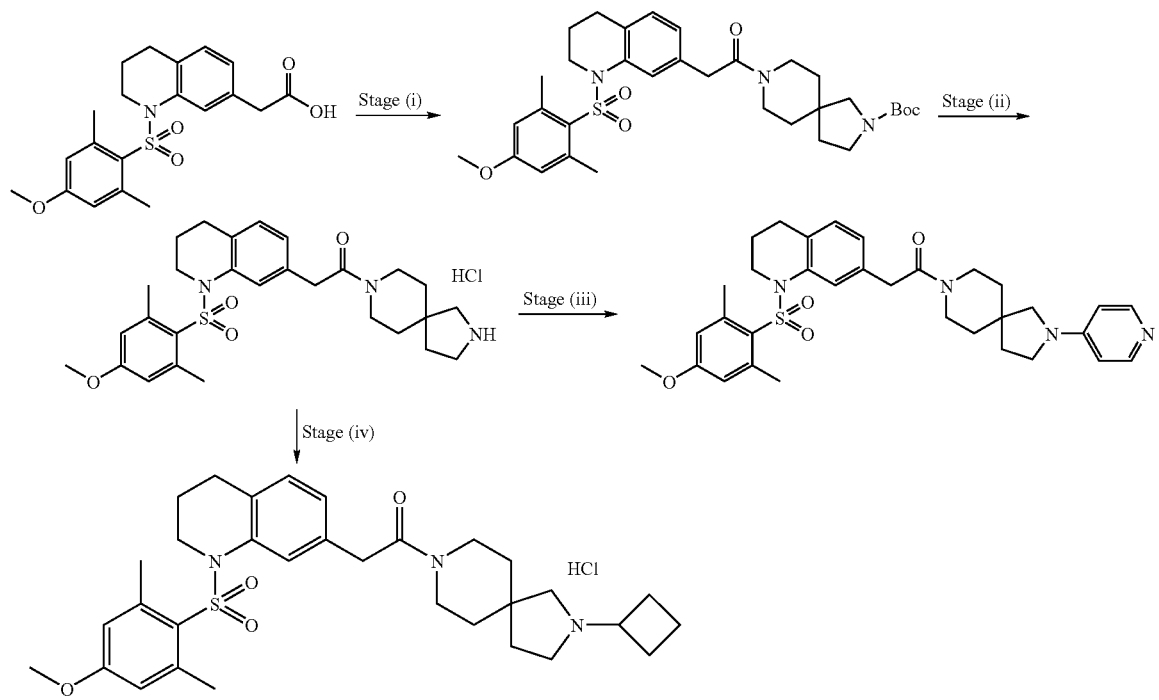

Stage (i): tert-Butyl 8-(2-(1-(4-methoxy-2,6-dimethylphenylsulfonyl)-1,2,3,4-tetrahydroquinolin-7-yl)acetyl)-2,8-diazaspiro[4.5]decane-2-carboxylate The target compound was prepared according to general working procedure GWP X (TBTU coupling) from the starting materials 2-(1-(4-methoxy-2,6-dimethylphenyl-sulfonyl)-1,2,3,4-tetrahydroquinolin-7-yl)acetic acid (E-10) and tert-butyl 2,8-diazaspiro[4.5]decane-2-carboxylate (F-26). Yield: 53%

Stage (ii): 2-(1-(4-Methoxy-2,6-dimethylphenylsulfonyl)-1,2,3,4-tetrahydroquinolin-7-yl)-1-(2,8-diazaspiro[4.5]decan-8-yl)ethanone hydrochloride Hydrogen chloride (1.25 M solution in methanol, 6.5 ml) was added at room temperature to a solution of tert-butyl 8-(2-(1-(4-methoxy-2,6-dimethylphenylsulfonyl)-1,2,3,4-tetrahydroquinolin-7-yl)acetyl)-2,8-diazaspiro[4.5]decane-2-carboxylate (0.5 g, 0.817 mmol) in methanol (5 ml), and the 1-butanol (7 ml). Saturated sodium hydrogen carbonate solution (20 ml) and ethyl acetate (50 ml) were then added, the phases were separated and the aqueous phase was extracted with ethyl acetate (2×50 ml). The combined organic phases were washed with saturated sodium chloride solution (20 ml), dried over magnesium sulfate and concentrated in vacuo. The crude product was purified by column chromatography (silica gel, ethyl acetate/dichloromethane/-methanol/ammonia (25% aq.), 300:100:50:1) and the desired exemplary compound G-09 was obtained. Yield: 0.1 g (62%). MS, $R_t$=3.3 min; m/z=589.1 [MH]$^+$ Stage (iv): 1-(2-Cyclobutyl-2,8-diazaspiro[4.5]decan-8-yl)-2-(1-(4-methoxy-2,6-dimethylphenylsulfonyl)-1,2,3,4-tetrahydroquinolin-7-yl)ethanone hydrochloride (G-10)

2-(1-(4-Methoxy-2,6-dimethylphenylsulfonyl)-1,2,3,4-tetrahydroquinolin-7-yl)-1-(2,8-diazaspiro[4.5]decan-8-yl)ethanone hydrochloride (from stage (ii)) (140 mg, 0.255 mmol), triethylamine (0.04 ml, 0.255 mmol) and cyclobutanone (0.02 ml, 0.255 mmol) were dissolved in 1,2-dichloroethane (5 ml), and sodium triacetoxy-borohydride (75 mg, 0.358 mmol) and glacial acetic acid (15 mg, 0.255 mmol) were added thereto. The reaction mixture was stirred for 15 h and then diluted with dichloromethane, and saturated sodium hydrogen carbonate solution (10 ml) was added thereto. After phase separation, the aqueous phase was extracted with dichloromethane (3×30 ml). The combined organic phases were washed with saturated sodium chloride solution (30 ml), dried over magnesium sulfate and concentrated in vacuo. The crude product was purified by column chromatography (silica gel, ethyl acetate/dichloromethane/methanol/ammonia (25% aq.), 300:100:25:1). Finally, the hydrochloride was precipitated from ethereal solution (plus a small amount of acetone) with hydrogen chloride in ether (2 M) and the desired exemplary compound G-10 was thus obtained. Yield: 100 mg (65%). MS, $R_f$=3.4 min; m/z=566.1 [MH]$^+$ Exemplary compound G-14: (5-(4-Methoxy-2,6-dimethylphenylsulfonyl)-4,5,6,7-tetrahydrothieno[3,2-c]pyridin-2-yl)(9-(pyridin-4-yl)-3,9-diazaspiro[5.5]undecan-3-yl)methanone
and
Exemplary Compound G-15: ((5-(2-Chlorobenzoyl)-4,5,6,7-tetrahydrothieno[3,2-c]-pyridin-2-yl)(9-(pyridin-4-yl)-3,9-diazaspiro[5.5]undecan-3-yl)methanone Stage (i): tert-Butyl 2-(9-(pyridin-4-yl)-3,9-diazaspiro[5.5]undecane-3-carbonyl)-6,7-dihydrothieno[3,2-c]pyridine-5(4H)-carboxylate 1,1'-Carbonyldiimidazole (119 mg, 0.741 mmol) and 5-(tert-butoxycarbonyl)-4,5,6,7-tetrahydrothieno[3,2-c]pyridine-2-carboxylic acid (200 mg, 0.706 mmol) were dissolved in dichloromethane (5 ml) and N,N-dimethylformamide (3 ml) and stirred for 1 h at room temperature. 3-(Pyridin-4-yl)-3,9-diazaspiro[5.5]undecane dihydrochloride (322 mg, 1.059 mmol), dissolved in a mixture of dichloromethane (5 ml) and triethylamine (0.293 ml, 2.118 mmol), was then added dropwise and the reaction mixture was stirred for 3 days at room temperature. The mixture was diluted with dichloromethane (50 ml) and washed with saturated sodium hydrogen carbonate solution (3×10 ml) and with saturated sodium chloride solution (10 ml), dried over sodium sulfate and concentrated in vacuo. The crude product was purified by column chromatography (silica gel, ethyl acetate/methanol, 5:1). Yield: 280 mg (80%)

Stage (ii): (9-(Pyridin-4-yl)-3,9-diazaspiro[5.5]undecan-3-yl)(4,5,6,7-tetrahydrothieno[3,2-c]pyridin-2-yl)methanone hydrochloride Hydrogen chloride in methanol (2.3 ml, 2.82 mmol, 1.25 mol/l) was added at room temperature to a solution of tert-

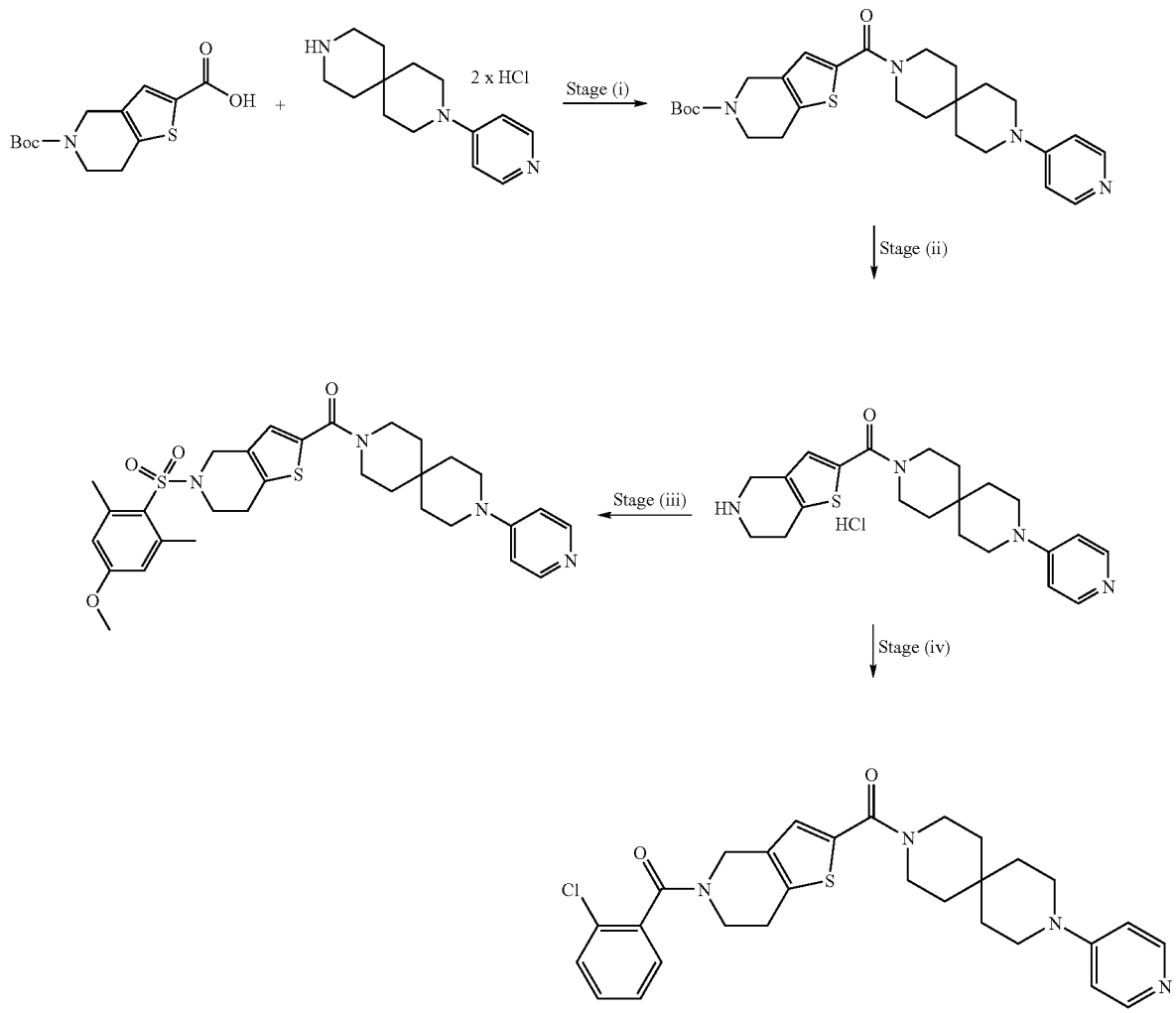

butyl 2-(9-(pyridin-4-yl)-3,9-diazaspiro[5.5]undecane-3-carbonyl)-6,7-dihydrothieno[3,2-c]pyridine-5(4H)-carboxylate (280 mg, 0.564 mmol) in methanol (2 ml), and the reaction mixture was refluxed for 2 h. The solvent was removed in vacuo, the residue was taken up in a small amount of ethanol (3 ml), and diethyl ether (50 ml) was added thereto. Cooling was then carried out for 30 min. in an ice bath, and the resulting solid was filtered out, washed with diethyl ether and dried in vacuo. Yield: 180 mg (73%)

Stage (iii): (5-(4-Methoxy-2,6-dimethylphenylsulfonyl)-4,5,6,7-tetrahydrothieno-[3,2-c]pyridin-2-yl)(9-(pyridin-4-yl)-3,9-diazaspiro[5.5]undecan-3-yl)methanone (G-14)

(9-(Pyridin-4-yl)-3,9-diazaspiro[5.5]undecan-3-yl)(4,5,6,7-tetrahydrothieno[3,2-c]-pyridin-2-yl)methanone hydrochloride (89 mg, 0.208 mmol) was dissolved in dichloromethane (5 ml) and cooled, and triethylamine (0.07 ml, 0.52 mmol) was added thereto. At 0° C., a solution of 4-methoxy-2,6-dimethylbenzenesulfonyl chloride (50 mg, 0.208 mmol) in dichloromethane (5 ml) was added dropwise, and then stirring was carried out for 15 h at room temperature. Saturated sodium hydrogen carbonate solution (10 ml) was added, the mixture was stirred for 15 min. and the phases were separated. The aqueous phase was extracted with dichloromethane (30 ml), and then the combined organic phases were washed with saturated sodium chloride solution, dried over sodium sulfate and concentrated in vacuo. The crude product was purified by column chromatography (silica gel, ethyl acetate/methanol/-ammonia (25% aq.), 400:20:1). Yield: 70 mg (56%). MS, R=3.4 min; m/z=595.3 [MH]+

Stage (iv): ((5-(2-Chlorobenzoyl)-4,5,6,7-tetrahydrothieno[3,2-c]pyridin-2-yl)(9-(pyridin-4-yl)-3,9-diazaspiro[5.5]undecan-3-yl)methanone (G-15)

(9-(Pyridin-4-yl)-3,9-diazaspiro[5.5]undecan-3-yl)(4,5,6,7-tetrahydrothieno[3,2-c]-pyridin-2-yl)methanone hydrochloride (0.089 g, 0.208 mmol) was dissolved in dichloromethane (4 ml) and N,N-dimethylformamide (1 ml), and triethylamine (0.072 ml, 0.52 mmol) was added. The mixture was cooled with an ice bath, and 2-chlorobenzoyl chloride (0.036 g, 0.208 mmol), dissolved in dichloromethane (4 ml), was added slowly at 0° C. The cooling bath was removed and the reaction mixture was stirred for 15 h at RT. Saturated sodium hydrogen carbonate solution (15 ml) was then added and the phases were separated. The aqueous phase was extracted with dichloromethane (25 ml) and the combined organic phases were washed with saturated NaCl solution (10 ml) and saturated sodium chloride solution (10 ml), dried over sodium sulfate and concentrated in vacuo. The crude product was purified by column chromatography (silica gel, ethyl acetate/methanol/ammonia (25% aq.), 500:100:1). Yield: 80 mg (72%). MS, $R_f$=3.0 min; m/z=535.2 [MH]+

Exemplary Compound G-20: 2-(1-(4-Methoxy-2,6-dimethylphenylsulfonyl)indolin-6-yl)-1-(9-(pyridin-4-yl)-3,9-diazaspiro[5.5]undecan-3-yl)ethanone

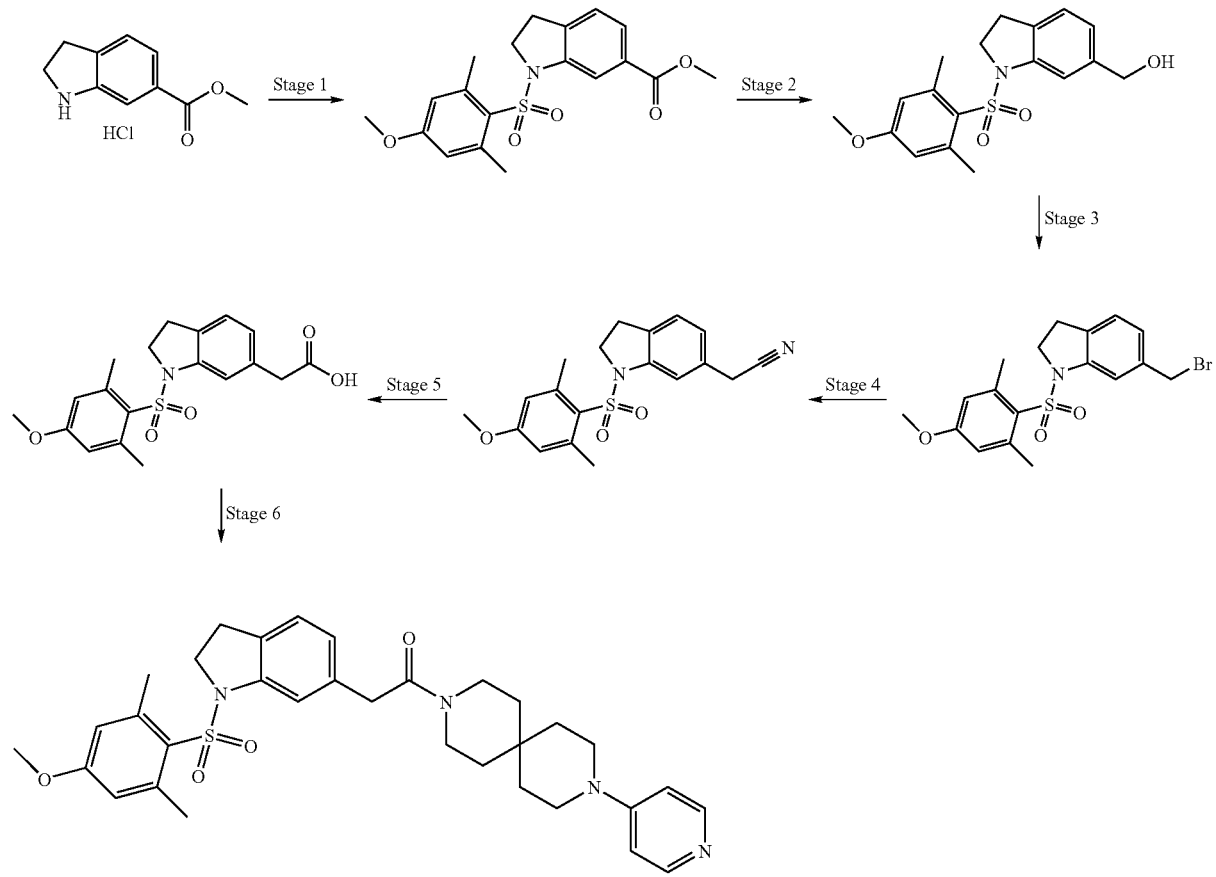

Stage 1: Methyl 1-(4-methoxy-2,6-dimethylphenylsulfonyl)indoline-6-carboxylate 4-Methoxy-2,6-dimethylbenzene-1-sulfonyl chloride (1.3 g, 0.0056 mol) was added at 25° C., under argon, to a solution of methyl indoline-6-carboxylate hydrochloride (1.2 g, 0.0056 mol) in dry pyridine (12 ml), and the resulting reaction mixture was stirred overnight at 70° C. The solvent was removed in vacuo, and the residue was taken up in dichloromethane and washed with water (2×), saturated copper sulfate solution (2×) and saturated sodium chloride solution, then dried (Na$_2$SO$_4$) and concentrated in vacuo. The resulting crude product was purified by column chromatography (silica gel, 10-30% ethyl acetate in hexane). Yield: 1.9 g (90%)

Stage 2: (1-(4-Methoxy-2,6-dimethylphenylsulfonyl)indolin-6-yl)methanol

Lithium borohydride (0.232 g, 0.0107 mol) was added at 0° C., under argon, to a solution of methyl 1-(4-methoxy-2,6-dimethylphenylsulfonyl)indoline-6-carboxylate (1 g, 0.0027 mol) in dry THF (30 ml), and the resulting reaction mixture was refluxed for 2 h. The solvent was removed in vacuo, water was added to the residue, and extraction with ethyl acetate was carried out. The organic phase was washed with water and saturated sodium chloride solution, then dried (Na$_2$SO$_4$) and concentrated in vacuo. The resulting crude product was used in the next stage without further purification. Yield: 0.9 g (97%).

Stage 3: 6-(Bromomethyl)-1-(4-methoxy-2,6-dimethylphenylsulfonyl)indoline

Phosphorus tribromide (0.9 ml, 0.0090 mol) was added at 0° C., under argon, to a solution of 1-(4-methoxy-2,6-dimethylphenylsulfonyl)indolin-6-yl)methanol (0.9 g, 0.0026 mol) in dry DMF (10 ml), and the resulting reaction mixture was stirred for 4 h. Ice was then added to the mixture, and extraction with ethyl acetate was carried out. The organic phase was washed with water (2×) and saturated sodium chloride solution, then dried (Na$_2$SO$_4$), filtered and concentrated in vacuo. The resulting crude product was used in the next stage without further purification. Yield: 0.7 g (66%).

Stage 4: 2-(1-(4-Methoxy-2,6-dimethylphenylsulfonyl)indolin-6-yl)acetonitrile Potassium cyanide (0.133 g, 0.0020 mol) was added to a solution of 6-(bromomethyl)-1-(4-methoxy-2,6-dimethylphenylsulfonyl)indoline (0.7 g, 0.0017 mol) in methanol (14 ml) and water (2 ml), and the resulting reaction mixture was refluxed for 4 h. The mixture was then diluted with ethyl acetate (400 ml) and washed with saturated sodium chloride solution (2×), water (2×), saturated iron sulfate solution and finally with saturated sodium chloride solution. It was then dried (Na$_2$SO$_4$), filtered and concentrated in vacuo. The resulting crude product was used directly in the following stage. Yield: 0.6 g (99%).

Stage 5: 2-(1-(4-Methoxy-2,6-dimethylphenylsulfonyl)indolin-6-yl)acetic acid (E-19)

45% potassium hydroxide solution (5 ml) was added to a solution of 2-(1-(4-methoxy-2,6-dimethylphenylsulfonyl)indolin-6-yl)acetonitrile (0.6 g, 0.0016 mol) in ethanol (12 ml), and the resulting reaction mixture was refluxed for 1 h. The solvent was removed in vacuo, water was added to the residue, and extraction with ethyl acetate was carried out. The aqueous phase was adjusted dropwise to pH ~2 with hydrochloric acid in cold solution and then extracted with ethyl acetate. The organic phase was washed with saturated sodium chloride solution, dried (Na$_2$SO$_4$), filtered and concentrated in vacuo. The resulting crude product was used directly in the following stage. Yield: 0.3 g (47%).

Stage 6: 2-(1-(4-Methoxy-2,6-dimethylphenylsulfonyl)indolin-6-yl)-1-(9-(pyridin-4-yl)-3,9-diazaspiro[5.5]undecan-3-yl)ethanone (G-20)

To a solution of 2-(1-(4-methoxy-2,6-dimethylphenylsulfonyl)indolin-6-yl)acetic acid (E-19) (150 mg, 0.4 mmol) in dichloromethane (10 ml/mmol) there was added at 0° C. diisopropylethylamine (0.3 ml, 1.6 mmol) followed by HOBT (54 mg, 0.48 mmol) and EDCl (115 mg, 0.6 mmol). The resulting reaction mixture was stirred for 16 h at 25° C. and then diluted with dichloromethane (30 ml) and washed with saturated ammonium chloride solution, saturated sodium chloride solution and saturated sodium hydrogen carbonate solution. Drying (Na$_2$SO$_4$) and concentration in vacuo were then carried out. The resulting crude product was purified by column chromatography (Alox-neutral, 0.5% methanol in dichloromethane). Yield: 150 mg (64%). MS, R$_t$=3.4 min; m/z=589.4 [MH]$^+$ Exemplary Compounds G-41 to G-43, G-45, G-47 to G-50, G-55, G-56, G-58 to G-63:

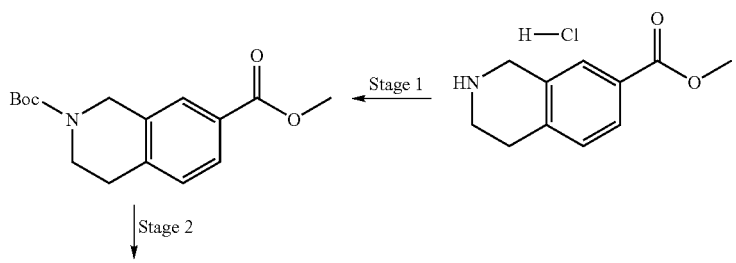

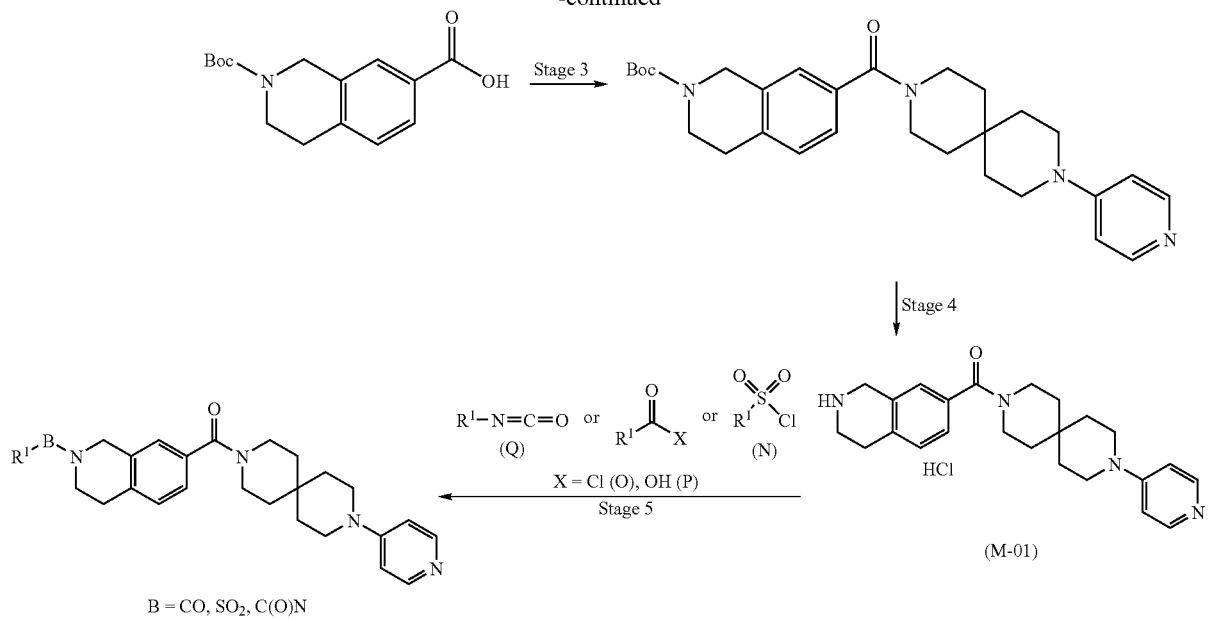

Stage 1: 2-tert-Butyl 7-methyl 3,4-dihydroisoquinoline-2,7(1H)-dicarboxylate Triethylamine (6.08 g, 0.0043 mol) and di-tert-butyl dicarbonate (5.6 g, 0.026 mol) were added at 0° C. to a solution of methyl 1,2,3,4-tetrahydroisoquinoline-7-carboxylate hydrochloride (5 g, 0.021 mol) in dichloromethane (42 ml), and the resulting reaction mixture was stirred for 16 h. Dist. water was added to the reaction mixture, and the phases were separated. The organic phase was washed 1× with each of 1 M HCl and sat. NaCl solution, dried (Na$_2$SO$_4$), filtered and concentrated in vacuo. The resulting crude product was used directly in the following stage. Yield: 7.9 g (>99%).

Stage 2: 2-(tert-Butoxycarbonyl) 1,2,3,4-tetrahydroisoquinoline-7-carboxylic acid Lithium hydroxide monohydrate (5.8 g, 0.136 mol) dissolved in water (73 ml) was added to a solution of 2-tert-butyl 7-methyl-3,4-dihydroisoquinoline-2,7(1H)-dicarboxylate (7.9 g, 0.027 mol) in methanol (110 ml), and the mixture was stirred for 4 h. The solvent was removed in vacuo. Water and diethyl ether were added to the residue, and the phases were separated. The aqueous phase was adjusted to an acidic pH with dilute aqueous HCl solution and extracted with ethyl acetate. The organic phase was dried over magnesium sulfate, filtered and concentrated in vacuo. The resulting crude product was used directly in the following stage. Yield: 5.8 g (76%).

Stage 3: tert-Butyl 7-(9-(pyridin-4-yl)-3,9-diazaspiro[5.5]undecane-3-carbonyl)-3,4-dihydroisoquinoline-2(1H)-carboxylate 2-(tert-Butoxycarbonyl)-1,2,3,4-tetrahydroisoquinoline-7-carboxylic acid (2 g, 0.0072 mol), O-(1H-benzotriazol-1-yl)-N,N,N',N'-tetramethyluronium tetrafluoroborate (2.3 g, 0.0072 mol) and 1-hydroxybenzotriazole hydrate (0.99 g, 0.0072 mol) were dissolved in tetrahydrofuran, under nitrogen, and the mixture was stirred for 30 min at RT. A solution of 3-(pyridin-4-yl)-3,9-diazaspiro[5.5]undecane dihydrochloride (F-09) (2.18 g, 0.0072 mol) and diisopropylethylamine (DIPEA) (4.28 g, 0.025 mol) in tetrahydrofuran was added, and the reaction mixture was stirred for 15 h at RT. Tetrahydrofuran was then removed in vacuo, the residue was taken up in ethyl acetate and sat. sodium hydrogen carbonate solution, and the phases were separated. The aqueous phase was extracted with ethyl acetate, and the combined organic phases were in turn washed with sat. sodium chloride solution, dried over sodium sulfate and concentrated in vacuo. The crude product was purified by column chromatography (ethyl acetate/methanol 20:1+1% 25% ammonia solution (aq.)). Yield: 1.91 g (54%).

Stage 4: (9-(Pyridin-4-yl)-3,9-diazaspiro[5.5]undecan-3-yl)(1,2,3,4-tetrahydroisoquinolin-7-yl)methanone (M-01)

1.25 M hydrogen chloride in methanol (15.5 ml, 19.36 mmol) was added at RT to a solution of tert-butyl 7-(9-(pyridin-4-yl)-3,9-diazaspiro[5.5]undecane-3-carbonyl)-3,4-dihydroisoquinoline-2(1H)-carboxylate (1.9 g, 3.87 mmol) in methanol (4 ml), and the reaction mixture was refluxed for 1.5 h. The solvent was removed in vacuo, the residue was taken up in a small amount of ethanol (3 ml), and diethyl ether (50 ml) was added. The mixture was then cooled for 30 min in an ice bath, and the resulting solid was filtered out, washed with diethyl ether and dried in vacuo. Yield: 1.56 g (94%).

Stage 5: General Working Procedure GWA [A]:

(9-(Pyridin-4-yl)-3,9-diazaspiro[5.5]undecan-3-yl)(1,2,3,4-tetrahydroisoquinolin-7-yl)methanone (M-01) (1 equiv.) was dissolved in dichloromethane and cooled, and triethylamine (2 equiv.) was added. At 0° C., a solution of the acid chloride (O) (1 equiv.) in dichloromethane was added dropwise, and then the mixture was stirred for 15 h at RT. Sat. sodium hydrogen carbonate solution was added, and the phases were separated. The aqueous phase was extracted with dichloromethane, and then the combined organic phases were washed with sat. sodium chloride solution, dried over sodium sulfate and concentrated in vacuo. Purification of the crude product was carried out by column chromatography (silica gel).

General Working Procedure GWP [B]:

(9-(Pyridin-4-yl)-3,9-diazaspiro[5.5]undecan-3-yl)(1,2,3,4-tetrahydroisoquinolin-7-yl)methanone (M-01) (1 equiv.) was dissolved in dichloromethane and cooled, and triethylamine (2.5 equiv.) was added. At 0° C., a solution of the sulfonyl chloride (N) (1.2 equiv.) in dichloromethane was added dropwise, and then the mixture was stirred for 15 h at RT. Saturated sodium hydrogen carbonate solution was added, and the phases were separated. The aqueous phase was extracted with dichloromethane, and then the combined organic phases were washed with saturated sodium chloride solution, dried over sodium sulfate and concentrated in vacuo. Purification of the crude product was carried out by column chromatography (silica gel).

General Working Procedure GWP [C]:

The carboxylic acid (P) (1 equiv.), O-(1H-benzotriazol-1-yl)-N,N,N',N'-tetramethyluronium tetrafluoroborate (1 equiv.) and 1-hydroxybenzotriazole hydrate (1 equiv.) were placed in tetrahydrofuran, under protecting gas, and stirred for 30 min at RT. A solution of (9-(pyridin-4-yl)-3,9-diazaspiro[5.5]undecan-3-yl)(1,2,3,4-tetrahydroisoquinolin-7-yl)methanone (M-01) (1 equiv.) and diisopropylethylamine (DIPEA) (2 equiv.) in tetrahydrofuran was added, and the reaction mixture was stirred for 15 h at RT. Tetrahydrofuran was then removed in vacuo, the residue was taken up in dichloromethane and sat. sodium hydrogen carbonate solution, and the phases were separated. The aqueous phase was extracted with dichloromethane, and then the combined organic phases were washed with sat. sodium chloride solution, dried over sodium sulfate and concentrated in vacuo. Purification of the crude product was carried out by column chromatography (silica gel).

General Working Procedure GWP [D]:

(9-(Pyridin-4-yl)-3,9-diazaspiro[5.5]undecan-3-yl)(1,2,3,4-tetrahydroisoquinolin-7-yl)methanone (M-01) (1 equiv.) was dissolved in toluene and triethylamine (1.2 equiv.). The isocyanate (Q) (1 equiv.) was added, and the reaction mixture was refluxed for 4 h and stirred for 15 h at room temperature. Toluene was removed in vacuo, the residue was taken up in dichloromethane and sat. sodium hydrogen carbonate solution, and the phases were separated. The aqueous phase was extracted with dichloromethane, and then the combined organic phases were washed with sat. sodium chloride solution, dried over sodium sulfate and concentrated in vacuo. Purification of the crude product was carried out by column chromatography (silica gel).

| Example No. | Structure | Name | Intermediate (M) | (N), (O), (P) or (Q) | Yield | Analyzis (LC/MS)[1] | Synthesised according to/ Comments |
|---|---|---|---|---|---|---|---|
| G-41 | 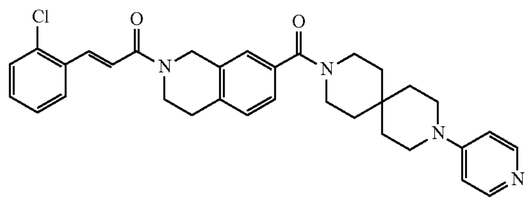 [SMILES: O=C(/C=C/c1ccccc1Cl)N1CCc2ccc(C(=O)N3CCC4(CC3)CCN(c3ccncc3)CC4)cc2C1] | 3-(2-Chlorophenyl)-1-(7-(9-(pyridin-4-yl)-3,9-diazaspiro[5.5]undecan-3-carbonyl)-3,4-dihydroisoquinolin-2(1H)-yl)prop-2-en-1-one (G-41) | (9-(Pyridin-4-yl)-3,9-diazaspiro[5.5]undecan-3-yl)(1,2,3,4-tetrahydroisoquinolin-7-yl)methanone hydrochloride (M-01) | (E)-3-(2-Chlorophenyl)acryloyl chloride (O-01) | 77% (0.18 mmol) | $R_t$ = 3.4 min; m/z = 555.4 [MH]$^+$ | GWP [A] |
| G-42 | 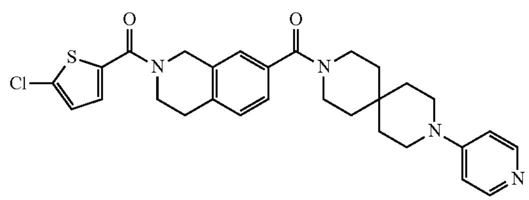 [SMILES: O=C(c1ccc2c(c1)CN(C(=O)c1ccc(Cl)s1)CC2)N1CCC2(CC1)CCN(c1ccncc1)CC2] | (5-Chlorothiophen-2-yl)(7-(9-(pyridin-4-yl)-3,9-diazaspiro[5.5]undecane-3-carbonyl)-3,4-dihydroisoquinolin-2(1H)-yl)methanone (G-42) | (9-(Pyridin-4-yl)-3,9-diazaspiro[5.5]undecan-3-yl)(1,2,3,4-tetrahydroisoquinolin-7-yl)methanone hydrochloride (M-01) | 5-Chlorothiophene-2-carboxylic acid (P-01) | 96% (0.34 mmol) | $R_t$ = 3.1 min; m/z = 535.3 [MH]$^+$ | GWP [C] |
| G-43 | 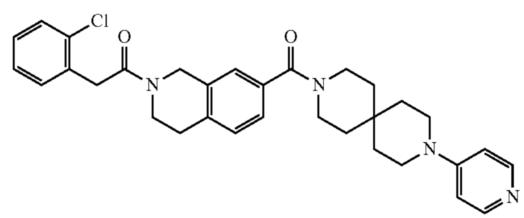 [SMILES: O=C(Cc1ccccc1Cl)N1CCc2ccc(C(=O)N3CCC4(CC3)CCN(c3ccncc3)CC4)cc2C1] | 2-(2-Chlorophenyl)-1-(7-(9-(pyridin-4-yl)-3,9-diazaspiro[5.5]undecane-3-carbonyl)-3,4-dihydroisoquinolin-2(1H)-yl)ethanone (G-43) | (9-(Pyridin-4-yl)-3,9-diazaspiro[5.5]undecan-3-yl)(1,2,3,4-tetrahydroisoquinolin-7-yl)methanone hydrochloride (M-01) | 2-(2-Chlorophenyl)acetyl chloride (O-02) | 71% (0.17 mmol) | $R_t$ = 3.4 min; m/z = 543.4 [MH]$^+$ | GWP [A] |
| G-45 | 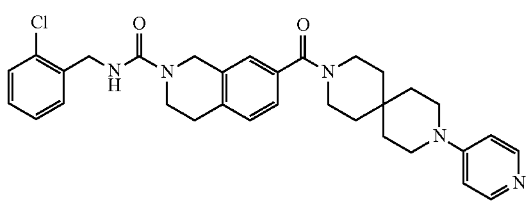 [SMILES: O=C(NCc1ccccc1Cl)N1CCc2ccc(C(=O)N3CCC4(CC3)CCN(c3ccncc3)CC4)cc2C1] | N-[(2-Chlorophenyl)-methyl]-7-(9-pyridin-4-yl-3,9-diazaspiro[5.5]undecane-3-carbonyl)-1,2,3,4-tetrahydro-isoquinoline-2-carboxylic acid amide (G-45) | (9-(Pyridin-4-yl)-3,9-diazaspiro[5.5]undecan-3-yl)(1,2,3,4-tetrahydroisoquinolin-7-yl)methanone hydrochloride (M-01) | 1-Chloro-2-(isocyanatomethyl)-benzene (Q-01) | 45% (0.13 mmol) | $R_t$ = 3.0 min; m/z = 558.4 [MH]$^+$ | GWP [D] |

-continued

| Example No. | Structure | Name | Intermediate (M) | (N), (O), (P) or (Q) | Yield | Analyzis (LC/MS)[1] | Synthesised according to/ Comments |
|---|---|---|---|---|---|---|---|
| G-47 | 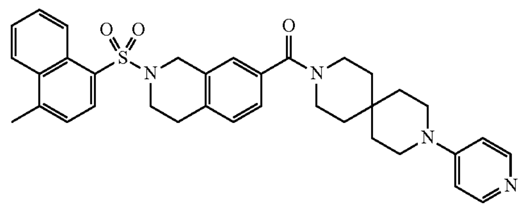 [SMILES: Cc1ccc(S(=O)(=O)N2CCc3ccc(C(=O)N4CCC5(CC4)CCN(c4ccncc4)CC5)cc3C2)c2ccccc12] | [2-[(4-Methyl-naphthalin-1-yl)sulfonyl]-1,2,3,4-tetrahydro-isoquinolin-7-yl]-(9-pyridin-4-yl-3,9-diazaspiro[5.5]undecan-3-yl)-methanone (G-47) | (9-(Pyridin-4-yl)-3,9-diazaspiro[5.5]undecan-3-yl](1,2,3,4-tetrahydroisoquinolin-7-yl)methanone hydrochloride (M-01) | 4-Methylnaphthalene-1-sulfonyl chloride (N-01) | 77% (0.26 mmol) | R$_t$ = 3.7 min; m/z = 595.3 [MH]$^+$ | GWP [B] |
| G-48 | 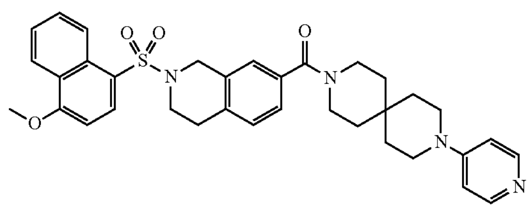 [SMILES: COc1ccc(S(=O)(=O)N2CCc3ccc(C(=O)N4CCC5(CC4)CCN(c4ccncc4)CC5)cc3C2)c2ccccc12] | [2-[(4-Methoxy-naphthalin-1-yl)sulfonyl]-1,2,3,4-tetrahydro-isoquinolin-7-yl]-(9-pyridin-4-yl-3,9-diazaspiro[5.5]undecan-3-yl)-methanone (G-48) | (9-(Pyridin-4-yl)-3,9-diazaspiro[5.5]undecan-3-yl](1,2,3,4-tetrahydroisoquinolin-7-yl)methanone hydrochloride (M-01) | 4-Methoxy-naphthalene-1-sulfonyl chloride (N-02) | 76% (0.21 mmol) | R$_t$ = 3.7 min; m/z = 611.3 [MH]$^+$ | GWP [B] |
| G-49 | 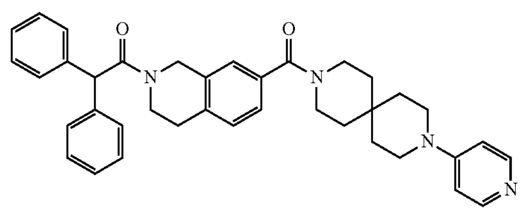 [SMILES: O=C(c1ccc2c(c1)CN(C(=O)C(c1ccccc1)c1ccccc1)CC2)N1CCC2(CC1)CCN(c1ccncc1)CC2] | 2,2-Diphenyl-1-[7-(9-pyridin-4-yl-3,9-diazaspiro[5.5]undecane-3-carbonyl)-1,2,3,4-tetrahydro-isoquinolin-2-yl]-ethanone (G-49) | (9-(Pyridin-4-yl)-3,9-diazaspiro[5.5]undecan-3-yl](1,2,3,4-tetrahydroisoquinolin-7-yl)methanone hydrochloride (M-01) | 2,2-Diphenylacetyl chloride (O-03) | 85% (0.24 mmol) | R$_t$ = 3.5 min; m/z = 585.4 [MH]$^+$ | GWP [A] |
| G-50 | 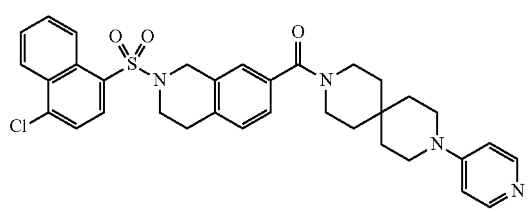 [SMILES: O=C(c1ccc2c(c1)CN(S(=O)(=O)c1ccc(Cl)c3ccccc13)CC2)N1CCC2(CC1)CCN(c1ccncc1)CC2] | [2-[(4-Chloro-naphthalin-1-yl)sulfonyl]-1,2,3,4-tetrahydro-isoquinolin-7-yl]-(9-pyridin-4-yl-3,9-diazaspiro[5.5]undecan-3-yl)-methanone (G-50) | (9-(Pyridin-4-yl)-3,9-diazaspiro[5.5]undecan-3-yl](1,2,3,4-tetrahydroisoquinolin-7-yl)methanone hydrochloride (M-01) | 4-Chloronaphthalene-1-sulfonyl chloride (N-03)) | 52% (0.15 mmol) | R$_t$ = 3.9 min; m/z = 615.3 [MH]$^+$ | GWP [B] |

-continued

| Example No. | Structure | Name | Intermediate (M) | (N), (O), (P) or (Q) | Yield | Analyzis (LC/MS)[1] | Synthesised according to/ Comments |
|---|---|---|---|---|---|---|---|
| G-55 | 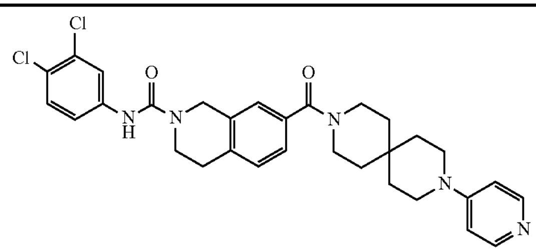 | N-(3,4-Dichlorophenyl)-7-(9-pyridin-4-yl-3,9-diazaspiro[5.5]undecane-3-carbonyl)-1,2,3,4-tetrahydroisoquinoline-2-carboxylic acid amide (G-55) | (9-(Pyridin-4-yl)-3,9-diazaspiro[5.5]undecan-3-yl)(1,2,3,4-tetrahydroisoquinolin-7-yl)methanone hydrochloride (M-01) | 1,2-Dichloro-4-isocyanatobenzene (Q-02) | 49% (0.13 mmol) | $R_t$ = 3.5 min; m/z = 578.3 [MH]+ | GWP [D] |
| G-56 | 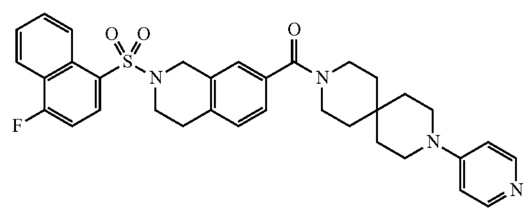 [SMILES: O=C(c1ccc2c(c1)CN(S(=O)(=O)c1ccc(F)c3ccccc13)CC2)N1CCC2(CC1)CCN(c1ccncc1)CC2] | [2-[(4-Fluoro-naphthalin-1-yl)sulfonyl]-1,2,3,4-tetrahydro-isoquinolin-7-yl]-(9-pyridin-4-yl-3,9-diazaspiro[5.5]undecan-3-yl)-methanone (G-56) | (9-(Pyridin-4-yl)-3,9-diazaspiro[5.5]undecan-3-yl)(1,2,3,4-tetrahydroisoquinolin-7-yl)methanone hydrochloride (M-01) | 4-Fluoro-naphthalene-1-sulfonyl chloride (N-04) | 53% (0.15 mmol) | $R_t$ = 3.6 min; m/z = 599.3 [MH]+ | GWP [B] |
| G-58 | 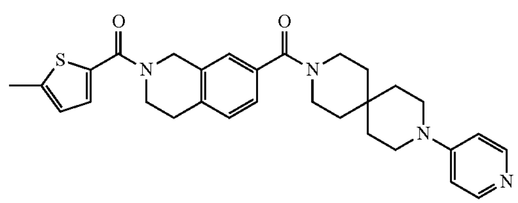 [SMILES: Cc1ccc(C(=O)N2CCc3ccc(C(=O)N4CCC5(CC4)CCN(c4ccncc4)CC5)cc3C2)s1] | [2-(5-Methyl-thiophene-2-carbonyl)-1,2,3,4-tetrahydro-isoquinolin-7-yl]-(9-pyridin-4-yl-3,9-diazaspiro[5.5]undecan-3-yl)-methanone (G-58) | (9-(Pyridin-4-yl)-3,9-diazaspiro[5.5]undecan-3-yl)(1,2,3,4-tetrahydroisoquinolin-7-yl)methanone hydrochloride (M-01) | 5-Methylthiophene-2-carbonyl chloride (O-04) | 83% (0.23 mmol) | $R_t$ = 3.0 min; m/z = 515.3 [MH]6+ | GWP [A] |
| G-59 | 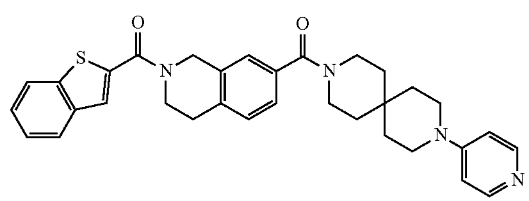 [SMILES: O=C(c1ccc2c(c1)CN(C(=O)c1cc3ccccc3s1)CC2)N1CCC2(CC1)CCN(c1ccncc1)CC2] | [2-(Benzo[b]thiophene-2-carbonyl)-1,2,3,4-tetrahydro-isoquinolin-7-yl]-(9-pyridin-4-yl-3,9-diazaspiro[5.5]undecan-3-yl)-methanone (G-59) | (9-(Pyridin-4-yl)-3,9-diazaspiro[5.5]undecan-3-yl)(1,2,3,4-tetrahydroisoquinolin-7-yl)methanone hydrochloride (M-01) | Benzo[b]thiophene-2-carbonyl chloride (O-05) | 32% (0.09 mmol) | $R_t$ = 3.3 min; m/z = 551.3 [MH]+ | GWP [A] |

-continued

| Example No. | Structure | Name | Intermediate (M) | (N), (O), (P) or (Q) | Yield | Analyzis (LC/MS)[1] | Synthesised according to/ Comments |
|---|---|---|---|---|---|---|---|
| G-60 | 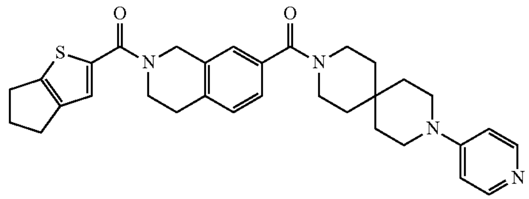 [SMILES: O=C(c1ccc2c(c1)CN(C(=O)c1cc3c(s1)CCC3)CC2)N1CCC2(CC1)CCN(c1ccncc1)CC2] | [2-(5,6-Dihydro-4H-cyclopenta[b]thiophene-2-carbonyl)-1,2,3,4-tetrahydro-isoquinolin-7-yl]-(9-pyridin-4-yl-3,9-diazaspiro[5.5]undecan-3-yl)-methanone (G-60) | (9-(Pyridin-4-yl)-3,9-diazaspiro[5.5]undecan-3-yl)(1,2,3,4-tetrahydroisoquinolin-7-yl)methanone hydrochloride (M-01) | 5,6-Dihydro-4H-cyclopenta[b]-thiophene-2-carbonyl chloride (O-06) | 46% (0.13 mmol) | R$_t$ = 3.2 min; m/z = 541.3 [MH]$^+$ | GWP [A] |
| G-61 | 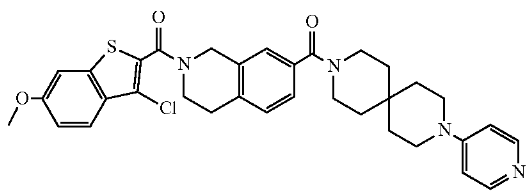 [SMILES: COc1ccc2c(Cl)c(C(=O)N3CCc4ccc(C(=O)N5CCC6(CC5)CCN(c5ccncc5)CC6)cc4C3)sc2c1] | [2-(3-Chloro-6-methoxy-benzo[b]thiophene-2-carbonyl)-1,2,3,4-tetrahydro-isoquinolin-7-yl]-(9-pyridin-4-yl-3,9-diazaspiro[5.5]undecan-3-yl)-methanone (G-61) | (9-(Pyridin-4-yl)-3,9-diazaspiro[5.5]undecan-3-yl)(1,2,3,4-tetrahydroisoquinolin-7-yl)methanone hydrochloride (M-01) | 3-Chloro-6-methoxybenzo[b]-thiophene-2-carbonyl chloride (O-07) | 46% (0.16 mmol) | R$_t$ = 3.7 min; m/z = 615.2 [MH]$^+$ | GWP [A] |
| G-62 | 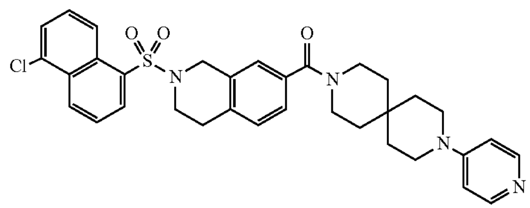 [SMILES: O=C(c1ccc2c(c1)CN(S(=O)(=O)c1cccc3c(Cl)cccc13)CC2)N1CCC2(CC1)CCN(c1ccncc1)CC2] | [2-[(5-Chloro-naphthalin-1-yl)sulfonyl]-1,2,3,4-tetrahydro-isoquinolin-7-yl]-(9-pyridin-4-yl-3,9-diazaspiro[5.5]undecan-3-yl)-methanone (G-62) | (9-(Pyridin-4-yl)-3,9-diazaspiro[5.5]undecan-3-yl)(1,2,3,4-tetrahydroisoquinolin-7-yl)methanone hydrochloride (M-01) | 5-Chloronaphthalene-1-sulfonyl chloride (N-05) | 46% (0.13 mmol) | R$_t$ = 3.9 min; m/z = 615.3 [MH]$^+$ | GWP [B] |
| G-63 | 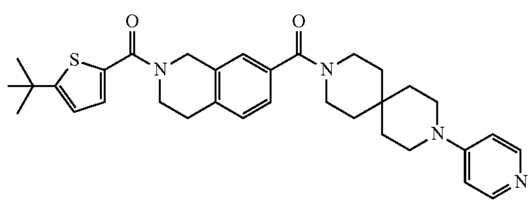 [SMILES: CC(C)(C)c1ccc(C(=O)N2CCc3ccc(C(=O)N4CCC5(CC4)CCN(c4ccncc4)CC5)cc3C2)s1] | [2-(5-tert-Butyl-thiophene-2-carbonyl)-1,2,3,4-tetrahydro-isoquinolin-7-yl]-(9-pyridin-4-yl-3,9-diazaspiro[5.5]undecan-3-yl)-methanone (G-63) | (9-(Pyridin-4-yl)-3,9-diazaspiro[5.5]undecan-3-yl)(1,2,3,4-tetrahydroisoquinolin-7-yl)methanone hydrochloride (M-01) | 5-tert-Butylthiophene-2-carbonyl chloride (O-08) | 68% (0.27 mmol) | R$_t$ = 3.8 min; m/z = 557.3 [MH]$^+$ | GWP [A] |

Exemplary Compounds G-67 to G-69 and G-73:

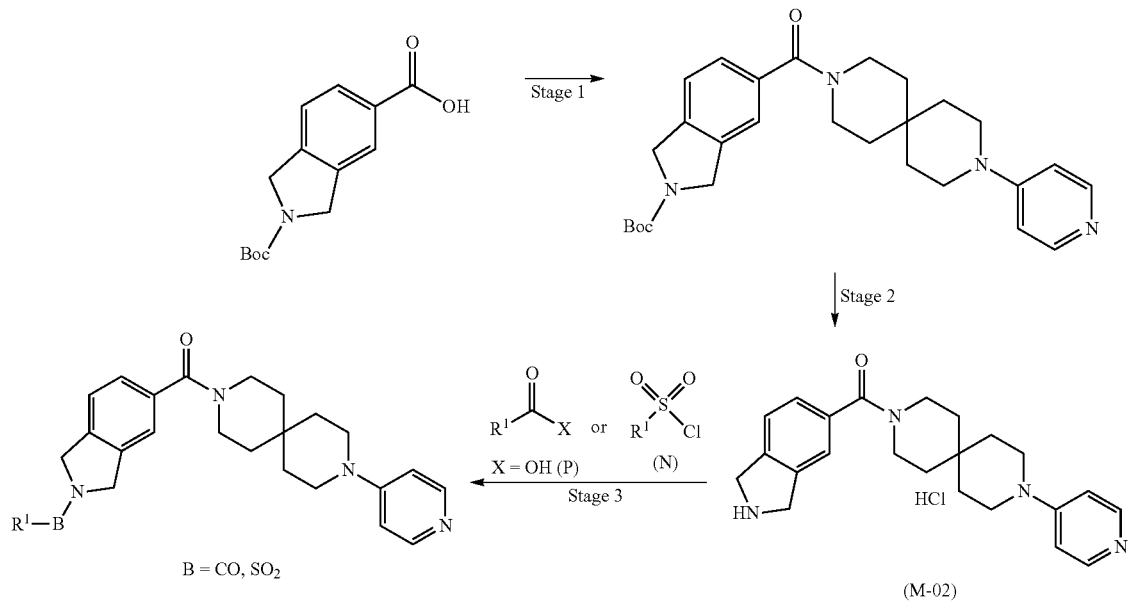

Stage 1: tert-Butyl 5-(9-(pyridin-4-yl)-3,9-diazaspiro[5.5]undecane-3-carbonyl)isoindoline-2-carboxylate 2-(tert-Butoxycarbonyl)isoindoline-5-carboxylic acid (0.5 g, 0.0019 mol) ([CAS: 149353-71-9] available commercially from Milestone, for example), O-(1H-benzotriazol-1-yl)-N,N,N',N'-tetramethyluronium tetrafluoroborate (0.6 g, 0.0019 mol) and 1-hydroxybenzotriazole hydrate (0.26 g, 0.0019 mol) were dissolved in tetrahydrofuran, under protecting gas, and stirred for 30 min at RT. A solution of 3-(pyridin-4-yl)-3,9-diazaspiro[5.5]undecane dihydrochloride (F-09) (0.5 g, 0.0019 mol) and diisopropylethylamine (DIPEA) (0.86 g, 0.066 mol) in tetrahydrofuran was added, and the reaction mixture was stirred for 15 h at RT. Tetrahydrofuran was then removed in vacuo, the residue was taken up in ethyl acetate and sat. sodium hydrogen carbonate solution, and the phases were separated. The aqueous phase was extracted with ethyl acetate and the combined organic phases were in turn washed with sat. sodium chloride solution, dried over sodium sulfate and concentrated in vacuo. The crude product was purified by column chromatography (ethyl acetate/methanol 10:1+1% ammonia solution (25% aq.)). Yield: 0.85 g (94%)

Stage 2: Isoindolin-5-yl(9-(pyridin-4-yl)-3,9-diazaspiro[5.5]undecan-3-yl)methanone (M-02)

1.25 M hydrogen chloride in methanol (7.1 ml, 8.92 mmol) was added at RT to a solution of tert-butyl 5-(9-(pyridin-4-yl)-3,9-diazaspiro[5.5]undecane-3-carbonyl)isoindoline-2-carboxylate (0.85 g, 1.78 mmol) in methanol (1 ml), and the reaction mixture was refluxed for 1 h. The solvent was removed in vacuo, the residue was taken up in a small amount of ethanol (2 ml), and diethyl ether (50 ml) was added. The mixture was then cooled for 30 min in an ice bath, and the resulting solid was filtered out, washed with diethyl ether and dried in vacuo. Yield: 0.74 g (92%).

Stage 3: General Working Procedure GWP [E]:

Isoindolin-5-yl(9-(pyridin-4-yl)-3,9-diazaspiro[5.5]undecan-3-yl)methanone (M-02) (1 equiv.) was dissolved in dichloromethane and cooled, and triethylamine (3 equiv.) was added. At 0° C., a solution of the sulfonyl chloride (N) (1 equiv.) in dichloromethane was added dropwise, then stirring was carried out for 1 h at RT. Sat. sodium hydrogen carbonate solution was added, and the phases were separated. The aqueous phase was extracted with dichloromethane, and the combined organic phases were dried over sodium sulfate and concentrated in vacuo. The crude product was purified by column chromatography (silica gel).

General Working Procedure GWP [F]:

The carboxylic acid (P) (1 equiv.), O-(1H-benzotriazol-1-yl)-N,N,N',N'-tetramethyluronium tetrafluoroborate (1 equiv.) and 1-hydroxybenzotriazole hydrate (1 equiv.) were placed in tetrahydrofuran, under protecting gas, and stirred for 30 min at RT. A solution of isoindolin-5-yl(9-(pyridin-4-yl)-3,9-diazaspiro[5.5]undecan-3-yl)methanone (M-02) (1 equiv.) and diisopropylethylamine (DIPEA) (2.5 equiv.) in tetrahydrofuran was added, and the reaction mixture was stirred for 15 h at RT. Tetrahydrofuran was then removed in vacuo, the residue was taken up in dichloromethane and sat. sodium hydrogen carbonate solution, and the phases were separated. The aqueous phase was extracted with dichloromethane, and the combined organic phases were then washed with sat. sodium chloride solution, dried over sodium sulfate and concentrated in vacuo. Purification of the crude product was carried out by column chromatography (silica gel).

General Working Procedure GWP [G]:

Isoindolin-5-yl(9-(pyridin-4-yl)-3,9-diazaspiro[5.5]undecan-3-yl)methanone (M-02) (1 equiv.) was placed in DMF and 4-methylmorpholine (4 equiv.), and the carboxylic acid (P) (1 equiv.) was added, followed by benzotriazol-1-yloxytris(dimethylamino)-phosphonium hexafluorophosphate (1.3 equiv.). The reaction mixture was stirred for 15 h at RT, and then the solvent was removed in vacuo. The residue was taken up in dichloromethane and sat. sodium hydrogen carbonate solution, and the phases were separated. The aqueous phase was extracted with dichloromethane, and the combined organic phases were dried over magnesium sulfate and concentrated in vacuo. The crude product was purified by column chromatography (silica gel).

| Example No. | Structure | Name | Intermediate (M) | (N), (O), or (P) | Yield | Analyzis (LC/MS)[1] | Synthesised according to/ Comments |
|---|---|---|---|---|---|---|---|
| G-67 | 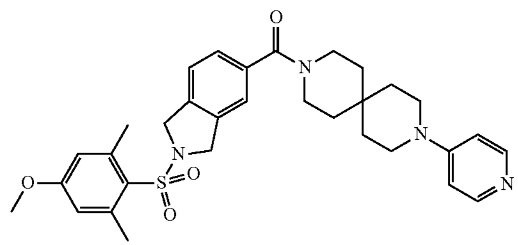 [SMILES: COc1cc(C)c(S(=O)(=O)N2Cc3ccc(C(=O)N4CCC5(CC4)CCN(c4ccncc4)CC5)cc3C2)c(C)c1] | [2-[(4-Methoxy-2,6-dimethyl-phenyl)sulfonyl]-2,3-dihydro-1H-isoindol-5-yl]-(9-pyridin-4-yl-3,9-diazaspiro[5.5]undecan-3-yl)-methanone (G-67) | Isoindolin-5-yl(9-(pyridin-4-yl)-3,9-diazaspiro[5.5]undecan-3-yl)methanone hydrochloride (M-02) | 4-Methoxy-2,6-dimethylphenyl-1-sulfonyl chloride (N-06) | 78% (0.34 mmol) | $R_t$ = 3.8 min; m/z = 575.3 [MH]$^+$ | GWP [E] |
| G-68 | 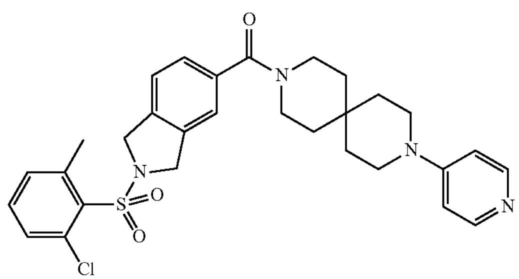 [SMILES: Cc1cccc(Cl)c1S(=O)(=O)N1Cc2ccc(C(=O)N3CCC4(CC3)CCN(c3ccncc3)CC4)cc2C1] | [2-[(2-Chloro-6-methyl-phenyl)sulfonyl]-2,3-dihydro-1H-isoindol-5-yl]-(9-pyridin-4-yl-3,9-diazaspiro[5.5]undecan-3-yl)-methanone (G-68) | Isoindolin-5-yl(9-(pyridin-4-yl)-3,9-diazaspiro[5.5]undecan-3-yl)methanone hydrochloride (M-02) | 2-Chloro-6-methylphenyl-1-sulfonyl chloride (N-07) | 72% (0.32 mmol) | $R_t$ = 3.8 min; m/z = 565.2 [MH]$^+$ | GWP [E] |
| G-69 | 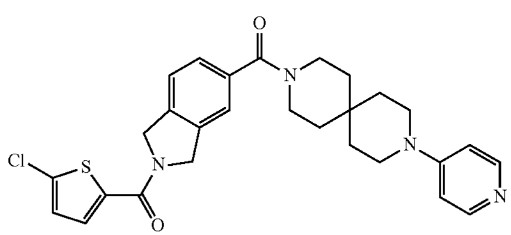 [SMILES: O=C(c1ccc2c(c1)CN(C(=O)c1ccc(Cl)s1)C2)N1CCC2(CC1)CCN(c1ccncc1)CC2] | [2-(5-Chloro-thiophene-2-carbonyl)-2,3-dihydro-1H-isoindol-5-yl]-(9-pyridin-4-yl-3,9-diazaspiro[5.5]undecan-3-yl)methanone (G-69) | Isoindolin-5-yl(9-(pyridin-4-yl)-3,9-diazaspiro[5.5]undecan-3-yl)methanone hydrochloride (M-02) | 5-Chlorothiophene-2-carboxylic acid (P-01) | 80% (0.23 mmol) | $R_t$ = 3.4 min; m/z = 521.2 [MH]$^+$ | GWP [F] |

-continued

| Example No. | Structure | Name | Intermediate (M) | (N), (O), or (P) | Yield | Analyzis (LC/MS)[1] | Synthesised according to/ Comments |
|---|---|---|---|---|---|---|---|
| G-73 | 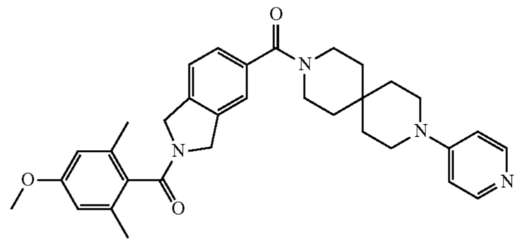 [SMILES: COc1cc(C)c(C(=O)N2Cc3ccc(C(=O)N4CCC5(CC4)CCN(c4ccncc4)CC5)cc3C2)c(C)c1] | [2-[(4-Methoxy-2,6-dimethyl-benzoyl)-2,3-dihydro-1H-isoindol-5-yl]-(9-pyridin-4-yl-3,9-diazaspiro[5.5]undecan-3-yl)-methanone (G-73) | Isoindolin-5-yl(9-(pyridin-4-yl)-3,9-diazaspiro[5.5]undecan-3-yl)methanone hydrochloride (M-02) | 4-Methoxy-2,6-dimethylbenzoic acid (P-02) | 17% (0.07 mmol) | $R_t$ = 3.3 min; m/z = 539.3 $[MH]^+$ | GWP [G] |

Exemplary Compounds G-36 to G-38 and G-44:

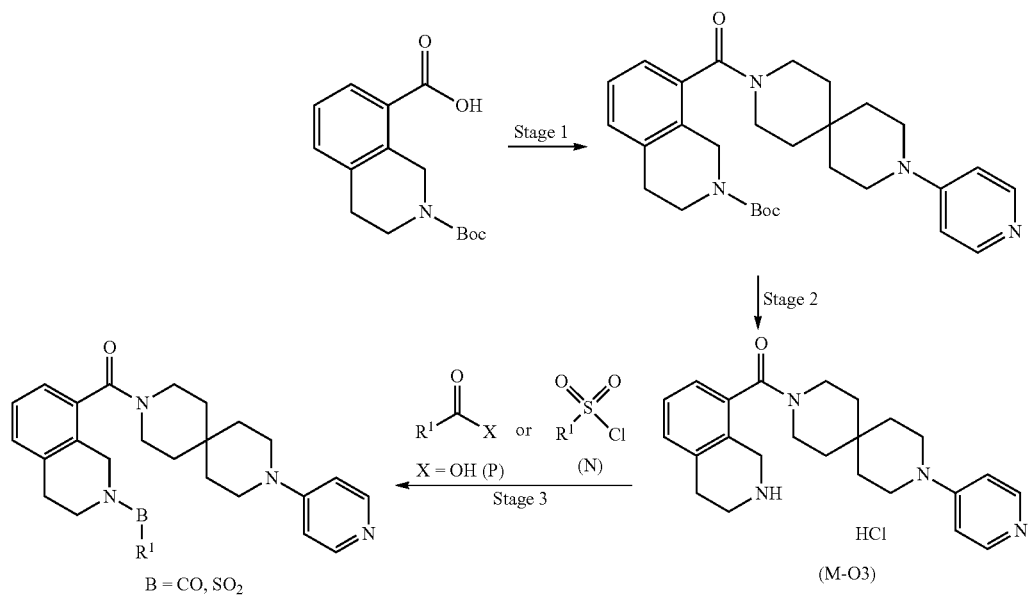

Stage 1: tert-Butyl 8-(9-(pyridin-4-yl)-3,9-diazaspiro[5.5]undecane-3-carbonyl)-3,4-dihydroisoquinoline-2(1H)-carboxylate 3-(Pyridin-4-yl)-3,9-diazaspiro[5.5]undecane dihydrochloride (F-09) (0.49 g, 1.62 mmol) was dissolved in DMF and triethylamine (0.45 g, 3.25 mmol), and 2-(tert-butoxycarbonyl)-1,2,3,4-tetrahydroisoquinoline-8-carboxylic acid (0.45 g, 1.62 mmol) (available commercially from Ennova, for example) was added, followed by benzotriazol-1-yloxytris(dimethylamino)phosphonium hexafluorophosphate (0.93 g, 2.11 mmol) and 4-methylmorpholine (0.53 g, 4.87 mmol). The reaction mixture was stirred for 15 h at RT, and then the solvent was removed in vacuo. The residue was taken up in ethyl acetate and sat. sodium hydrogen carbonate solution, and the phases were separated. The aqueous phase was extracted with ethyl acetate, and the combined organic phases were washed with sat. sodium hydrogen carbonate solution and sat. sodium chloride solution, dried over magnesium sulfate and concentrated in vacuo. The crude product was purified by column chromatography (silica gel, ethyl acetate/methanol 20:1+ammonia solution (25% aq.)). Yield: 0.78 g (98%).

Stage 2: (9-(Pyridin-4-yl)-3,9-diazaspiro[5.5]undecan-3-yl)(1,2,3,4-tetrahydroisoquinolin-8-yl)methanone (M-03)

1.25 M hydrogen chloride in methanol (9.4 ml, 11.7 mmol) was added at RT to a solution of tert-butyl 8-(9-(pyridin-4-yl)-3,9-diazaspiro[5.5]undecane-3-carbonyl)-3,4-dihydroisoquinoline-2(1H)-carboxylate (0.77 g, 1.57 mmol) in methanol (2 ml), and the reaction mixture was refluxed for 1 h. The solvent was removed in vacuo, the residue was taken up in a small amount of ethanol (2 ml), and diethyl ether (50 ml) was added. The mixture was then cooled for 30 min in an ice bath, and the resulting solid was filtered out, washed with diethyl ether and dried in vacuo. Yield: 0.56 g (83%).

Stage 3: General Working Procedure GWP [H]:

The carboxylic acid (P) (1.2 equiv.), O-(1H-benzotriazol-1-yl)-N,N,N',N'-tetramethyluronium tetrafluoroborate (1 equiv.) and 1-hydroxybenzotriazole hydrate (1 equiv.) were placed in tetrahydrofuran, under protecting gas, and stirred for 30 min at RT. A solution of (9-(pyridin-4-yl)-3,9-diazaspiro[5.5]undecan-3-yl)(1,2,3,4-tetrahydroisoquinolin-8-yl)methanone (M-03) (1 equiv.) and diisopropylethylamine (DIPEA) (2 equiv.) in tetrahydrofuran was added, and the reaction mixture was stirred for 15 h at RT. Tetrahydrofuran was then removed in vacuo, the residue was taken up in dichloromethane and sat. sodium hydrogen carbonate solution, and the phases were separated. The aqueous phase was extracted with dichloromethane, and the combined organic phases were then washed with sat. sodium chloride solution, dried over sodium sulfate and concentrated in vacuo. Purification of the crude product was carried out by column chromatography (silica gel).

General Working Procedure GWP [I]:

(9-(Pyridin-4-yl)-3,9-diazaspiro[5.5]undecan-3-yl)(1,2,3,4-tetrahydroisoquinolin-8-yl)methanone (M-03) (1 equiv.) was dissolved in dichloromethane and cooled, and triethylamine (2.5 equiv.) was added. At 0° C., a solution of the sulfonyl chloride (N) (1 equiv.) in dichloromethane was added dropwise, and then the mixture was stirred for 15 h at RT. Sat. sodium hydrogen carbonate solution was added, and the phases were separated. The aqueous phase was extracted with dichloromethane, and the combined organic phases were dried over sodium sulfate and concentrated in vacuo. Purification of the crude product was carried out by column chromatography (silica gel).

| Example No. | Structure | Name | Intermediate (M) | (N), (O), or (P) | Yield | Analyzis (LC/MS)[1] | Synthesised according to/ Comments |
|---|---|---|---|---|---|---|---|
| G-36 | 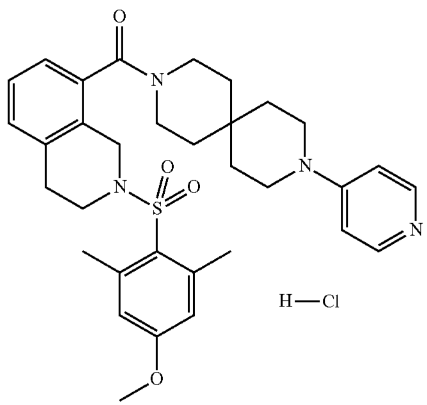 [SMILES: COc1cc(C)c(S(=O)(=O)N2CCc3cccc(C(=O)N4CCC5(CC4)CCN(c4ccncc4)CC5)c3C2)c(C)c1 ; Cl] | (2-(4-Methoxy-2,6-dimethylphenylsulfonyl)-1,2,3,4-tetrahydroisoquinolin-8-yl)(9-(pyridin-4-yl)-diazaspiro[5.5]undecan-3-yl)methanone hydrochloride (G-36) | (9-(Pyridin-4-yl)-3,9-diazaspiro[5.5]undecan-3-yl)(1,2,3,4-tetrahydroisoquinolin-8-yl)methanone hydrochloride (M-03) | 4-Methoxy-2,6-dimethylphenyl-1-sulfonyl chloride (N-06) | 48% (0.16 mmol) | $R_t$ = 3.4 min; m/z = 589.4 [MH]+ | GWP [I] The hydrochloride was precipitated with 2M HCl in diethyl ether. |
| G-37 | 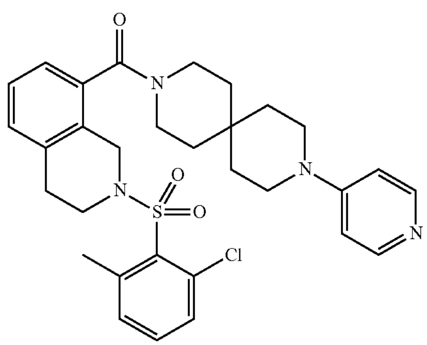 [SMILES: Cc1cccc(Cl)c1S(=O)(=O)N1CCc2cccc(C(=O)N3CCC4(CC3)CCN(c3ccncc3)CC4)c2C1] | (2-(2-Chloro-6-methylphenylsulfonyl)-1,2,3,4-tetrahydroisoquinolin-8-yl)(9-(pyridin-4-yl)-3,9-diazaspiro[5.5]undecan-3-yl)methanone (G-37) | (9-(Pyridin-4-yl)-3,9-diazaspiro[5.5]undecan-3-yl)(1,2,3,4-tetrahydroisoquinolin-8-yl)methanone hydrochloride (M-03) | 2-Chloro-6-methylphenyl-1-sulfonyl chloride (N-07) | 85% (0.26 mmol) | $R_t$ = 3.5 min; m/z = 579.3 [MH]+ | GWP [I] |

| Example No. | Structure | Name | Intermediate (M) | (N), (O), or (P) | Yield | Analyzis (LC/MS)[1] | Synthesised according to/ Comments |
|---|---|---|---|---|---|---|---|
| G-38 | 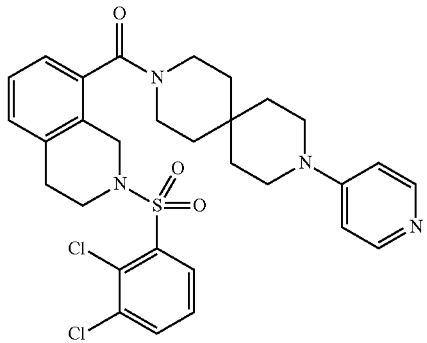 [SMILES: O=C(c1cccc2c1CN(S(=O)(=O)c1cccc(Cl)c1Cl)CC2)N1CCC2(CC1)CCN(c1ccncc1)CC2] | (2-(2,3-Dichlorophenylsulfonyl)-1,2,3,4-tetrahydroisoquinolin-8-yl)(9-(pyridin-4-yl)-3,9-diazaspiro[5.5]undecan-3-yl)methanone (G-38) | (9-(Pyridin-4-yl)-3,9-diazaspiro[5.5]undecan-3-yl)(1,2,3,4-tetrahydroisoquinolin-8-yl)methanone hydrochloride (M-03) | 2,3-Dichlorophenyl-1-sulfonyl chloride (N-10) | 88% (0.27 mmol) | $R_t$ = 3.5 min; m/z = 599.2 [MH]+ | GWP [I] |
| G-44 | 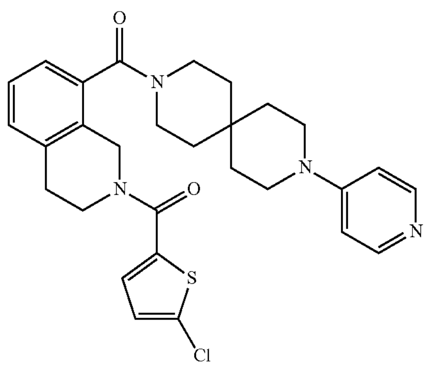 [SMILES: O=C(c1ccc(Cl)s1)N1CCc2cccc(C(=O)N3CCC4(CC3)CCN(c3ccncc3)CC4)c2C1] | [2-(5-Chloro-thiophene-2-carbonyl)-1,2,3,4-tetrahydro-isoquinolin-8-yl]-(9-pyridin-4-yl-3,9-diazaspiro[5.5]undecan-3-yl)-methanone (G-44) | (9-(Pyridin-4-yl)-3,9-diazaspiro[5.5]undecan-3-yl)(1,2,3,4-tetrahydroisoquinolin-8-yl)methanone hydrochloride (M-03) | 5-Chlorothiophene-2-carboxylic acid (P-01) | 80% (0.28 mmol) | $R_t$ = 3.2 min; m/z = 535.3 [MH]+ | GWP [H] |

Exemplary compound G-46: N-(3,4-Dichlorophenyl)-3-(9-pyridin-4-yl-3,9-diazaspiro[5.5]undecane-3-carbonyl)-4,5,6,7-tetrahydro-isoxazolo[4,5-c]pyridine-5-carboxylic acid amide hydrochloride

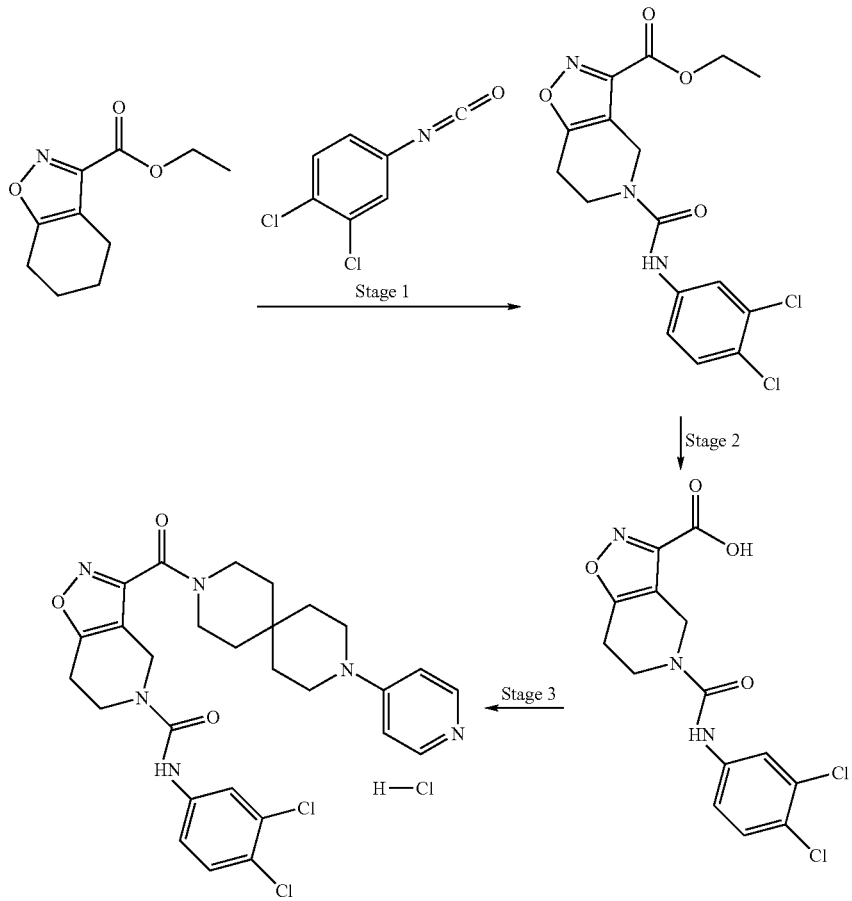

Stage 1: Ethyl 5-(3,4-dichlorophenylcarbamoyl)-4,5,6,7-tetrahydroisoxazolo-[4,5-c]pyridine-3-carboxylate Ethyl 4,5,6,7-tetrahydroisoxazolo[4,5-c]pyridine-3-carboxylate (A-06) (for synthesis see above) (0.5 g, 2.55 mmol) was dissolved in toluene (25 ml), and 1,2-dichloro-4-isocyanatobenzene (0.48 g, 2.55 mmol) was added. The reaction mixture was refluxed for 2 h. Toluene was removed in vacuo, the residue was taken up in ethyl acetate and sat. sodium hydrogen carbonate solution, and the phases were separated. The aqueous phase was extracted with ethyl acetate, and then the combined organic phases were washed with sat. sodium chloride solution, dried over sodium sulfate and concentrated in vacuo. Purification of the crude product was carried out by column chromatography (silica gel, diethyl ether/hexane 2:1). Yield: 1.2 g (>99%)

Stage 2: 5-(3,4-Dichlorophenylcarbamoyl)-4,5,6,7-tetrahydroisoxazolo-[4,5-c]pyridine-3-carboxylic acid Lithium hydroxide monohydrate (56%) (0.25 g, 6.038 mmol) dissolved in water (8 ml) was added to a solution of ethyl 5-(3,4-dichlorophenylcarbamoyl)-4,5,6,7-tetrahydroisoxazolo[4,5-c]pyridine-3-carboxylate (1.2 g, 3.019 mmol) in methanol (25 ml), and the mixture was stirred for 15 h. The solvent was removed in vacuo. The aqueous phase was adjusted to an acidic pH value with dilute HCl solution (aq.) and extracted with ethyl acetate. The organic phase was dried over sodium sulfate, filtered and concentrated in vacuo. The resulting crude product was used directly in the following stage. Yield: 0.94 g (87%).

Stage 3: N-(3,4-Dichlorophenyl)-3-(9-(pyridin-4-yl)-3,9-diazaspiro[5.5]undecane-3-carbonyl)-6,7-dihydroisoxazolo[4,5-c]pyridine-5(4H)-carboxamide (G-46)

3-(Pyridin-4-yl)-3,9-diazaspiro[5.5]undecane dihydrochloride (0.17 g, 0.562 mmol) was dissolved in DMF (8.6 ml) and triethylamine (0.15 ml, 1.123 mmol), and 4-methylmorpholine (0.17 g, 1.685 mmol) was added, followed by 5-(3,4-dichlorophenylcarbamoyl)-4,5,6,7-tetrahydroisoxazolo[4,5-c]pyridine-3-carboxylic acid (0.2 g, 0.562 mmol) and benzotriazol-1-yloxytris(dimethylamino)phosphonium hexafluorophosphate (0.32 g, 1.3 mmol). The reaction mixture was stirred for 15 h at RT, and then the solvent was removed in vacuo. The residue was taken up in ethyl acetate and sat. sodium hydrogen carbonate solution, and the phases were separated. The aqueous phase was extracted with ethyl acetate, and then the combined organic phases were washed with sat. sodium chloride solution and sat. sodium hydrogen carbonate solution, dried over magnesium sulfate and concentrated in vacuo. The crude product was purified by column chromatography (silica gel, ethyl acetate/methanol 20:1+1% ammonia solution (25% aq.)). The purified product was dissolved in methyl ethyl ketone (2 ml); 2 M hydrogen chloride in diethyl ether (4 equiv.) was added at 0° C., and stirring was carried out for 1 h in an ice bath. The solid was filtered out with suction, washed with diethyl ether and dried in vacuo. Yield: 0.16 g (47%). MS, $R_t$=3.4 min; m/z=569.3 $[MH]^+$ Exemplary Compound G-71: [7-(5-Chloro-thiophene-2-carbonyl)-5,6,7,8-tetrahydro-imidazo[1,2-a]pyrazin-2-yl]-(9-pyridin-4-yl-3,9-diazaspiro[5.5]undecan-3-yl)-methanone

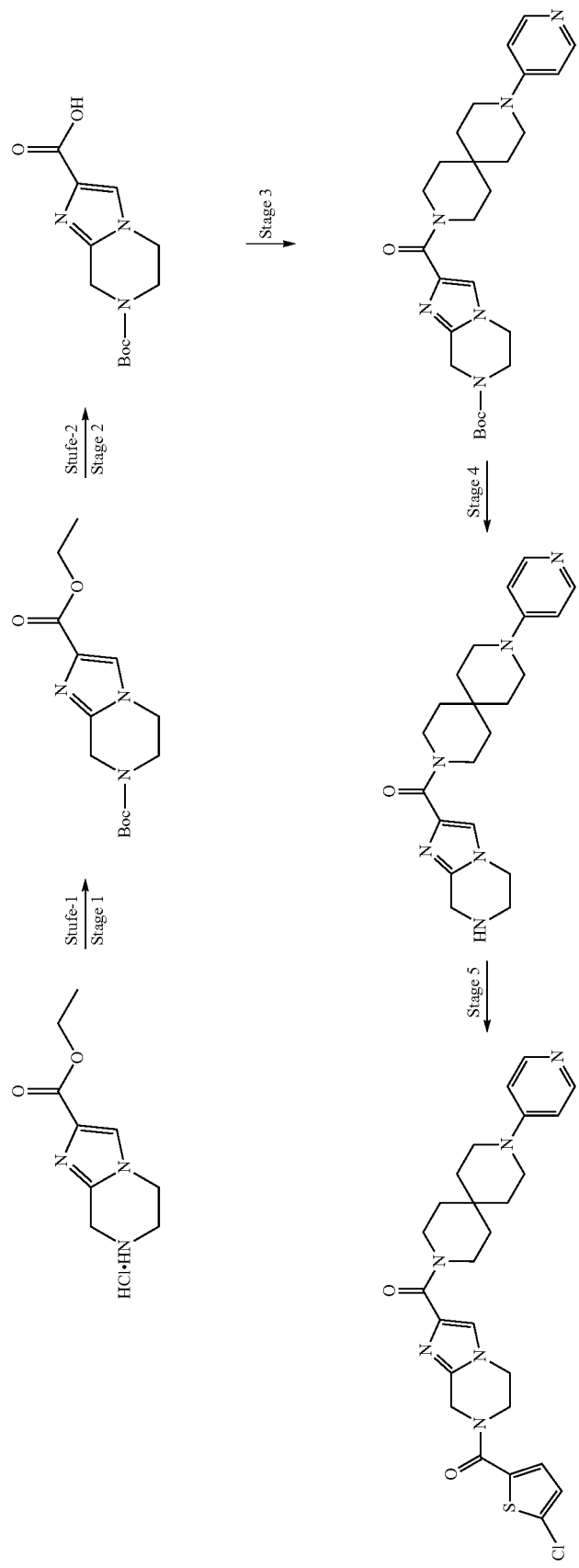

Stage 1: 7-tert-Butyl 2-ethyl 5,6-dihydroimidazo[1,2-a]pyrazine-2,7(8H)-dicarboxylate Et$_3$N (8.33 mmol, 2.5 equiv.) was added at 0° C. to a solution of ethyl 5,6,7,8-tetrahydroimidazo[1,2-a]pyrazine-2-carboxylate hydrochloride (3.33 mmol, 1.0 equiv.) in DCM (25 ml), and the mixture was stirred for 10 min. Boc anhydride (4.99 mmol, 1.5 equiv.) was then added dropwise at 0° C. to the mixture, and stirring was then carried out for 16 h at 25° C. The reaction mixture was diluted with DCM (100 ml) and extracted with water (2×50 ml) and sat. NaCl solution (2×50 ml). The organic phase was dried over Na$_2$SO$_4$ and concentrated in vacuo. The crude product was purified by column chromatography (35% ethyl acetate in hexane) and the desired product was thus obtained in the form of a white solid. Yield: 66%.

Stage 2: 7-(tert-Butoxycarbonyl)-5,6,7,8-tetrahydroimidazo[1,2-a]pyrazine-2-carboxylic acid LiOH.H$_2$O (8.8 mmol, 4.0 equiv.) was added at 0° C. to a solution of 7-tert-butyl 2-ethyl-5,6-dihydroimidazo[1,2-a]pyrazine-2,7(8H)-dicarboxylate (2.2 mmol, 1.0 equiv.) in methanol/water (2.5:1, 35 ml), and the mixture was then stirred for 2 h at 25° C. When the reaction was complete (TLC monitoring), the methanol was removed in vacuo, the residue was diluted with water (40 ml), and extraction with ethyl acetate (2×40 ml) was carried out. The aqueous phase was then adjusted to pH 2-3 with 1N HCl solution, and the resulting solid was filtered out. The solid was taken up in toluene, and the solvent was then removed in vacuo (2×) to yield the desired product in the form of a white solid. Yield: 68%.

Stage 3: tert-Butyl 2-(9-(pyridin-4-yl)-3,9-diazaspiro[5.5]undecane-3-carbonyl)-5,6-dihydroimidazo[1,2-a]pyrazine-7(8H)-carboxylate DIPEA (5.96 mmol, 4.0 equiv.), EDCl (2.24 mmol, 1.5 equiv.) and HOBt (2.24 mmol, 1.5 equiv.) were added at 0° C. to a solution of 7-(tert-butoxycarbonyl)-5,6,7,8-tetrahydroimidazo[1,2-a]pyrazine-2-carboxylic acid (1.49 mmol, 1.0 equiv.) in DCM (20 ml), and the mixture was stirred for 30 min. A solution of 3-(pyridin-4-yl)-3,9-diazaspiro[5.5]undecane (F-19) (1.49 mmol, 1.0 equiv.) in DCM (5 ml) was added at 0° C., and then the reaction mixture was stirred for 16 h at 25° C. The mixture was diluted with DCM (100 ml) and washed with sat. sodium carbonate solution (65 ml), sat. ammonium chloride solution (65 ml), water (50 ml) and sat. sodium chloride solution (50 ml), dried over Na$_2$SO$_4$ and concentrated in vacuo. The resulting crude product was used directly in the following stage. Yield: 63%

Stage 4: (9-(Pyridin-4-yl)-3,9-diazaspiro[5.5]undecan-3-yl)(5,6,7,8-tetrahydroimidazo[1,2-a]pyrazin-2-yl)methanone TFA (2.5 ml) was added to a cooled (0° C.) solution of tert-butyl 2-(9-(pyridin-4-yl)-3,9-diazaspiro[5.5]undecane-3-carbonyl)-5,6-dihydroimidazo[1,2-a]pyrazine-7(8H)-carboxylate (0.86 mmol, 1.0 equiv.) in DCM (10 ml), and the mixture was stirred for 2 h at 25° C. When the reaction was complete (TLC monitoring), the solvent was removed in vacuo in order thus to yield the desired product in the form of a yellow solid. This was used directly in the next stage without further purification.

Stage 5: [7-(5-Chloro-thiophene-2-carbonyl)-5,6,7,8-tetrahydro-imidazo-[1,2-a]pyrazin-2-yl]-(9-pyridin-4-yl-3,9-diazaspiro[5.5]undecan-3-yl)-methanone EDCl (1.29 mmol, 1.5 equiv.), HOBt (1.29 mmol, 1.5 equiv.) and DIPEA (3.44 mmol, 4 equiv.) were added at 0° C. to a solution of 5-chlorothiophene-2-carbonyl chloride (0.86 mmol, 1.0 equiv.) in DCM (20 ml), and the mixture was stirred for 30 min. A solution of tert-butyl 2-(9-(pyridin-4-yl)-3,9-diazaspiro[5.5]undecane-3-carbonyl)-5,6-dihydroimidazo[1,2-a]pyrazine-7(8H)-carboxylate (0.86 mmol, 1.0 equiv.) in DCM (5 ml) was then added, the ice bath was removed, and stirring was carried out for 16 h at 25° C. The reaction mixture was diluted with dichloromethane (100 ml) and washed with sat. sodium carbonate solution (65 ml), sat. ammonium chloride solution (65 ml), water (50 ml) and sat. sodium chloride solution (50 ml), dried over Na$_2$SO$_4$ and concentrated in vacuo. The crude product was purified by column chromatography (8% methanol in DCM) and the desired product was thus obtained in the form of a white solid. Yield: 11%. MS, R$_t$=2.7 min; m/z=525.2 [MH]$^+$ Library Syntheses 7) Parallel Synthesis of the Compounds of the General Formula I According to the Invention

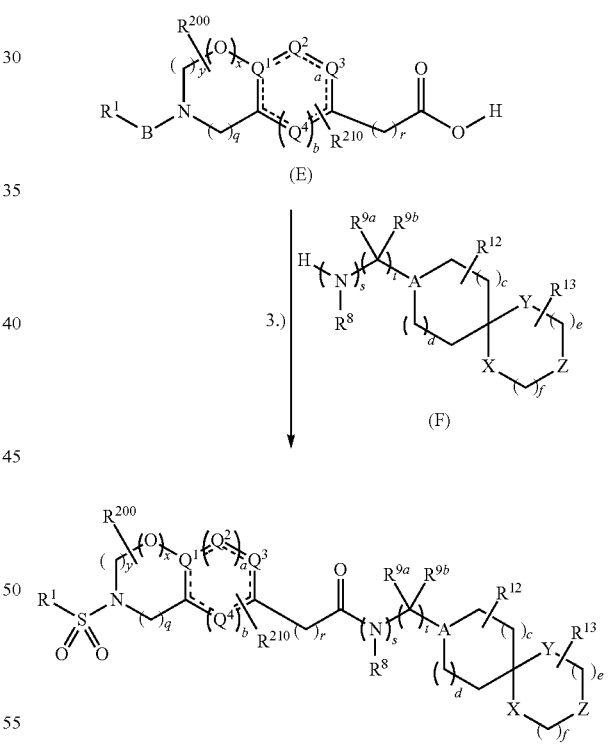

1)

According to the above scheme, the acid structural units E are reacted in parallel synthesis with the amines F to give the spiroamides of the general formula (I) according to the invention. The correlation of product to reagent, structural unit and method is to be found in the synthesis matrix. The crude products of the parallel synthesis were analyzed by HPLC- MS[1] and then purified by means of reverse phase HPLC-MS[1]. The identity of the products could be demonstrated by analytical HPLC-MS measurements[3].

[1] Equipment and methods for HPLC-MS analysis: Parallel synthesis method: HPLC: Waters Alliance 2795 with PDA Waters 2996; MS: ZQ 2000 MassLynx Single Quadrupol MS Detector; column: Atlantis dC18 30×2.1 mm, 3 µm; column temperature: 40° C., eluant A: purified water+0.1% formic acid; eluant B: methanol (gradient grade)+0.1% formic acid; gradient: 0% B to 100% B in 2.3 min, 100% B for 0.4 min, 100% B to 0% B in 0.01 min, 0% B for 0.8 min; flow: 1.0 ml/min; ionisation: ES+, 25V; make up: 100 µl/nnin 70% methanol+0.2% formic acid; UV: 200-400 nm.

[3] Equipment and methods for HPLC-MS analysis: HPLC: Waters Alliance 2795 with PDA Waters 2998; MS: Micromass Quattro Micro™ API; column: Waters Atlantis® T3, 3 µm, 100 Å, 2.1×30 mm; col. temp.: 40° C., eluant A: purified water+0.1% formic acid; eluant B: acetonitrile (gradient grade)+0.1% formic acid; gradient: 0% B to 100% B in 8.8 min, 100% B for 0.4 min, 100% B to 0% B in 0.01 min, 0% B for 0.8 min; flow: 1.0 ml/min; ionisation: ES+, 25 V; make up: 100 µl/min 70% methanol+0.2% formic acid; UV: 200-400 nm.

2.)

To a solution of amine F (100 µM), Hünig base (600 µM) and HOBT (5 µM) in 1 ml of tetrahydrofuran there were added first a solution of the corresponding acid E (100 µM) in 1 ml of tetrahydrofuran and then a solution of TBTU (125 µM) in 1 ml of acetonitrile. The reaction mixture was shaken for 18 h at room temperature. For working up, 3 ml of a ½ saturated sodium hydrogen carbonate solution and 3 ml of ethyl acetate were added to the batches. Further working up was carried out on a Myriad-Allex working-up system (Mettler-Toledo). After thorough mixing, the organic phase was separated off, the aqueous phase was washed with 2×3 ml of ethyl acetate, and the organic phases were combined. Removal of the solvent was carried out in vacuo in a vacuum centrifuge (GeneVac). Final purification was carried out by HPLC-MS[3]. Final analysis was carried out by means of LC-MS[2].

[1] Equipment and methods for HPLC-MS analyzis:

Parallel synthesis method: HPLC: Waters Alliance 2795 with PDA Waters 2996; MS: ZQ 2000 MassLynx Single Quadrupol MS Detector; column : Atlantis dC18 30×2.1 mm, 3µm; column temperature: 40° C., eluant A: purified water +0.1% formic acid; eluant B: methanol (gradient grade) +0.1% formic acid; gradient: 0% B to 100% in B in 2.3 min, 100% B for 0.4 min, 100% B to 0% B in 0.01 min, 0% B for 0.8 min; flow: 1.0 ml/min; ionisation: ES+, 25V; make up: 100 µl/min 70% menthanol +0.2% formic acid; UV: 200-400nm.

[2] Equipment and methods for HPLC-MS purification: prep pump: Waters 2525; make up pump:

Waters 515; auxiliary detector: Waters DAD 2487; MS detector: Waters Micromass ZQ; injector/fraction collector: Waters Sample Manager 2767; gradient: initial: 60% water 40% methanol->12-14.5 min: 0% water 100% methanol->14.5-15 min: 60% water 40% methanol; flow: 35 ml/min column: Macherey-Nagel, C18 Gravity, 100×21 mm, 5µ.

[3] Equipment and methods for HPLC-MS analvzis: HPLC: Waters Alliance 2795 with PDA Waters 2998; MS: Micromass Quattro Micro™ API; column: Waters Atlantis® T3, 3 µm, 100 Å, 2.1×30 mm; col. temp.: 40° C., eluant A: purified water+0.1% formic acid; eluant B: acetonitrile (gradient grade)+0.1% formic acid; gradient: 0% B to 100% B in 8.8 min, 100% B for 0.4 min, 100% B to 0% B in 0.01 min, 0% B for 0.8 min; flow: 1.0 ml/min; ionisation: ES+, 25 V; make up: 100 µl/min 70% methanol+0.2% formic acid; UV: 200-400 nm.

| Example No. | Structure | Name | Amino acid (E) | Amino acid (F) | Yield | Analyzis (LC/MS)[1] |
|---|---|---|---|---|---|---|
| G_CC-006 | 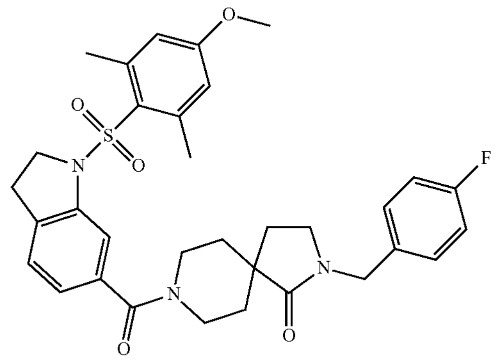 [SMILES: COc1cc(C)c(S(=O)(=O)N2CCc3ccc(C(=O)N4CCC5(CC4)CCN(Cc4ccc(F)cc4)C5=O)cc32)c(C)c1] | 2-(4-Fluorobenzyl)-8-(1-(4-methoxy-2,6-dimethylphenylsulfonyl)indoline-6-carbonyl)-2,8-diazaspiro[4.5]decan-1-one | 1-(4-Methoxy-2,6-dimethylphenylsulfonyl)-indoline-6-carboxylic acid (E-01) | 2-(4-Fluorobenzyl)-2,8-diazaspiro[4.5]decan-1-one hydrochloride (F-17) | | $R_t$ = 2.5 min; m/z = 606.1 [MH]$^+$ |
| G_CC-007 | 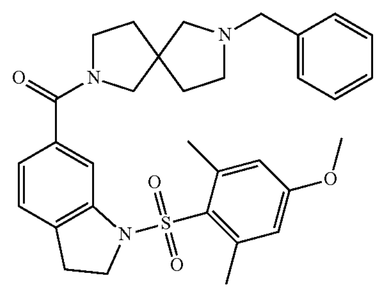 [SMILES: COc1cc(C)c(S(=O)(=O)N2CCc3ccc(C(=O)N4CCC5(CCN(Cc6ccccc6)C5)C4)cc32)c(C)c1] | (7-Benzyl-2,7-diazaspiro[4.4]nonan-2-yl)(1-(4-methoxy-2,6-dimethylphenylsulfonyl)indolin-6-yl)methanone | 1-(4-Methoxy-2,6-dimethylphenylsulfonyl)-indoline-6-carboxylic acid (E-01) | 2-Benzyl-2,7-diazaspiro[4.4]nonane (F-19) | | $R_t$ = 2.0 min; m/z = 560.1 [MH]$^+$ |
| G_CC-008 | 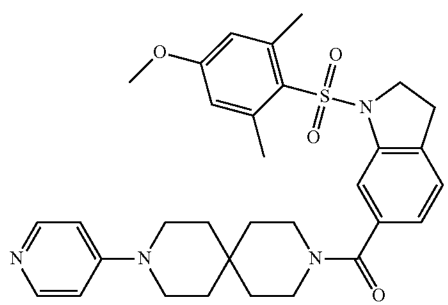 [SMILES: COc1cc(C)c(S(=O)(=O)N2CCc3ccc(C(=O)N4CCC5(CC4)CCN(c4ccncc4)CC5)cc32)c(C)c1] | (1-(4-Methoxy-2,6-dimethylphenylsulfonyl)indolin-6-yl)(9-(pyridin-4-yl)-3,9-diazaspiro[5.5]undecan-3-yl)methanone | 1-(4-Methoxy-2,6-dimethylphenylsulfonyl)-indoline-6-carboxylic acid (E-01) | 3-(Pyridin-4-yl)-3,9-diazaspiro[5.5]-undecane dihydrochloride (F-09) | | $R_t$ = 2.0 min; m/z = 575.1 [MH]$^+$ |

-continued

| Example No. | Structure | Name | Amino acid (E) | Amino acid (F) | Yield | Analyzis (LC/MS)[1] |
|---|---|---|---|---|---|---|
| G_CC-009 | 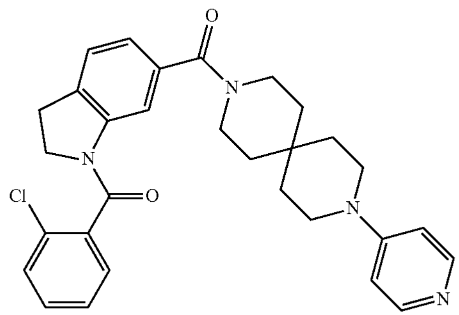 [SMILES: O=C(c1ccc2c(c1)N(C(=O)c1ccccc1Cl)CC2)N1CCC2(CC1)CCN(c1ccncc1)CC2] | (1-(2-Chlorobenzoyl)indolin-6-yl)(9-(pyridin-4-yl)-3,9-diazaspiro[5.5]undecan-3-yl)methanone | 1-(2-Chlorobenzoyl)indoline-6-carboxylic acid (E-02) | 3-(Pyridin-4-yl)-3,9-diazaspiro[5.5]undecane dihydrochloride (F-09) | | $R_t$ = 1.9 min; m/z = 515.1 [MH]$^+$ |
| G_CC-013 | 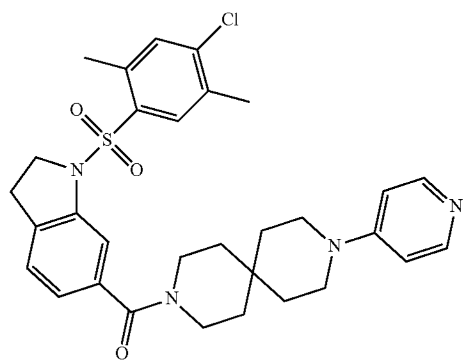 [SMILES: Cc1cc(S(=O)(=O)N2CCc3ccc(C(=O)N4CCC5(CC4)CCN(c4ccncc4)CC5)cc32)c(C)cc1Cl] | (1-(4-Chloro-2,5-dimethylphenylsulfonyl)indolin-6-yl)(9-(pyridin-4-yl)-3,9-diazaspiro[5.5]undecan-3-yl)methanone | 1-(4-Chloro-2,5-dimethylphenylsulfonyl)-indoline-6-carboxylic acid (E-03) | 3-(Pyridin-4-yl)-3,9-diazaspiro[5.5]undecane dihydrochloride (F-09) | | $R_t$ = 2.1 min; m/z = 579.1 [MH]$^+$ |
| G_CC-018 | 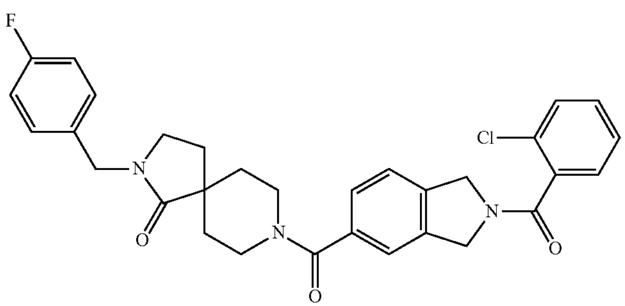 [SMILES: O=C(c1ccc2c(c1)CN(C(=O)c1ccccc1Cl)C2)N1CCC2(CC1)CCN(Cc1ccc(F)cc1)C2=O] | 8-(2-(2-Chlorobenzoyl)isoindoline-5-carbonyl)-2-(4-fluorobenzyl)-2,8-diazaspiro[4.5]decan-1-one | 2-(2-Chlorobenzoyl)isoindoline-5-carboxylic acid (E-05) | 2-(4-Fluorobenzyl)-2,8-diazaspiro[4.5]decan-1-one hydrochloride (F-17) | | $R_t$ = 2.3 min; m/z = 546.1 [MH]$^+$ |

-continued

| Example No. | Structure | Name | Amino acid (E) | Amino acid (F) | Yield | Analyzis (LC/MS)[1] |
|---|---|---|---|---|---|---|
| G_CC-025 | 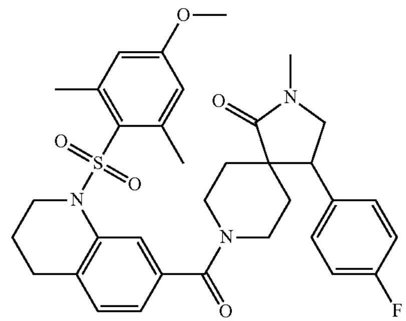 [SMILES: COc1cc(C)c(S(=O)(=O)N2CCCc3ccc(C(=O)N4CCC5(CC4)C(=O)N(C)CC5c4ccc(F)cc4)cc32)c(C)c1] | 4-(4-Fluorophenyl)-8-(1-(4-methoxy-2,6-dimethylphenylsulfonyl)-1,2,3,4-tetrahydroquinoline-7-carbonyl)-2-methyl-2,8-diazaspiro[4.5]decan-1-one | 1-(4-Methoxy-2,6-dimethylphenylsulfonyl)-1,2,3,4-tetrahydroquinoline-7-carboxylic acid (E-07) | 4-(4-Fluorophenyl)-2-methyl-2,8-diazaspiro[4.5]decan-1-one hydrochloride (F-16) | | $R_t$ = 2.5 min; m/z = 620.1 [MH]$^+$ |
| G_CC-026 | 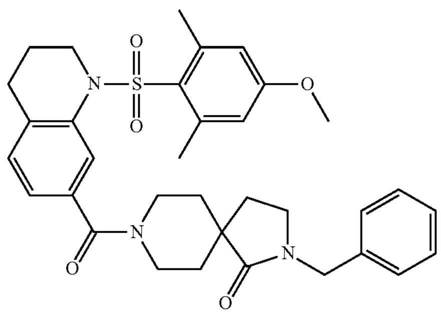 [SMILES: COc1cc(C)c(S(=O)(=O)N2CCCc3ccc(C(=O)N4CCC5(CC4)CCN(Cc4ccccc4)C5=O)cc32)c(C)c1] | 2-Benzyl-8-(1-(4-methoxy-2,6-dimethylphenylsulfonyl)-1,2,3,4-tetrahydroquinoline-7-carbonyl)-2,8-diazaspiro[4.5]decan-1-one | 1-(4-Methoxy-2,6-dimethylphenylsulfonyl)-1,2,3,4-tetrahydroquinoline-7-carboxylic acid (E-07) | 2-Benzyl-2,8-diazaspiro[4.5]decan-1-one hydrochloride (F-18) | | $R_t$ = 2.5 min; m/z = 602.1 [MH]$^+$ |
| G_CC-027 | 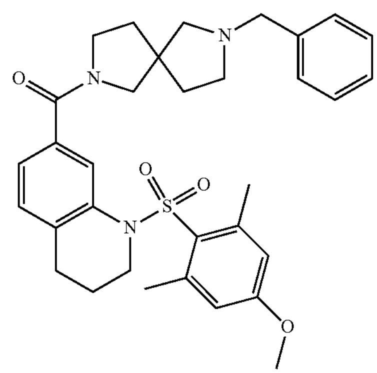 [SMILES: COc1cc(C)c(S(=O)(=O)N2CCCc3ccc(C(=O)N4CCC5(CCN(Cc6ccccc6)C5)C4)cc32)c(C)c1] | (7-Benzyl-2,7-diazaspiro[4.4]nonan-2-yl)(1-(4-methoxy-2,6-dimethylphenylsulfonyl)-1,2,3,4-tetrahydroquinolin-7-yl)methanone | 1-(4-Methoxy-2,6-dimethylphenylsulfonyl)-1,2,3,4-tetrahydroquinoline-7-carboxylic acid (E-07) | 2-Benzyl-2,7-diazaspiro[4.4]nonane (F-19) | | $R_t$ = 2.0 min; m/z = 574.1 [MH]$^+$ |

| Example No. | Structure | Name | Amino acid (E) | Amino acid (F) | Yield | Analyzis (LC/MS)[1] |
|---|---|---|---|---|---|---|
| G_CC-039 | 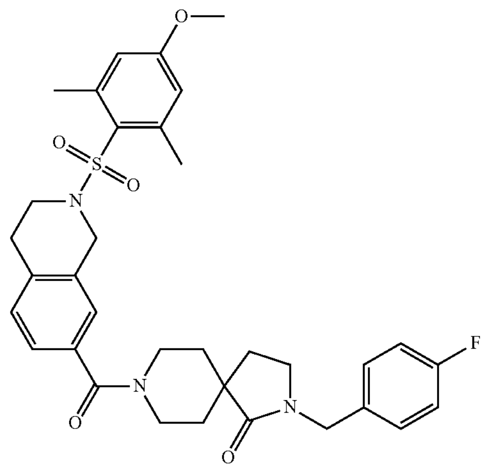 [SMILES: COc1cc(C)c(S(=O)(=O)N2CCc3ccc(C(=O)N4CCC5(CC4)CCN(Cc4ccc(F)cc4)C5=O)cc3C2)c(C)c1] | 2-(4-Fluorobenzyl)-8-(2-(4-methoxy-2,6-dimethylphenylsulfonyl)-1,2,3,4-tetrahydroisoquinoline-7-carbonyl)-2,8-diazaspiro[4.5]decan-1-one | 2-(4-Methoxy-2,6-dimethylphenylsulfonyl)-1,2,3,4-tetrahydroisoquinoline-7-carboxylic acid (E-08) | 2-(4-Fluorobenzyl)-2,8-diazaspiro[4.5]decan-1-one hydrochloride (F-17) | | $R_t$ = 2.5 min; m/z = 620.1 $[MH]^+$ |
| G_CC-040 | 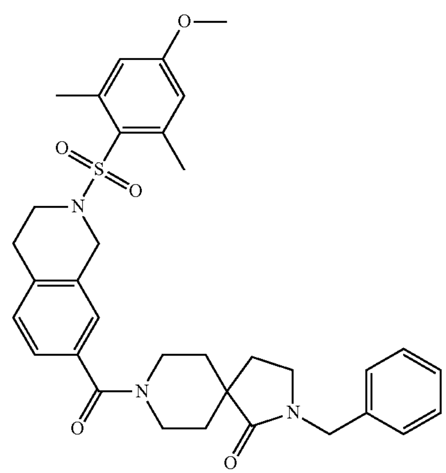 [SMILES: COc1cc(C)c(S(=O)(=O)N2CCc3ccc(C(=O)N4CCC5(CC4)CCN(Cc4ccccc4)C5=O)cc3C2)c(C)c1] | 2-Benzyl-8-(2-(4-methoxy-2,6-dimethylphenylsulfonyl)-1,2,3,4-tetrahydroisoquinoline-7-carbonyl)-2,8-diazaspiro[4.5]decan-1-one | 2-(4-Methoxy-2,6-dimethylphenylsulfonyl)-1,2,3,4-tetrahydroisoquinoline-7-carboxylic acid (E-08) | 2-Benzyl-2,8-diazaspiro[4.5]decan-1-one hydrochloride (F-18) | | $R_t$ = 2.5 min; m/z = 602.1 $[MH]^+$ |

-continued

| Example No. | Structure | Name | Amino acid (E) | Amino acid (F) | Yield | Analyzis (LC/MS)[1] |
|---|---|---|---|---|---|---|
| G_CC-041 | 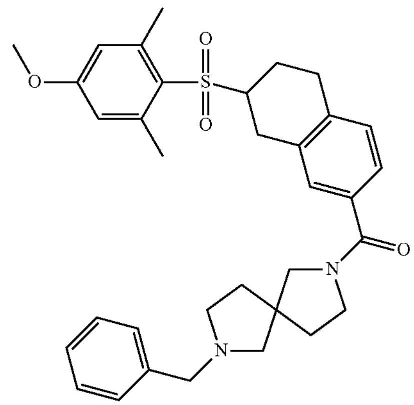 [SMILES: COc1cc(C)c(S(=O)(=O)C2CCc3ccc(C(=O)N4CCC5(CCN(Cc6ccccc6)C5)C4)cc3C2)c(C)c1] | (7-Benzyl-2,7-diazaspiro[4.4]nonan-2-yl)(2-(4-methoxy-2,6-dimethylphenylsulfonyl)-1,2,3,4-tetrahydroisoquinolin-7-yl)methanone | 2-(4-Methoxy-2,6-dimethylphenylsulfonyl)-1,2,3,4-tetrahydroisoquinoline-7-carboxylic acid (E-08) | 2-Benzyl-2,7-diazaspiro[4.4]nonane (F-19) | | $R_t$ = 2.0 min; m/z = 574.2 [MH]$^+$ |
| G_CC-043 | 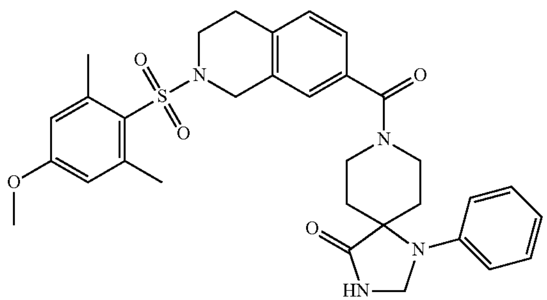 [SMILES: COc1cc(C)c(S(=O)(=O)N2CCc3ccc(C(=O)N4CCC5(CC4)C(=O)NCN5c4ccccc4)cc3C2)c(C)c1] | 8-(2-(4-Methoxy-2,6-dimethylphenylsulfonyl)-1,2,3,4-tetrahydroisoquinoline-7-carbonyl)-1-phenyl-1,3,8-triazaspiro[4.5]decan-4-one | 2-(4-Methoxy-2,6-dimethylphenylsulfonyl)-1,2,3,4-tetrahydroisoquinoline-7-carboxylic acid (E-08) | 1-Phenyl-1,3,8-triazaspiro[4.5]decan-4-one (F-14) | | $R_t$ = 2.4 min; m/z = 589.1 [MH]$^+$ |

| Example No. | Structure | Name | Amino acid (E) | Amino acid (F) | Yield | Analyzis (LC/MS)[1] |
|---|---|---|---|---|---|---|
| G_CC-045 | 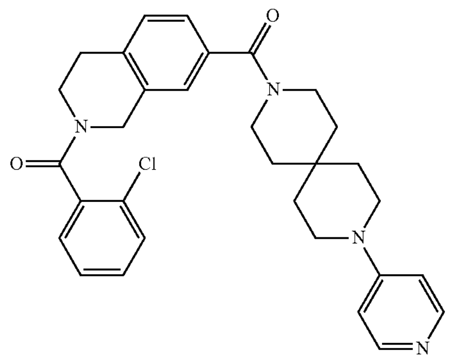 [SMILES: O=C(c1ccc2c(c1)CN(C(=O)c1ccccc1Cl)CC2)N1CCC2(CC1)CCN(c1ccncc1)CC2] | (2-(2-Chlorobenzoyl)-1,2,3,4-tetrahydroisoquinolin-7-yl)(9-(pyridin-4-yl)-3,9-diazaspiro[5.5]undecan-3-yl)methanone | 2-(2-Chlorobenzoyl)-1,2,3,4-tetrahydroisoquinoline-7-carboxylic acid (E-09) | 3-(Pyridin-4-yl)-3,9-diazaspiro[5.5]-undecane dihydrochloride (F-09) | | $R_t$ = 1.9 min; m/z = 529.1 $[MH]^+$ |
| G_CC-053 | 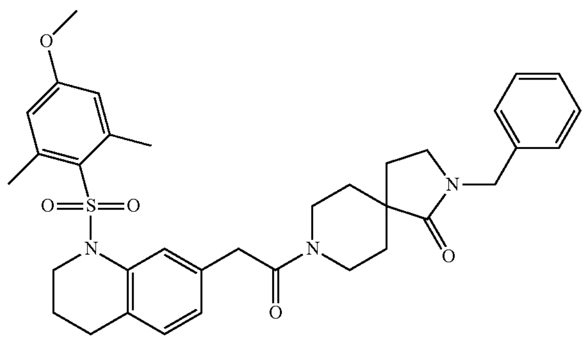 [SMILES: COc1cc(C)c(S(=O)(=O)N2CCCc3ccc(CC(=O)N4CCC5(CC4)CCN(Cc4ccccc4)C5=O)cc32)c(C)c1] | 2-Benzyl-8-(2-(1-(4-methoxy-2,6-dimethylphenylsulfonyl)-1,2,3,4-tetrahydroquinolin-7-yl)acetyl)-2,8-diazaspiro[4.5]decan-1-one | 2-(1-(4-Methoxy-2,6-dimethylphenylsulfonyl)-1,2,3,4-tetrahydroquinolin-7-yl)acetic acid (E-10) | 2-Benzyl-2,8-diazaspiro[4.5]decan-1-one hydrochloride (F-18) | | $R_t$ = 2.5 min; m/z = 616.1 $[MH]^+$ |
| G_CC-054 | 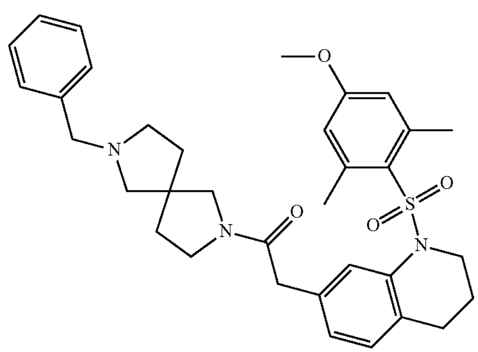 [SMILES: COc1cc(C)c(S(=O)(=O)N2CCCc3ccc(CC(=O)N4CCC5(CCN(Cc6ccccc6)C5)C4)cc32)c(C)c1] | 1-(7-Benzyl-2,7-diazaspiro[4.4]nonan-2-yl)-2-(1-(4-methoxy-2,6-dimethylphenylsulfonyl)-1,2,3,4-tetrahydroquinolin-7-yl)ethanone | 2-(1-(4-Methoxy-2,6-dimethylphenylsulfonyl)-1,2,3,4-tetrahydroquinolin-7-yl)acetic acid (E-10) | 2-Benzyl-2,7-diazaspiro[4.4]nonane (F-19) | | $R_t$ = 2.0 min; m/z = 588.2 $[MH]^+$ |

-continued

| Example No. | Structure | Name | Amino acid (E) | Amino acid (F) | Yield | Analyzis (LC/MS)[1] |
|---|---|---|---|---|---|---|
| G_CC-055 | 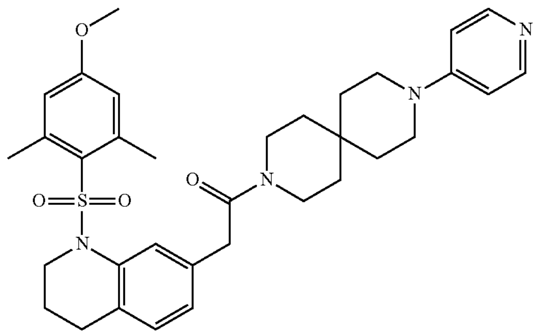 [SMILES: COc1cc(C)c(S(=O)(=O)N2CCCc3ccc(CC(=O)N4CCC5(CC4)CCN(c4ccncc4)CC5)cc32)c(C)c1] | 2[1-[(4-Methoxy-2,6-dimethyl-phenyl)sulfonyl]-1,2,3,4-tetrahydro-quinolin-7-yl]-1-(3-pyridin-4-yl-3,9-diazaspiro[5.5]undecan-9-yl)-ethanone | 2-(1-(4-Methoxy-2,6-dimethylphenylsulfonyl)-1,2,3,4-tetrahydroquinolin-7-yl)acetic acid (E-10) | 3-(Pyridin-4-yl)-3,9-diazaspiro[5.5]undecane dihydrochloride (F-09) | | $R_t$ = 2.0 min; m/z = 603.2 [MH]$^+$ |
| G_CC-056 | 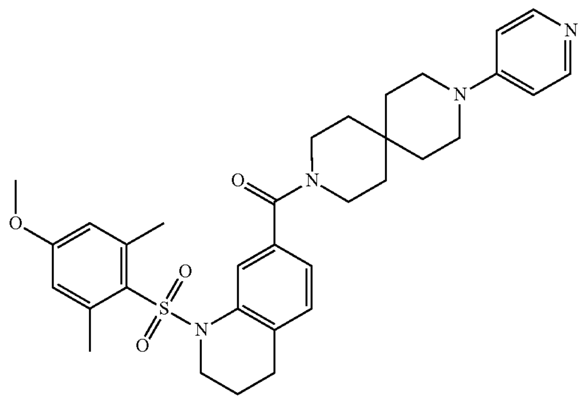 [SMILES: COc1cc(C)c(S(=O)(=O)N2CCCc3ccc(C(=O)N4CCC5(CC4)CCN(c4ccncc4)CC5)cc32)c(C)c1] | [1-[(4-Methoxy-2,6-dimethyl-phenyl)sulfonyl]-1,2,3,4-tetrahydro-quinolin-7-yl]-(3-pyridin-4-yl-3,9-diazaspiro[5.5]undecan-9-yl)-methanone | 1-(4-Methoxy-2,6-dimethylphenylsulfonyl)-1,2,3,4-tetrahydroquinoline-7-carboxylic acid (E-07) | 3-(Pyridin-4-yl)-3,9-diazaspiro[5.5]undecane dihydrochloride (F-09) | | $R_t$ = 2.0 min; m/z = 589.2 [MH]$^+$ |

Pharmacological Data

The pharmacological data were determined as described above. The following data are given by way of example in the table below:

| Compound | B1R antagonism, rat [10 μM] % inhibition | B1R antagonism, human [10 μM] % inhibition |
|---|---|---|
| G-04 | 99 | 97 |
| G-09 | 96 | 96 |
| G-10 | 80 | 97 |
| G-11 | 99 | 99 |
| G-12 | 102 | 100 |
| G-13 | 94 | 100 |
| G-14 | 97 | 97 |
| G-15 | 81 | 66 |
| G-16 | 100 | 98 |
| G-17 | 89 | 97 |
| G-18 | 98 | 97 |
| G-19 | 100 | 100 |
| G-20 | 102 | 100 |
| G-21 | 101 | 95 |
| G-24 | 100 | 99 |
| G-25 | 98 | 100 |
| G-26 | 95 | 99 |
| G-30 | 98 | 46 |
| G-32 | 102 | 91 |
| G-33 | 73 | 65 |
| G-34 | 86 | 18 |
| G-35 | 101 | 79 |
| G-36 | 99 | 99 |
| G-37 | 90 | 99 |
| G-38 | 91 | 97 |
| G-39 | 89 | 99 |
| G-40 | 102 | 100 |
| G-41 | 90 | 99 |
| G-42 | 102 | 100 |
| G-43 | 102 | 99 |
| G-44 | 62 | 99 |
| G-45 | 97 | 97 |
| G-46 | 57 | 35 |
| G-47 | 80 | 72 |
| G-48 | 95 | 73 |
| G-49 | 106 | 99 |
| G-50 | 91 | 69 |
| G-51 | 106 | 100 |
| G-52 | 106 | 98 |
| G-53 | 105 | 95 |
| G-54 | 55 | 57 |
| G-55 | 94 | 92 |
| G-56 | 90 | 87 |
| G-57 | 101 | 100 |
| G-58 | 91 | 100 |
| G-59 | 95 | 86 |
| G-60 | 91 | 98 |
| G-61 | 91 | 77 |
| G-62 | 78 | 44 |
| G-63 | 80 | 83 |
| G-64 | 96 | 59 |
| G-66 | 100 | 98 |
| G-67 | 101 | 100 |
| G-68 | 81 | 90 |
| G-69 | 70 | 99 |
| G-70 | 101 | 88 |
| G-71 | 80 | 91 |
| G-72 | 104 | 100 |
| G-73 | 13 | 85 |
| G_CC-006 | 71 | |
| G_CC-007 | 59 | |
| G_CC-008 | 100 | |
| G_CC-009 | 78 | |
| G_CC-013 | 99 | 87 |
| G_CC-018 | 51 | |
| G_CC-025 | 51 | |
| G_CC-026 | 58 | |
| G_CC-027 | 58 | |
| G_CC-039 | 71 | |
| G_CC-040 | 70 | |
| G_CC-041 | 64 | |
| G_CC-043 | 74 | |
| G_CC-045 | 92 | |
| G_CC-053 | 84 | |
| G_CC-054 | 71 | |
| G_CC-055 | 98 | 96 |
| G_CC-056 | 100 | 98 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to the formula:

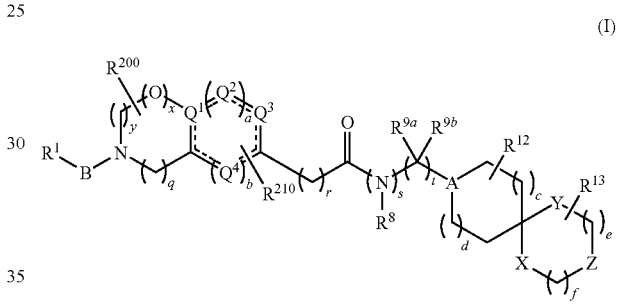

(I)

wherein

B represents C(=O), S(=O)$_2$ or —C(=O)—N(R$^4$), wherein the nitrogen atom thereof is bonded to R$^1$;

q represents 0;

y represents 2 or 3; or q represents 1 and y represents 1 or 2;

r represents 0 or 1;

R$^1$ represents aryl, heteroaryl or an aryl or heteroaryl bonded via a C$_{1-3}$-alkylene group or C$_{2-6}$-alkenylene group, wherein aryl and heteroaryl in each case optionally may be fused with a 4-, 5-, 6- or 7-membered cycle or heterocycle, wherein the cycle and heterocycle in each case is saturated or at least monounsaturated but is not aromatic and in each case optionally may be substituted on one or more of its carbon ring members by one or more substituents independently selected from the group consisting of F, Cl, Br, I, —CF$_3$, —O—CF$_3$, C$_{1-6}$-alkyl and O—C$_{1-6}$-alkyl and wherein the heterocycle contains one or more heteroatoms or heteroatom groups independently selected from the group consisting of N, NR$^{50}$, O, S, S=O and S(=O)$_2$; wherein R$^{50}$ denotes H, C$_{1-6}$-alkyl, —C(=O)—R$^{51}$, C$_{3-8}$-cycloalkyl, aryl, heteroaryl or a C$_{3-8}$-cycloalkyl, aryl or heteroaryl bonded via a C$_{1-3}$-alkylene group, and R$^{51}$ denotes C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group;

R$^4$ represents H, C$_{1-6}$-alkyl, aryl or an aryl bonded via a C$_{1-3}$-alkylene group;

$R^{200}$ represents from 0 to 4 substituents independently selected from the group consisting of $C_{1-6}$-alkyl, F, Cl, $CF_3$ and $OCF_3$;

$R^{210}$ represents from 0 to 4 substituents independently selected from the group consisting of $C_{1-6}$-alkyl, O—$C_{1-6}$-alkyl, F, Cl, $CF_3$ and $OCF_3$;

c, d, e and f each independently denote 0, 1 or 2;

$R^{12}$ and $R^{13}$ each independently represent from 0 to 4 substituents each independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent $R^{13}$ form a fused aryl or heteroaryl ring structure;

X represents $CR^{14a}R^{14b}$, $NR^{15}$ or O;

Y represents $CR^{16a}R^{16b}$, $NR^{17}$ or O;

with the proviso that if Y is $NR^{17}$, then X is not $NR^{15}$, and with the proviso that X and Y are not simultaneously O;

wherein $R^{14a}$, $R^{14b}$, $R^{16a}$ and $R^{16b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group, and/or $R^{14a}$ and $R^{14b}$ and/or $R^{16a}$ and $R^{16b}$, respectively, together may represent =O;

$R^{15}$ and $R^{17}$ each independently represent H, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group;

Z represents $CR^{18a}R^{18b}$, $NR^{19}$ or O; or if X represents O and f represents 0, then Z may denote —(C($R^{124}$)=C($R^{125}$))— or (=N($CR^{126}$))— wherein the N atom is singly bonded to the O atom, and wherein $R^{124}$ and $R^{125}$, together with the carbon atoms joining them, form a fused aryl or heteroaryl ring structure;

$R^{126}$ represents H, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group;

$R^{18a}$ represents H, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group, or $R^{18a}$ represents a structure corresponding to formula (II):

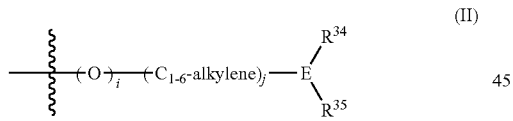

(II)

wherein i and j each independently represent 0 or 1;

E represents N or CH, with the proviso that if i is 1 and j is 0, then E is CH;

$R^{34}$ and $R^{35}$ each independently denote H, $C_{1-6}$-alkyl, $C_{3-8}$-cycloalkyl, aryl or heteroaryl, or an aryl, heteroaryl or $C_{3-8}$-cycloalkyl group bonded via a $C_{1-3}$-alkylene group; or $R^{34}$ and $R^{35}$ together with E form a 5- or 6-membered aryl or heteroaryl ring structure; or $R^{34}$ and $R^{35}$ together with E form a saturated heterocycle corresponding to formula (III):

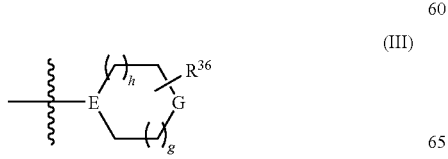

(III)

wherein h and g each independently denote 0, 1 or 2;

G represents $CR^{37a}R^{37b}$, $NR^{38}$, O, S, S=O or S(=O)$_2$, with the proviso that if E is CH, then G is not $CR^{37a}R^{37b}$;

$R^{36}$ represents from 0 to 4 substituents each independently selected from the group consisting of F, Cl, Br, I, OH, SH, =O, O—$C_{1-6}$-alkyl, $C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent substituents $R^{36}$ together represent a fused aryl or heteroaryl ring structure;

$R^{37a}$ and $R^{37b}$ each independently denote H, F, Cl, Br, I, OH, SH, =O, O—$C_{1-6}$-alkyl, $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group;

$R^{38}$ represents H, $C_{1-6}$-alkyl, $C_{3-8}$-cycloalkyl, aryl or heteroaryl, or an aryl, heteroaryl or $C_{3-8}$-cycloalkyl group bonded via a $C_{1-3}$-alkylene group;

$R^{18b}$ represents H, OH, $C_{1-6}$-alkyl, $C_{3-8}$-cycloalkyl, O—$C_{1-6}$-alkyl, O—($C_{3-8}$-cycloalkyl), ($C_{1-6}$-alkylene)-O—$C_{1-6}$-alkyl, ($C_{1-6}$-alkylene)-O—($C_{3-8}$-cycloalkyl), aryl, heteroaryl, O-aryl or O-heteroaryl, or an aryl, O-aryl, heteroaryl or O-heteroaryl group bonded via a $C_{1-6}$-alkylene group; or $R^{18b}$ represents a structure corresponding to formula (IV):

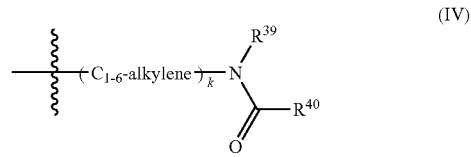

(IV)

wherein

K represents 0 or 1;

$R^{39}$ represents H, $C_{1-6}$-alkyl, $C_{3-8}$-cycloalkyl, aryl or heteroaryl, or a $C_{3-8}$-cycloalkyl, aryl or heteroaryl group bonded via a $C_{1-3}$-alkylene group;

$R^{40}$ represents $C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group; or $R^{39}$ and $R^{40}$ together with the N—C(=O)— group joining them form a ring structure corresponding to formula (V):

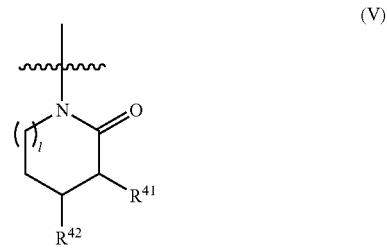

(V)

wherein l represents 0, 1 or 2; and $R^{41}$ and $R^{42}$ together with the carbon atoms joining them form a fused aryl or heteroaryl ring structure;

$R^{19}$ represents H; or $(P)_z$—$R^{22}$, wherein
z represents 0 or 1;
P represents (C=O), S(=O)$_2$ or C(=O)—N(R$^{24}$), wherein the N atom is bonded to R$^{22}$, and R$^{24}$ represents H, $C_{1-6}$-alkyl, $C_{3-8}$-cycloalkyl, or an aryl, heteroaryl or $C_{3-8}$-cycloalkyl group bonded via a $C_{1-3}$-alkylene group;
$R^{22}$ represents $C_{1-6}$-alkyl, aryl or heteroaryl, or an aryl or heteroaryl group bonded via a $C_{1-6}$-alkylene group; or
$R^{22}$ represents a structure corresponding to formula (VI):

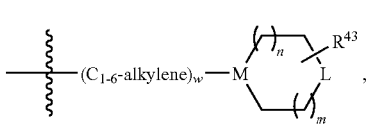

wherein
n represents 0, 1 or 2;
m represents 0, 1 or 2;
w represents 0 or 1;
M represents CH or N;
with the proviso that if P is C(=O)—NR$^{24}$ and w is 0, then M is CH; and
with the proviso that if z and w are both 0, then M is CH;
$R^{43}$ represents from 0 to 4 substituents each independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group; and/or two adjacent substituents $R^{43}$ together represent a fused aryl or heteroaryl ring structure;
L represents CR$^{44a}$R$^{44b}$, NR$^{45}$, O, S, S=O or S(=O)$_2$; wherein
$R^{44a}$ and $R^{44b}$ each independently represent H, F, Cl, Br, I, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group; or
$R^{44a}$ and $R^{44b}$ together represent =O; and
$R^{45}$ represents H, $C_{1-6}$-alkyl, $C_{3-8}$-cycloalkyl, aryl or heteroaryl, or an aryl, heteroaryl or $C_{3-8}$-cycloalkyl group bonded via a $C_{1-3}$-alkylene group;
wherein the aforementioned $C_{1-6}$-alkyl, $C_{1-3}$-alkylene, $C_{1-6}$-alkylene, $C_{2-6}$-alkenylene or $C_{3-8}$-cycloalkyl, in each case can be unsubstituted or mono- or polysubstituted by identical or different radicals, selected from the group consisting of F, Cl, Br, CF$_3$, OCF$_3$, CN NH$_2$, NH—$C_{1-6}$-alkyl, NH—$C_{1-6}$-alkylene-OH, $C_{1-6}$-alkyl, N($C_{1-6}$-alkyl)2, N($C_{1-6}$-alkylene-OH)2, NO$_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, OC$_2$H, CO2-$C_{1-6}$-alkyl, phenyl, pneyonxy, benzyl, naphthyl, furyl, thienyl and pyridinyl, and the abovementioned radicals aryl and heteroaryl groups in each case may be unsubstituted, monosubstituted or identically or differently polysubstituted by radicals selected from the group consisting of F, Cl, CN, CF$_3$, CH$_3$, OCH$_3$ and OCF$_3$, and the aforementioned $C_{1-6}$-alkyl, $C_{1-3}$-alkylene, $C_{1-6}$-alkylene and $C_{2-6}$-alkenylene groups in each case may be branched or unbranched;
or a physiologically acceptable salt thereof.

2. A compound according to claim 1, wherein said compound is in the form of a mixture of stereoisomers.

3. A compound according to claim 2, wherein said mixture is a racemic mixture.

4. A compound according to claim 1, wherein $R_1$ represents phenyl, naphthyl, chromanyl, indolyl, benzofuranyl, benzothiophenyl, 5,6-dihydro-4H-cyclopenta[b]thiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl, or a phenyl or naphthyl group bonded via a $C_{1-3}$-alkylene group or a $C_{2-3}$-alkenylene group,
wherein the foregoing aryl or heteroaryl groups may be unsubstituted, monosubstituted or identically or differently polysubstituted by substituents independently selected from the group consisting of —O—$C_{1-3}$-alkyl, $C_{1-6}$-alkyl, F, Cl, Br, I, CF$_3$, OCF$_3$, OH, SH, phenyl, phenoxy, naphthyl, furyl, thienyl and pyridinyl; and
wherein the foregoing alkylene and alkenylene groups in each case may be unsubstituted, monosubstituted or identically or differently polysubstituted by substituents independently selected from the group consisting of —O—$C_{1-3}$-alkyl, F, Cl, Br, I, CF$_3$, OCF$_3$, OH, SH, phenyl, phenoxy, naphthyl, furyl, thienyl and pyridinyl.

5. A compound according to claim 4, wherein $R^1$ represents phenyl, naphthyl, chromanyl, benzothiophenyl, 5,6-dihydro-4H-cyclopenta[b]thiophenyl, benzooxadiazolyl, thienyl, pyridinyl, imidazothiazolyl, dibenzofuranyl, or a phenyl group bonded via a $C_{1-3}$-alkylene group or a $C_{2-3}$-alkenylene group.

6. A compound according to claim 1, wherein said compound is in the form of an isolated stereoisomer.

7. A compound according to claim 1, wherein B represents S(=O)$_2$.

8. A compound according to claim 1, wherein
X represents CR$^{14a}$R$^{14b}$, NR$^{15}$ or O;
Y represents CR$^{16a}$R$_{6b}$;
$R^{14a}$, $R^{14b}$, $R^{16a}$ and $R^{16b}$ each independently denote H, F, Cl, OH, $C_{1-6}$-alkyl, O—$C_{1-6}$-alkyl, $C_{3-8}$-cycloalkyl, aryl or heteroaryl, or a $C_{3-8}$-cycloalkyl, aryl or heteroaryl group bonded via a $C_{1-6}$-alkylene group, and/or R$^{14a}$ and R$^{14b}$ and/or R$^{16a}$ and R$^{16b}$, respectively, may together represent =O;
$R^{15}$ represents H, $C_{1-6}$-alkyl, $C_{3-8}$-cycloalkyl, aryl or heteroaryl, or denotes a $C_{3-8}$-cycloalkyl, aryl or heteroaryl group bonded via a $C_{1-6}$-alkylene group;
Z represents CR$^{18a}$R$^{18b}$ or NR$^{19}$; or
if X is O and f is 0, then Z is =(N(CR$^{126}$))—, wherein
the N atom is singly bonded to the O atom, and
$R^{126}$ represents H, $C_{1-6}$-alkyl, $C_{3-8}$-cycloalkyl, aryl or heteroaryl, or denotes a $C_{3-8}$-cycloalkyl, aryl or heteroaryl group bonded via a $C_{1-6}$-alkylene group;
$R^{18a}$ represents H, $C_{1-6}$-alkyl, $C_{3-8}$-cycloalkyl, —NH($C_{1-6}$-alkyl), —N($C_{1-6}$-alkyl)$_2$, phenyl, pyridyl, imidazolyl, triazolyl, pyrimidyl, thiazolyl or thienyl, in each case unsubstituted or mono- or poly-substituted; or represents phenyl, pyridyl, imidazolyl, triazolyl, pyrimidyl, thiazolyl or thienyl group bonded via a —(O)$_{0-1}$-$C_{1-6}$-alkylene group, in each case unsubstituted or mono- or poly-substituted; or $R^{18a}$ represents a structure corresponding to formula (VII):

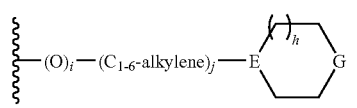

wherein
i represents 0 or 1;
j represents 0 or 1;
h represents 0 or 1;
E represents N or CH; with the proviso that if i is 1 and j is 0, then E is CH;
G represents $CR^{37a}R^{37b}$ or $NR^{38}$; wherein
  $R^{37a}$ and $R^{37b}$ each independently represent H, F or $C_{1-6}$-alkyl, in each case unsubstituted or mono- or poly-substituted by identical or different substituents;
  $R^{38}$ represents H; $C_{1-6}$-alkyl, $C_{3-6}$-alkyl or pyridyl;
$R^{18b}$ represents H, OH, $C_{1-6}$-alkyl, phenyl, pyridyl, imidazolyl, triazolyl, pyrimidyl, thiazolyl or thienyl, in each case unsubstituted or mono- or poly-substituted by identical or different substituents; phenyl, pyridyl, imidazolyl, triazolyl, pyrimidyl, thiazolyl or thienyl bonded via a $C_{1-6}$-alkylene group, in each case unsubstituted or mono- or poly-substituted by identical or different substituents; O-phenyl or O-pyridyl, in each case unsubstituted or mono- or poly-substituted by identical or different substituents; or $C_{1-6}$-alkylene-NH(C=O)-bridged phenyl, pyridyl or thienyl, in each case unsubstituted or mono- or poly-substituted by identical or different substituents;
$R^{19}$ represents H, $C_{1-6}$-alkyl, $C_{3-8}$-cycloalkyl, —(C=O)-$C_{1-6}$-alkyl, phenyl, pyridyl, thienyl, thiazolyl, triazolyl, pyrimidinyl or imidazolyl; in each case unsubstituted or mono- or poly-substituted by identical or different substituents; or phenyl, pyridyl, thienyl, thiazolyl, pyrimidinyl, triazolyl or imidazolyl bonded via a $C_{1-6}$-alkylene group, in each case unsubstituted or mono- or poly-substituted by identical or different substituents; or
$R^{19}$ represents a structure corresponding to formula (VIII):

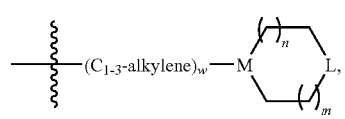

wherein
w represents 0 or 1;
n represents 0 or 1;
m represents 0 or 1;
M represents CH or N, with the proviso that if w is 0, then M is CH;
L represents $CR^{44a}R^{44b}$ or $NR^{45}$; wherein
  $R^{44a}$ and $R^{44b}$ each independently represent H, F or $C_{1-6}$-alkyl, in each case unsubstituted or mono- or poly-substituted by identical or different substituents; and
  $R^{45}$ represents H, $C_{1-6}$-alkyl, $C_{3-6}$-alkyl or pyridyl.

9. A compound according to claim 1, wherein the following partial structure:

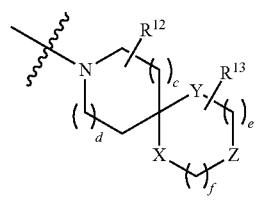

is selected from the group consisting of:

SP 1
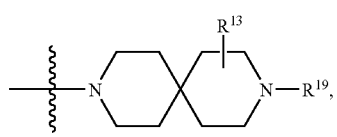

SP 2
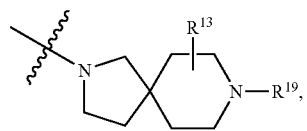

SP 3
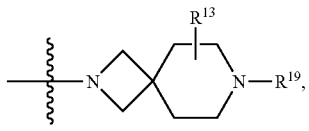

SP 4
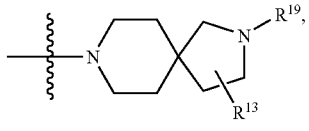

SP 5
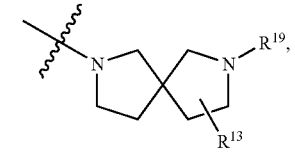

SP 6
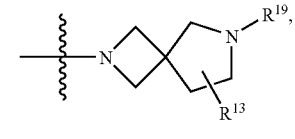

SP 7
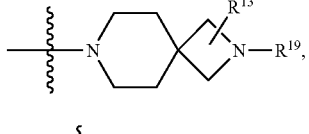

SP 8
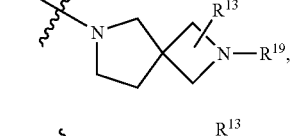

SP 9
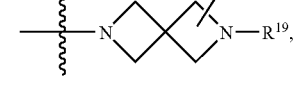

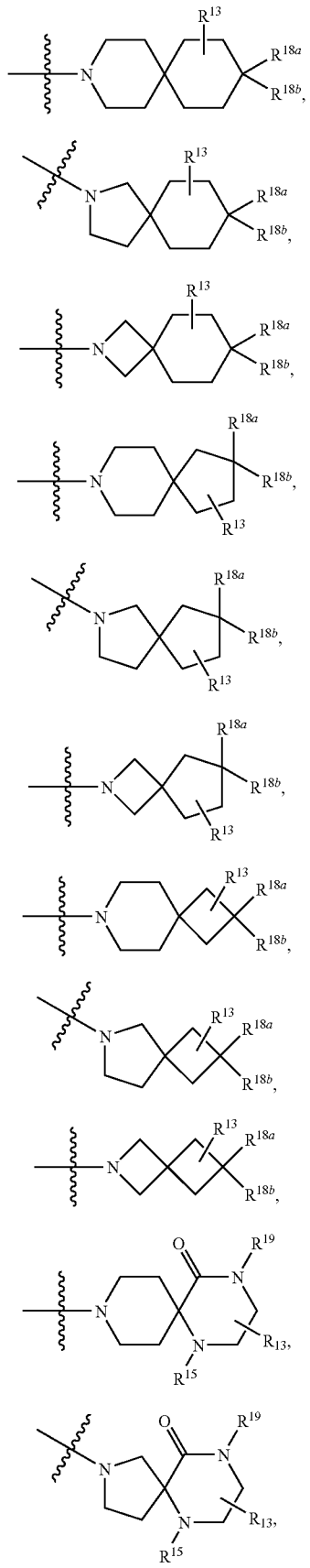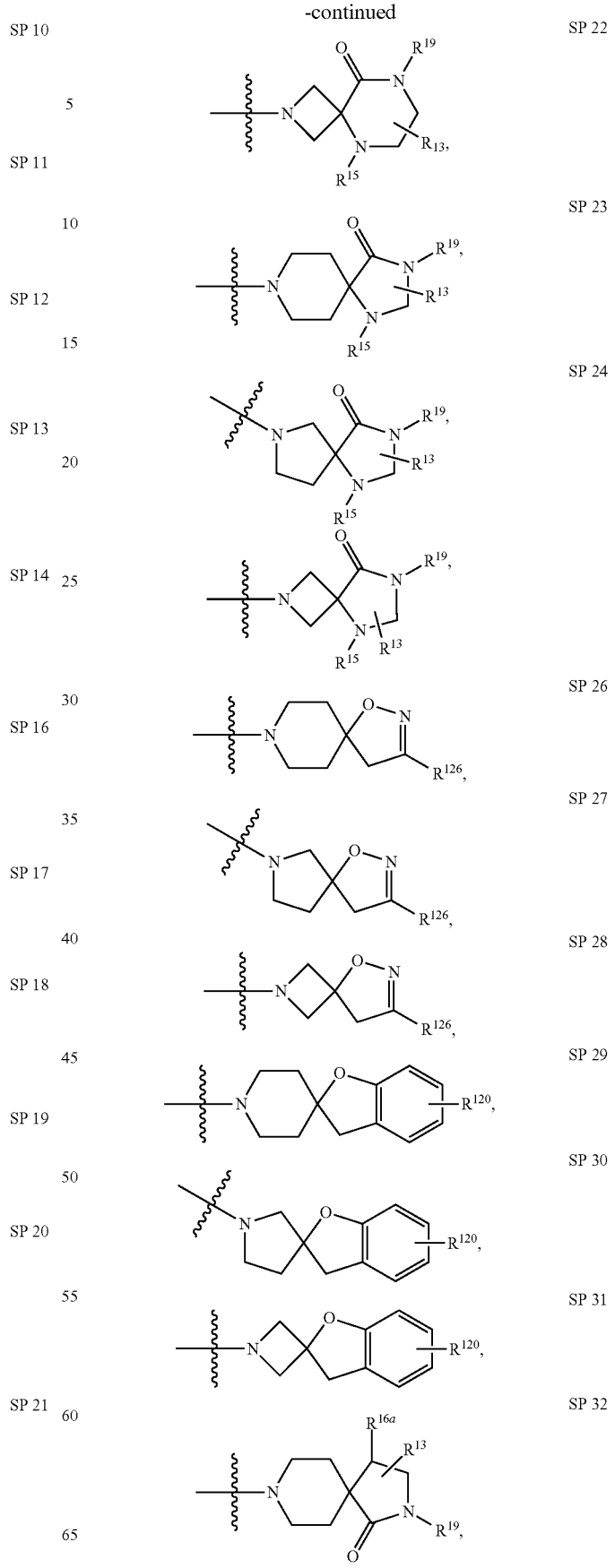

-continued

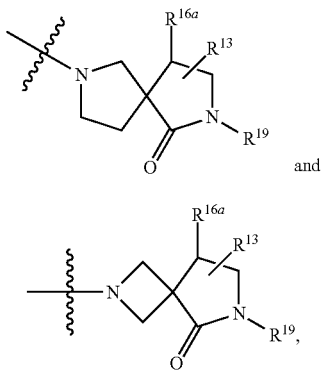

SP 33 and

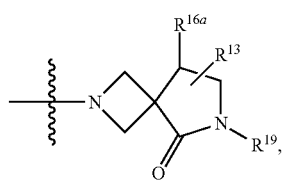

SP 34 wherein
R<sup>13</sup> represents 1 or 2 substituents selected from the group consisting of H and unsubstituted, monosubstituted or identically or differently polysubstituted phenyl; and/or two $R^{13}$ together form =O and/or two adjacent $R^{13}$ together form a fused aryl or heteroaryl ring structure, in each case unsubstituted or mono-or poly-substituted by identical or different substituents;
$R^{15}$ represents H, $C_{1-6}$-alkyl, $C_{3-8}$-cycloalkyl, phenyl or pyridyl, in each case unsubstituted or mono- or poly-substituted by identical or different substituents; or phenyl or pyridyl bonded via a $C_{1-6}$-alkylene group and in each case unsubstituted or mono- or poly-substituted by identical or different substituents;
$R^{16a}$ represents H, $C_{1-6}$-alkyl, phenyl or pyridyl, in each case unsubstituted or mono- or poly-substituted by identical or different substituents;
$R^{18a}$ represents H, $C_{1-6}$-alkyl, $C_{3-8}$-cycloalkyl, $N(C_{1-6}$-alkyl)$_2$, $NH(C_{1-6}$-alkyl), azetidinyl, pyrrolidinyl, piperidinyl, 4-($C_{1-6}$-alkyl)-piperazinyl, phenyl or pyridyl, in each case unsubstituted or mono- or poly-substituted by identical or different substituents; or $N(C_{1-6}$-alkyl)$_2$, $NH(C_{1-6}$-alkyl), azetidinyl, pyrrolidinyl, piperidinyl, 4-($C_{1-6}$-alkyl)-piperazinyl, phenyl, imidazolyl, triazolyl, or pyridyl bonded via a —(O)$_{0/I}$—$C_{1-6}$-alkylene group and in each case unsubstituted or mono- or poly-substituted by identical or different substituents;
$R^{18b}$ presents H, OH, $C_{1-6}$-alkyl, phenyl or pyridyl, in each case unsubstituted or mono- or poly-substituted by identical or different substituents; O-phenyl or O-pyridyl, in each case unsubstituted or mono- or poly-substituted by identical or different substituents; or a phenyl or pyridyl group bonded via a $C_{1-6}$-alkylene group and in each case unsubstituted or mono- or poly-substituted by identical or different substituents;
$R^{19}$ represents H, $C_{1-6}$-alkyl, $C_{3-8}$-cycloalkyl, phenyl, pyridyl, thienyl, imidazolyl, thiazolyl or triazolyl, in each case unsubstituted or mono- or poly-substituted by identical or different substituents; or phenyl or pyridyl bonded via a $C_{1-6}$-alkylene group and in each case unsubstituted or mono- or poly-substituted by identical or different substituents;
$R^{120}$ represents H, F, Cl, OH, OCH$_3$, O—CF$_3$, $C_{1-6}$-alkyl, CF$_3$ or unsubstituted or mono- or poly-substitutedphenyl; and
$R^{126}$ represents H, $C_{1-6}$-alkyl, $C_{3-6}$-cycloalkyl, phenyl or pyridyl; or $C_{3-6}$-cycloalkyl, phenyl or pyridyl bonded via a $C_{1-3}$-alkylene group and in each case unsubstituted or mono- or poly-substituted by identical or different substituents.

10. A compound according to claim 1, wherein the following partial structure:

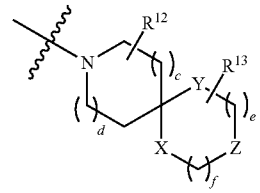

is selected from the group consisting of:

(B.1.)

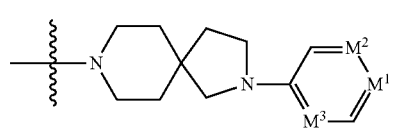
(B.2.)

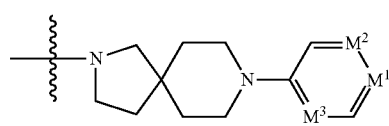
(B.3.)

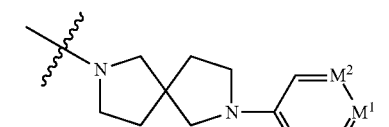
(B.4.)

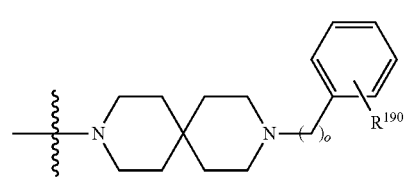
(B.5.)

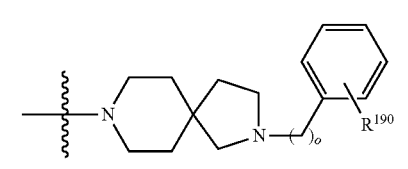
(B.6.)

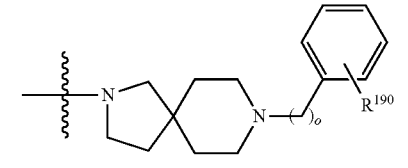
(B.7.)

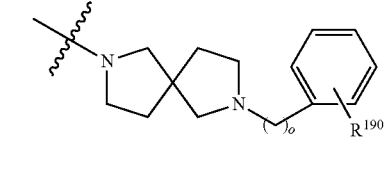
(B.8.)

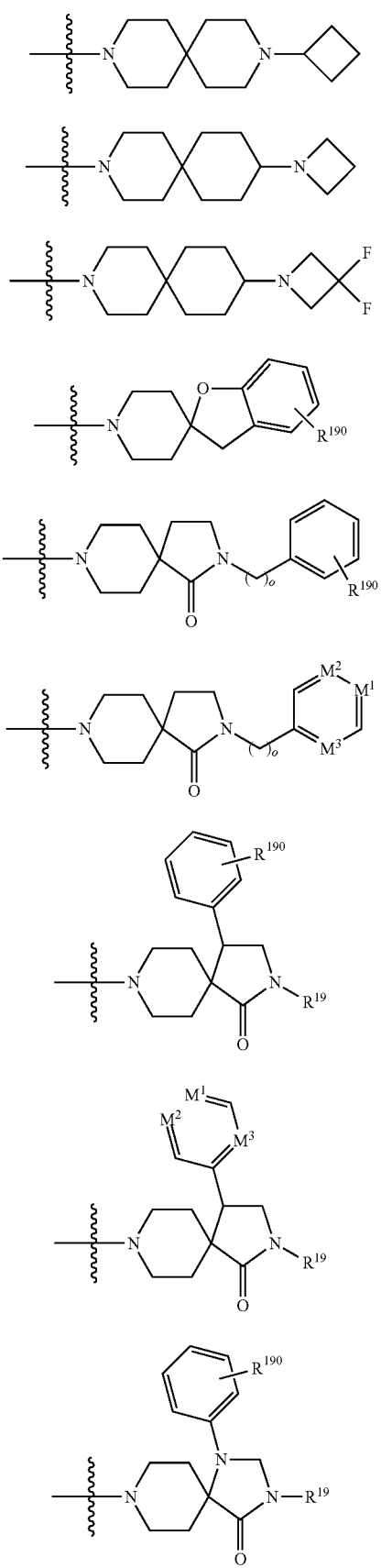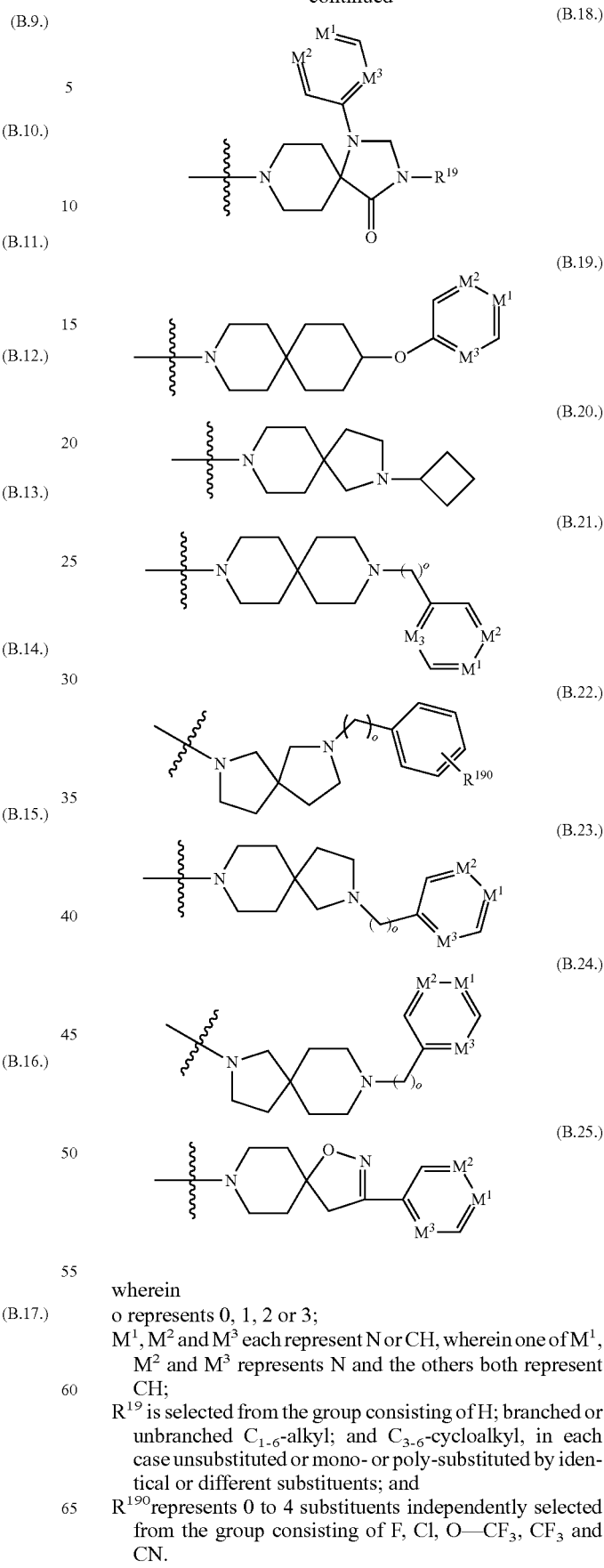

wherein
o represents 0, 1, 2 or 3;
$M^1$, $M^2$ and $M^3$ each represent N or CH, wherein one of $M^1$, $M^2$ and $M^3$ represents N and the others both represent CH;
$R^{19}$ is selected from the group consisting of H; branched or unbranched $C_{1-6}$-alkyl; and $C_{3-6}$-cycloalkyl, in each case unsubstituted or mono- or poly-substituted by identical or different substituents; and
$R^{190}$ represents 0 to 4 substituents independently selected from the group consisting of F, Cl, O—$CF_3$, $CF_3$ and CN.

11. A compound according to claim 1, selected from the group consisting of:

(2-(4-Methoxy-2,6-dimethylphenylsulfonyl)-1,2,3,4-tetrahydroisoquinolin-7-yl)(9-(pyridin-4-yl)-3,9-diazaspiro[5.5]undecan-3-yl)methanone, 2-(1-(4-Methoxy-2,6-dimethylphenylsulfonyl)-1,2,3,4-tetrahydroquinolin-7-yl)-1-(2-(pyridin-4-yl)-2,8-diazaspiro[4.5]decan-8-yl)ethanone, 1-(2-Cyclobutyl-2,8-diazaspiro[4.5]decan-8-yl)-2-(1-(4-methoxy-2,6-dimethylphenylsulfonyl)-1,2,3,4-tetrahydroquinolin-7-yl)ethanone, 2-(1-(4-Methoxy-2,6-dimethylphenylsulfonyl)-1,2,3,4-tetrahydroquinolin-7-yl)-1-(8-(pyridin-4-yl)-2,8-diazaspiro[4.5]decan-2-yl)ethanone, 2-(1-(4-Methoxy-2,6-dimethylphenylsulfonyl)-1,2,3,4-tetrahydroquinolin-7-yl)-1-(7-(pyridin-4-yl)-2,7-diazaspiro[4.4]nonan-2-yl)ethanone, 1-(9-(Pyridin-4-yl)-3,9-diazaspiro[5.5]undecan-3-yl)-2-(1-(2-(trifluoromethyl)phenylsulfonyl) -1,2,3,4-tetrahydroquinolin-7-yl)ethanone, 2-(1-(Naphthalin-1-ylsulfonyl)-1,2,3,4-tetrahydroquinolin-7-yl)-1-(9-(pyridin-4-yl)-3,9-diazaspiro[5.5]undecan-3-yl)ethanone, 2-(1-(2-Chloro-6-methylphenylsulfonyl)-1,2,3,4-tetrahydroquinolin-7-yl)-1-(9-(pyridin-4-yl)-3,9-diazaspiro[5.5]undecan-3-yl)ethanone, 2-(1-(4-Methoxy-2,6-dimethylphenylsulfonyl)indolin-6-yl)-1-(9-(pyridin-4-yl)-3,9-diazaspiro[5.5]undecan-3-yl)ethanone, (1-(2-Chlorobenzoyl)-1,2,3,4-tetrahydroquinolin-7-yl)(9-(pyridin-4-yl)-3,9-diazaspiro[5.5]undecan-3-yl)methanone, (1-(4-Methoxy-2,6-dimethylphenylsulfonyl)-1,2,3,4-tetrahydroquinolin-7-yl)(9-(pyridin-4-yl)-3,9-diazaspiro[5.5]undecan-3-yl)methanone, 2-(1-(4-Methoxy-2,6-dimethylphenylsulfonyl)-1,2,3,4-tetrahydroquinolin-7-yl)-1-(9-(pyridin-4-yl)-3,9-diazaspiro[5.5]undecan-3-yl)ethanone, 2-(1-(4-Methoxy-2,6-dimethylphenylsulfonyl)-1,2,3,4-tetrahydroquinolin-7-yl)-1-(9-(pyridin-4-yloxy)-3-azaspiro[5.5]undecan-3-yl)ethanone, 1-(9-(Azetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone, 1-(9-(3,3-Difluoroazetidin-1-yl)-3-azaspiro[5.5]undecan-3-yl)-2-(1-(4-methoxy-2,6-dimethylphenylsulfonyl)-1,2,3,4-tetrahydroquinolin-7-yl)ethanone, 2-(1-(2-Chloro-4-(trifluoromethoxy)phenylsulfonyl)-1,2,3,4-tetrahydroquinolin-7-yl)-1-(9-(pyridin-4-yl)-3,9-diazaspiro[5.5]undecan-3-yl)ethanone, 2-(2-(4-Methoxy-2,6-dimethylphenylsulfonyl)-1,2,3,4-tetrahydroisoquinolin-7-yl)-1-(9-(pyridin-4-yl)-3,9-diazaspiro[5.5]undecan-3-yl)ethanone, (2-(4-Methylnaphthalin-1-ylsulfonyl)-1,2,3,4-tetrahydroisoquinolin-7-yl)(9-(pyridin-4-yl)-3,9-diazaspiro[5.5]undecan-3-yl)methanone, (2-(4-Methoxynaphthalin-1-ylsulfonyl)-1,2,3,4-tetrahydroisoquinolin-7-yl)(9-(pyridin-4-yl)-3,9-diazaspiro[5.5]undecan-3-yl)methanone, (2-(4-Chloronaphthalin-1-ylsulfonyl)-1,2,3,4-tetrahydroisoquinolin-7-yl)(9-(pyridin-4-yl)-3,9-diazaspiro[5.5]undecan-3-yl)methanone, 2-(1-(2-Chloro-6-methylphenylsulfonyl)-1,2,3,4-tetrahydroquinolin-7-yl)-1-(8-(pyridin-4-yl)-2,8-diazaspiro[4.5]decan-2-yl)ethanone, 2-(1-(Naphthalin-1-ylsulfonyl)-1,2,3,4-tetrahydroquinolin-7-yl)-1-(8-(pyridin-4-yl)-2,8-diazaspiro[4.5]decan-2-yl)ethanone, 2-(1-(Naphthalin-1-ylsulfonyl)-1,2,3,4-tetrahydroquinolin-7-yl)-1-(7-(pyridin-4-yl)-2,7-diazaspiro[4.4]nonan-2-yl)ethanone, 1-(9-(Azetidin-1-yl)-3-azaspiro[5.5]undecan-3-yl)-2-(1-(naphthalin-1-ylsulfonyl)-1,2,3,4-tetrahydroquinolin-7-yl)ethanone, (2-(4-Fluoronaphthalin-1-ylsulfonyl)-1,2,3,4-tetrahydroisoquinolin-7-yl)(9-(pyridin-4-yl)-3,9-diazaspiro[5.5]undecan-3-yl)methanone, 1-(8-(Pyridin-4-yl)-2,8-diazaspiro[4.5]decan-2-yl)-2-(1-(2-(trifluoromethyl)phenylsulfonyl)-1,2,3,4-tetrahydroquinolin-7-yl)ethanone, (2-(5-Chloronaphthalin-1-ylsulfonyl)-1,2,3,4-tetrahydroisoquinolin-7-yl)(9-(pyridin-4-yl)-3,9-diazaspiro[5.5]undecan-3-yl)methanone, 2-[1-(2-Chloro-benzoyl)-1,2,3,4-tetrahydro-quinolin-7-yl]-1-(9-pyridin-4-yl-3,9-diazaspiro[5.5]undecan-3-yl)-ethanone, 2-[1-[(2,6-Dichloro-3-methyl-phenyl)sulfonyl]-1,2,3,4-tetrahydro-quinolin-7-yl]-1-(9-pyridin-4-yl-3,9-diazaspiro[5.5]undecan-3-yl)-ethanone,

[2-[(4-Methoxy-2,6-dimethyl-phenyl)sulfonyl]-2,3-dihydro-1H-isoindol-5-yl]-(9-pyridin-4-yl-3,9-diazaspiro[5.5]undecan-3-yl)-methanone,

[2-[(2-Chloro-6-methyl-phenyl)sulfonyl]-2,3-dihydro-1H-isoindol-5-yl]-(9-pyridin-4-yl-3,9-diazaspiro[5.5]undecan-3-yl)-methanone,

[2-(5-Chloro-thiophene-2-carbonyl)-2,3-dihydro-1H-isoindol-5-yl]-(9-pyridin-4-yl-3,9-diazaspiro[5.5]undecan-3-yl)-methanone,

[2-(4-Methoxy-2,6-dimethyl-benzoyl)-2,3-dihydro-1H-isoindol-5-yl]-(9-pyridin-4-yl-3,9-diazaspiro[5.5]undecan-3-yl)-methanone, 2-(4-Fluorobenzyl)-8-(1-(4-methoxy-2,6-dimethylphenylsulfonyl)indoline-6-carbonyl)-2,8-diazaspiro[4.5]decan-1-one, (7-Benzyl-2,7-diazaspiro[4.4]nonan-2-yl)(1-(4-methoxy-2,6-dimethylphenylsulfonyl)indoline -6-yl)methanone, (1-(4-Methoxy-2,6-dimethylphenylsulfonyl)indolin-6-yl)(9-(pyridin-4-yl)-3,9-diazaspiro[5.5]undecan-3-yl) methanone, (1-(2-Chlorobenzoyl)indolin-6-yl)(9-(pyridin-4-yl)-3,9-diazaspiro[5.5]undecan-3-yl)methanone, (1-(4-Chloro-2,5-dimethylphenylsulfonyl)indolin-6-yl)(9-(pyridin-4-yl)-3,9-diazaspiro[5.5]undecan-3-yl) methanone, 8-(2-(2-Chlorobenzoyl)isoindoline-5-carbonyl)-2-(4-fluorobenzyl)-2,8-diazaspiro[4.5]decan-1-one, 4-(4-Fluorophenyl)-8-(1-(4-methoxy-2,6-dimethylphenylsulfonyl)-1,2,3,4-tetrahydroquinoline-7-carbonyl)-2-methyl-2,8-diazaspiro[4.5]decan-1-one, 2-Benzyl-8-(1-(4-methoxy-2,6-dimethylphenylsulfonyl)-1,2,3,4-tetrahydroquinoline-7-carbonyl)-2,8-diazaspiro[4.5]decan-1-one, (7-Benzyl-2,7-diazaspiro[4.4]nonan-2-yl)(1-(4-methoxy-2,6-dimethylphenylsulfonyl)-1,2,3,4-tetrahydroquinolin-7-yl)methanone, 2-(4-Fluorobenzyl)-8-(2-(4-methoxy-2,6-dimethylphenylsulfonyl)-1,2,3,4-tetrahydroisoquinoline-7-carbonyl)-2,8-diazaspiro[4.5]decan-1-one, 2-Benzyl-8-(2-(4-methoxy-2,6-dimethylphenylsulfonyl)-1,2,3,4-tetrahydroisoquinoline-7-carbonyl)-2,8-diazaspiro[4.5]decan-1-one, (7-Benzyl-2,7-diazaspiro[4.4]nonan-2-yl)(2-(4-methoxy-2,6-dimethylphenylsulfonyl)-1,2,3,4-tetrahydroisoquinolin-7-yl)methanone, (2-(2-Chlorobenzoyl)-1,2,3,4-tetrahydroisoquinolin-7-yl)(9-(pyridin-4-yl)-3,9-diazaspiro[5.5]undecan-3-yl)methanone, 2-Benzyl-8-(2-(1-(4-methoxy-2,6-dimethylphenylsulfonyl)-1,2,3,4-tetrahydroquinolin-7-yl)acetyl)-2,8-diazaspiro[4.5]decan-1-one, 1-(7-Benzyl-2,7-diazaspiro[4.4]nonan-2-yl)-2-(1-(4-methoxy-2,6-dimethylphenylsulfonyl)-1,2,3,4-tetrahydroquinolin-7-yl)ethanone, 2-[1-[(4-Methoxy-2,6-dimethyl-phenyl)sulfonyl]-1,2,3,4-tetrahydro-quinolin-7-yl]-1-(3-pyridin-4-yl-3,9-diazaspiro[5.5]undecan-9-yl)-ethanone, and

[1-[(4-Methoxy-2,6-dimethyl-phenyl)sulfonyl]-1,2,3,4-tetrahydro-quinolin-7-yl]-(3-pyridin-4-yl-3,9-diazaspiro[5.5]undecan-9-yl)-methanone, or a physiologically compatible salt thereof.

12. A pharmaceutical composition comprising a compound according to claim 1 and at least one pharmaceutically acceptable carrier or auxiliary substance.

* * * * *

UNITED STATES PATENT AND TRADEMARK OFFICE
CERTIFICATE OF CORRECTION

PATENT NO. : 8,357,717 B2
APPLICATION NO. : 12/700857
DATED : January 22, 2013
INVENTOR(S) : Schunk et al.

It is certified that error appears in the above-identified patent and that said Letters Patent is hereby corrected as shown below:

In the Claims:

Claim 1 at column 170, lines 25-35 should appear as follows:

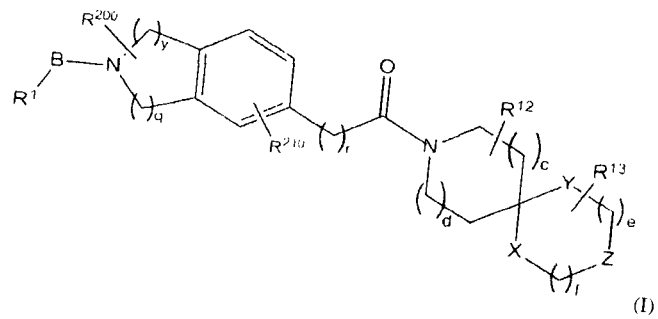

Claim 9 at column 178, lines 23-28 should appear as follows:

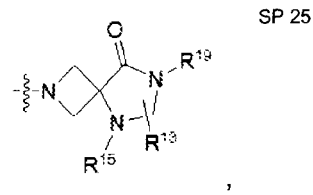

Signed and Sealed this
Third Day of September, 2013

Teresa Stanek Rea
*Acting Director of the United States Patent and Trademark Office*